(12) United States Patent
Cai et al.

(10) Patent No.: US 9,024,017 B2
(45) Date of Patent: May 5, 2015

(54) OCTAHYDRO-CYCLOPENTAPYRROLYL ANTAGONISTS OF CCR2

(71) Applicant: Janssen Pharmaceutica NV, Beerse (BE)

(72) Inventors: Chaozhong Cai, North Wales, PA (US); David F. McComsey, Warminster, PA (US); Zhihua Sui, Norristown, PA (US); Fu-An Kang, Collegeville, PA (US)

(73) Assignee: Janssen Pharmaceutica NV, Belgium (BE)

( * ) Notice: Subject to any disclaimer, the term of this patent is extended or adjusted under 35 U.S.C. 154(b) by 0 days.

(21) Appl. No.: 13/943,099

(22) Filed: Jul. 16, 2013

(65) Prior Publication Data
US 2014/0024646 A1 Jan. 23, 2014

Related U.S. Application Data
(60) Provisional application No. 61/673,383, filed on Jul. 19, 2012.

(51) Int. Cl.
| C07D 471/02 | (2006.01) |
| A61K 31/5377 | (2006.01) |
| C07D 471/04 | (2006.01) |
| C07D 405/12 | (2006.01) |
| C07D 405/14 | (2006.01) |

(52) U.S. Cl.
CPC ............ C07D 471/04 (2013.01); C07D 471/02 (2013.01); A61K 31/5377 (2013.01); C07D 405/12 (2013.01); C07D 405/14 (2013.01)

(58) Field of Classification Search
CPC .......................... C07D 471/02; A61K 31/5377
USPC ........................................ 544/127; 514/234.5
See application file for complete search history.

(56) References Cited

FOREIGN PATENT DOCUMENTS

| WO | WO 01/19360 | 3/2001 |
| WO | WO 03/093266 | 11/2003 |
| WO | WO 2005/079496 | 9/2005 |
| WO | WO 2005/120505 | 12/2005 |
| WO | WO 2006012396 | 2/2006 |
| WO | WO 2006/098959 | 9/2006 |
| WO | WO 2009/033281 | 3/2009 |

OTHER PUBLICATIONS

Kubinyi (3D QSAR in Drug Design: Ligand-Protein Interactions and Molecular Similarity, vol. 2-3, Springer, 1998, 800 pages). p. 243-44 provided.*
Cai et al. (Bioorganic & Medicinal Chemistry Letters 24 (2014) 1239-1242).*
Kalliomaki et al. (Scandinavian Journal of Pain 4 (2013) 77-83).*
Wermuth, The Practice of Medicinal Chemsitry, 2d ed. (2003), 768 pages. Chs. 9-10 provided.*

Dawson J, et al., Targeting monocyte chemoattractant protein-1 signaling in disease, *Expert Opin. Ther. Targets*, Feb. 7, 2003 (1):35-48.
Rollins B J, Monocyte chemoattractant protein 1: a potential regulator of monocyte recruitment in inflammatory disease, *Mol. Med. Today*, 1996, 2:198.
Tanaka, K.; et. al., "A New Approach for the Total Synthesis of L-y-Carboxyglutamic Acid: Utility of Ruthenium Tetroxide Oxidation" Nitta, Y. *Chem. Pharm. Bull.* 1986, 34(9), 3879-84.
Nordmann, R.; et. al., "115. Synthesis and Conformation of (5R,8R,10R)-8-(Methylthiomethyl)ergoline-6-carboxamidine", *Helv. Chim. Acta*, 1985, 68(4), 1025-32.
Smith, M. E. B. et. al., "Highly selective directed hydrogenation of enantiopure 4-(tert-butoxycarbonylamino_cyclopent-1-enecarboxylic acid methyl esters" *Tetrahedron Lett.* 2001, 42(7), 1347-50.
Garbrecht, W. L. et. al., "The Synthesis of Certain 5-Aminotetrazole Derivatives", *J. Org. Chem.*, 1953, 18, 1003-1013.
Regainia, Z. et al., "Synthesis of 1,2,5-Thiadiazolidines 1,1-dioxides (Cyclosulfamides) Starting from Amino acids and Chlorosulfonyl Isocyanate", *Tetrahedron* 2000, 56(3), 381-7.
Sarges, R.; et al., "Sulfamylurea Hypoglycemic Agents. 6. High-Potency Derivatives", *J. Med. Chem.* 1976, 19(5), 695-709.
Abdaoui, M. et al., "Synthese et Structure de 2-chloroethylnitrososulfamides (CENS) derives D'Aminoacides. Partie 5", *Tetrahedron* 2000, 56(16), 2427-35.
Gillaspy, M. et al., "A Simple Method for the Formation of Cyclopropylamines: The First Synthesis of Tricyclopropylamine", *Tetrahedron Lett.* 1995, 36(41), 7399-402.
Lyons, T. W. et. al., "Palladium-Catalyzed Ligand-Directed C-H Functionalization Reactions", *Chem. Rev.* 2010, 110(2), 1147-69.
Levins, C. et. al., "Efficient Phosphonium-Mediated Synthesis of 2-Amino-1,3,4-oxadiazoles", *Org. Lett.* 2008, 10(9), 1755-1758.
Hiltmann, R. et al., "Stereochemische Untersuchungen uber Arzneimittel. 4. Mitt. (*)", *Eur. J. Med. Chem.* 1977, 12(1), 63-8.
Hackler, R. E. et. al., "Synthetic Communications: An International Journal for Rapid Communication of Synthetic Organic Chemistry", *Syn. Comm.* 1975, 5(2), 143-6.
King, J. A. et. al., "The Preparation of Some a-Benzylamino-B,B-dialkoxypropionic Acid Derivatives", *J Amer. Chem. Soc.* 1950, 72, 1236-40.

(Continued)

*Primary Examiner* — Robert Havlin
(74) *Attorney, Agent, or Firm* — Mary A. Appollina

(57) ABSTRACT

The present invention comprises compounds of Formula (I).

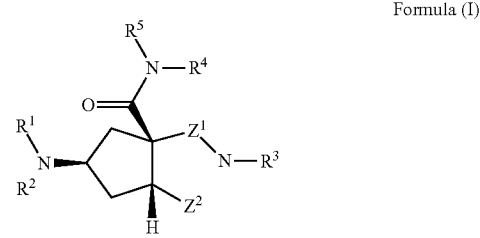

Formula (I)

wherein: $R^1$, $R^2$, $R^3$, $R^4$, $R^5$, $Z^1$ and $Z^2$ are as defined in the specification. The invention also comprises a method of preventing, treating or ameliorating a syndrome, disorder or disease, wherein said syndrome, disorder or disease is type II diabetes, obesity and asthma. The invention also comprises a method of inhibiting CCR2 activity in a mammal by administration of a therapeutically effective amount of at least one compound of Formula (I).

13 Claims, No Drawings

(56) References Cited

OTHER PUBLICATIONS

Rembarz, G. et al., "Reaktionen mit Natriumdicyanimid", J. *fuer Prak. Chem*, 1964, 26(5-6), 314-8.

Cory, et al., "Reduction of Carbonyl Compounds with Chiral Oxazaborolidine Catalysts: A New Paradigm for entioslsctice Catalysis and a powerful New Snythetic Method", Angewandte Chemie., 1998, vol. 37, No. 15, pp. 1986-2012.

Cho B. T., et al., Catalytic Enantioselective Reactions. Part 15. Oxazaborolidine Catalyzed Asymmetric Reduction of—Keto Acetals with N,N-Diethylaniline-Barone (DEANB) Complex, Bull. Korean Chem soc., 1999, 20:397.

International Search Report, PCT.US2013/050665, dated, Oct. 21, 2013.

International Search Report, PCT/US2013/035396, dated Aug. 8, 2013.

* cited by examiner

OCTAHYDRO-CYCLOPENTAPYRROLYL ANTAGONISTS OF CCR2

CROSS REFERENCE

This application claims priority from U.S. Provisional Application Ser. No. 61/673,383 filed Jul. 19, 2012, the contents of which is hereby incorporated by reference in its entirety.

FIELD OF THE INVENTION

The invention is directed to substituted fused cyclopentyl compounds, which are antagonists to the chemoattractant cytokine receptor 2 (CCR2), pharmaceutical compositions, and methods for use thereof. More particularly, the CCR2 antagonists are compounds useful for preventing, treating or ameliorating a CCR2 mediated syndrome, disorder or disease.

BACKGROUND OF THE INVENTION

CCR2 is a member of the GPCR family of receptors, as are all known chemokine receptors, and are expressed by monocytes and memory T-lymphocytes. The CCR2 signaling cascade involves activation of phospholipases (PLCβ2), protein kinases (PKC), and lipid kinases (PI-3 kinase).

Chemoattractant cytokines (i.e., chemokines) are relatively small proteins (8-10 kD), which stimulate the migration of cells. The chemokine family is divided into four subfamilies based on the number of amino acid residues between the first and second highly conserved cysteines.

Monocyte chemotactic protein-1 (MCP-1) is a member of the CC chemokine subfamily (wherein CC represents the subfamily having adjacent first and second cysteines) and binds to the cell-surface chemokine receptor 2 (CCR2). MCP-1 is a potent chemotactic factor, which, after binding to CCR2, mediates monocyte and lymphocyte migration (i.e., chemotaxis) toward a site of inflammation. MCP-1 is also expressed by cardiac muscle cells, blood vessel endothelial cells, fibroblasts, chondrocytes, smooth muscle cells, mesangial cells, alveolar cells, T-lymphocytes, marcophages, and the like.

After monocytes enter the inflammatory tissue and differentiate into macrophages, monocyte differentiation provides a secondary source of several proinflammatory modulators, including tumor necrosis factor-α (TNF-α), interleukin-1 (IL-1), IL-8 (a member of the CXC chemokine subfamily, wherein CXC represents one amino acid residue between the first and second cysteines), IL-12, arachidonic acid metabolites (e.g., $PGE_2$ and $LTB_4$), oxygen-derived free radicals, matrix metalloproteinases, and complement components.

Animal model studies of chronic inflammatory diseases have demonstrated that inhibition of binding between MCP-1 and CCR2 by an antagonist suppresses the inflammatory response. The interaction between MCP-1 and CCR2 has been implicated (see Rollins B J, Monocyte chemoattractant protein 1: a potential regulator of monocyte recruitment in inflammatory disease, *Mol. Med. Today*, 1996, 2:198; and Dawson J, et al., Targeting monocyte chemoattractant protein-1 signaling in disease, *Expert Opin. Ther. Targets*, 2003 Feb. 7 (1):35-48) in inflammatory disease pathologies such as psoriasis, uveitis, atherosclerosis, rheumatoid arthritis (RA), multiple sclerosis, Crohn's Disease, nephritis, organ allograft rejection, fibroid lung, renal insufficiency, type II diabetes and diabetic complications, diabetic nephropathy, diabetic retinopathy, diabetic retinitis, diabetic microangiopathy, tuberculosis, sarcoidosis, invasive staphylococcia, inflammation after cataract surgery, allergic rhinitis, allergic conjunctivitis, chronic urticaria, Chronic Obstructive Pulmonary Disease (COPD), allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, and stomach.

Monocyte migration is inhibited by MCP-1 antagonists (either antibodies or soluble, inactive fragments of MCP-1), which have been shown to inhibit the development of arthritis, asthma, and uveitis. Both MCP-1 and CCR2 knockout (KO) mice have demonstrated that monocyte infiltration into inflammatory lesions is significantly decreased. In addition, such KO mice are resistant to the development of experimental allergic encephalomyelitis (EAE, a model of human MS), cockroach allergen-induced asthma, atherosclerosis, and uveitis. Rheumatoid arthritis and Crohn's Disease patients have improved during treatment with TNF-α antagonists (e.g., monoclonal antibodies and soluble receptors) at dose levels correlated with decreases in MCP-1 expression and the number of infiltrating macrophages.

MCP-1 has been implicated in the pathogenesis of seasonal and chronic allergic rhinitis, having been found in the nasal mucosa of most patients with dust mite allergies. MCP-1 has also been found to induce histamine release from basophils in vitro. During allergic conditions, both allergens and histamines have been shown to trigger (i.e. to up-regulate) the expression of MCP-1 and other chemokines in the nasal mucosa of people with allergic rhinitis, suggesting the presence of a positive feedback loop in such patients.

There remains a need for small molecule CCR2 antagonists for preventing, treating or ameliorating a CCR2 mediated inflammatory syndrome, disorder or disease resulting from MCP-1 induced monocyte and lymphocyte migration to a site of inflammation.

All documents cited herein are incorporated by reference.

SUMMARY OF THE INVENTION

The present invention relates to the compounds of Formula (I)

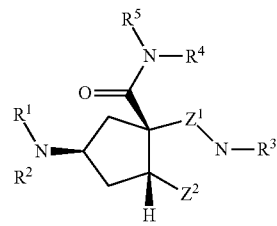

wherein $R^1$ is $C_{(1-4)}$alkyl$OC_{(1-4)}$alkyl, cyclohexyl, or tetrahydropyranyl, wherein said cyclohexyl or tetrahydropyranyl may be optionally substituted with one substituent selected from the group consisting of: $OC_{(1-4)}$alkyl, OH, $CH_2CH_3$, —CN, $NH_2$, $NH(CH_3)$, $N(CH_3)_2$, or $OCF_3$;

$R^2$ is H, $C(S)NHCH_2CH(CH_3)_2$, or $C(S)NHCH_3$;

$R^3$ is

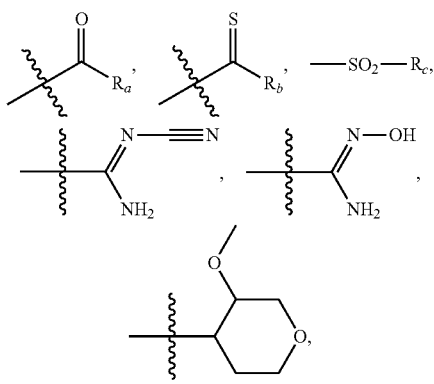

H, —CN, $C_{(1-4)}$alkyl, $C_{(1-4)}$alkylN$A^1A^2$, $C_{(1-3)}$alkylC(O)N$A^1A^2$, $C_{(3-6)}$cycloalkyl, oxetan-3-yl, —(CH$_2$)$_n$Ph-R$_{aa}$, —C$_{(1-4)}$alkylCO$_2$C$_{(1-4)}$alkyl, 4,5 dihydro thiazolyl, 4,5 dihydro oxazolyl, thiazolyl, oxazolyl, pyrimidinyl, pyridyl, pyrazyl, furyl, or 3-methyl 1,2,4 oxadiazol-5-yl; wherein said 4,5 dihydro thiazolyl, 4,5 dihydro oxazolyl, thiazolyl, oxazolyl, pyrimidinyl, pyridyl, pyrazyl, and furyl may be optionally substituted with up to two substituent independently selected from $R_{aa}$.

n is 0, 1, 2, or 3;

$R_a$ is H, N$A^1A^2$, NHCH$_2$CH$_2$NA$_1$A$_2$, $C_{(1-4)}$alkylN$A^1A^2$, OC$_{(1-4)}$alkylN$A^1A^2$, $C_{(1-6)}$alkyl, OC$_{(1-6)}$alkyl, —CN, —CH$_2$CH$_2$Ph, —CH$_2$OPh, —CH$_2$OC(O)C$_{(1-4)}$alkyl, —CH$_2$OC$_{(1-4)}$alkyl, —CH$_2$NHBoc, —OCH$_2$CH=CH$_2$, —OCH$_2$CH$_2$CF$_3$, —OCH$_2$CH$_2$C(CH$_3$)$_2$OH, —OCH$_2$CH$_2$OC$_{(1-4)}$alkyl, —OCH$_2$CH$_2$CN, —OPh-R$_{aa}$,

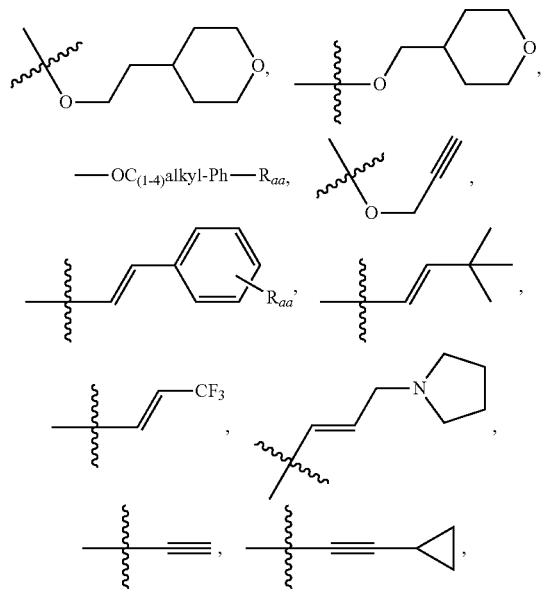

phenyl-R$_{aa}$, oxazol-2-yl, oxazol-4-yl, isoxazol-5-yl, or thiazol-2-yl;

$R_{aa}$ is H, OC$_{(1-4)}$alkyl, OCF$_3$, —CO$_2$H, Cl, Br, F, or —CN;

$R_b$ is N$A^1A^2$;

$R_c$ is N$A^1A^2$, CH$_2$Ph, CH$_2$CH$_2$Ph, or $C_{(1-4)}$alkyl;

$A^1$ is H, $C_{(1-6)}$alkyl, Ph-R$_{aa}$, C(O)CH$_3$, CH$_2$Ph-R$_{aa}$, or $C_{(1-4)}$alkylOC$_{(1-4)}$alkyl;

$A^2$ is H, $C_{(1-6)}$alkyl; or $A^1$ and $A^2$ may be taken together with the nitrogen to which they are attached to form a ring selected from the group consisting of:

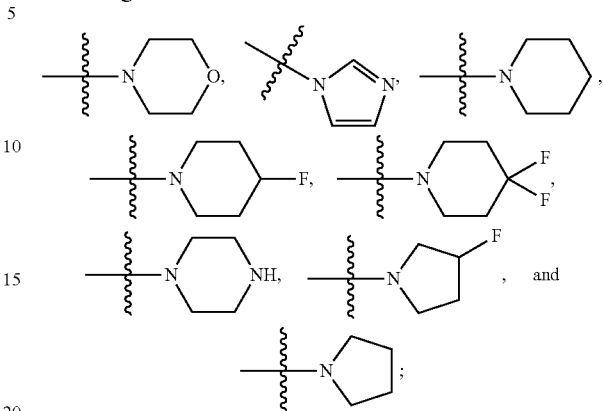

$R^4$ is CH$_2$Ph, wherein said Ph is optionally substituted with up to two groups selected from CF$_3$, OCF$_3$, and F;

$R^5$ is H; or $R^4$ and $R^5$ are taken together with their attached nitrogen to form a pair of fused rings selected from the group consisting of:

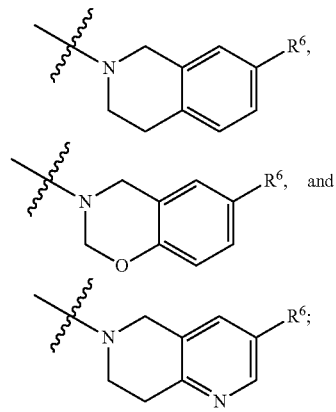

$R^6$ is CF$_3$, or OCF$_3$;

$Z^1$ is CH$_2$ or C=O;

$Z^2$ is CH$_2$ or $Z^2$ may be C=O provided that $Z^1$ and $Z^2$ are not both simultaneously C=O;

and pharmaceutically acceptable salts thereof.

DETAILED DESCRIPTION OF THE INVENTION

The present invention comprises compounds of Formula (I)

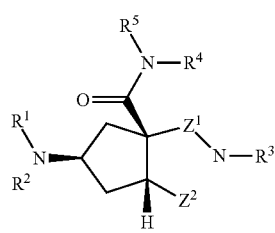

wherein
$R^1$, $R^2$, $R^3$, $R^4$, $R^5$; $Z^1$ and $Z^2$ are as defined above.

In an embodiment of the invention:
$R^1$ is $C_{(1-4)}$alkylOCH$_3$, cyclohexyl, 1-methoxy cyclohex-2-yl, tetrahydropyran-4-yl, or 3-$C_{(1-4)}$alkoxy tetrahydropyran-4-yl;
$R^3$ is

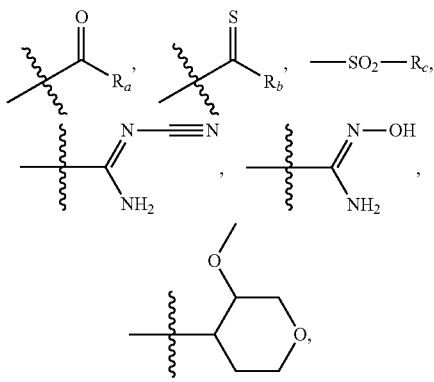

H, —CN, $C_{(1-4)}$alkyl, $C_{(1-4)}$alkylNA$^1$A$^2$, $C_{(1-3)}$alkylC(O)N(C$_{(1-2)}$alkyl)$_2$, $C_{(1-6)}$cycloalkyl, oxetan-3-yl, —(CH$_2$)$_n$Ph, —C$_{(1-4)}$alkylCO$_2$C$_{(1-4)}$alkyl, 4,5 dihydro thiazolyl, 4,5 dihydro oxazolyl, thiazolyl, oxazolyl, pyrimidinyl, pyridyl, pyrazyl, furyl, or 3-methyl 1,2,4 oxadiazol-5-yl;
n is 0, 1, 2, or 3;
$R_a$ is H, NA$^1$A$^2$, NHCH$_2$CH$_2$NA$_1$A$_2$, $C_{(1-4)}$alkylNA$^1$A$^2$, OC$_{(1-4)}$alkylNA$^1$A$^2$, $C_{(1-6)}$alkyl, OC$_{(1-6)}$alkyl, —CN, —CH$_2$CH$_2$Ph, —CH$_2$OPh, —CH$_2$OC(O)C$_{(1-4)}$alkyl, —CH$_2$OC$_{(1-4)}$alkyl, —CH$_2$NHBoc, —OCH$_2$CH=CH$_2$, —OCH$_2$CH$_2$CF$_3$, —OCH$_2$CH$_2$C(CH$_3$)$_2$OH, —OCH$_2$CH$_2$OC$_{(1-4)}$alkyl, —OCH$_2$CH$_2$CN, —OPh,

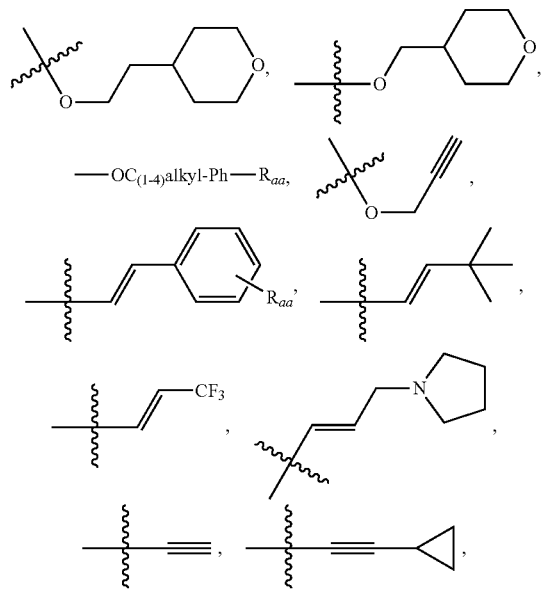

phenyl, oxazol-2-yl, oxazol-4-yl, isoxazol-5-yl, or thiazol-2-yl;
$R_{aa}$ is H, OC$_{(1-4)}$alkyl, —CO$_2$H, Cl, Br, F, or —CN;
$R_b$ is NA$^1$A$^2$;

$R_c$ is NH$_2$, NHCH$_2$Ph, CH$_2$Ph, CH$_2$CH$_2$Ph, or $C_{(1-4)}$alkyl;
$A^1$ is H, $C_{(1-6)}$alkyl, Ph-R$_{aa}$, or C(O)CH$_3$, CH$_2$Ph-R$_{aa}$, $C_{(1-4)}$alkylOC$_{(1-4)}$alkyl; $A^2$ is H, $C_{(1-6)}$alkyl; or $A^1$ and $A^2$ may be taken together with the nitrogen to which they are attached to form a ring selected from the group consisting of:

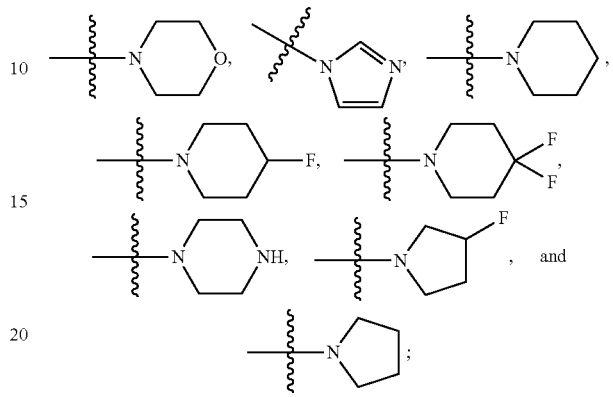

$R^4$ is CH$_2$Ph, wherein said Ph is optionally substituted with up to two groups selected from CF$_3$, OCF$_3$, and F;
$R^5$ is H; or
$R^4$ and $R^5$ are taken together with their attached nitrogen to form a pair of fused rings selected from the group consisting of:

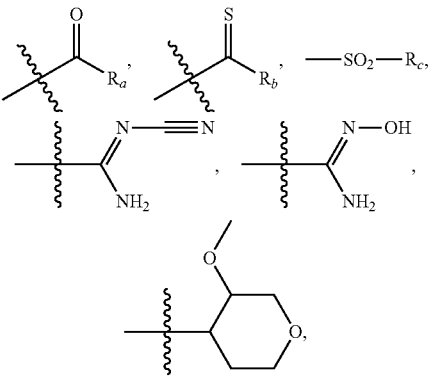

and pharmaceutically acceptable salts thereof.

In another embodiment of the invention:
$R^1$ is $C_{(1-4)}$alkylOCH$_3$, 3-$C_{(1-4)}$alkoxy tetrahydropyran-4-yl, or tetrahydropyran-4-yl;
$R^2$ is H, C(S)NHCH$_2$CH(CH$_3$)$_2$, or C(S)NHCH$_3$;
$R^3$ is

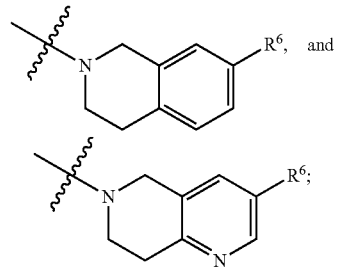

H, —CN, $C_{(1-4)}$alkyl, —$C_{(1-3)}$alkylC(O)N($C_{(1-2)}$alkyl)$_2$, $C_{(3-6)}$cycloalkyl, oxetan-3-yl, —(CH$_2$)$_n$Ph, —$C_{(1-4)}$alkylCO$_2$C$_{(1-4)}$alkyl, 4,5 dihydro thiazolyl, 4,5 dihydro oxazolyl, thiazolyl, oxazolyl, pyrimidinyl, pyridyl, pyrazyl, furyl, or 3-methyl 1,2,4 oxadiazol-5-yl;

n is 0, 1, 2, or 3;

$R_a$ is H, NA$^1$A$^2$, NHCH$_2$CH$_2$NA$_1$A$_2$, $C_{(1-4)}$alkylNA$^1$A$^2$, OC$_{(1-4)}$alkylNA$^1$A$^2$, $C_{(1-6)}$alkyl, OC$_{(1-6)}$alkyl, —CN, —CH$_2$CH$_2$Ph, —CH$_2$OPh, —CH$_2$OC(O)C$_{(1-4)}$alkyl, —CH$_2$OC$_{(1-4)}$alkyl, —CH$_2$NHBoc, —OCH$_2$CH=CH$_2$, —OCH$_2$CH$_2$CF$_3$, —OCH$_2$CH$_2$C(CH$_3$)$_2$OH, —OCH$_2$CH$_2$OCH$_3$, —OCH$_2$CH$_2$CN, —OPh,

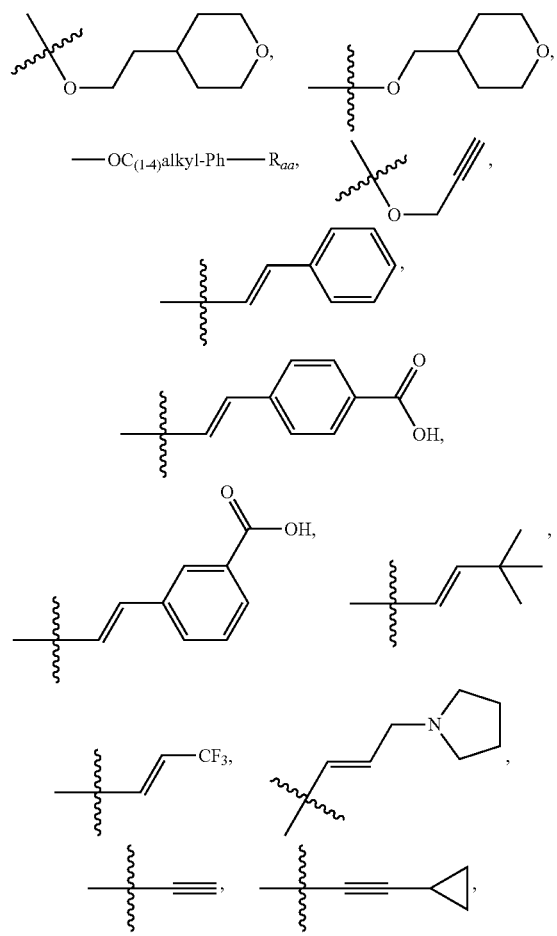

—OC$_{(1-4)}$alkyl-Ph—$R_{aa}$, phenyl, oxazol-2-yl, oxazol-4-yl, isoxazol-5-yl, or thiazol-2-yl;

$R_{aa}$ is H, OC$_{(1-4)}$alkyl, or —CN;

$R_b$ is

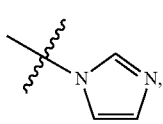 [SMILES: *n1ccnc1]

NH$_2$, NHCH$_3$, NHCH$_2$Ph, or NHCH$_2$CH(CH$_3$)$_2$;

$R_c$ is NH$_2$, NHCH$_2$Ph, CH$_2$Ph, CH$_2$CH$_2$Ph, or CH$_3$;

A$^1$ is H, $C_{(1-6)}$alkyl, Ph, C(O)CH$_3$, CH$_2$Ph, or $C_{(1-4)}$alkyl OC$_{(1-4)}$alkyl;

A$^2$ is H, $C_{(1-6)}$alkyl; or

A$^1$ and A$^2$ may be taken together with the nitrogen to which they are attached to form a ring selected from the group consisting of:

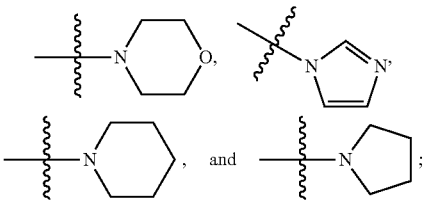

R$^4$ is CH$_2$Ph, wherein said Ph is optionally substituted with up to two groups selected from CF$_3$, OCF$_3$, and F;

R$^5$ is H; or R$^4$ and R$^5$ are taken together with their attached nitrogen to form a pair of fused rings selected from the group consisting of:

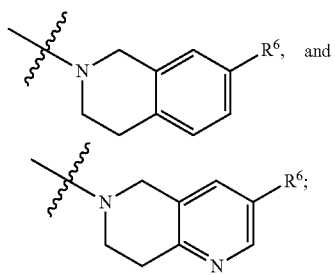

R$^6$ is CF$_3$, or OCF$_3$;

Z$^1$ is CH$_2$ or C=O;

Z$^2$ is CH$_2$ or Z$^2$ may be C=O provided that Z$^1$ and Z$^2$ are not both simultaneously C=O;

and pharmaceutically acceptable salts thereof.

In another embodiment of the invention:

R$^1$ is CH$_2$CH$_2$OCH$_3$, 3-$C_{(1-4)}$alkoxy tetrahydropyran-4-yl, or tetrahydropyran-4-yl;

R$^2$ is H, C(S)NHCH$_2$CH(CH$_3$)$_2$, or C(S)NHCH$_3$;

R$^3$ is

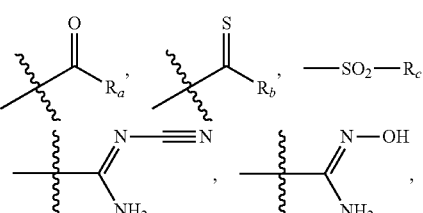

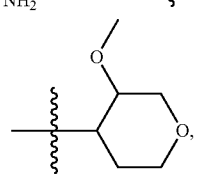

H, —CN, $C_{(1-4)}$alkyl, —$C_{(1-3)}$alkylC(O)N($C_{(1-2)}$alkyl)$_2$, cyclopropyl, cyclobutanyl, oxetan-3-yl, —(CH$_2$)$_n$Ph, —$C_{(1-4)}$ alkylCO$_2$C$_{(1-4)}$alkyl, 4,5 dihydro thiazol-2-yl, 4,5 dihydro oxazol-2-yl, thiazol-2-yl, pyrimidin-2-yl, or 3-methyl 1,2,4 oxadiazol-5-yl;

n is 0, 1, 2, or 3;

$R_a$ is H, $NA^1A^2$, $NHCH_2CH_2NA_1A_2$, $C_{(1-4)}alkylNA^1A^2$, $OC_{(1-4)}alkylNA^1A^2$, $C_{(1-6)}alkyl$, $OC_{(1-6)}alkyl$, —CN, —$CH_2CH_2Ph$, —$CH_2OPh$, —$CH_2NHBoc$, —$OCH_2Ph$, —$CH_2OC(O)C_{(1-4)}alkyl$, —$CH_2OC_{(1-4)}alkyl$, —$OCH_2Ph$-CN, —$OCH_2Ph$-$OCH_3$, —$OCH_2CH=CH_2$, —$OCH_2CH_2CF_3$, —$OCH_2CH_2C(CH_3)_2OH$, —$OCH_2CH_2OCH_3$, —$OCH_2CH_2CN$, —OPh,

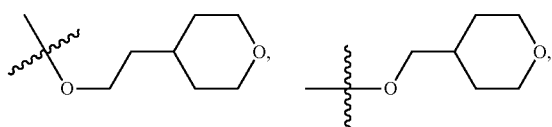

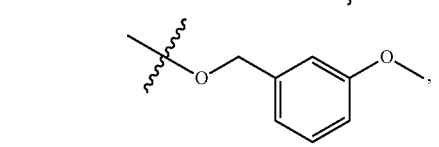

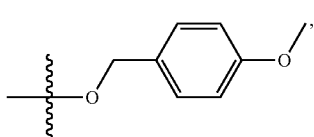

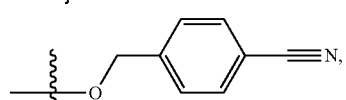

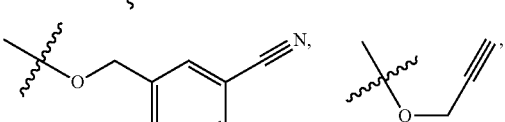

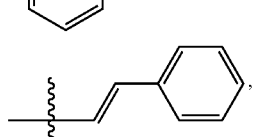

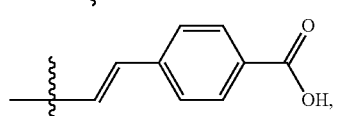

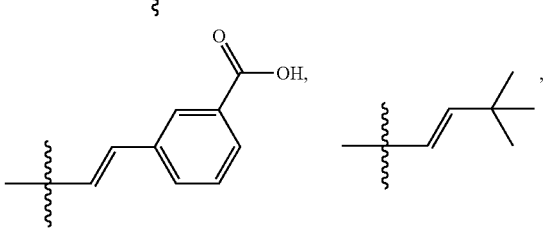

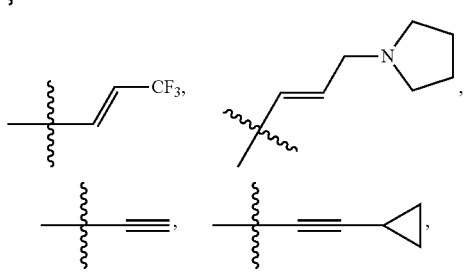

phenyl, oxazol-2-yl, oxazol-4-yl, isoxazol-5-yl, or thiazol-2-yl;

$R_b$ is

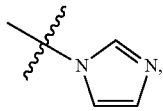 [SMILES: *n1ccnc1]

$NH_2$, $NHCH_3$, $NHCH_2Ph$, or $NHCH_2CH(CH_3)_2$;
$R_c$ is $NH_2$, $NHCH_2Ph$, $CH_2Ph$, $CH_2CH_2Ph$, or $CH_3$;
$A^1$ is H, $C_{(1-6)}alkyl$, Ph, or $C(O)CH_3$, $CH_2Ph$, $C_{(1-4)}alkyl$ $OC_{(1-4)}alkyl$;
$A^2$ is H, $C_{(1-4)}alkyl$; or
$A^1$ and $A^2$ may be taken together with the nitrogen to which they are attached to form a ring selected from the group consisting of:

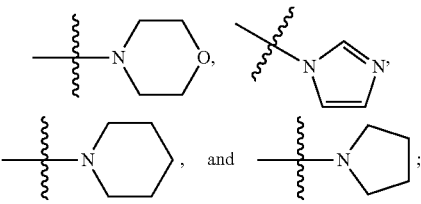

$R^4$ is $CH_2Ph$, wherein said Ph is optionally substituted with up to two groups selected from $CF_3$, $OCF_3$, and F;
$R^5$ is H; or $R^4$ and $R^5$ are taken together with their attached nitrogen to form a pair of fused rings selected from the group consisting of:

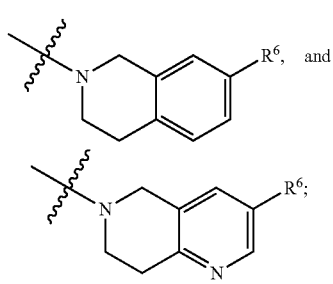

$R^6$ is $CF_3$, or $OCF_3$;
$Z^1$ is $CH_2$ or C=O;
$Z^2$ is $CH_2$ or $Z^2$ may be C=O provided that $Z^1$ and $Z^2$ are not both simultaneously C=O;
and pharmaceutically acceptable salts thereof.
In another embodiment of the invention:
$R^1$ is $CH_2CH_2OCH_3$, 3-$C_{(1-2)}alkoxy$ tetrahydropyran-4-yl, or tetrahydropyran-4-yl;
$R^2$ is H, $C(S)NHCH_2CH(CH_3)_2$, or $C(S)NHCH_3$;
$R^3$ is

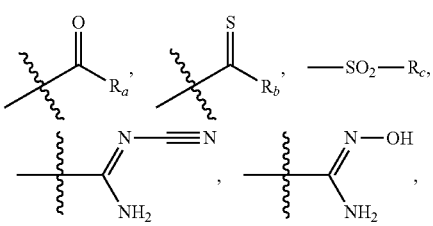

-continued

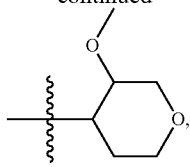

H, —CN, C$_{(1-3)}$alkyl, —CH$_2$C(O)N(CH$_3$)$_2$, cyclopropyl, oxetan-3-yl, —(CH$_2$)$_n$Ph, —CH$_2$CO$_2$CH$_3$, 4,5 dihydro thiazol-2-yl, 4,5 dihydro oxazol-2-yl, thiazol-2-yl, pyrimidin-2-yl, or 3-methyl 1,2,4 oxadiazol-5-yl;

n is 0, 1, 2, or 3;

R$_a$ is H, NH$_2$, NHCH$_3$, N(CH$_3$)$_2$, NHCH$_2$CH(CH$_3$)$_2$, NHCH(CH$_3$)$_2$, NHCH$_2$C(CH$_3$)$_3$, NHCH$_2$CH$_2$OCH$_3$, NHCH$_2$CH$_2$NA$_1$A$_2$, NHPh, NHCH$_2$Ph, CH$_2$CH$_2$N(CH$_3$)$_2$, CH$_2$CH$_2$CH$_2$N(CH$_3$)$_2$, —CN, —CH$_3$, —CH$_2$CH$_2$Ph, —CH$_2$OPh, —CH$_2$OC(O)CH$_3$, —CH$_2$OCH$_3$, —CH$_2$OC(CH$_3$)$_3$, —CH$_2$NHC(O)CH$_3$, —CH$_2$N(CH$_3$)$_2$, —CH$_2$NHBoc, —OCH$_3$, —OCH$_2$C(CH$_3$)$_3$, —OCH$_2$CH(CH$_3$)$_2$, —OCH$_2$CH$_2$CH$_3$, —OCH$_2$Ph, —OCH$_2$Ph-CN, —OCH$_2$Ph-OCH$_3$, —OCH$_2$CH═CH$_2$, —OCH$_2$CH$_2$CF$_3$, —OCH$_2$CH$_2$C(CH$_3$)$_2$OH, —OCH$_2$CH$_2$OCH$_3$, —OCH$_2$CH$_2$CN, —OCH$_2$CH$_2$N(C$_{(1-2)}$alkyl)$_2$, —OCH$_2$CH$_2$NHC(O)CH$_3$, —OPh,

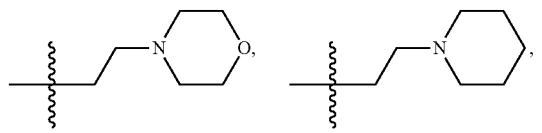

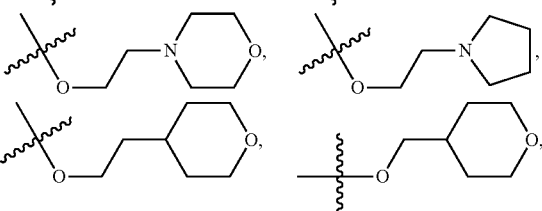

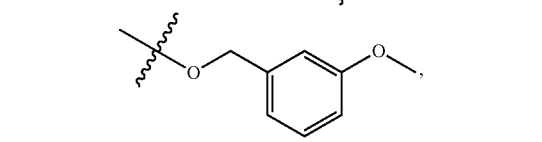

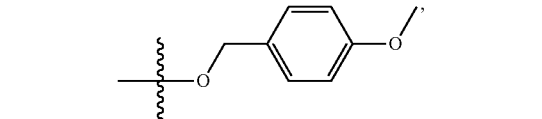

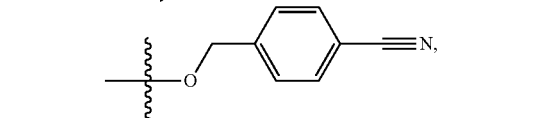

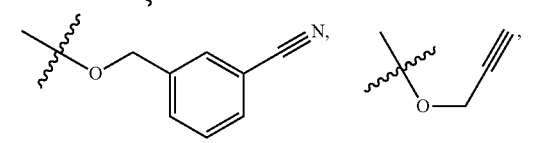

-continued

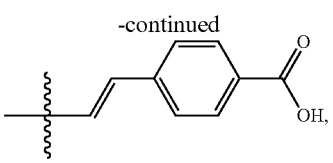

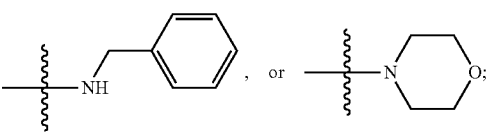

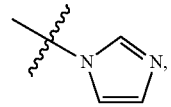 [SMILES: *n1ccnc1]

phenyl, oxazol-2-yl, oxazol-4-yl, isoxazol-5-yl, thiazol-2-yl,

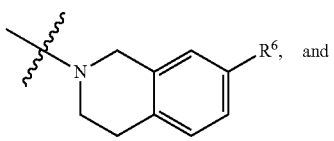

R$_b$ is

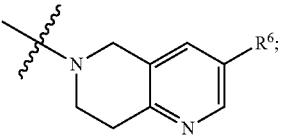

NH$_2$, NHCH$_3$, NHCH$_2$Ph, or NHCH$_2$CH(CH$_3$)$_2$;

R$_c$ is NH$_2$, NHCH$_2$Ph, CH$_2$Ph, CH$_2$CH$_2$Ph, or CH$_3$;

R$^4$ is 1,3-bis(trifluoromethyl)benz-5-yl, 1-fluoro-3-(trifluoromethyl)benz-5-yl, or 1-(trifluoromethyl)benz-5-yl;

R$^5$ is H; or R$^4$ and R$^5$ are taken together with their attached nitrogen to form a pair of fused rings selected from the group consisting of:

R$^6$ is CF$_3$, or OCF$_3$;

Z$^1$ is CH$_2$ or C═O;

Z$^2$ is CH$_2$ or Z$^2$ may be C═O provided that Z$^1$ and Z$^2$ are not both simultaneously C═O;

and pharmaceutically acceptable salts thereof.

Another embodiment of the invention comprises a compound of Formula (I), selected from the group consisting of:

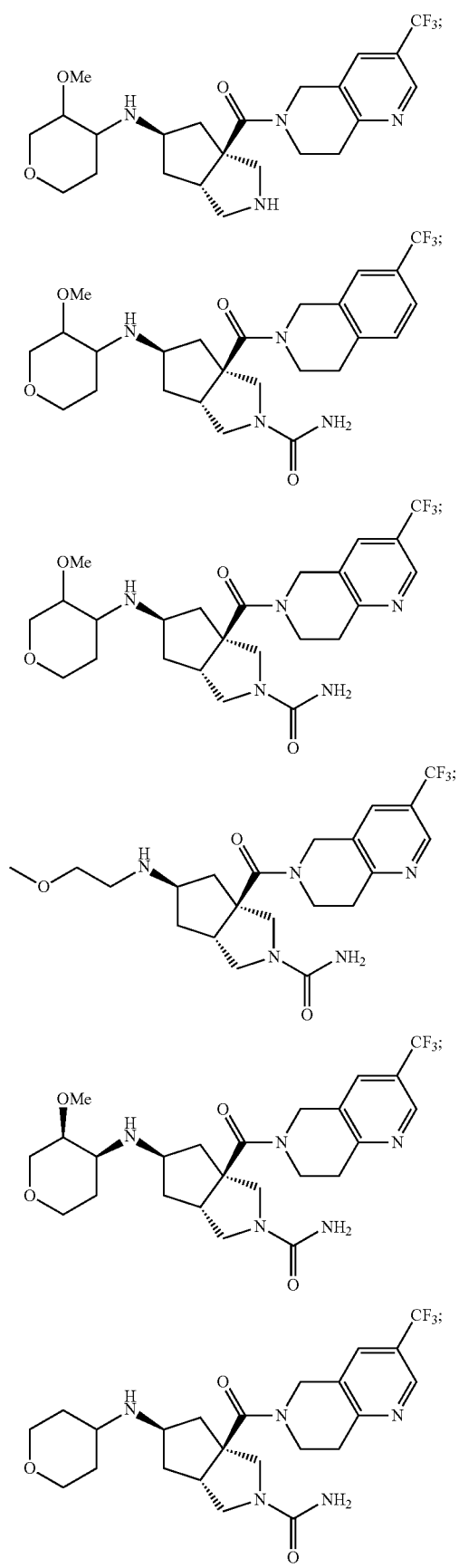
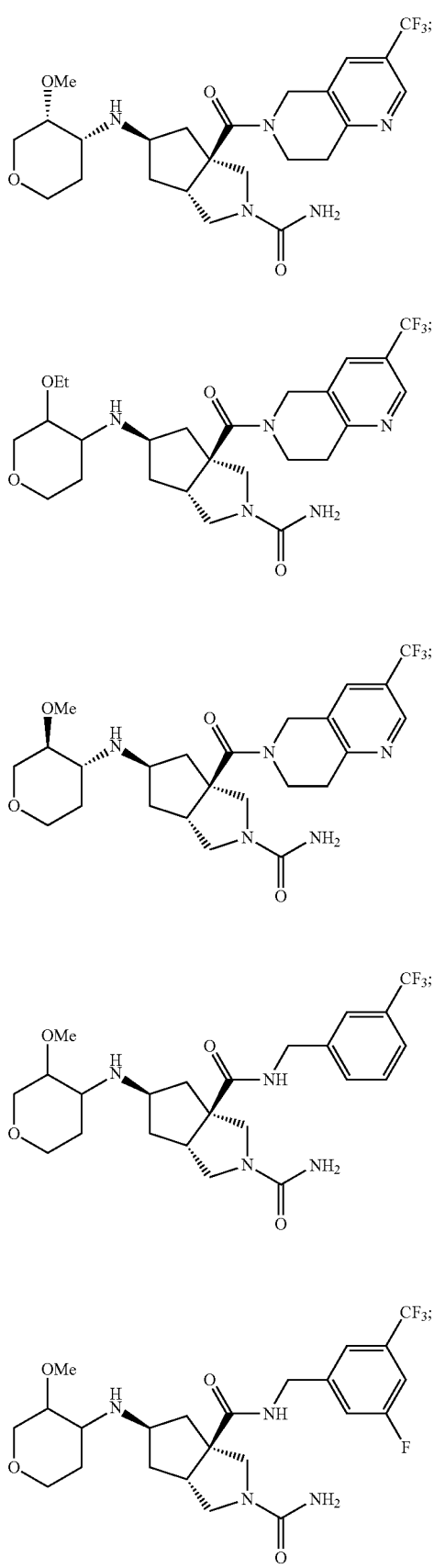

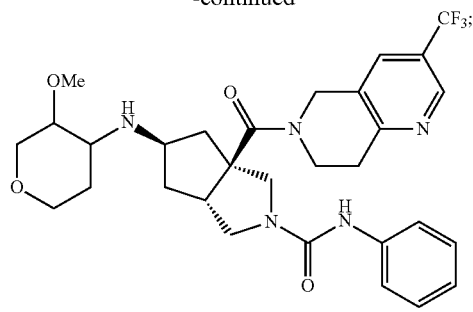
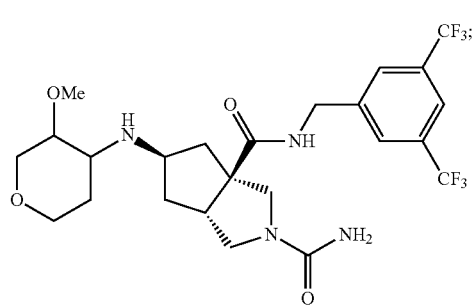
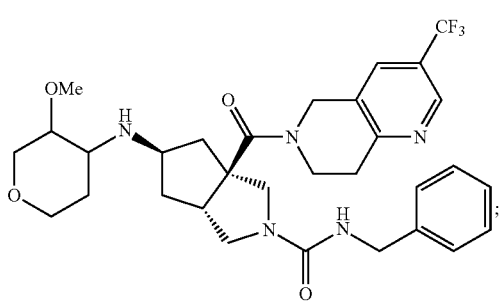
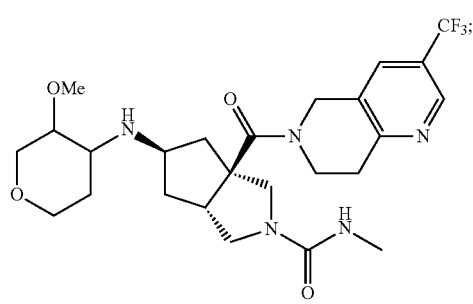
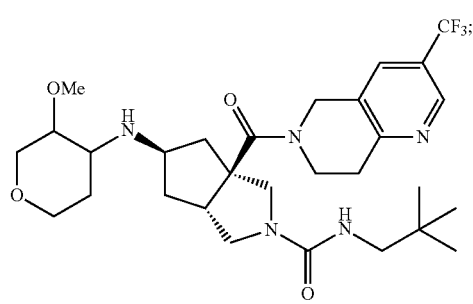
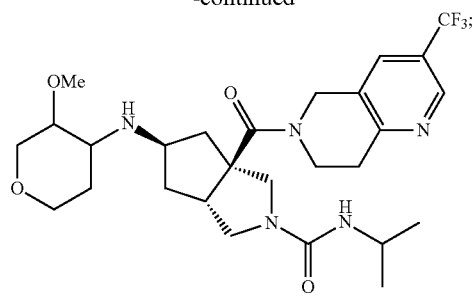
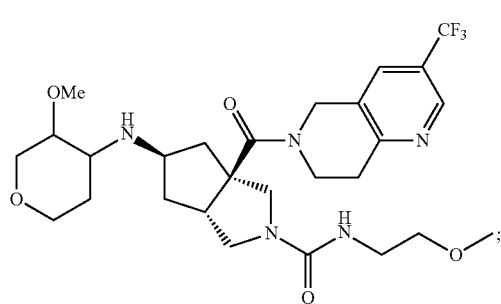
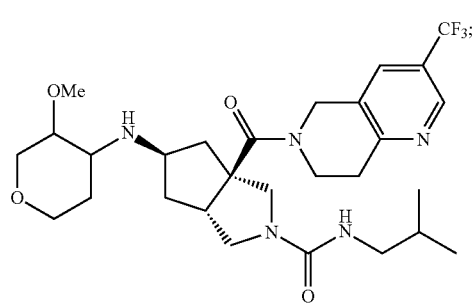
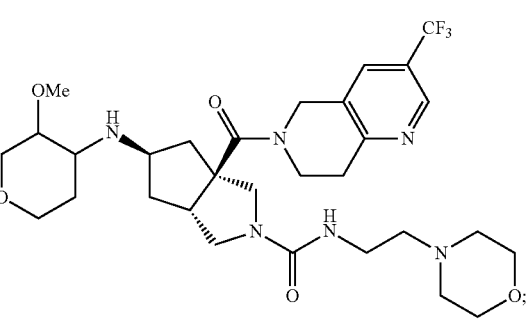
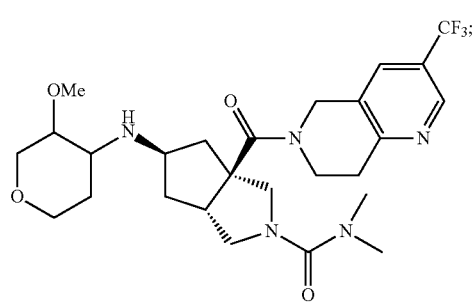

17
-continued
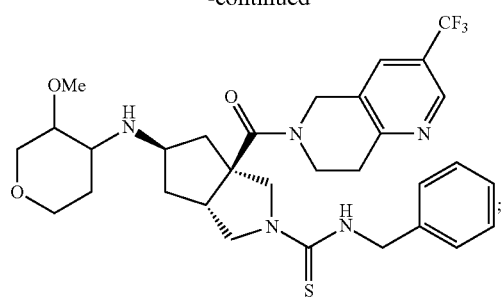
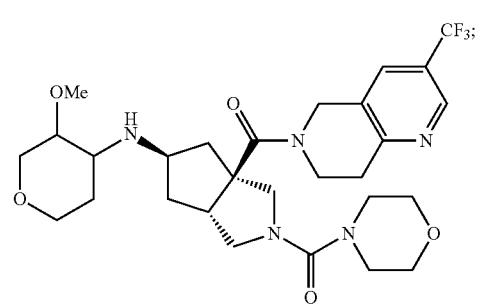
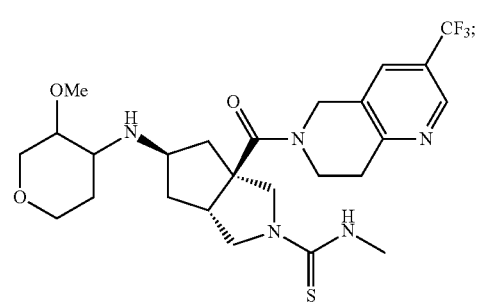
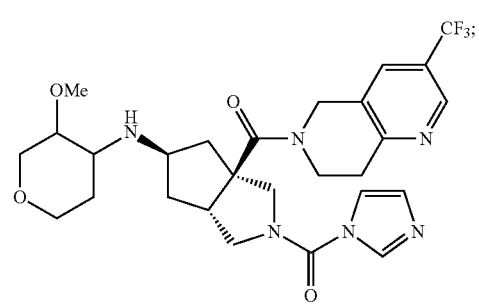
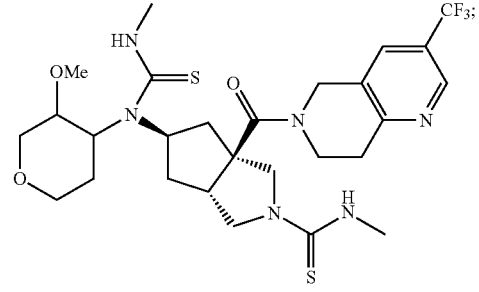
18
-continued
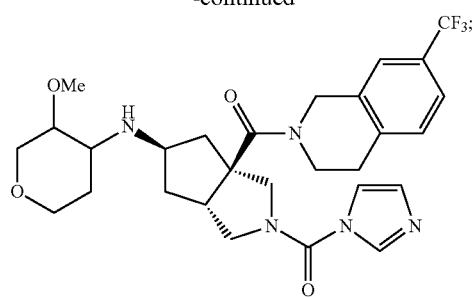
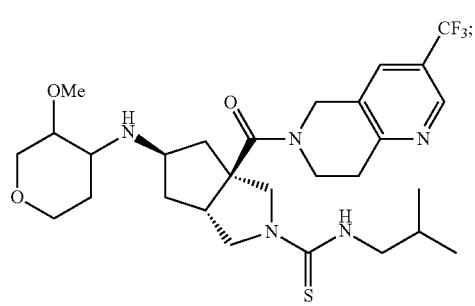
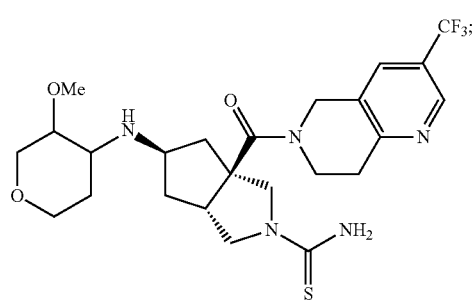
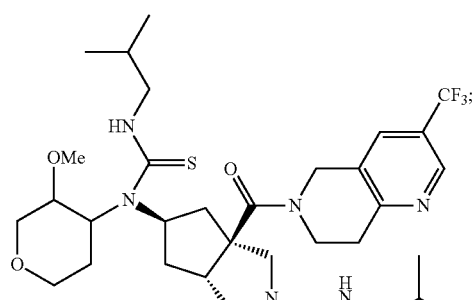
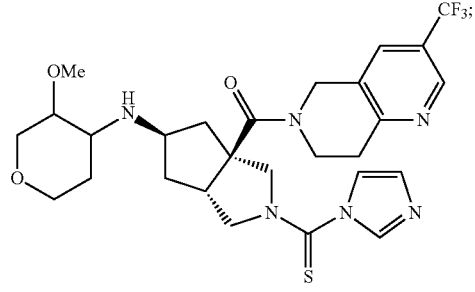

19
-continued
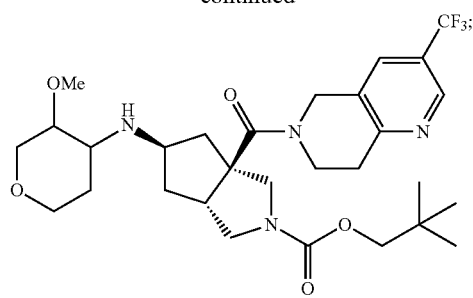
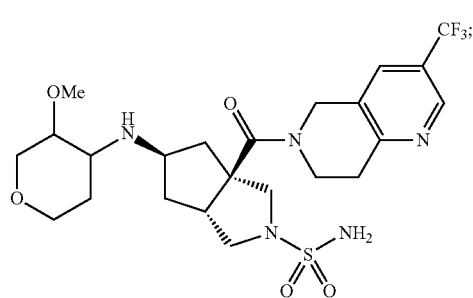
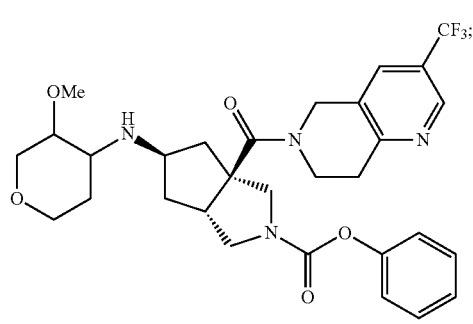
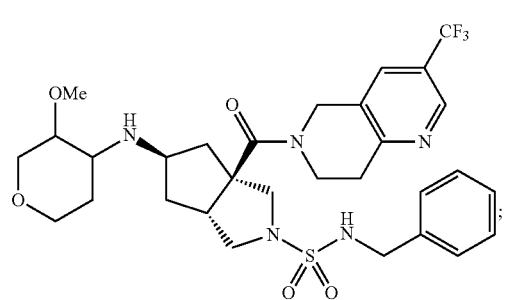
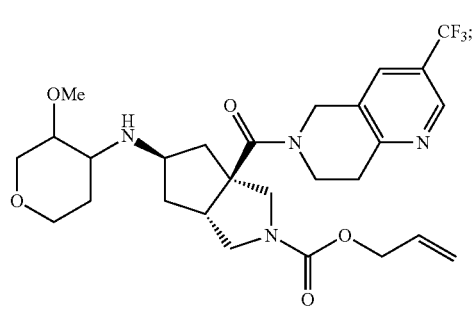
20
-continued
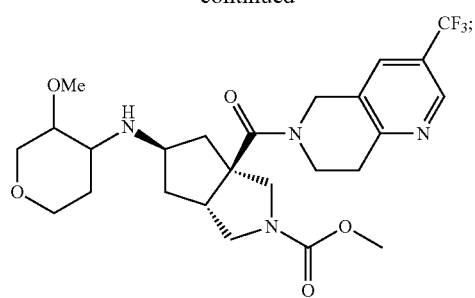
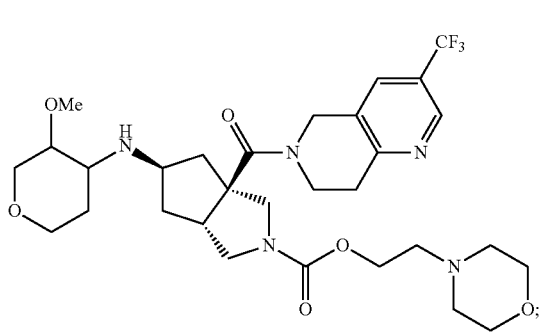
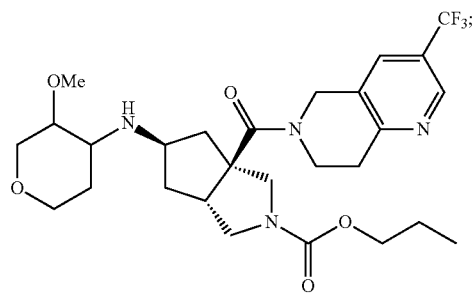
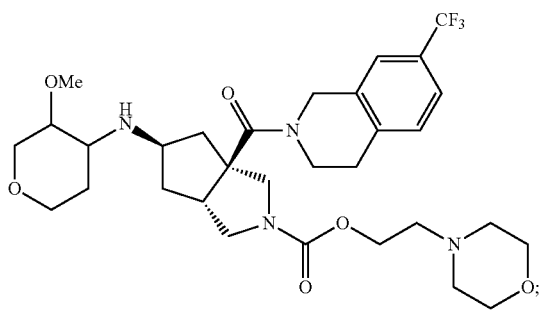
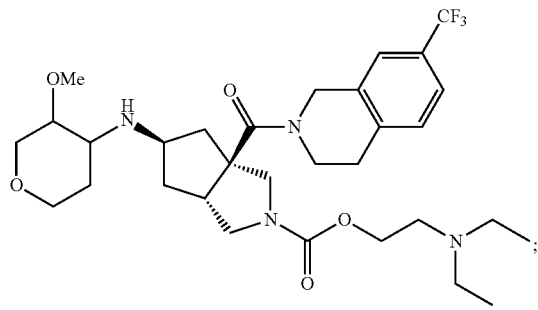

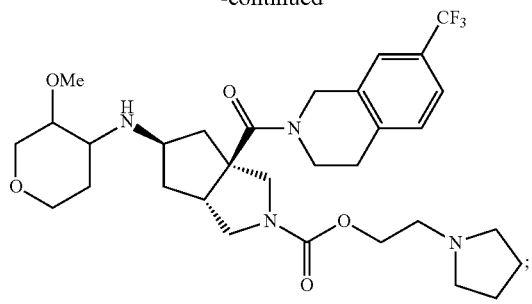
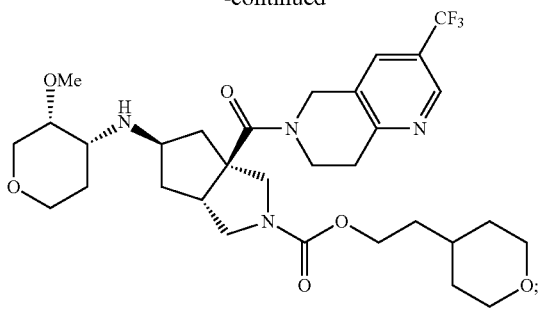
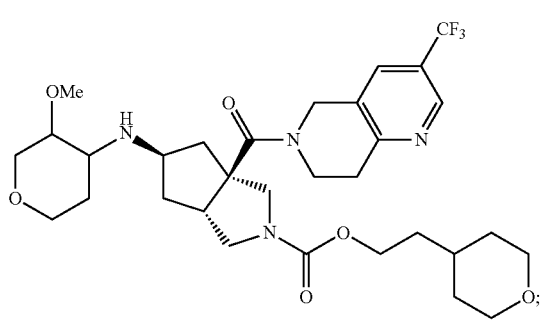
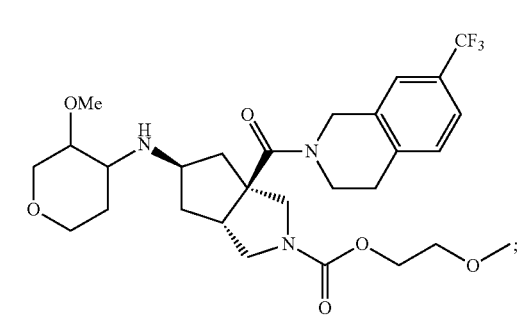
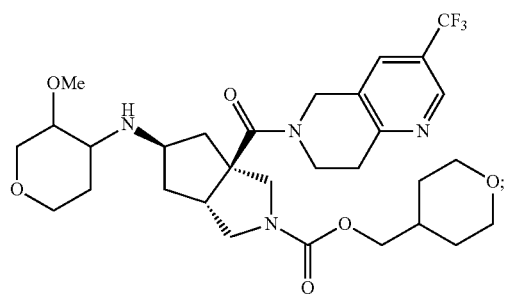
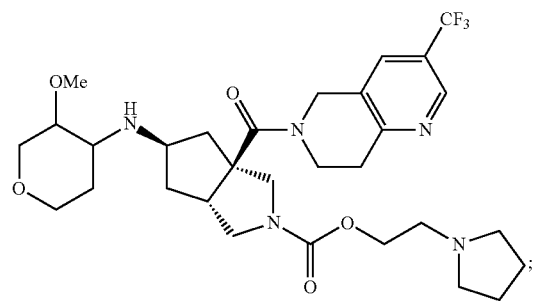
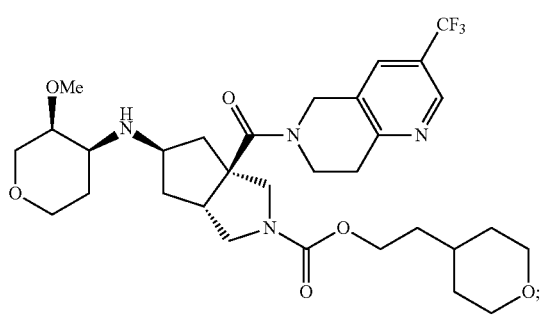
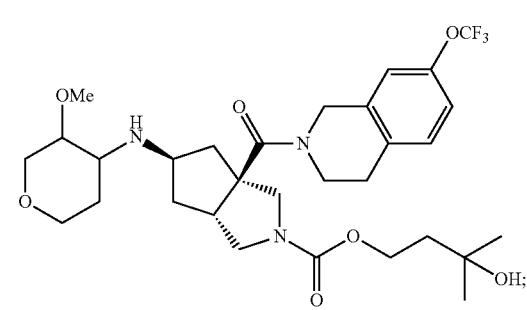
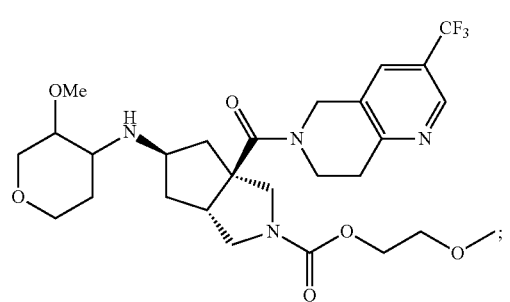
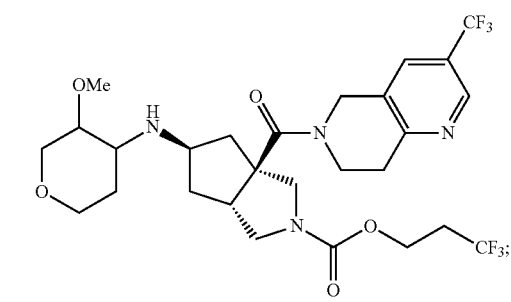

-continued
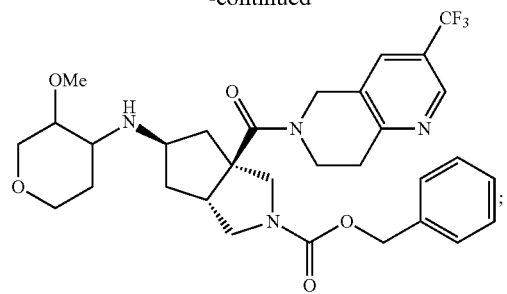
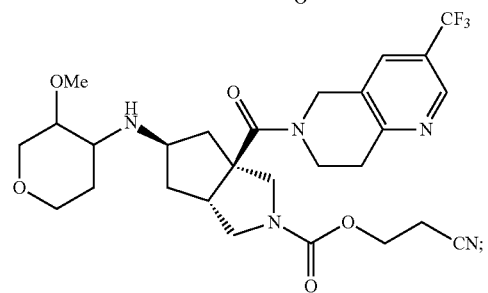
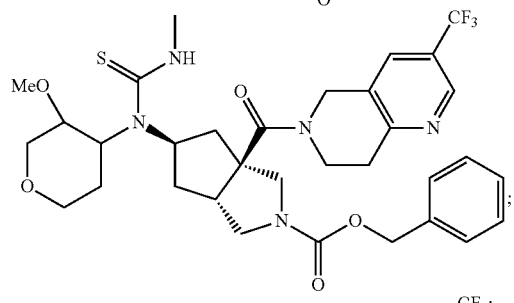
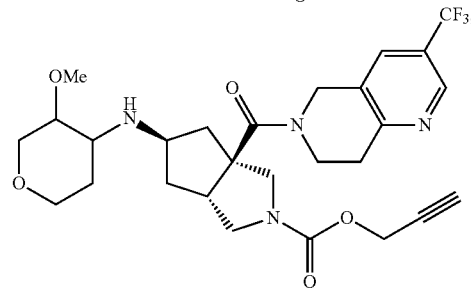
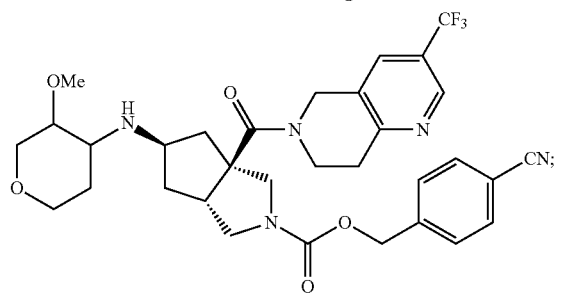
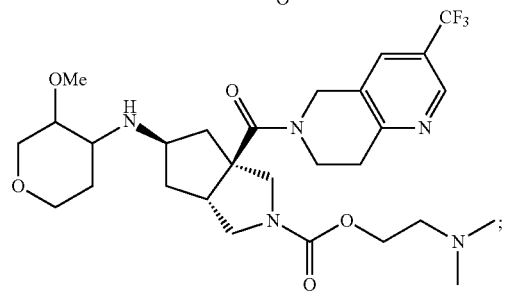
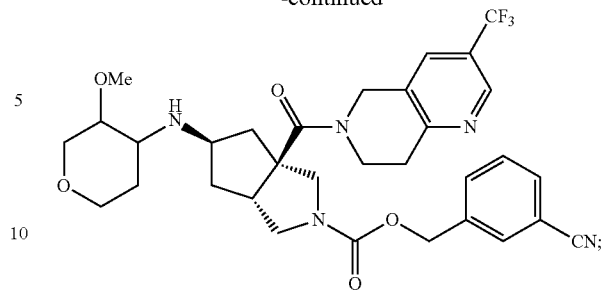
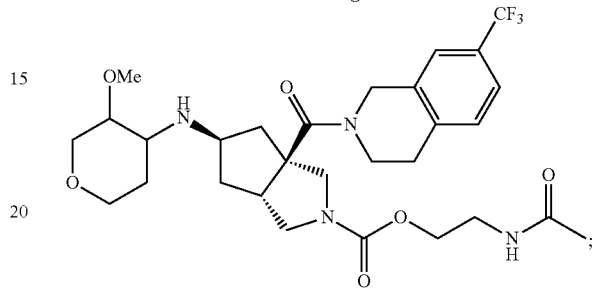
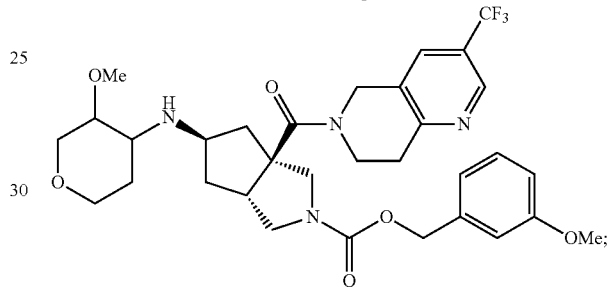
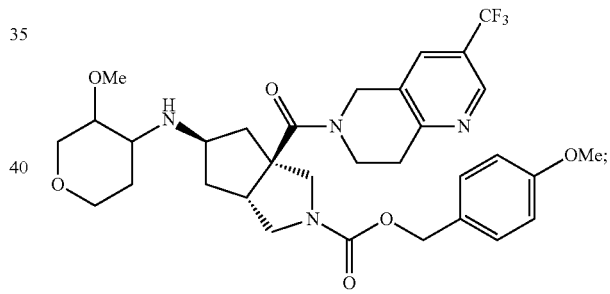
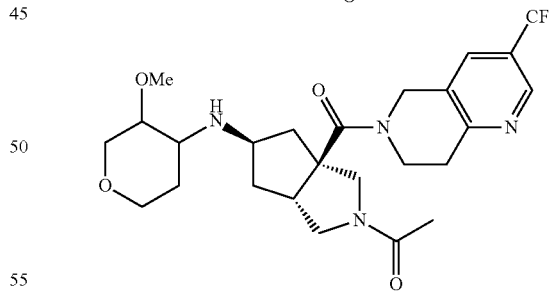
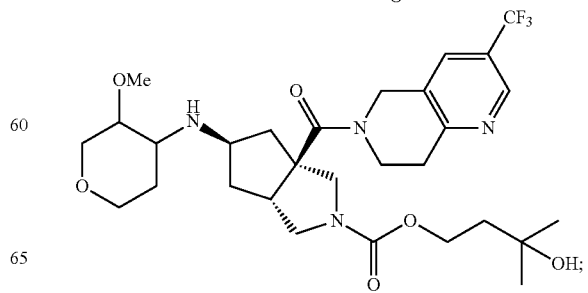

25
-continued
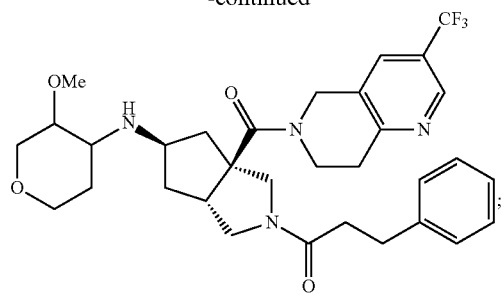
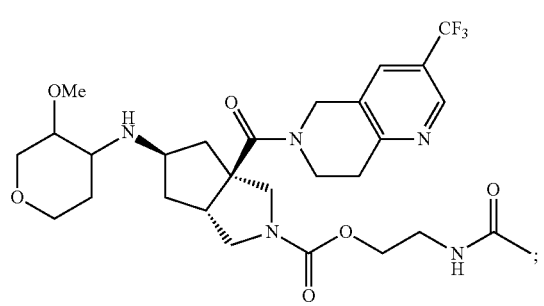
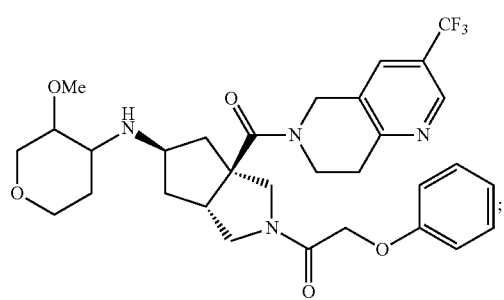
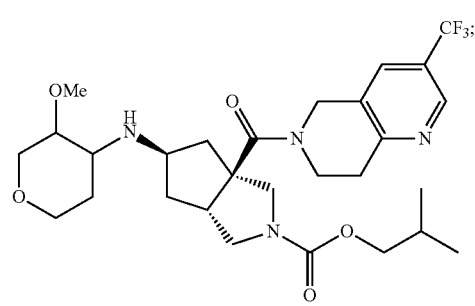
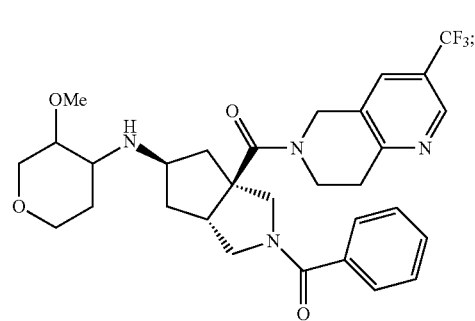
26
-continued
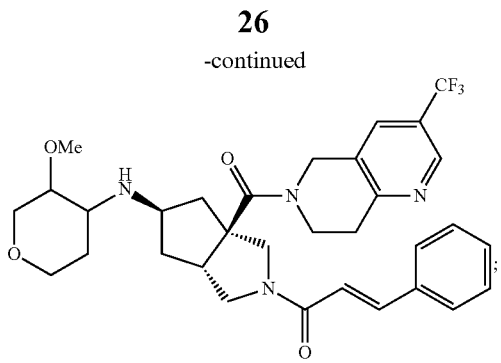
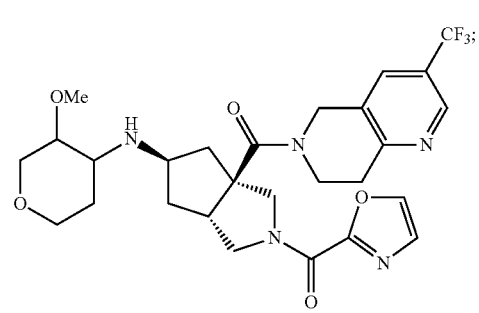
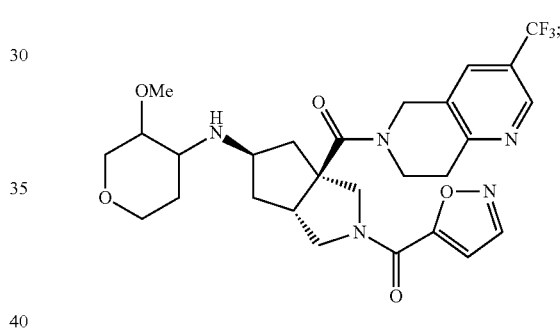
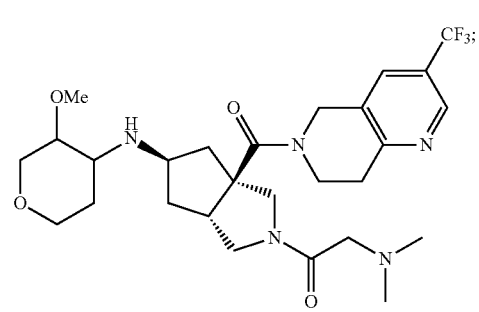
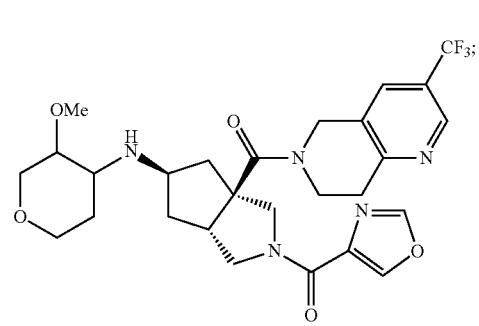

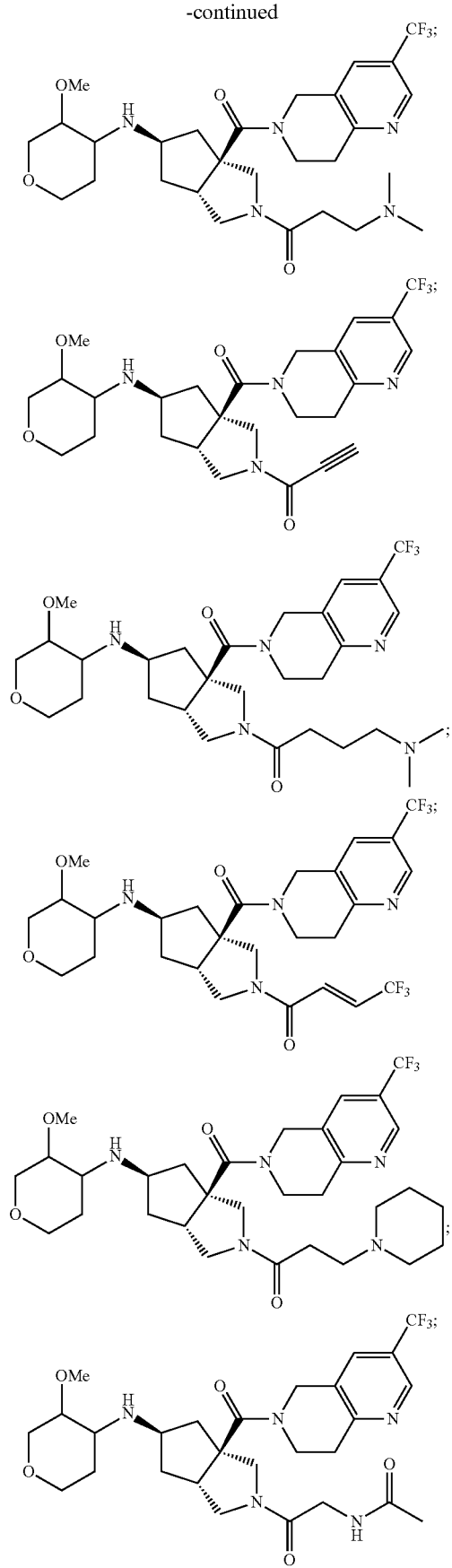
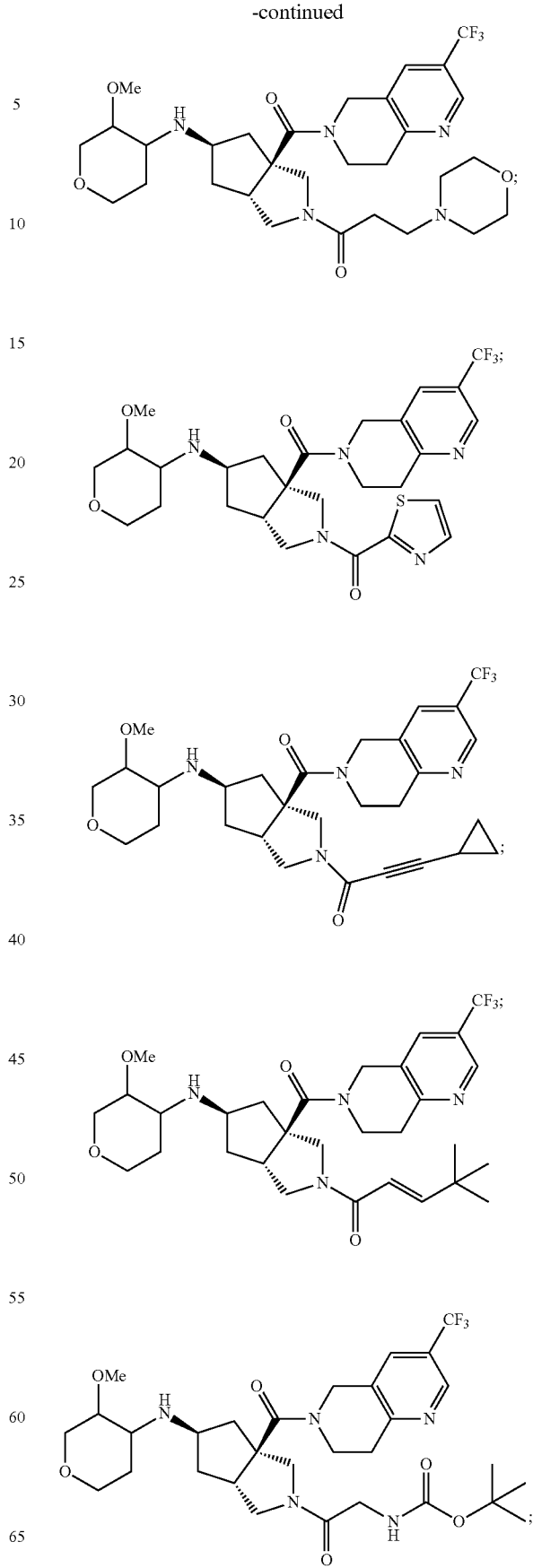

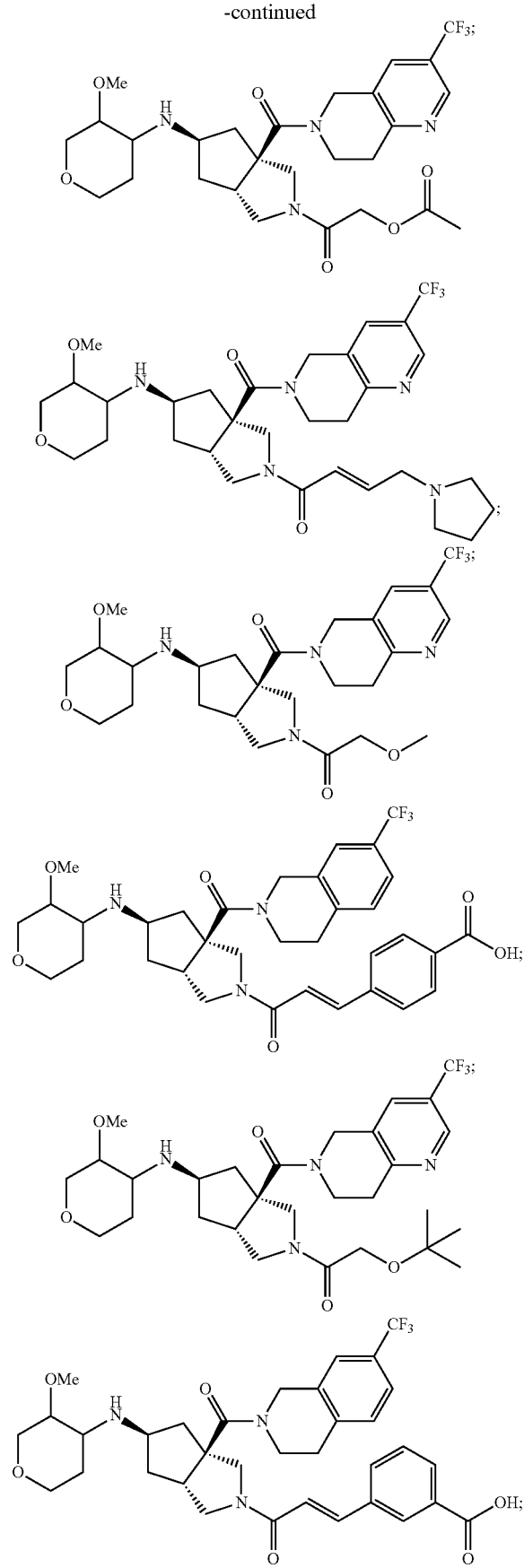
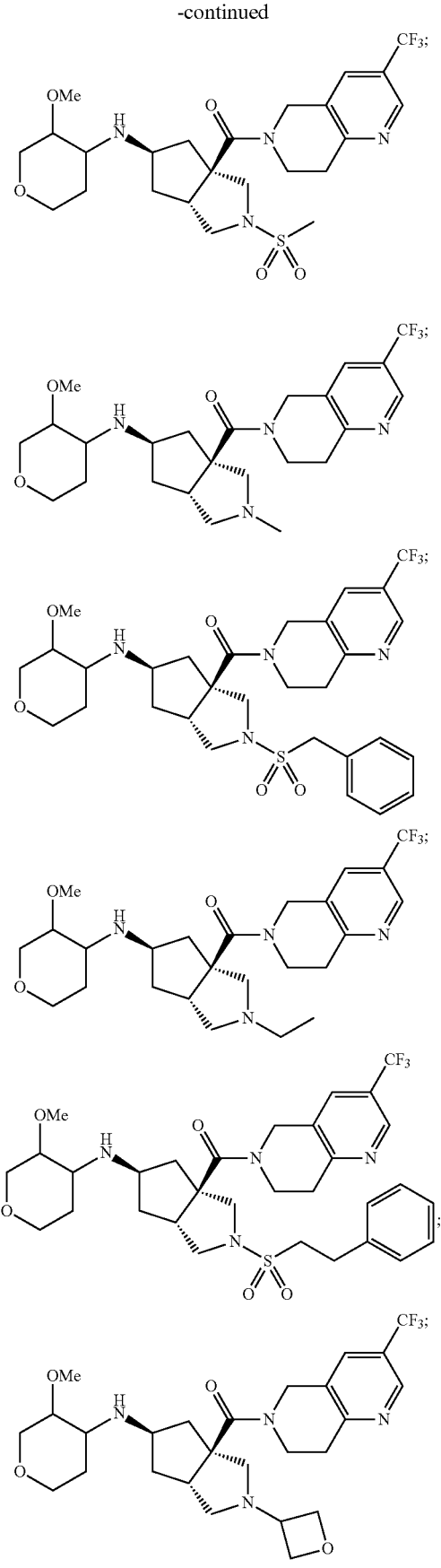

31
-continued
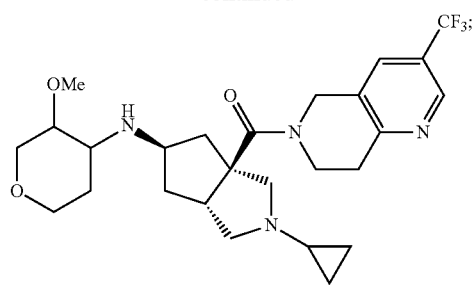
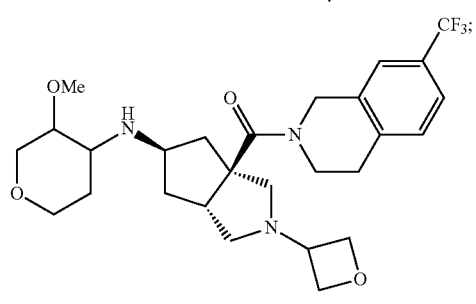
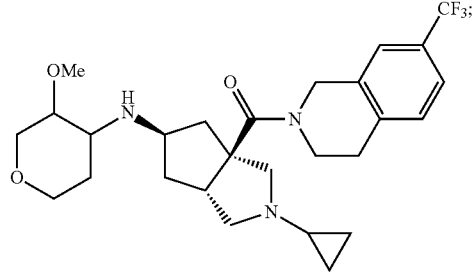
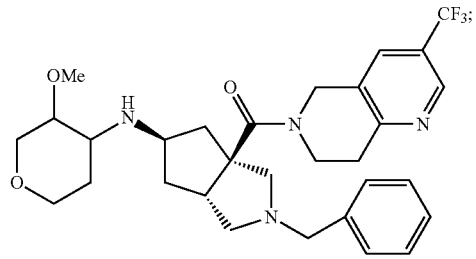
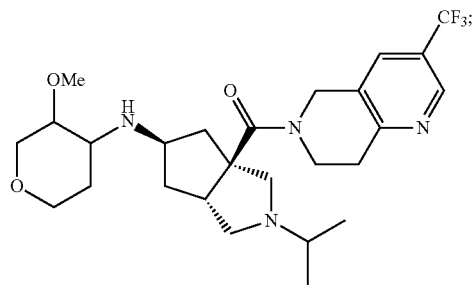
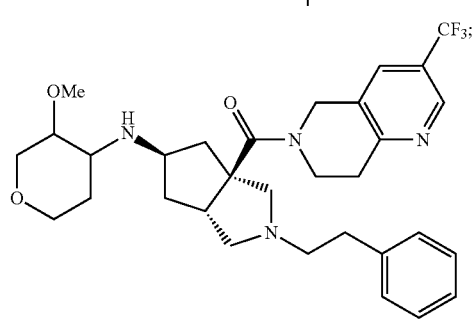
32
-continued
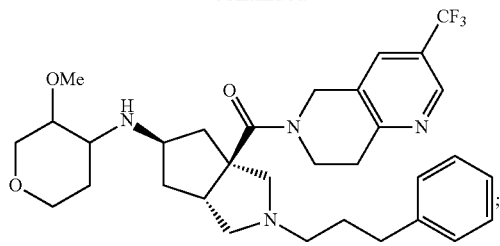
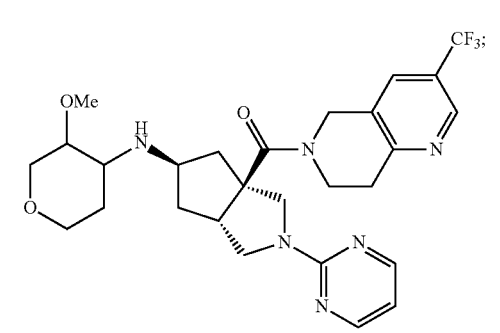
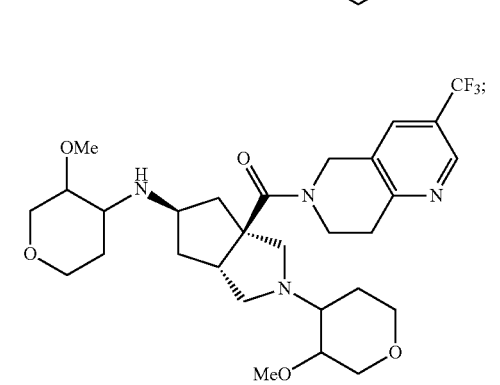
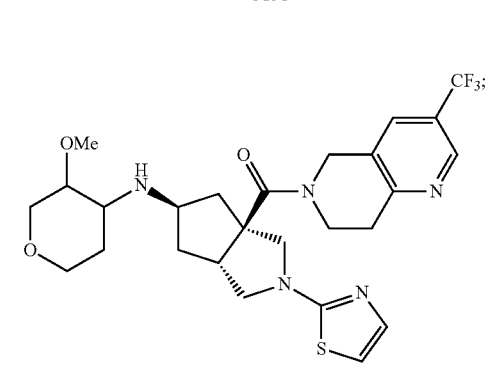
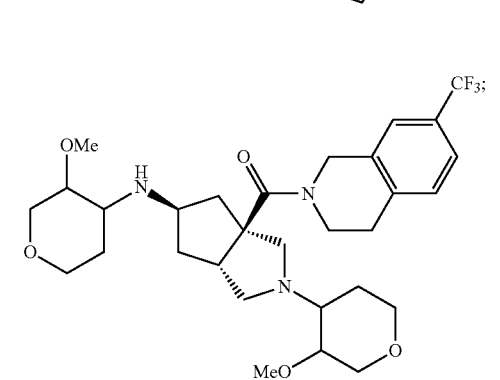

33
-continued
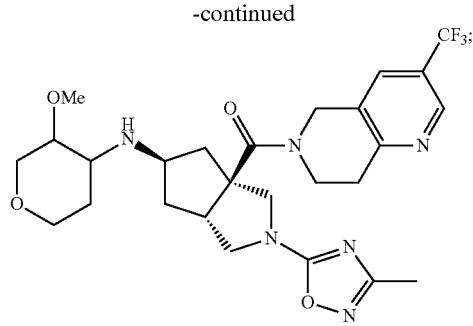
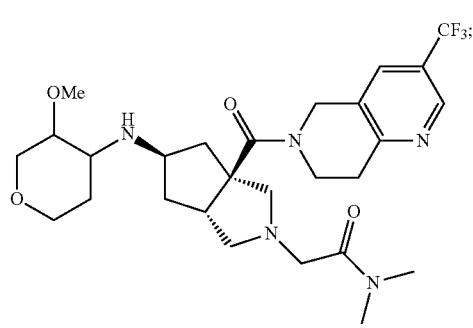
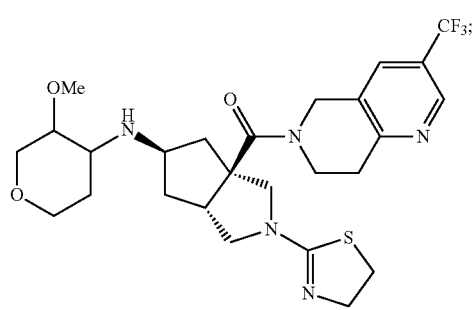
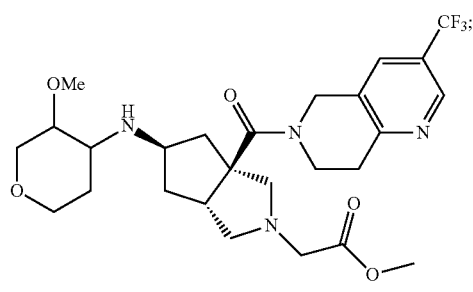
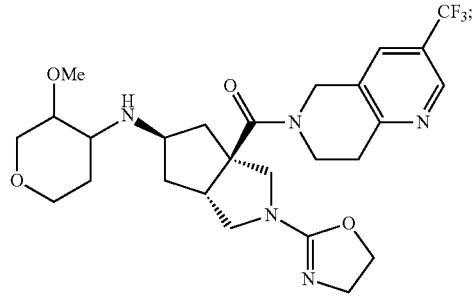
34
-continued
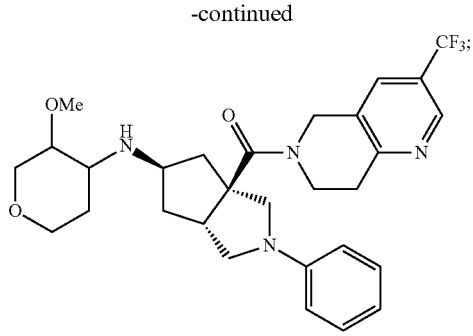
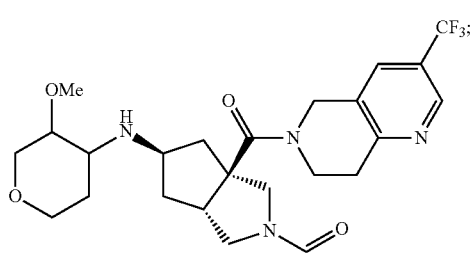
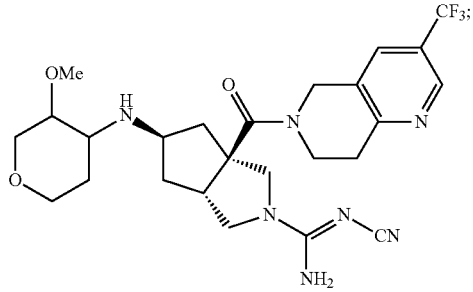
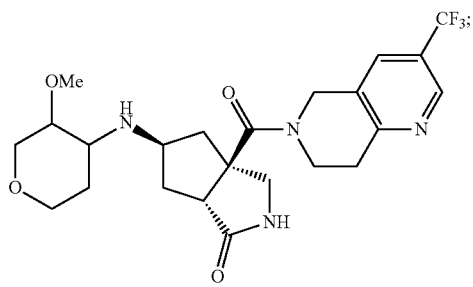
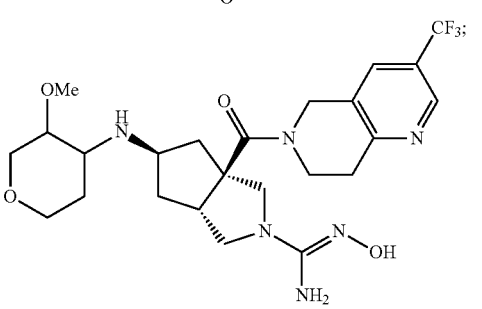
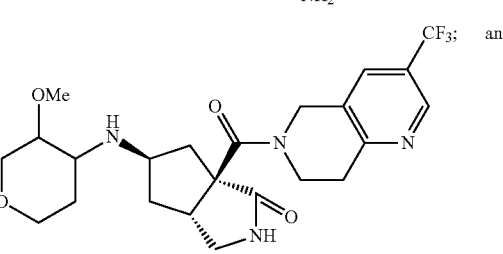

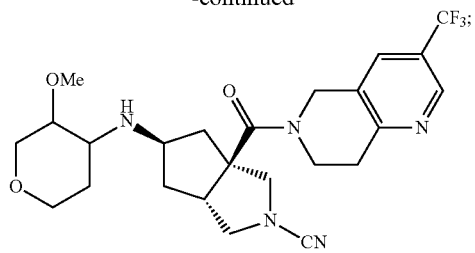

and pharmaceutically acceptable salts thereof.

In another embodiment, the invention relates to a pharmaceutical composition, comprising a compound of formula (I) and a pharmaceutically acceptable carrier.

In another embodiment, the invention relates to a pharmaceutical composition made by mixing a compound of formula (I) and a pharmaceutically acceptable carrier.

In another embodiment, the invention relates to a process for making a pharmaceutical composition comprising mixing a compound of formula (I) and a pharmaceutically acceptable carrier.

The present invention is further directed to a product prepared according to any of the processes described herein.

In another embodiment, the present invention is directed to a process for the preparation of a compound of formula (I), as described in more detail in the Schemes and Examples which follow herein.

In another embodiment, the invention relates to a method for preventing, treating or ameliorating a CCR2 mediated syndrome, disorder or disease comprising administering to a subject in need thereof a therapeutically effective amount of a compound of formula (I).

In another embodiment, the invention relates to a method for preventing, treating or ameliorating a CCR2 mediated inflammatory syndrome, disorder or disease wherein the syndrome, disorder or disease is associated with elevated MCP-1 expression or MCP-1 overexpression, or is an inflammatory condition that accompanies syndromes, disorders or diseases associated with elevated MCP-1 expression or MCP-1 overexpression comprising administering to a subject in need thereof an effective amount of a compound of claim 1.

In another embodiment, the invention relates to a method of preventing, treating or ameliorating a syndrome, disorder or disease, wherein said syndrome, disorder or disease is selected from the group consisting of: Chronic Obstructive Pulmonary Disease (COPD), ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type-I diabetes, type II diabetes, diabetic complications, diabetic nephropathy, diabetic retinopathy, diabetic retinitis, diabetic microangiopathy, overweight, obesity, obesity-associated insulin resistance, metabolic syndrome, tuberculosis, sarcoidosis, invasive staphyloccocia, inflammation after cataract surgery, allergic rhinitis, allergic conjunctivitis, chronic urticaria, asthma, allergic asthma, periodontal diseases, periodontis, gingivitis, gum disease, diastolic cardiomyopathies, cardiac infarction, myocarditis, chronic heart failure, angiostenosis, restenosis, reperfusion disorders, aortic abdominal aneurism, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach and chronic neuroinflammatory disorders including, but not limited to, Alzheimer's disease, ischemic stroke, spinal cord injury, nerve crush injury and traumatic brain injury comprising administering to a subject in need thereof an effective amount of a compound of formula (I).

In another embodiment, the invention relates to a method of preventing, treating or ameliorating a syndrome, disorder or disease, wherein said syndrome, disorder or disease is selected from the group consisting of: type I diabetes, type II diabetes, diabetic complications, diabetic nephropathy, diabetic retinopathy, diabetic retinitis, diabetic microangiopathy, obesity, obesity-associated insulin resistance, metabolic syndrome, asthma, and allergic asthma, comprising administering to a subject in need thereof a therapeutically effective amount of a compound of formula (I).

In another embodiment, the invention relates to a method of treating a disorder selected from the group consisting of type II diabetes, obesity and asthma comprising administering to a subject in need thereof a therapeutically effective amount of a compound of formula (I).

DEFINITIONS

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "cycloalkyl" refers to a saturated or partially unsaturated monocyclic or bicyclic hydrocarbon ring radical derived by the removal of one hydrogen atom from a single ring carbon atom. Examples of cycloalkyl radicals include, but are not limited to cyclopropyl, cyclobutyl, cyclopentyl, cyclopentenyl, cyclohexyl, cyclohexenyl, cycloheptyl and cyclooctyl. Additional examples include $C_{(3-8)}$cycloalkyl, $C_{(5-8)}$cycloalkyl, $C_{(3-12)}$cycloalkyl, $C_{(3-20)}$cycloalkyl, decahydronaphthalenyl, and 2,3,4,5,6,7-hexahydro-1H-indenyl.

The term "heteroaryl" refers to a radical derived by the removal of one hydrogen atom from a ring carbon atom of a heteroaromatic ring system. A heteroaromatic ring system shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure. Examples of heteroaryl radicals include, but are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolizinyl, indolyl, isoindolyl, benzo[b]furyl, benzo[b]thienyl, indazolyl, benzimidazolyl, benzthiazolyl, purinyl, 4H-quinolizinyl, quinolinyl, isoquinolinyl, cinnolinyl, phthalzinyl, quinazolinyl, quinoxalinyl, 1,8-naphthyridinyl, and pteridinyl.

For use in medicines, the salts of the compounds of this invention refer to non-toxic "pharmaceutically acceptable salts." FDA approved pharmaceutically acceptable salt forms (Ref. International J. Pharm. 1986, 33, 201-217; J. Pharm. Sci., 1977, January, 66(1), p 1) include pharmaceutically acceptable acidic/anionic or basic/cationic salts.

Throughout this specification, compounds are described as being separated, usually by silica gel column, although preporatory thin layer chromatography, or high or low pressure liquid choromatography may also be used. It is generally accepted that when eluting compounds through a silica gel-type separation medium, that the least polar compounds elute before the more polar compounds. Therefore, the term "less polar isomer", refers to the isomer that will elute first from a silica gel type separation medium.

Abbreviations

Herein and throughout this application, the following abbreviations may be used.

ACN acetonitrile
BOC or Boc tert-butyloxycarbonyl
BOP (Benzotriazole-1-yl-oxy-tris-(dimethylamino)-phosphonium hexafluorophosphate)
DBU diazabicycloundecene
DCC dicyclohexylcarbodiimide
DCM dicholomethane
DIAD diisopropylazodicarboxylate
DIPEA diisopropylethylamine
DMAP dimethylaminopyridine
DME dimethoxyethane
DMF dimethylformamide
DMSO dimethylsulfoxide
EDAC 1-Ethyl-3-[3-dimethylaminopropyl]carbodiimide hydrochloride
Et ethyl
EtOAc ethyl acetate
eq equivalents
HOBt hydroxybenzotriazole
M moles/liter
Me methyl
min. minutes
OAc acetate
Ph phenyl
PyBop Benzotriazol-1-yloxy)tripyrrolidinophosphonium Hexafluorophosphate
PyBrop bromo-tris-pyrrolidinophosphonium hexafluorophosphate
rt room temperature
TEA triethylamine
TFA trifluoroacetic acid
THF tetrahydrofuran
TLC thin layer chromatography
TPP triphenyl phosphine Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate (SEH), sodium hydroxide, triethanolamine or zinc.

Methods of Use

The present invention is directed to a method for preventing, treating or ameliorating a CCR2 mediated syndrome, disorder or disease comprising administering to a subject in need thereof an effective amount of a compound of Formula (I) or a form, composition or medicament thereof.

Examples of a CCR2 mediated syndrome, disorder or disease for which the compounds of Formula (I) are useful include chronic obstructive pulmonary disorder (COPD), ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type-I diabetes, type II diabetes, diabetic complications, diabetic nephropathy, diabetic retinopathy, diabetic retinitis, diabetic microangiopathy, overweight, obesity, obesity-associated insulin resistance, metabolic syndrome, tuberculosis, chronic obstructive pulmonary disease, sarcoidosis, invasive staphyloccocia, inflammation after cataract surgery, allergic rhinitis, allergic conjunctivitis, chronic urticaria, asthma, allergic asthma, periodontal diseases, periodontis, gingivitis, gum disease, diastolic cardiomyopathies, cardiac infarction, myocarditis, chronic heart failure, angiostenosis, restenosis, reperfusion disorders, aortic abdominal aneurism, multiple sclerosis, glomerulonephritis, solid tumors and cancers, chronic lymphocytic leukemia, chronic myelocytic leukemia, multiple myeloma, malignant myeloma, Hodgkin's disease, carcinomas of the bladder, breast, cervix, colon, lung, prostate, or stomach, and chronic neuroinflammatory disorders including, but not limited to, Alzheimer's disease, ischemic stroke, spinal cord injury, nerve crush injury and traumatic brain injury.

Some of the quantitative expressions given herein are qualified with the term "about". It is understood that whether the term "about" is used explicitly or not, every quantity given herein is meant to refer to both the actual given value and the approximation to such given value that would reasonably be inferred based on the ordinary skill in the art, including approximations due to the experimental and/or measurement conditions for such given value. In addition, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

The term "administering" with respect to the methods of the invention, means a method for therapeutically or prophylactically preventing, treating or ameliorating a syndrome, disorder or disease as described herein by using a compound of Formula (I) or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be animal, typically a mammal, typically a human, which has been the object of treatment, observation or experiment. In one aspect of the invention, the subject is at risk of (or susceptible to) developing a syndrome, disorder or disease that is associated with elevated MCP-1 expression or MCP-1 overexpression, or a patient with an inflammatory condition that accompanies syndromes, disorders or diseases associated with elevated MCP-1 expression or MCP-1 overexpression.

The term "therapeutically effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

The term "uveitis" generically refers to any inflammatory disease involving the eye. Uveitis can be divided into clinically distinct subtypes based on the part of the eye in which the inflammation is present (percentages correspond to patients known to fit these categories): anterior (51%), intermediate (13%), posterior (20%), or panuveitis (16%) and, according to the course of the disease, as either acute (16%), recurring (26%), or chronic (58%). Those with anterior uveitis (19%) eventually develop irreparable vision damage despite aggressive treatment such as unilateral blindness (9%), bilateral blindness (2%), or unilateral or bilateral vision impairment (8%). Most cases of uveitis are idiopathic, but known causes include infection (e.g., toxoplasmosis, cytomegalovirus, and the like) or development as a component of a systemic inflammatory and/or autoimmune disorder (e.g., juvenile RA, HLA-B27 associated spondyloarthropathies, sarcoidosis, and the like). (HLA-B27: Human Leukocyte Antigen B*27—is a class I surface antigen encoded by the B locus in the major histocompatibility complex (MHC) on chromosome 6 and presents micobial antigens to T cells. HLA-B27 is strongly associated with a certain set of autoimmune diseases referred to as the seronegative spondyloarthropathies.)

When employed as CCR2 inhibitors, the compounds of the invention may be administered in an effective amount within the dosage range of about 0.5 mg to about 10 g, or any amount or range therein, preferably between about 0.5 mg to about 5 g, or any amount or range therein, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula (I) may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula (I) include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention. As used herein, the term "composition" is intended to encompass a product comprising the specified ingredients in the specified amounts, as well as any product which results, directly or indirectly, from combinations of the specified ingredients in the specified amounts.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in the Examples of Formula (I) for use as a medicament.

In another embodiment, the invention relates to the use of a compound as described in the Examples of Formula (I) for the preparation of a medicament for the treatment of a disease associated with an elevated or inappropriate CCR2 activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

General Reaction Scheme

Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art. The following schemes describe general synthetic methods whereby intermediate and target compounds of the present invention may be prepared. Additional representative compounds and stereoisomers, racemic mixtures, diastereomers and enantiomers thereof can be synthesized using the intermediates prepared in accordance to the general schemes and other materials, compounds and reagents known to those skilled in the art. All such compounds, steroisomers, racemic mixtures, diastereomers and enantiomers thereof are intended to be encompassed within the scope of the present invention.

Certain intermediates may be prepared according to the process outlined in Schemes A-FF below.

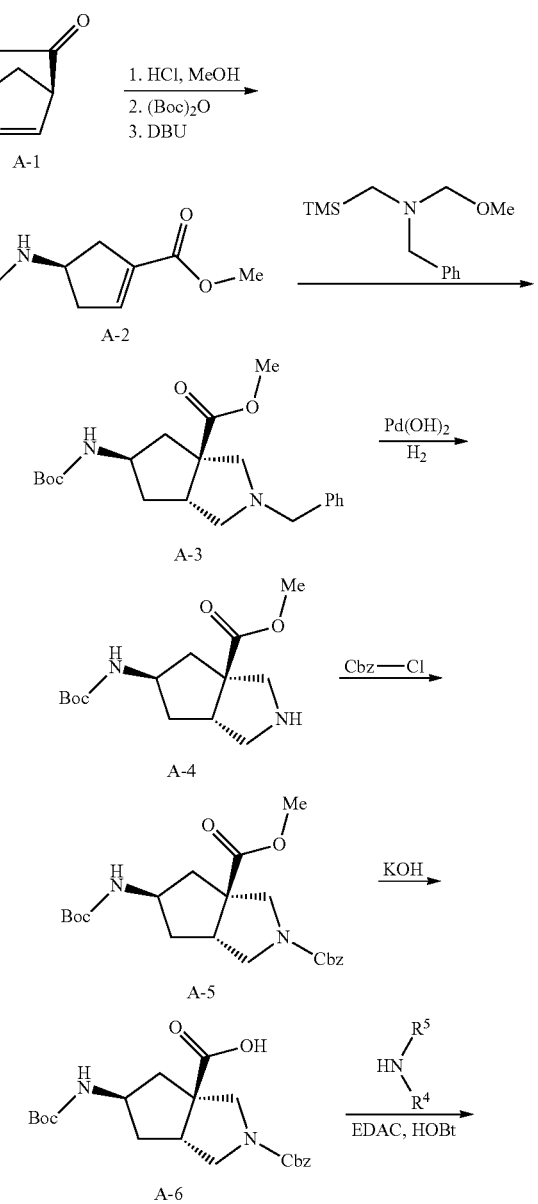

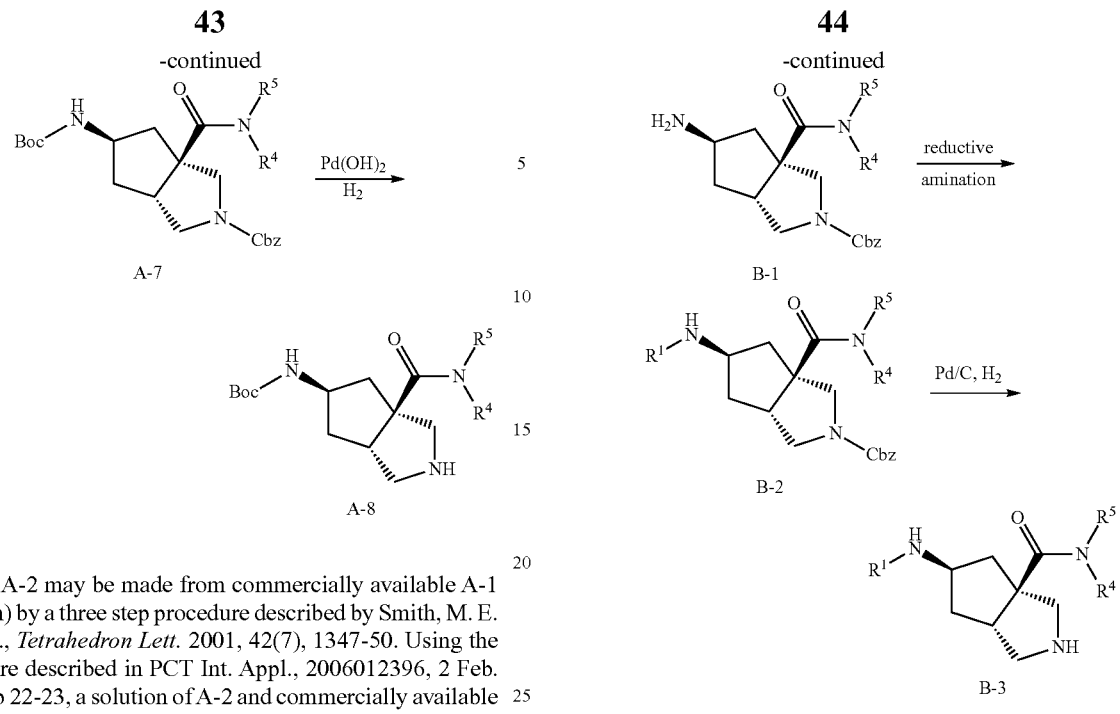

Ester A-2 may be made from commercially available A-1 (Aldrich) by a three step procedure described by Smith, M. E. B. et. al., *Tetrahedron Lett.* 2001, 42(7), 1347-50. Using the procedure described in PCT Int. Appl., 2006012396, 2 Feb. 2006, pp 22-23, a solution of A-2 and commercially available N-(methoxymethyl)-N-(trimethylsilylmethyl)benzylamine in an organic solvent such as DCM may be treated with a dilute (for example 0.5%) solution of TFA in the same solvent at a temperature in the range of about 0° C. to about 25° C. to give compound A-3. Hydrogenation of A-3 in the present of a catalyst such as Pd(OH)$_2$ or 5-10% Pd/C in an organic solvent such as methanol or ethanol at a temperature in the range of about 25° C. to about 50° C. at the pressure in the range of about 1 atm to 3 atm yielded amine A-4. The amine A-4 may be then treated with commercially available benzyl chloroformate in the presence of an organic base such as triethylamine or diethylpropylamine, in an organic solvent such as dichloromethane or THF at a temperature in the range of about 0° C. to about 25° C. to give Compound A-5. The carboxylic acid A-5 may be obtained by saponification of A-6 with an aqueous inorganic base such as KOH or NaOH in an organic solvent such methanol or THF at a temperature in the range of about 0° C. to about 25° C. and then coupled with suitable, commercially available amines HNR$^4$R$^5$ in the presence of coupling reagents such as EDAC/HOBt, PyBOP, PyBrop, or DCC in an organic solvent such as THF, dichloromethane or 1,2-dichloroethane, at a temperature in the range of about 0° C. to about 25° C. to give the amide A-7. The resulting amide A-7 may be treated with hydrogen gas under pressure from 1 atm to 3 atm, catalyzed by a catalyst such as 5-10% Pd/C, in an organic solvent such as methanol, ethanol, ethyl acetate or THF, at a temperature in the range of about 0° C. to about 25° C., to yield intermediate A-8.

The Boc protecting group on compound A-7 may be removed using acids such as TFA or HCl according to reported protocols in the scientific literature to form a corresponding salt of compound B-1, which may be substituted using reductive amination with an appropriately substituted aldehyde or ketone in the presence of a hydride source, such as sodium borohydride or sodium triacetoxyborohydride, to provide compounds of formula B-2. A Cbz protecting in formula B-2 may be removed by, for instance, hydrogenation in the presence of a palladium catalyst, to afford a required intermediate amine of formula B-3.

Scheme C

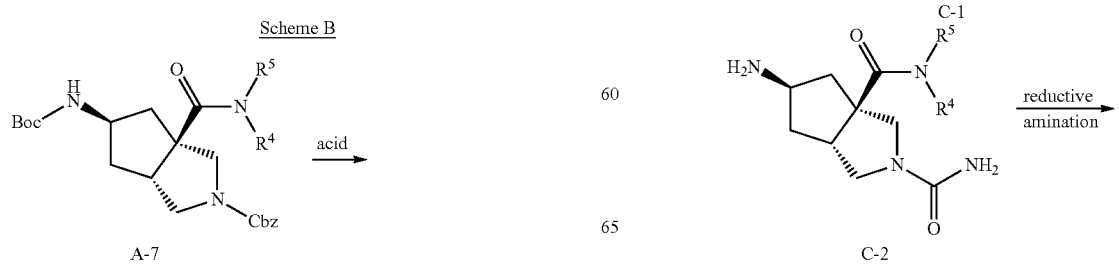

Scheme B

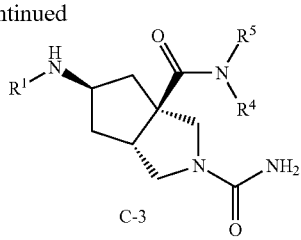

Compound A-8 may be cyanated by suitable cyanogen reagents such as cyanogen bromide to give a compound of formula C-1 (Garbrecht, W. L.; Herbst, R. M. *J. Org. Chem.*, 1953, 18, 1003-1013). Treatment with an acid such as TFA will remove the Boc protecting group and also convert the cyano group on N to urea as shown in compound C-2. A compound of formula C-2 may be further elaborated via a reductive amination as described above to provide compounds of formula C-3.

thiourea). Further reaction with ammonia (when $A^1$ and $A^2$ are H) or a suitably substituted amine, or with suitable carbamoyl chloride (for urea) or thiocarbamoyl chloride (for thiourea) gives urea or thiourea D-1. Compound D-1 may be further deprotected to give compound D-2 and substituted to afford compound D-3 by using the methods described above.

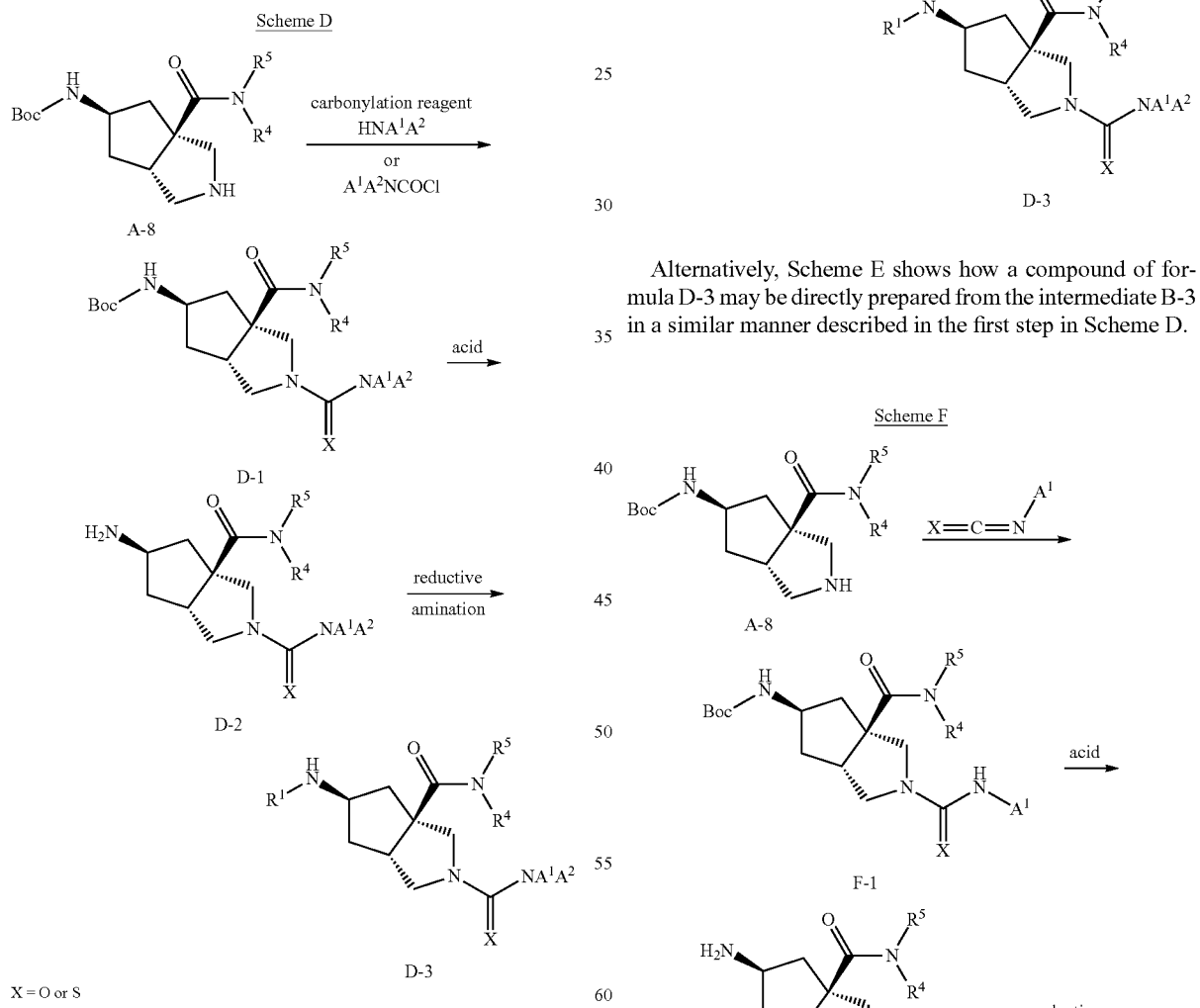

Compound A-8 may be reacted with a carbonylation reagent, either commercially or prepared by reported protocols in the scientific literature, such as N,N'-carbonydiimidazole, phosgene, trichlorophosgen (for urea) or N,N'-thiocarbonydiimidazole, di-2-pyridyl thionocarbonate (for Alternatively, Scheme E shows how a compound of formula D-3 may be directly prepared from the intermediate B-3 in a similar manner described in the first step in Scheme D.

47

-continued

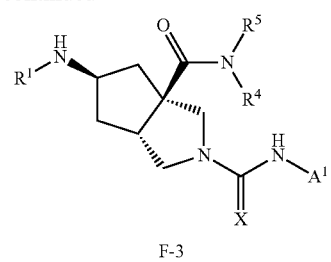

F-3

X = O or S

Scheme F demonstrates an alternative method for preparation of certain compound F-3. A compound of formula A-8 may be treated with a commercially available isocyanate or isothiocyanate in an aprotic solvent such as DCM or THF at ambient temperature to generate compound F-1. Compound F-3 may be obtained via the deprotection of the Boc group in compound F-1 and subsequent reductive amination of compound F-2 by using the methods described above.

Scheme G

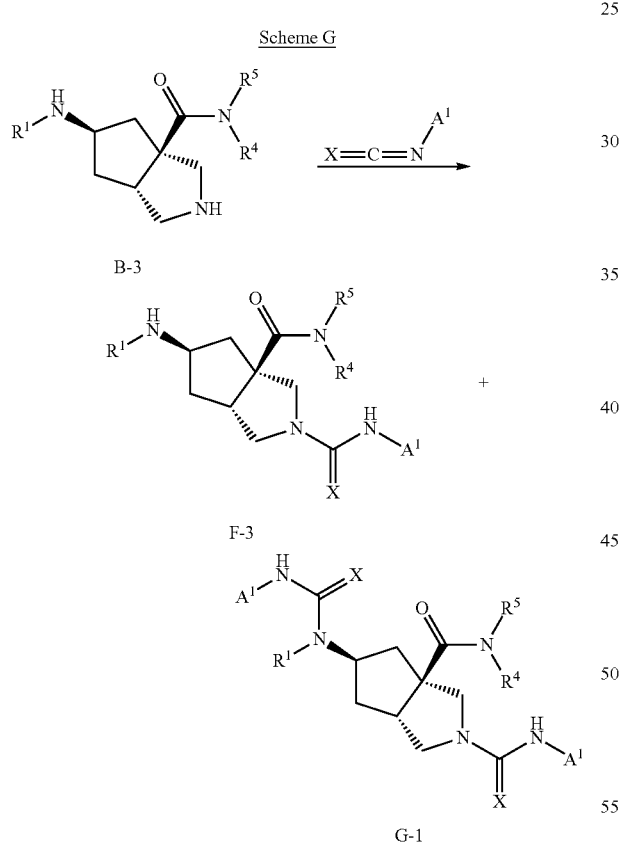

G-1

X = O or S

A compound of formula F-3 may be synthesized directly from compound B-3 by treatment of a commercially available isocyanate or isothiocyanate in an aprotic solvent such as DCM or THF at ambient temperature. When an excess amount of cyanate or thiocyanate is used or reaction is processed in a longer time, a by-product of formula G-1 may be produced.

48

Scheme H

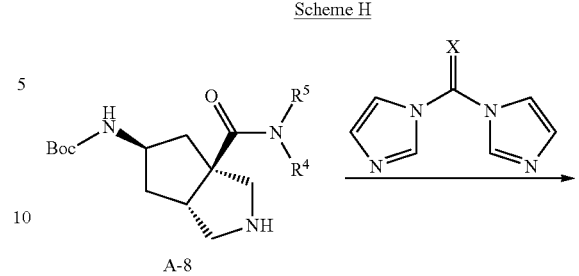

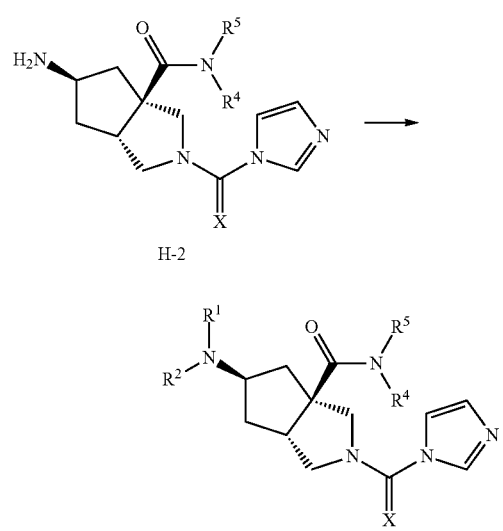

X = O or S

Compound A-8 may be treated with N,N'-carbonydiimidazole or N,N'-thiocarbonydiimidazole in an aprotic medium such as DCM or THF at ambient temperature to give a compound of formula H-1, which may be further converted to compound H-3 in a similar manner described previously.

Scheme I

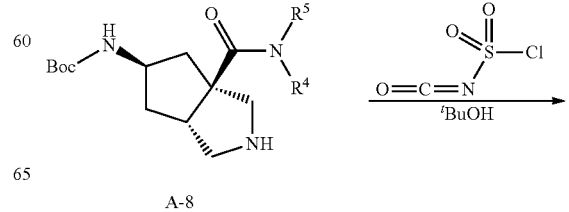

A-8

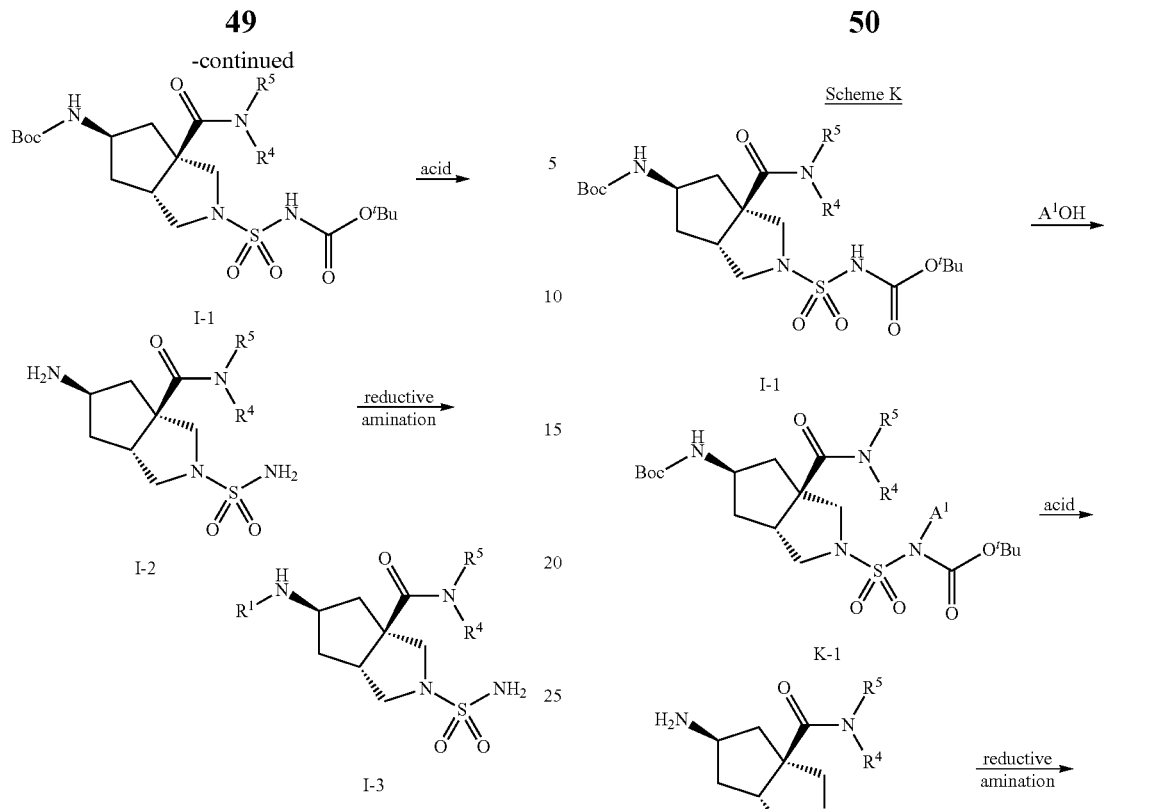

Compound A-8 may be treated with chlorosulfonyl isocyanate and tert-butanol in an aprotic solvent such as DCM or THF at a range of 0° C. to ambient temperature (Regainia, Z. et al. *Tetrahedron* 2000, 56(3), 381-7) to generate compound I-1. Compound I-3 may be obtained via the deprotection of the Boc groups in compound I-1 and subsequent reductive amination of compound I-2 by using the methods described above.

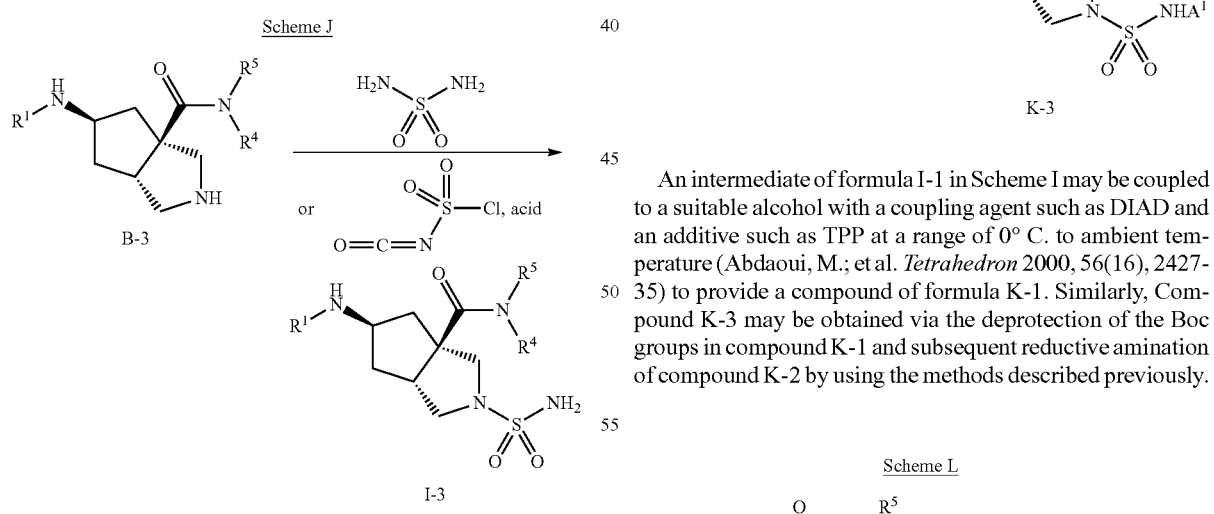

Compound of formula B-3 may be condensed with sulfamide upon heating to afford a compound of formula I-3 as reported in (Sarges, R.; et al. *J. Med. Chem.* 1976, 19(5), 695-709). Alternatively, compound I-3 may be generated by treating B-3 with chlorosulfonyl isocyanate and tert-butanol in an aprotic solvent such as DCM or THF at a range of 0° C. to ambient temperature (Regainia, Z. et al. *Tetrahedron* 2000, 56(3), 381-7).

An intermediate of formula I-1 in Scheme I may be coupled to a suitable alcohol with a coupling agent such as DIAD and an additive such as TPP at a range of 0° C. to ambient temperature (Abdaoui, M.; et al. *Tetrahedron* 2000, 56(16), 2427-35) to provide a compound of formula K-1. Similarly, Compound K-3 may be obtained via the deprotection of the Boc groups in compound K-1 and subsequent reductive amination of compound K-2 by using the methods described previously.

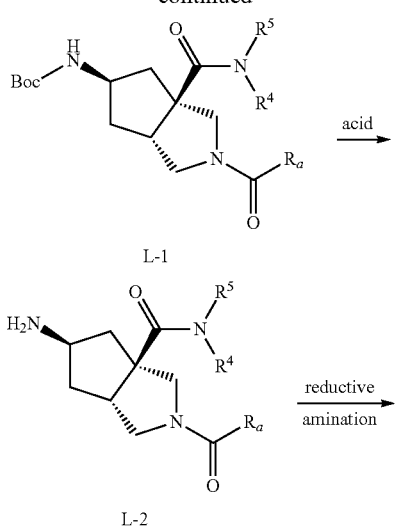

L-1

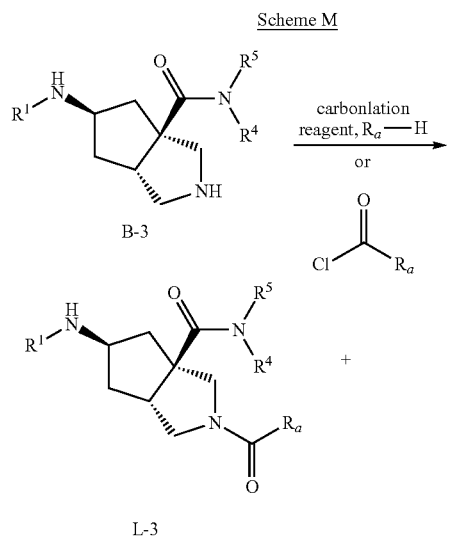

L-2

L-3

Compounds of Formula I wherein $R^3$ is $C(O)R_a$, and $R_a$ is alkoxyl or phenoxyl may be made according to Schemes L, and M. Compound A-8 may be treated with an available carbonylation reagent such as N,N'-disuccinimidyl carbonate and an additive such as DMAP, or with an available chloroformate and a base such as TEA, DIPEA in aprotic mediums such as DCM, acetonitrile, DMF at ambient temperature to give a carbamate of formula L-1. Compound L-1 may be further deprotected to give compound L-2 and substituted to afford compound L-3 by using the methods described previously.

Scheme M

B-3

L-3

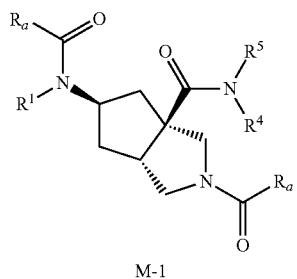

M-1

Alternatively, one skilled in the art will recognize that a compound of formula L-3 may be directly made from a compound of formula B-3 by using known methods presented in Scheme L. However, a second product of formula M-1 may be obtained an excess amount of chloroformate is used or reaction is processed in a longer time.

Scheme N

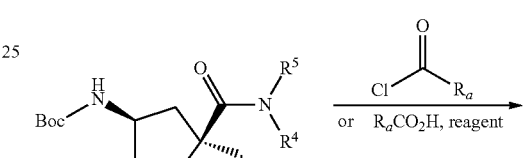

A-8

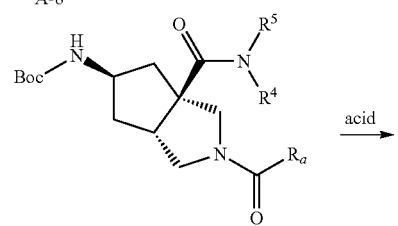

N-1

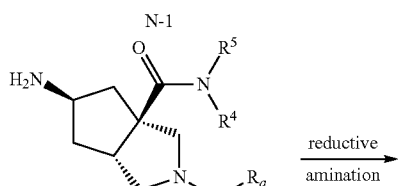

N-2

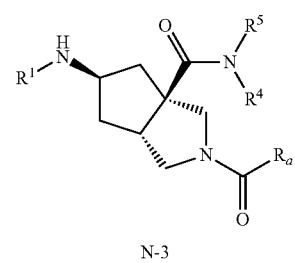

N-3

Schemes N and O show the synthesis of N-3, wherein $R_a$ is as defined in Formula I. A compound of formula A-8 may be coupled to a carbonyl chloride, available either commercially or prepared according to reported protocols in the scientific literature, or to a carboxylic acid with a coupling agent such as EDAC, BOP and an additive such as HOBt, in the presence of a base such as TEA, DIPEA to provide the amide of formula N-1. Compound N-1 may be finally elaborated to N-3 by removal of the protecting Boc group and subsequent substitution.

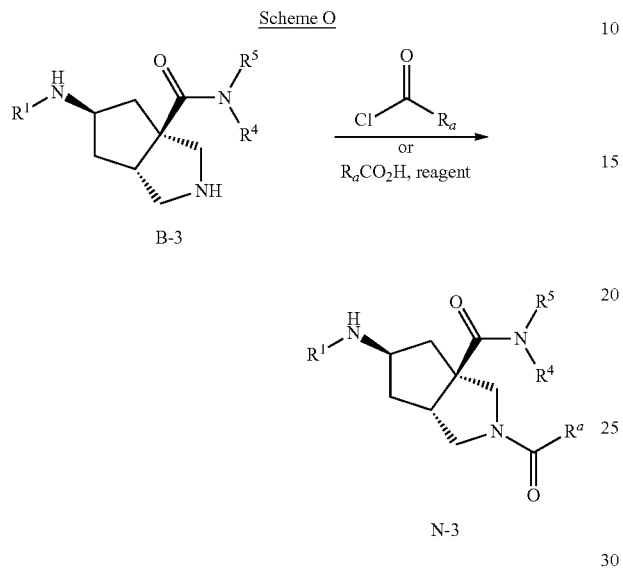

Alternatively, the compound N-3 may also be prepared from the compound B-3 by coupling to a carbonyl chloride or a carboxylic acid in a same method presented in Scheme N.

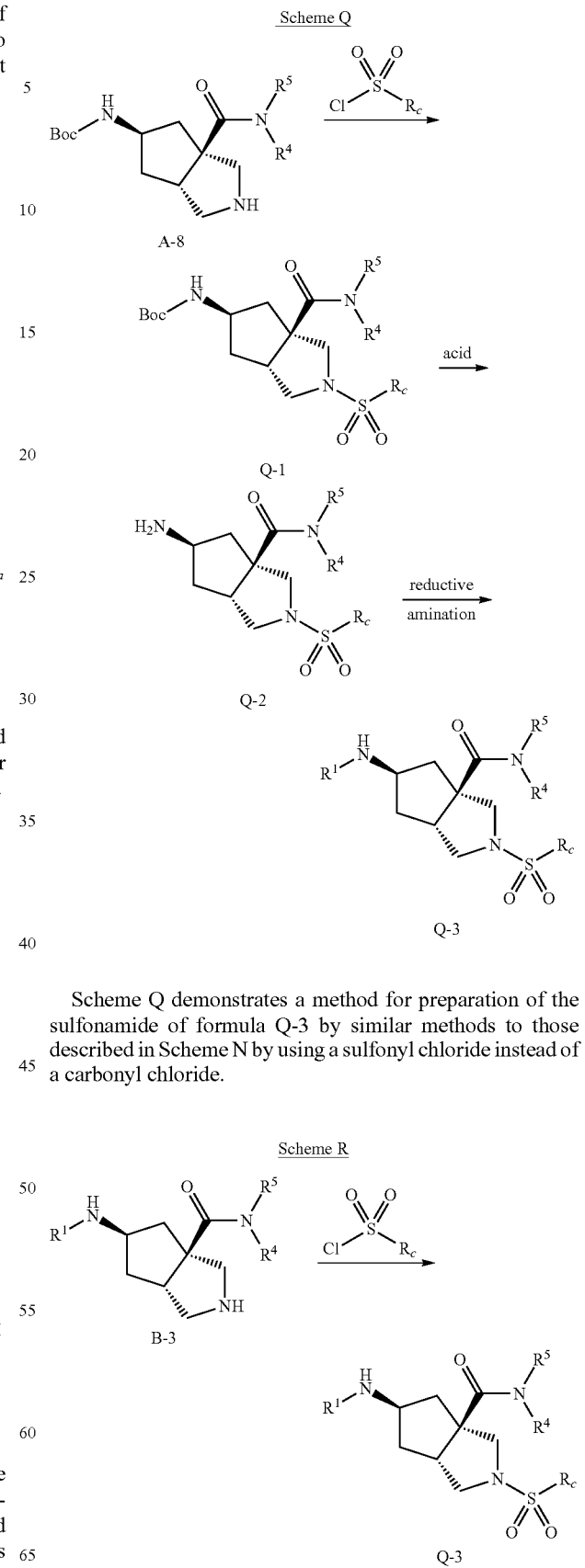

A compound of formula P-1 with a carboxylic ester on the phenyl ring, which may be made either via the method presented in Scheme N or Scheme O, may be further hydrolyzed to compound P-2 by using an aqueous inorganic base such as NaOH, LiOH, KOH in a solvent such as methanol, THF at a range of 0° C. to room temperature.

Scheme Q demonstrates a method for preparation of the sulfonamide of formula Q-3 by similar methods to those described in Scheme N by using a sulfonyl chloride instead of a carbonyl chloride.

Alternatively, the compound Q-3 may also be prepared from the compound B-3 by coupling to a carbonyl chloride in the same method presented in Scheme Q.

Alternatively, a compound of formula S-3 may be directly prepared via a substitution such as reductive amination from a compound of formula B-3.

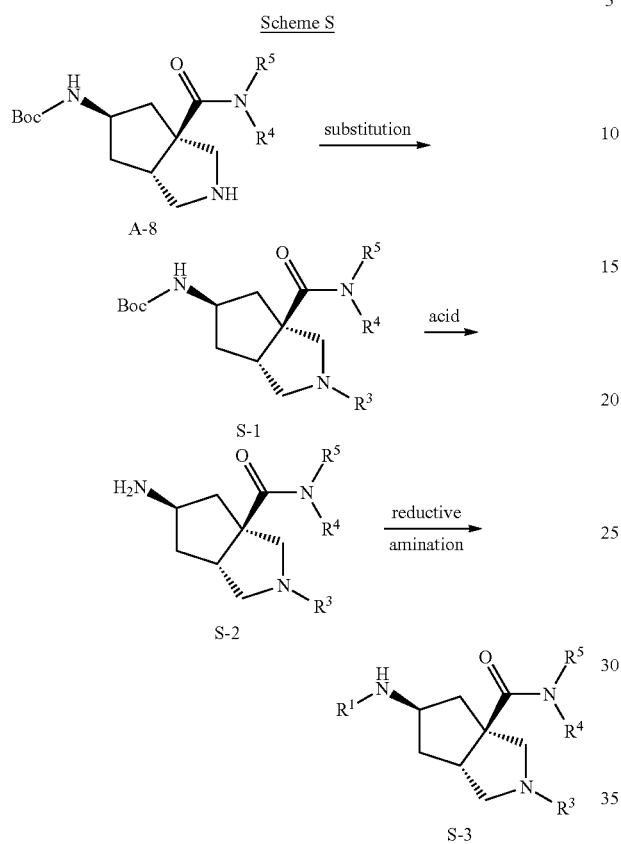

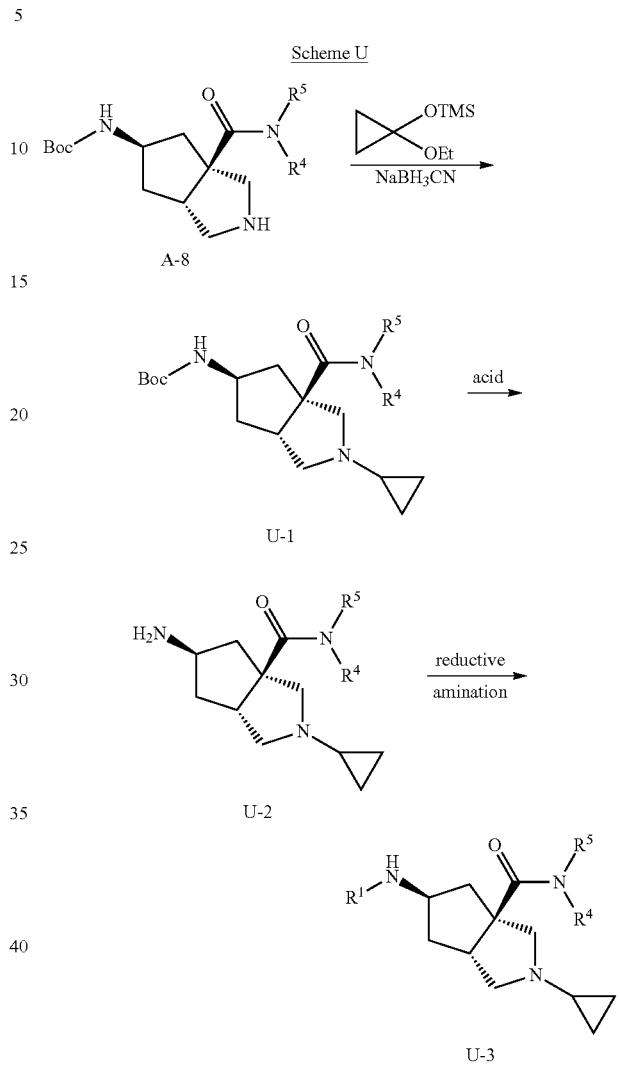

Compound A-8 may be converted to a compound of formula S-1 by a variety chemical routes which utilize conventional chemical methods known to those skilled in the art. For example, a reductive amination of compound A-8 with an aldehyde or ketone in the presence of a hydride source, such as sodium borohydride or sodium triacetoxyborohydride, to provide compounds of formula S-1. As demonstrated previously, Compound S-1 may be elaborated to S-3 by removal of the protecting Boc group and subsequent substitution.

A compound of formula U-1 (where $R^3$ is a cyclopropyl group) may be made by using (1-ethoxycyclopropoxy)-trimethylsilane in the presence of a hydride source such as sodium cyanoborohydride and an acid such as acetic acid in a solvent such as methanol at a elevated temperature around 80° C. (Gillaspy, M. et al. *Tetrahedron Lett.* 1995, 36(41), 7399-402). Subsequent deprotection and reductive amination may convert compound U-1 to compound U-3 as described previously.

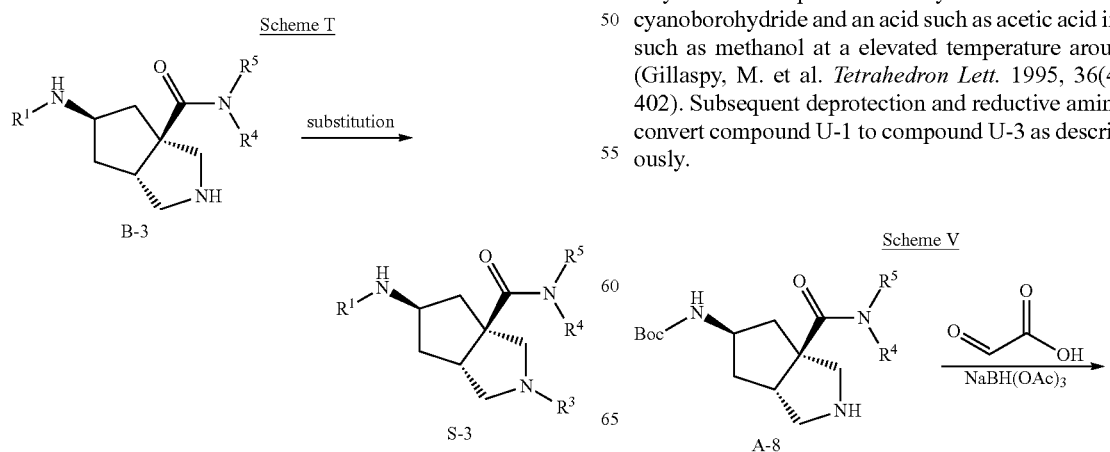

-continued

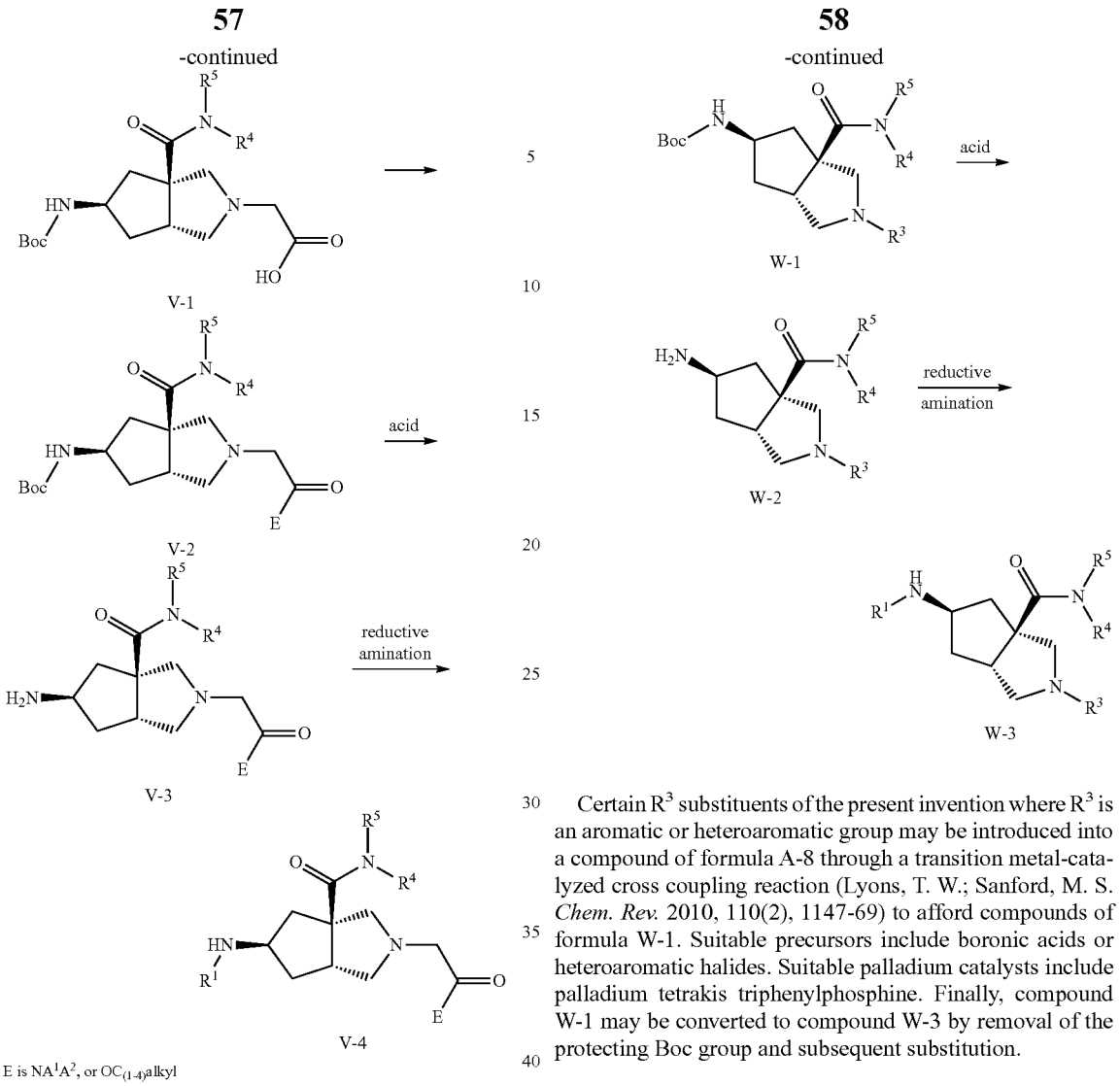

wherein E is NA$^1$A$^2$, or OC$_{(1-4)}$alkyl

Compounds of Formula I wherein R$_3$ is C$_{(1-3)}$alkylC(O)NA$^1$A$^2$ or C$_{(1-4)}$alkylCO$_2$C$_{(1-4)}$alkyl may be synthesized according to Scheme V. A compound of formula A-8 may participate in a reductive amination with glyoxylic acid (or other alkyl group substituted with both aldehyde and acid moieties) in the presence of a hydride source such as sodium triacetoxyborohydride at an ambient temperature to afford an acid of formula V-1. One skilled in the art will recognize that the transformation of compound V-1 to the corresponding ester or the corresponding amide (where X is N) of formula V-2 using standard literature protocols. Compound V-4 may be generated by following previously described method.

Scheme W

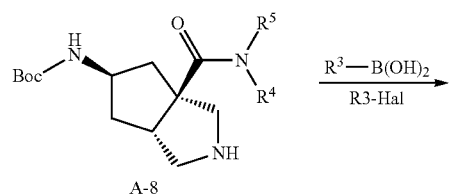

Certain R$^3$ substituents of the present invention where R$^3$ is an aromatic or heteroaromatic group may be introduced into a compound of formula A-8 through a transition metal-catalyzed cross coupling reaction (Lyons, T. W.; Sanford, M. S. *Chem. Rev.* 2010, 110(2), 1147-69) to afford compounds of formula W-1. Suitable precursors include boronic acids or heteroaromatic halides. Suitable palladium catalysts include palladium tetrakis triphenylphosphine. Finally, compound W-1 may be converted to compound W-3 by removal of the protecting Boc group and subsequent substitution.

Scheme X

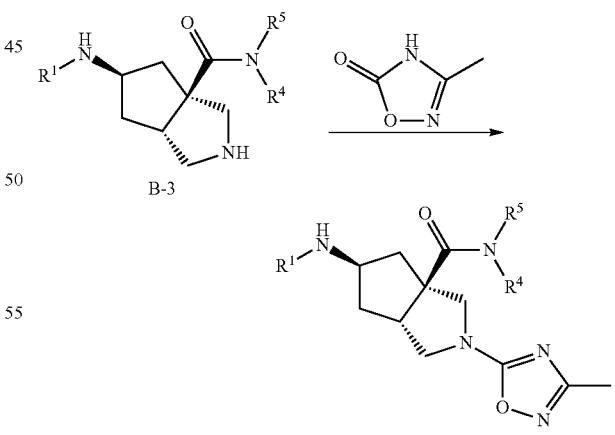

A compound of formula X-1 where R3 is an oxadiazole or substituted oxadiazole may be obtained via a phosphonium-mediated cross-coupling from a compound of formula B-3 and the corresponding oxadiazol-2-one as described in Levins, C.; Wan, Z-K. *Org. Lett.* 2008, 10(9), 1755-1758.

Scheme Y

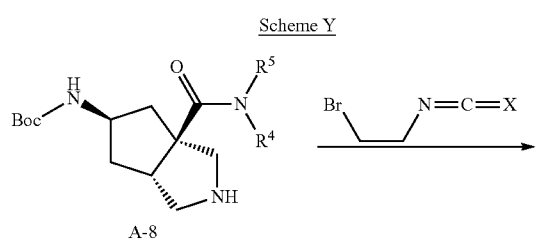

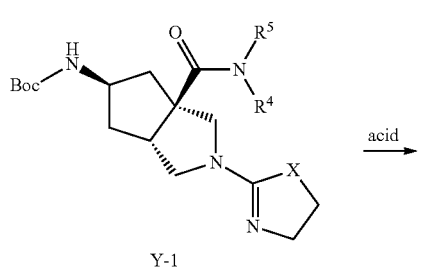

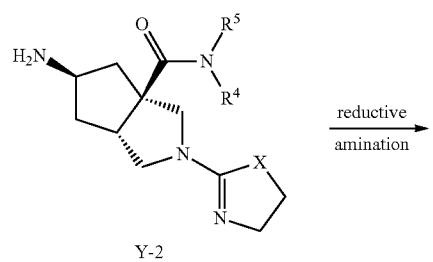

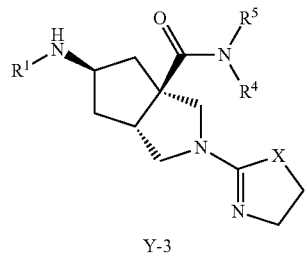

X = O or S

A compound of formula Y-1 may be formed by treatment of compound A-8 with 2-bromoethyl isocyanate (where X is O) (Hiltmann, R. et al. *Eur. J. Med. Chem.* 1977, 12(1), 63-8) or 2-bromoethyl isothiocyanate (where X is S) (Hackler, R. E.; Balko, T. W. *Syn. Comm.* 1975, 5(2), 143-6) in the presence of a base such as TEA in an aprotic solvent such as DCM at an ambient temperature. Subsequent deprotection and substitution with reductive amination may lead to a compound of formula Y-3.

Scheme Z

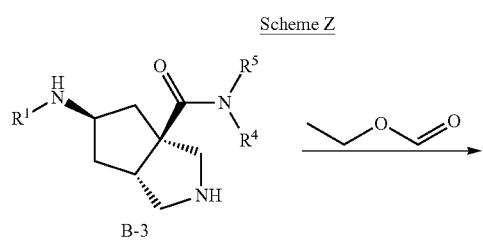

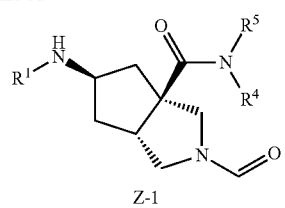

Using the procedure described in King, J. A.; McMillan, F. H. *J. Amer. Chem. Soc.* 1950, 72, 1236-40, a compound of formula Z-1 may be formed by condensation of a compound B-3 with ethyl formate at an elevated temperature around 70° C.

Scheme AA

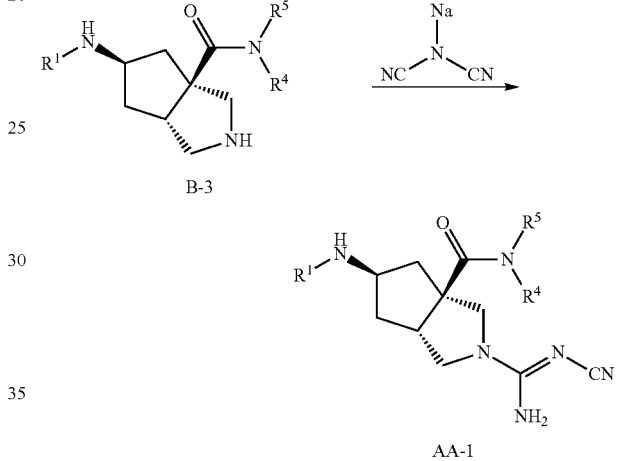

Formation of certain compounds of formula AA-1 may be achieved by heating a mixture of B-3 and sodium dicyanamide in 5% water in isopropyl alcohol at an elevated temperature around 120° C. under an inert atmosphere (Rembarz, G. et al. *J. fuer Prak. Chem.*, 1964, 26(5-6), 314-8).

Scheme BB

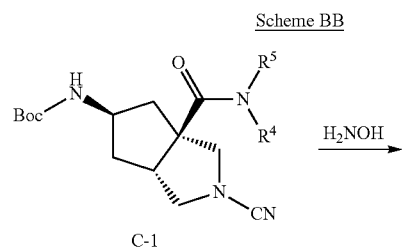

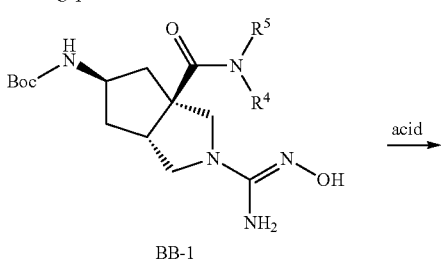

-continued

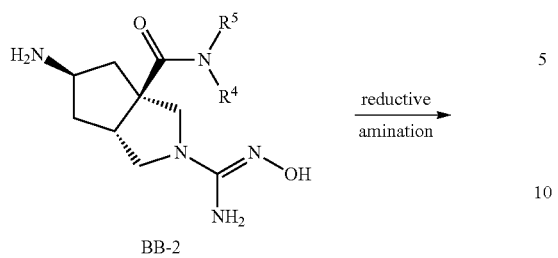

BB-2

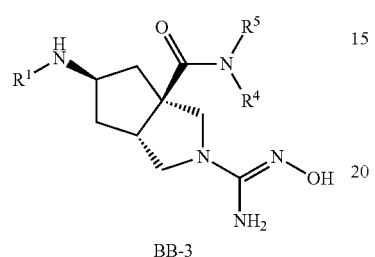

BB-3

A mixture of compound C-1 with hydroxylamine in a solvent such as ethanol at an elevated temperature around 80° C. under an inert atmosphere may be condensed to a compound of formula BB-1 as described in Nordmann, R.; Loosli, H. R. *Helv. Chim. Acta,* 1985, 68(4), 1025-32. Subsequent deprotection compound of BB-1 and substitution of the resulting compound BB-2 with reductive amination may lead to a compound of formula BB-3 as described previously.

Scheme CC

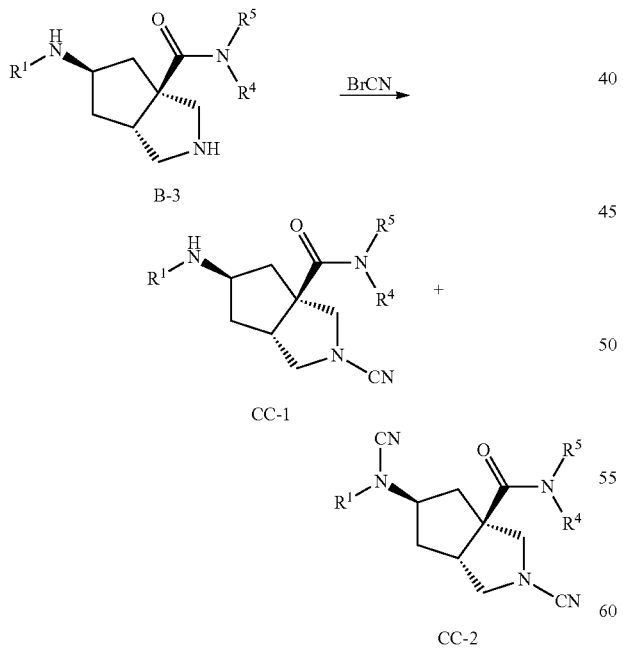

A compound of formula B-3 may undergo a cyanation reaction as described in Scheme C to generate mono-cyanated compound CC-1 or/and dicyanated compound CC-2 where an excess amount of cyanating agent is used.

Scheme DD

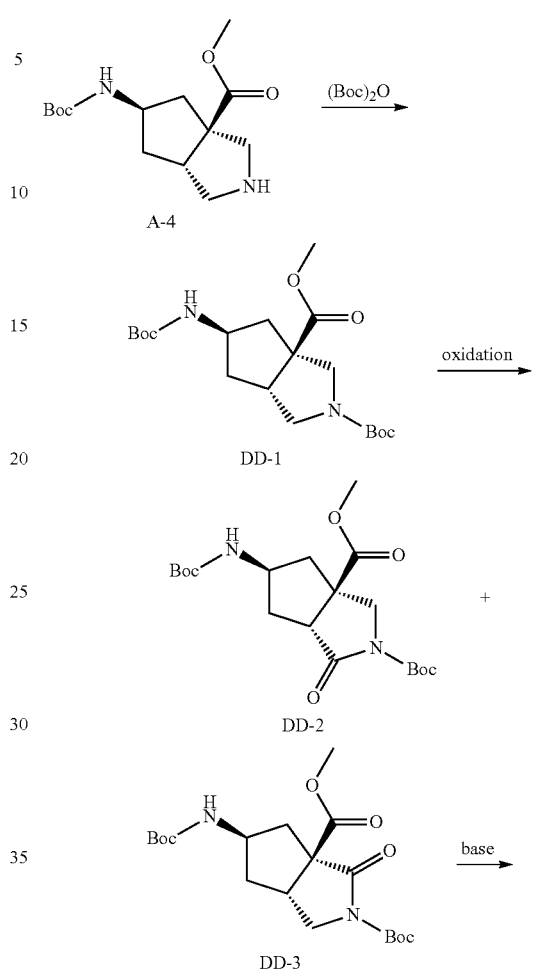

-continued

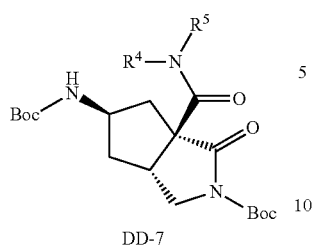

DD-7

A compound of formula A-4 may be protected by a Boc group to lead a compound of formula DD-1, which may be further oxidized to a mixture of two isomers DD-2 and DD-3 by a suitable oxidizing agent such as sodium bromate and in the presence of an additive such as ruthenium(III) chloride (Tanaka, K.; Yoshifuji, S.; Nitta, Y. *Chem. Pharm. Bull.* 1986, 34(9), 3879-84). One skilled in the art will recognize that the mixture of formulas DD-2 and DD-3 may be hydrolyzed to their corresponding carboxylic acids of formulas DD-4 and DD-5, followed by coupling to certain amines to afford separable amides of formulas DD-6 and DD-7.

Scheme EE

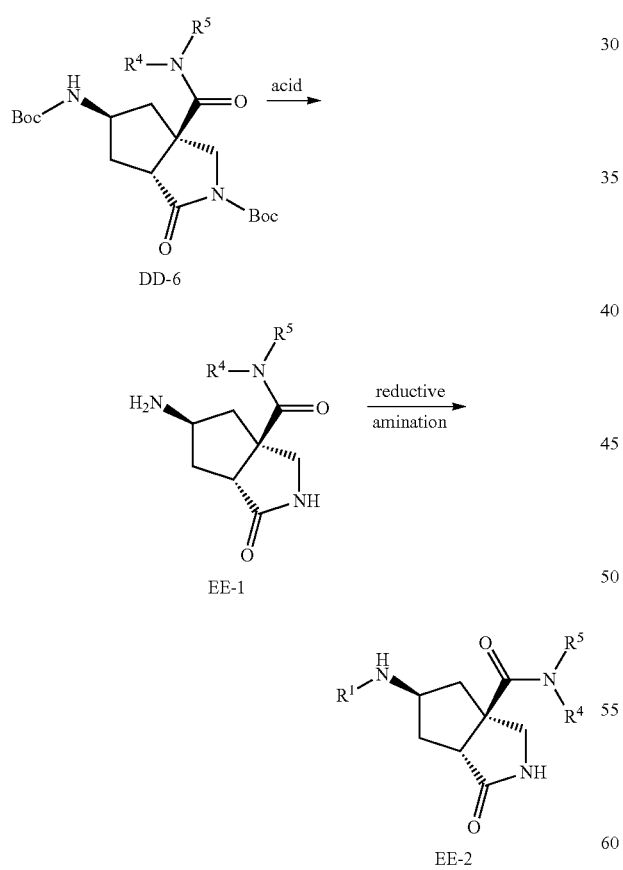

Both Boc protecting groups in the compound of formula DD-6, prepared in Scheme DD, may be removed by an acid such as TFA to generate a compound of formula EE-1. A compound of formula EE-1 may then be substituted by reductive amination to a compound EE-2 as described previously.

Scheme FF

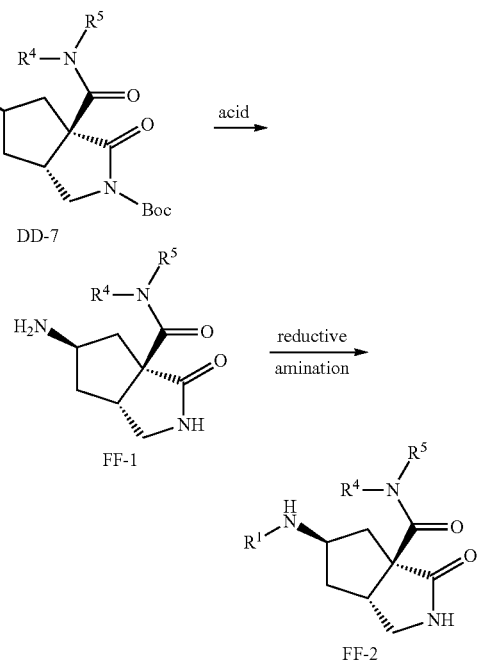

In a similar manner, transformation of a compound of formula FF-2 from a compound DD-7 may be achieved using conditions described in Scheme EE.

SPECIFIC EXAMPLES

Specific compounds which are representative of this invention were prepared as per the following examples and reactions sequences; the examples and the diagrams depicting the reaction sequences are offered by the way of illustration, to aid in the understanding of the invention and should not be construed to limit in any way the invention set forth in the claims which follow thereafter. The instant compounds may also be used as intermediates in subsequent examples to produce additional compounds of the present invention. No attempt has been made to optimize the yields obtained in any of the reactions. One skilled in the art would know how to increase such yields through routine variations in reaction times, temperatures, solvents and/or reagents.

Intermediate 1 tert-Butyl((3aR,5R,6aR)-3a-(3-(trifluoromethyl)-5,6,7,8-tetrahydro-1,6-naphthyridine-6-carbonyl)octahydrocyclopenta[c]pyrrol-5-yl)carbamate

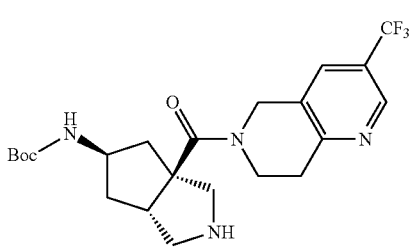 [SMILES: CC(C)(C)OC(=O)N[C@@H]1C[C@H]2CNC[C@@]2(C(=O)N2CCc3ncc(C(F)(F)F)cc3C2)C1]

Step A. (1R,4S)-Methyl 4-((tert-butoxycarbonyl)amino)cyclopent-2-enecarboxylate A solution of (1S,4R)-2-azabicyclo[2.2.1]hept-5-en-3-one (5 g, 98%, 45.8 mmol, Aldrich) and concentrated hydrochloric acid (9.2 mL) in methanol (115 mL) in a sealed tube was heated with stirring for 16 h. After cooling to rt, the solvents were removed by rotary evaporation. The residue was triturated with Et$_2$O and stirred. Filtration and evaporation to dryness gave the HCl salt as a white solid, which was dissolved in DCM (228 mL) and cooled to 0° C. To the cooled solution was added di-tert-butyl dicarbonate (11.14 g, 49.5 mmol), followed by addition of TEA (6.95 mL, 49.5 mmol) over 1 h. The reaction mixture was stirred at rt overnight and quenched by the addition of aqueous NH$_4$Cl solution. The organic phase was washed with cool 0.5 N HCl solution and dried over Na$_2$SO$_4$. Evaporation and purification by column chromatography (eluent: 20% EtOAc in hexanes to 40%) gave the product as a colorless oil. 10.2 g, 92.3%. LC/MS: C$_{12}$H$_{19}$NO$_4$: m/z 264.0 (M+Na).

Step B. (R)-Methyl-4-((tert-butoxycarbonyl)amino)cyclopent-1-enecarboxylate

A mixture of the product from Step A (9.8 g, 40.6 mmol) and DBU (9 mL, 60 mmol) in DCM (70 mL) was stirred at rt overnight. The mixture was cooled to 0° C. and washed with 1N HCl aqueous solution and brine, dried over Na$_2$SO$_4$. Evaporation and purification by column chromatography (eluent: 20% EtOAc in hexanes to 40%) gave the product as a white solid. $^1$H-NMR (400 MHz, CDCl$_3$): δ 1.44 (s, 9H), 2.36-2.47 (m, 2H), 2.88-2.99 (m, 2H), 3.74 (s, 3H), 4.36 (br s, 1H), 4.71 (br s, 1H), 6.71-6.72 (m, 1H). LC/MS: C$_{12}$H$_{19}$NO$_4$: m/z 264.0 (M+Na).

Step C. (3aR,5R,6aR)-Methyl 2-benzyl-5-((tert-butoxycarbonyl)amino)octahydro-cyclopenta[c]pyrrole-3a-carboxylate To a solution of the product from Step B (5.51 g, 20 mmol) and N-(methoxymethyl)-N-(trimethylsilylmethyl)benzylamine (6.4 mL, 24 mmol, Aldrich) in DCM (40 mL) was added 1M TFA in DCM (2.4 mL, 2.4 mmol) slowly. The resulting mixture was stirred at rt overnight and quenched by the addition of saturated aqueous NaHCO$_3$ solution. The organic phase was washed with brine, dried over Na$_2$SO$_4$. Evaporation and purification by column chromatography (eluent: 10% EtOAc in hexanes to 20%) gave the desired isomer as a colorless gel. $^1$H-NMR (400 MHz, CDCl$_3$) of the desired isomer: δ 1.38 (s, 9H), 1.66-1.86 (m, 2H), 1.86-1.96 (m, 1H), 1.96-2.08 (m, 1H), 2.29-2.63 (m, 3H), 2.71-2.93 (m, 2H), 3.43-3.56 (m, 2H), 3.58-3.74 (s, 3H), 4.08-4.29 (m, 1H), 4.78 (d, J=6.6 Hz, 1H), 7.11-7.31 (m, 5H). LC/MS: C$_{24}$H$_{28}$N$_2$O$_4$: m/z 375.2 (M+H).

Step D. (3aR,5R,6aR)-Methyl 5-((tert-butoxycarbonyl)amino)octahydrocyclopenta[c]-pyrrole-3a-carboxylate To a solution of the product from Step C (28.6 g, 76.4 mmol) in methanol (200 mL) was added 5% palladium hydroxide on carbon (0.26 g). Hydrogenation proceeded overnight in Parr shaker at rt at 50 psi. Filtration and evaporation to dryness gave the product as a yellow gel. $^1$H-NMR (400 MHz, CDCl$_3$): δ 1.44 (s, 9H), 1.72-1.90 (m, 2H), 1.93-2.05 (m, 1H), 2.05-2.17 (m, 1H), 2.67 (dd, J=11.6, 5.8 Hz, 1H), 2.77 (d, J=12.1 Hz, 1H), 2.82-2.94 (m, 1H), 3.30 (dd, J=11.6, 8.1 Hz, 1H), 3.44-3.57 (m, 2H), 3.68-3.79 (m, 3H), 4.14 (d, J=6.3 Hz, 1H), 4.85 (d, J=5.8 Hz, 1H). LC/MS: C$_{14}$H$_{24}$N$_2$O$_4$: m/z 285.2 (M+H).

Step E. (3aR,5R,6aR)-2-Benzyl 3a-methyl 5-((tert-butoxycarbonyl)amino)-hexahydrocyclopenta[c]pyrrole-2,3a(1H)-dicarboxylate To a solution of the product from Step D (21.5 g, 75.6 mmol) in DCM (400 mL) was added TEA (31.6 mL, 226.8 mmol) and benzyl chloroformate (14.5 mL, 95%, 98.3 mmol) at 0° C. under Ar. The mixture was stirred at rt for 3 h and quenched by the addition of aqueous NaHCO$_3$ solution. The aqueous phase was extracted with DCM (3×) and the combined organic phases were dried over Na$_2$SO$_4$. Evaporation and purification by column chromatography (eluent: 20% EtOAc in hexanes to 30%) gave the product as a colorless gel. $^1$H-NMR (400 MHz, CDCl$_3$): δ 1.43 (s, 9H), 1.89 (br. s., 2H), 2.13 (br. s., 2H), 2.99 (d, J=1.0 Hz, 1H), 3.22-3.57 (m, 2H), 3.59-3.83 (m, 4H), 3.99 (d, J=11.6 Hz, 1H), 4.23 (d, J=5.8 Hz, 1H), 4.85 (br. s., 1H), 5.12 (d, J=3.0 Hz, 2H), 7.28-7.42 (m, 5H). LC/MS: C$_{22}$H$_{30}$N$_2$O$_6$: m/z 441.2 (M+Na).

Step F. (3aR,5R,6aR)-2-(Benzyloxy)carbonyl)-5-((tert-butoxycarbonyl)amino)-octahydrocyclopenta[c]pyrrole-3a-carboxylic acid To a mixture of the product from Step E (10.8 g, 25.81 mmol) in THF (40 mL) was added 6N KOH aqueous solution (12.9 mL). After being stirred at rt overnight, the reaction mixture was condensed. The residue was acidified by a cooled 1N HCl solution to pH~3 and extracted with EtOAc, dried over Na$_2$SO$_4$. Filtration and evaporation to dryness gave the product as a white foam. LC/MS: C$_{21}$H$_{28}$N$_2$O$_6$: m/z 427.2 (M+Na).

Step G. (3aR,5R,6aR)-Benzyl 5-((tert-butoxycarbonyl)amino)-3a-(3-(trifluoromethyl)-5,6,7,8-tetrahydro-1,6-naphthyridine-6-carbonyl)hexahydrocyclopenta-[c]pyrrole-2(1H)-carboxylate To a solution of the product from Step F (9.25 g, 22.87 mmol) and 3-(trifluoromethyl)-5,6,7,8-tetrahydro-1,6-naphthyridine dihydrochloride (7.55 g, 27.44 mmol) in THF (80 mL) was added TEA (19.13 mL, 137.2 mmol), EDAC (5.7 g, 29.73 mol) and HOBt (4.02 g, 29.73 mmol). The resulting mixture was stirred at rt overnight. The reaction was quenched by addition of brine, extracted with EtOAc, and dried over Na$_2$SO$_4$. Evaporation and purification by column chromatography (eluent: 80% EtOAc in hexanes to 100%) gave the product as a yellow foam. $^1$H-NMR (400 MHz, CDCl$_3$): δ 1.31-1.40 (s, 9H), 1.61-1.70 (m, 1H), 1.84 (br. s., 3H), 2.40 (br. s., 1H), 3.13 (br. s., 2H), 3.30 (br. s., 1H), 3.58-3.89 (m, 5H), 4.24 (br. s., 1H), 4.53-4.78 (m, 2H), 4.89 (br. s., 1H), 5.05-5.16 (m, 2H), 7.31-7.42 (m, 5H), 7.69 (s, 1H), 8.72 (s, 1H); LC/MS: C$_{30}$H$_{35}$F$_3$N$_4$O$_5$: m/z 589.3 (M+H).

Step H. tert-Butyl((3aR,5R,6aR)-3a-(3-(trifluoromethyl)-5,6,7,8-tetrahydro-1,6-naphthyridine-6-carbonyl)octahydrocyclopenta[c]pyrrol-5-yl)carbamate A solution of the product from Step G (9.2 g, mmol) in methanol (60 mL) was bubbled with Ar for 15 min, and 10% Palladium on carbon (1 g) was added. The mixture was hydrogenated at 25 psi in Parr shaker overnight. Filtration and evaporation to dryness gave the product as yellow foam.

$^1$H-NMR (400 MHz, CDCl$_3$): δ 1.33-1.44 (m, 9H), 1.65-2.07 (m, 6H), 2.28 (dd, J=12.5, 5.7 Hz, 1H), 2.61 (dd, J=11.2, 5.7 Hz, 1H), 2.95-3.30 (m, 5H), 3.58-3.70 (m, 1H), 3.88 (br. s., 2H), 4.18 (d, J=6.3 Hz, 1H), 4.58-4.92 (m, 3H), 7.70 (s, 1H), 8.71 (s, 1H); LC/MS: C$_{22}$H$_{29}$F$_3$N$_4$O$_3$: m/z 455.3 (M+H).

Intermediate 2 tert-Butyl((3aR,5R,6aR)-3a-(7-(trifluoromethyl)-1,2,3,4-tetrahydroisoquinoline-2-carbonyl)octahydrocyclopenta[c]pyrrol-5-yl)carbamate

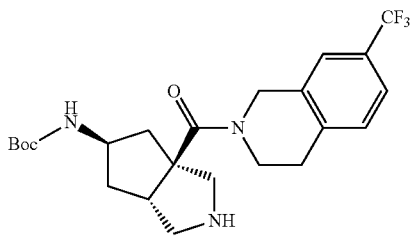 [SMILES: CC(C)(C)OC(=O)N[C@@H]1C[C@H]2CNC[C@@]2(C(=O)N2CCc3ccc(C(F)(F)F)cc3C2)C1]

Prepared according to the procedure of Intermediate 1, using 7-(trifluoromethyl)-1,2,3,4-tetrahydroisoquinoline hydrochloride instead of 3-(trifluoromethyl)-5,6,7,8-tetrahydro-1,6-naphthyridine dihydrochloride in Step G. $^1$H-NMR (400 MHz, CDCl$_3$): δ 1.34-1.43 (s, 9H), 1.66-1.98 (m, 2H), 2.25 (dd, J=12.9, 5.6 Hz, 3H), 2.62 (dd, J=11.4, 5.6 Hz, 1H), 2.86-3.10 (m, 3H), 3.16 (dd, J=11.1, 8.1 Hz, 2H), 3.59-3.91 (m, 3H), 4.18 (d, J=6.6 Hz, 1H), 4.57-4.89 (m, 3H), 7.21-7.27 (m, 1H), 7.35-7.49 (m, 2H); LC/MS: C$_{23}$H$_{30}$F$_3$N$_3$O$_3$: m/z 454.2 (M+H).

Intermediate 3 tert-Butyl((3aR,5R,6aR)-3a-(7-(trifluoromethoxy)-1,2,3,4-tetrahydroisoquinoline-2-carbonyl)octahydrocyclopenta[c]pyrrol-5-yl)carbamate

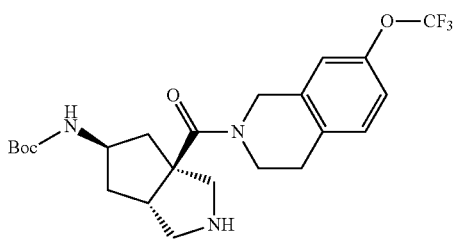 [SMILES: CC(C)(C)OC(=O)N[C@@H]1C[C@H]2CNC[C@@]2(C(=O)N2CCc3ccc(OC(F)(F)F)cc3C2)C1]

Prepared according to the procedure of Intermediate 1, using 7-(trifluoromethoxy)-1,2,3,4-tetrahydroisoquinoline hydrochloride instead of 3-(trifluoromethyl)-5,6,7,8-tetrahydro-1,6-naphthyridine dihydrochloride in Step G. $^1$H-NMR (400 MHz, CDCl$_3$): δ 1.32 (br. s., 9H), 1.89-2.29 (m, 4H), 2.48 (dd, J=13.4, 5.3 Hz, 1H), 2.90 (br. s., 2H), 3.21 (d, J=10.4 Hz, 1H), 3.32-3.50 (m, 2H), 3.69 (m, 3H), 3.96 (br. s., 1H), 4.24 (br. s., 1H), 4.63 (m, 2H), 4.80 (br. s., 1H), 7.06 (d, J=10.1 Hz, 2H), 7.17 (d, J=8.3 Hz, 1H); LC/MS: C$_{23}$H$_{30}$F$_3$N$_3$O$_4$: m/z 470.2 (M+H).

Intermediate 4 tert-Butyl((3aR,5R,6aR)-3a-((3-(trifluoromethyl)benzyl)carbamoyl)octahydrocyclopenta[c]pyrrol-5-yl)carbamate

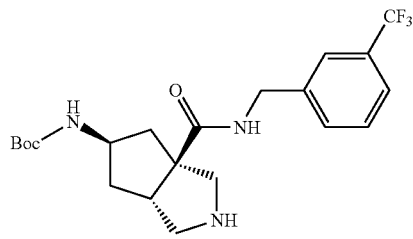 [SMILES: CC(C)(C)OC(=O)N[C@@H]1C[C@H]2CNC[C@@]2(C(=O)NCc2cccc(C(F)(F)F)c2)C1]

Prepared according to the procedure of Intermediate 1, using 3-(trifluoromethyl)benzylamine instead of 3-(trifluoromethyl)-5,6,7,8-tetrahydro-1,6-naphthyridine dihydrochloride in Step G. LC/MS: C$_{21}$H$_{28}$F$_3$N$_3$O$_3$: m/z 428.5 (M+H).

Intermediate 5 tert-Butyl((3aR,5R,6aR)-3a-((3-fluoro-5-(trifluoromethyl)benzyl)carbamoyl)-octahydrocyclopenta[c]pyrrol-5-yl)carbamate

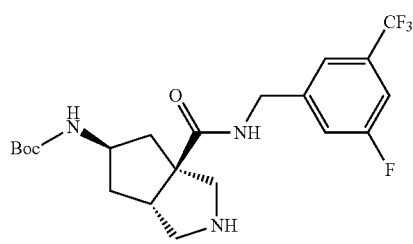 [SMILES: CC(C)(C)OC(=O)N[C@@H]1C[C@H]2CNC[C@@]2(C(=O)NCc2cc(F)cc(C(F)(F)F)c2)C1]

Prepared according to the procedure of Intermediate 1, using 3-fluoro-5-(trifluoromethyl)benzylamine instead of 3-(trifluoromethyl)-5,6,7,8-tetrahydro-1,6-naphthyridine dihydrochloride in Step G. LC/MS: C$_{21}$H$_{27}$F$_4$N$_3$O$_3$: m/z 446.5 (M+H).

Intermediate 6 tert-Butyl((3aR,5R,6aR)-3a-((3,5-bis(trifluoromethyl)benzyl)carbamoyl)octahydro-cyclopenta[c]pyrrol-5-yl)carbamate

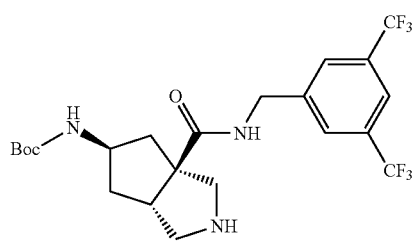 [SMILES: CC(C)(C)OC(=O)N[C@@H]1C[C@H]2CNC[C@@]2(C(=O)NCc2cc(C(F)(F)F)cc(C(F)(F)F)c2)C1]

Prepared according to the procedure of Intermediate 1, using 3,5-bis(trifluoromethyl)benzyl)amine instead of 3-(trifluoromethyl)-5,6,7,8-tetrahydro-1,6-naphthyridine dihydrochloride in Step G. LC/MS: $C_{22}H_{27}F_6N_3O_3$: m/z 496.5 (M+H).

Example 1

((3aR,5R,6aR)-5-(((3S*,4S*)-3-Methoxytetrahydro-2H-pyran-4-yl)amino)octahydrocyclopenta[c]pyrrol-3a-yl)(3-(trifluoromethyl)-7,8-dihydro-1,6-naphthyridin-6(5H)-yl)methanone

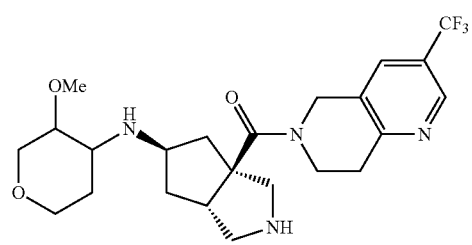 [SMILES: COC1COCCC1N[C@@H]1C[C@H]2CNC[C@@]2(C(=O)N2CCc3ncc(C(F)(F)F)cc3C2)C1]

Step A. (3aR,5R,6aR)-Benzyl 5-amino-3a-(3-(trifluoromethyl)-5,6,7,8-tetrahydro-1,6-naphthyridine-6-carbonyl)hexahydrocyclopenta[c]pyrrole-2(1H)-carboxylate A solution of the product from Step G in Intermediate 1 (80 mg, 0.136 mmol) in TFA (1 mL) and DCM (1 mL) was stirred at rt for 1.5 h. Concentration by rotary evaporation was followed by dilution with DCM and additional evaporation to give the product as a TFA salt. LC/MS: $C_{25}H_{27}F_3N_4O_3$: m/z 498.3 (M+H)

Step B. (3aR,5R,6aR)-Benzyl 5-((3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrole-2(1H)-carboxylate A mixture of the product from Step A (difluoroacetate, 97.45 mg, 0.136 mmol), 3-methoxydihydro-2H-pyran-4(3H)-one (35.4 mg, 0.272 mmol), 4 Å molecular sieves (60 mg) and TEA (0.19 mL, 1.36 mmol) in DCM (4 mL) was stirred at rt for 2 h, followed by addition of sodium triacetoxyborohydride (46.12 mg, 0.218 mmol). The resulting mixture was stirred at rt overnight. The reaction was quenched by addition of saturated NaHCO$_3$ aqueous solution, extracted with DCM, dried over Na$_2$SO$_4$. After removal of solvent, the residue was purified by column chromatography (eluent: 5% 7N NH$_3$ in MeOH in DCM) to give the product as a yellow foam. $^1$H-NMR (400 MHz, CDCl$_3$): δ 1.56-2.12 (m, 7H), 2.31 (br. s., 1H), 2.55-2.67 (m, 1H), 3.06-3.21 (m, 3H), 3.24-4.16 (m, 14H), 4.71 (br. s., 2H), 5.12 (s, 2H), 7.29-7.44 (m, 5H), 7.69 (br. s., 1H), 8.72 (br. s., 1H); LC/MS: $C_{31}H_{37}F_3N_4O_5$: m/z 603.0 (M+H).

Step C. ((3aR,5R,6aR)-5-(((3S*,4S*)-3-Methoxytetrahydro-2H-pyran-4-yl)amino)octahydro-cyclopenta[c]pyrrol-3a-yl)(3-(trifluoromethyl)-7,8-dihydro-1,6-naphthyridin-6(5H)-yl)methanone A solution of the product from Step B (1.53 g, 2.55 mmol) in methanol (18 mL) was bubbled with Ar for 15 min, and 10% Palladium on carbon (0.3 g) was added. The mixture was hydrogenated at 25 psi in Parr shaker overnight. Filtration and evaporation to dryness gave the product as yellow foam. $^1$H-NMR (400 MHz, CDCl$_3$): δ 1.37-2.04 (m, 7H), 2.21 (d, J=5.8 Hz, 1H), 2.47-2.63 (m, 1H), 2.66-2.86 (m, 1H), 2.86-3.54 (m, 12H), 3.60 (br. s., 1H), 3.66-4.21 (m, 4H), 4.61-5.05 (m, 2H), 7.70 (br. s., 1H), 8.71 (br. s., 1H); LC/MS: $C_{23}H_{31}F_3N_4O_3$: m/z 469.2 (M+H).

Example 2

(3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxamide

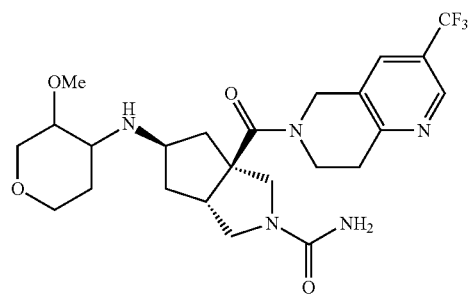 [SMILES: COC1COCCC1N[C@@H]1C[C@H]2CN(C(N)=O)C[C@@]2(C(=O)N2CCc3ncc(C(F)(F)F)cc3C2)C1]

Step A. tert-Butyl((3aR,5R,6aR)-2-cyano-3a-(3-(trifluoromethyl)-5,6,7,8-tetrahydro-1,6-naphthyridine-6-carbonyl)octahydrocyclopenta[c]pyrrol-5-yl)carbamate To a mixture of the product from Step H in Intermediate 1 (3.26 g, 7.17 mmol) and K$_2$CO$_3$ (1.19 g, 8.61 mmol) in acetonitrile (15 mL) was added cyanogen bromide (1.44 mL, 7.17 mmol). After being stirred at rt overnight, the mixture was filtered and the filtrate was condensed in vacuo. The residue was purified by column chromatography (eluent: 80% EtOAc in hexanes to 100%) gave the product as a white foam. $^1$H-NMR (400 MHz, CDCl$_3$): δ 1.31-1.44 (m, 9H), 1.77-1.93 (m, 2H), 2.05 (s, 1H), 2.37 (d, J=5.8 Hz, 1H), 3.14 (br. s., 2H), 3.24 (dd, J=9.9, 4.0 Hz, 1H), 3.50-3.89 (m, 6H), 4.24 (d, J=6.1 Hz, 1H), 4.49-5.02 (m, 3H), 7.71 (s, 1H), 8.73 (s, 1H); LC/MS: $C_{23}H_{28}F_3N_5O_3$: m/z 480.2 (M+H).

Step B. (3aR,5R,6aR)-5-amino-3a-(3-(trifluoromethyl)-5,6,7,8-tetrahydro-1,6-naphthyridine-6-carbonyl)hexahydrocyclopenta[c]pyrrol-2(1H)-carboxamide trifluoroacetate A solution of the product from Step A (0.19 g, 0.396 mmol) in TFA (1.5 mL) and DCM (1.5 mL) was stirred at rt for 1.5 h. Concentration by rotary evaporation was followed by dilution with DCM and additional evaporation to give the product as a TFA salt. LC/MS: $C_{18}H_{22}F_3N_5O_2$: m/z 398.3 (M+H).

Step C. (3aR,5R,6aR)-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydro-cyclopenta[c]pyrrole-2(1H)-carboxamide A mixture of the product from Step B (247.7 mg, 0.396 mmol), 3-methoxydihydro-2H-pyran-4(3H)-one (154.6 mg, 1.188 mmol), 4 Å molecular sieves (0.2 g) and TEA (0.165 mL, 1.188 mmol) in DCM (5 mL) was stirred at rt for 2 h, followed by addition of sodium triacetoxyborohydride (0.168 g, 0.792 mmol). The resulting mixture was stirred at rt overnight. The reaction was quenched by addition of saturated NaHCO$_3$ aqueous solution, extracted with DCM, dried over Na$_2$SO$_4$. After removal of solvent, the residue was purified by column chromatography (eluent: 5% 7N NH$_3$ in methanol in DCM) to give the product as a white foam. $^1$H-NMR (400 MHz, CDCl$_3$): δ 1.51-1.95 (m, 4H), 2.07-2.58 (m, 3H), 2.72 (br. s., 1H), 3.06-4.13 (m, 18H), 4.57-5.04 (m, 4H), 7.71 (br. s., 1H), 8.71 (br. s., 1H); LC/MS: C$_{24}$H$_{32}$F$_3$N$_5$O$_4$: m/z 512.3 (M+H).

Example 3

(3aR,5R,6aR)-5-(((3S,4S)-(3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrole-2(1H)-carboxamide

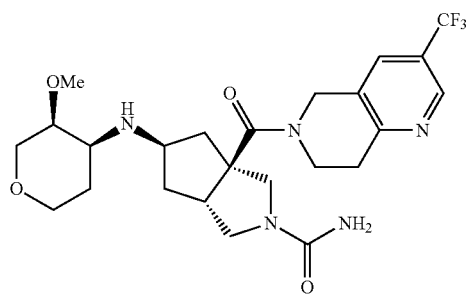 [SMILES: CO[C@@H]1COCC[C@@H]1N[C@@H]1C[C@H]2CN(C(N)=O)C[C@@]2(C(=O)N2CCc3ncc(C(F)(F)F)cc3C2)C1]

The 1$^{st}$ fraction of Example 2 from chiral HPLC (Kromasil K40813, 10-Amycoat, 30×250 mm; eluent: alcohol by EMD). $^1$H-NMR (400 MHz, CDCl$_3$): δ 0.79-0.96 (m, 1H), 1.14-1.23 (m, 1H), 1.60-2.03 (m, 5H), 2.40 (d, J=5.6 Hz, 1H), 2.79 (br. s., 1H), 3.07-4.19 (m, 17H), 4.56-5.19 (m, 4H), 7.74 (s, 1H), 8.70 (br. s., 1H); LC/MS: C$_{24}$H$_{32}$F$_3$N$_5$O$_4$: m/z 512.0 (M+H).

Example 4

(3aR,5R,6aR)-5-(((3R,4R)-(3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrole-2(1H)-carboxamide

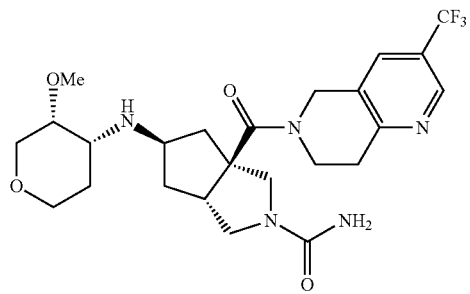 [SMILES: CO[C@H]1COCC[C@H]1N[C@@H]1C[C@H]2CN(C(N)=O)C[C@@]2(C(=O)N2CCc3ncc(C(F)(F)F)cc3C2)C1]

The 3$^{rd}$ fraction of Example 2 from chiral HPLC (Kromasil K40813, 10-Amycoat, 30×250 mm; eluent: alcohol by EMD). $^1$H-NMR (400 MHz, CDCl$_3$): δ 1.16-1.29 (m, 2H), 1.58-2.02 (m, 5H), 2.39 (br. s., 1H), 2.81 (br. s., 1H), 3.06-3.22 (m, 3H), 3.25-3.47 (m, 6H), 3.52-4.14 (m, 8H), 4.60-5.10 (m, 4H), 7.72 (s, 1H), 8.71 (br. s., 1H); LC/MS: C$_{24}$H$_{32}$F$_3$N$_5$O$_4$: m/z 512.0 (M+H).

Example 5

(3aR,5R,6aR)-5-(((3S*,4R*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrole-2(1H)-carboxamide

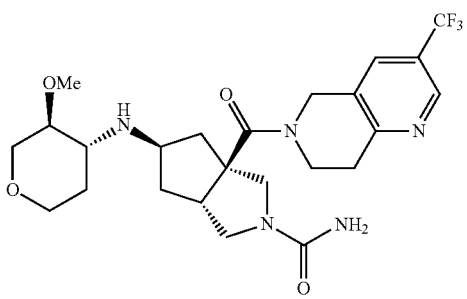 [SMILES: CO[C@@H]1COCC[C@H]1N[C@@H]1C[C@H]2CN(C(N)=O)C[C@@]2(C(=O)N2CCc3ncc(C(F)(F)F)cc3C2)C1]

The 2$^{nd}$ fraction of Example 2 (the minor product, a diastereoisomeric mixture) from chiral HPLC (Kromasil K40813, 10-Amycoat, 30×250 mm; eluent: alcohol by EMD). $^1$H-NMR (400 MHz, CDCl$_3$): δ 1.19-1.48 (m, 2H), 1.75-2.03 (m, 5H), 2.29-2.56 (m, 2H), 2.94-3.41 (m, 9H), 3.46-4.13 (m, 8H), 4.40-4.57 (m, 2H), 4.63-5.03 (m, 2H), 7.70 (br. s., 1H), 8.72 (br. s., 1H); LC/MS: C$_{24}$H$_{32}$F$_3$N$_5$O$_4$: m/z 512.0 (M+H).

Example 6

(3aR,5R,6aR)-5-(((3S*,4S*)-3-Methoxytetrahydro-2H-pyran-4-yl)amino)-3a-(7-(trifluoromethyl)-1,2,3,4-tetrahydroisoquinoline-2-carbonyl)hexahydrocyclopenta-[c]pyrrole-2(1H)-carboxamide

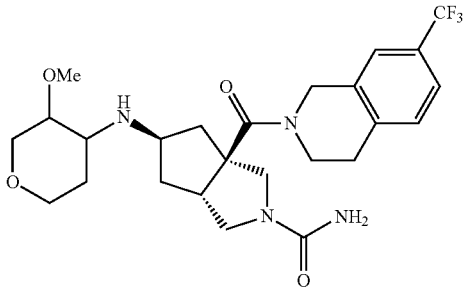 [SMILES: COC1COCCC1N[C@@H]1C[C@H]2CN(C(N)=O)C[C@@]2(C(=O)N2CCc3ccc(C(F)(F)F)cc3C2)C1]

Step A. tert-Butyl((3aR,5R,6aR)-2-Cyano-3a-(7-(trifluoromethyl)-1,2,3,4-tetrahydroisoquinoline-2-carbonyl)octahydrocyclopenta[c]pyrrol-5-yl)carbamate To a mixture of Intermediate 2 (0.46 g, 1.014 mmol) and K$_2$CO$_3$ (0.168 g, 1.217 mmol) in acetonitrile (2.6 mL) was added cyanogen bromide (0.203 mL, 1.014 mmol, 5M in acetonitrile) at rt. After being stirred at rt overnight, the mixture was filtered and the filtrate was condensed in vacuo. The residue was purified by column chromatography (eluent: 80% EtOAc in hexanes to 100%) to give the product as a colorless gel. $^1$H-NMR (400 MHz, CDCl$_3$): δ 1.31-1.46 (s, 9H), 1.87 (t, J=6.6 Hz, 2H), 2.36 (dd, J=13.4, 6.1 Hz, 1H), 2.85-3.08 (m, 2H), 3.23 (dd, J=9.6, 4.0 Hz, 1H), 3.44-3.99 (m, 6H), 4.23 (d, J=6.3 Hz, 1H), 4.45-4.80 (m, 3H), 7.28-7.34 (m, 1H), 7.35-7.44 (m, 1H), 7.46 (d, J=7.6 Hz, 1H); LC/MS: C$_{24}$H$_{29}$F$_3$N$_4$O$_3$: m/z 479.2 (M+H).

Step B. (3aR,5R,6aR)-5-Amino-3a-(7-(trifluoromethyl)-1,2,3,4-tetrahydroisoquinoline-2-carbonyl)hexahydrocyclopenta[c]pyrrole-2(1H)-carboxamide A solution of the product from Step A (0.03 g, 0.627 mmol) in TFA (1 mL) and DCM (1 mL) was stirred at rt for 1.5 h. The volatile organic compounds were removed by evaporation, and the residue was diluted with DCM and evaporated again to give the product as a TFA salt. LC/MS: C$_{19}$H$_{23}$F$_3$N$_4$O$_2$: m/z 397.2 (M+H).

Step C. (3aR,5R,6aR)-5-(((3S*,4S*)-3-Methoxytetrahydro-2H-pyran-4-yl)amino)-3a-(7-(trifluoromethyl)-1,2,3,4-tetrahydroisoquinoline-2-carbonyl)hexahydrocyclopenta-[c]pyrrole-2(1H)-carboxamide A mixture of the product from Step B (316 mg, 0.62 mmol), 3-methoxydihydro-2H-pyran-4(3H)-one (242 mg, 1.86 mmol), 4 Å molecular sieves (0.3 g) and TEA (0.259 mL, 1.86 mmol) in DCM (8 mL) was stirred at rt for 2 h, followed by addition of sodium triacetoxyborohydride (263 mg, 1.24 mmol). The resulting mixture was stirred at rt overnight. The reaction was quenched by the addition of saturated NaHCO$_3$ aqueous solution, extracted with DCM, and dried over Na$_2$SO$_4$. After removal of the solvent, the residue was purified by column chromatography (eluent: EtOAc to 15% 7N NH$_3$ in methanol in EtOAc) to give the product as a white foam. $^1$H-NMR (400 MHz, CDCl$_3$): δ 1.76 (br. s., 1H), 1.89-2.41 (m, 4H), 2.53 (br. s., 1H), 2.85-2.99 (m, 2H), 3.06-4.02 (m, 18H), 4.12 (q, J=7.1 Hz, 1H), 4.69 (br. s., 2H), 5.17-5.31 (m, 1H), 7.25 (d, J=7.8 Hz, 1H), 7.34-7.49 (m, 2H); LC/MS: C$_{25}$H$_{33}$F$_3$N$_4$O$_4$: m/z 511.0 (M+H).

Example 7

(3aR,5R,6aR)-5-(((2-Methoxyethyl)amino)-3a-(3-(trifluoromethyl)-5,6,7,8-tetrahydro-1,6-naphthyridine-6-carbonyl)hexahydrocyclopenta[c]pyrrole-2(1H)-carboxamide

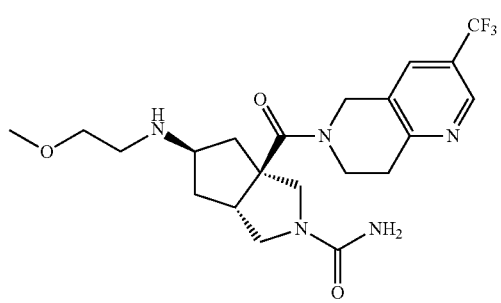 [SMILES: COCCN[C@@H]1C[C@H]2CN(C(N)=O)C[C@@]2(C(=O)N2CCc3ncc(C(F)(F)F)cc3C2)C1]

Prepared analogously to Example 6. $^1$H-NMR (400 MHz, CDCl$_3$): δ 1.70-1.98 (m, 4H), 2.38 (br. s., 1H), 2.58-2.81 (m, 2H), 3.04-3.21 (m, 3H), 3.26-3.35 (m, 3H), 3.36-3.51 (m, 3H), 3.59 (t, J=8.6 Hz, 1H), 3.64-3.92 (m, 5H), 4.55-4.73 (m, 3H), 4.89 (br. s., 1H), 7.70 (br. s., 1H), 8.71 (s, 1H); LC/MS: C$_{21}$H$_{28}$F$_3$N$_5$O$_3$: m/z 456.2 (M+H).

Example 8

(3aR,5R,6aR)-5-(Tetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxamide

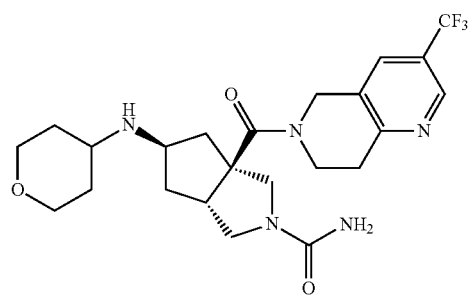 [SMILES: NC(=O)N1C[C@@H]2C[C@@H](NC3CCOCC3)C[C@]2(C(=O)N2CCc3ncc(C(F)(F)F)cc3C2)C1]

Prepared analogously to Example 6. $^1$H-NMR (400 MHz, CDCl$_3$): δ 1.29-1.92 (m, 8H), 2.37 (br. s., 1H), 2.64 (br. s., 1H), 3.03-3.25 (m, 3H), 3.26-3.46 (m, 2H), 3.47-3.67 (m, 2H), 3.65-4.03 (m, 7H), 4.44-5.04 (m, 4H), 7.69 (br. s., 1H), 8.72 (s, 1H); LC/MS: C$_{23}$H$_{30}$F$_3$N$_5$O$_3$: m/z 482.2 (M+H).

Example 9

(3aR,5R,6aR)-5-(((3S*,4S*)-3-Ethoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrole-2(1H)-carboxamide

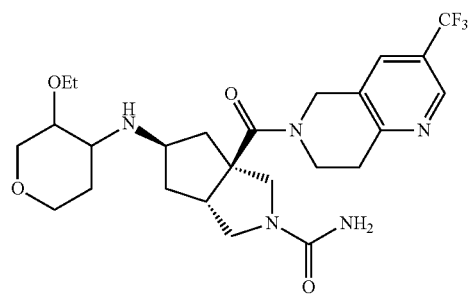

Prepared analogously to Example 6. $^1$H-NMR (400 MHz, CDCl$_3$): δ 1.11-1.22 (m, 3H), 1.53-1.94 (m, 5H), 2.09-2.47 (m, 2H), 2.63-2.81 (m, 1H), 3.06-4.04 (m, 16H), 4.63-5.01 (m, 4H), 5.64-6.10 (m, 1H), 7.71 (s, 1H), 8.71 (br. s., 1H); LC/MS: C$_{25}$H$_{34}$F$_3$N$_5$O$_4$: m/z 526.0 (M+H).

Example 10

(3aR,5R,6aR)-5-(((3S*,4S*)-3-Methoxytetrahydro-2H-pyran-4-yl)amino)-N³ᵃ-(3-(trifluoromethyl)benzyl)hexahydrocyclopenta[c]pyrrole-2,3a(1H)-dicarboxamide

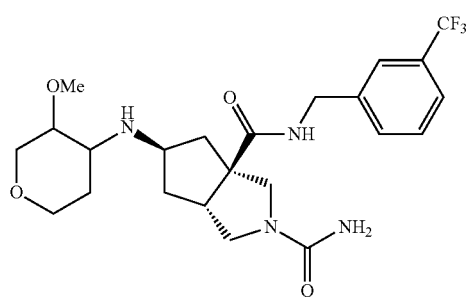 [SMILES: COC1COCCC1N[C@@H]1C[C@H]2CN(C(N)=O)C[C@@]2(C(=O)NCc2cccc(C(F)(F)F)c2)C1]

Prepared analogously to Example 6. ¹H-NMR (400 MHz, CDCl₃): δ 1.00-1.05 (m, 1H), 1.35-2.04 (m, 5H), 2.19 (dd, J=14.1, 9.9 Hz, 1H), 2.39-2.66 (m, 2H), 2.91-3.20 (m, 3H), 3.20-3.41 (m, 5H), 3.49-3.70 (m, 2H), 3.69-3.91 (m, 1H), 3.92-4.19 (m, 1H), 4.29-4.47 (m, 2H), 4.46-4.63 (m, 1H), 4.85 (s, 2H), 7.38-7.62 (m, 4H), 9.60-9.86 (m, 1H); LC/MS: C₂₃H₃₁F₃N₄O₄: m/z 485.2 (M+H).

Example 11

(3aR,5R,6aR)-N³ᵃ-(3-Fluoro-5-(trifluoromethyl)benzyl)-5-(((3S*,4S*)-3-methoxytetrahydro-2H-pyran-4-yl)amino)hexahydrocyclopenta[c]pyrrole-2,3a(1H)-dicarboxamide

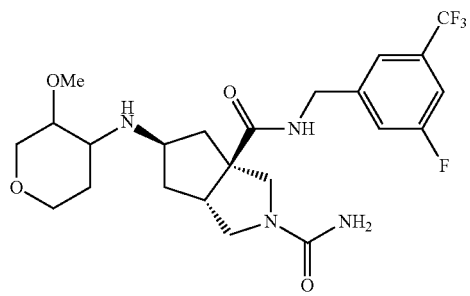 [SMILES: COC1COCCC1N[C@@H]1C[C@H]2CN(C(N)=O)C[C@@]2(C(=O)NCc2cc(F)cc(C(F)(F)F)c2)C1]

Prepared analogously to Example 6. ¹H-NMR (400 MHz, CDCl₃): δ 0.97-1.18 (m, 1H), 1.51-1.75 (m, 3H), 1.79-2.05 (m, 3H), 2.12-2.27 (m, 1H), 2.59 (dt, J=11.2, 4.1 Hz, 1H), 2.97-3.09 (m, 1H), 3.08-3.41 (m, 7H), 3.57 (ddd, J=10.9, 7.6, 3.7 Hz, 1H), 3.67 (d, J=15.2 Hz, 1H), 3.77-3.95 (m, 1H), 3.99-4.21 (m, 1H), 4.29-4.61 (m, 5H), 7.12-7.34 (m, 3H), 9.78-10.01 (m, 1H); LC/MS: C₂₃H₃₀F₄N₄O₄: m/z 503.0 (M+H).

Example 12

(3aR,5R,6aR)-N³ᵃ-(3,5-Bis(trifluoromethyl)benzyl)-5-(((3S*,4S*)-3-methoxytetrahydro-2H-pyran-4-yl)amino)hexahydrocyclopenta[c]pyrrole-2,3a(1H)-dicarboxamide

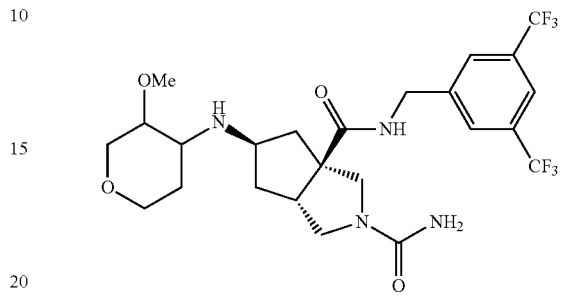

Prepared analogously to Example 6. ¹H-NMR (400 MHz, CDCl₃): δ 0.98-1.20 (m, 1H), 1.39-2.11 (m, 5H), 2.15-2.29 (m, 1H), 2.50-2.66 (m, 1H), 2.90-3.41 (m, 9H), 3.48-3.59 (m, 1H), 3.60-3.72 (m, 1H), 3.75-3.95 (m, 1H), 3.99-4.20 (m, 1H), 4.30-4.68 (m, 3H), 4.96 (br. s., 2H), 7.62-7.87 (m, 3H), 9.82-10.13 (m, 1H); LC/MS: C₂₄H₃₀F₆N₄O₄: m/z 553.3 (M+H).

Example 13

(3aR,5R,6aR)-5-(((3S*,4S*)-3-Methoxytetrahydro-2H-pyran-4-yl)amino)-N-methyl-3a-(3-(trifluoromethyl)-5,6,7,8-tetrahydro-1,6-naphthyridine-6-carbonyl)hexahydrocyclopenta-[c]pyrrole-2(1H)-carboxamide

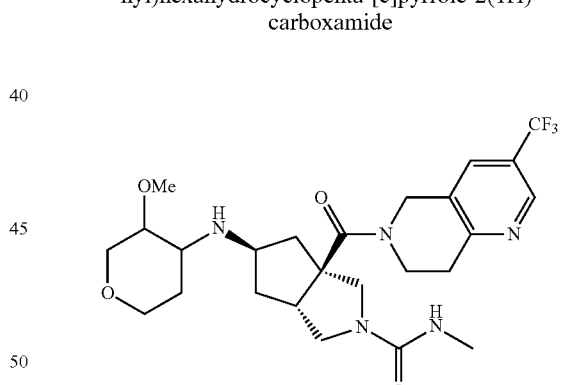

Step A. tert-Butyl((3aR,5R,6aR)-2-(methylcarbamoyl)-3a-(3-(trifluoromethyl)-5,6,7,8-tetrahydro-1,6-naphthyridine-6-carbonyl)octahydrocyclopenta[c]pyrrol-5-yl)carbamate To a solution of intermediate 1 (0.11 g, 0.242 mmol) in DCM (2 mL) or THF (2 mL) was added methyl isocyanate (16.9 mg, 0.29 mmol). The mixture was stirred at rt overnight. Aqueous workup and purification by CombiFlash (eluent: 8% methanol in DCM) gave the product as a colorless gel. ¹H-NMR (400 MHz, CDCl₃): δ 1.33-1.47 (m, 9H), 1.72-2.44 (m, 3H), 2.44 (br. s., 1H), 2.67-2.88 (m, 4H), 3.04-3.24 (m, 3H), 3.54 (t, J=8.6 Hz, 1H), 3.60-3.95 (m, 4H), 4.25 (br. s., 1H), 4.36-4.56 (m, 1H), 4.61-5.04 (m, 3H), 7.72 (s, 1H), 8.71 (br. s., 1H); LC/MS: $C_{24}H_{32}F_3N_5O_4$: m/z 512.3 (M+H).

Step B. (3aR,5R,6aR)-5-Amino-N-methyl-3a-(3-(trifluoromethyl)-5,6,7,8-tetrahydro-1,6-naphthyridine-6-carbonyl)hexahydrocyclopenta[c]pyrrole-2(1H)-carboxamide A solution of the product from Step A (0.08 g, 0.156 mmol) in TFA (1.5 mL) and DCM (1.5 mL) was stirred at rt for 1.5 h. The volatile organic compounds were removed by evaporation, and the residue was diluted with DCM and evaporated again to give the product as a TFA salt. LC/MS: $C_{19}H_{24}F_3N_5O_2$: m/z 412.5 (M+H).

Step C. (3aR,5R,6aR)-5-(((3S*,4S*)-(3-Methoxytetrahydro-2H-pyran-4-yl)amino)-N-methyl-3a-(3-(trifluoromethyl)-5,6,7,8-tetrahydro-1,6-naphthyridine-6-carbonyl)hexahydrocyclopenta-[c]pyrrole-2(1H)-carboxamide A mixture of the product from Step B (99.8 mg, 0.156 mmol), 3-methoxydihydro-2H-pyran-4(3H)-one (60.91 mg, 0.468 mmol), 4 Å molecular sieves (0.2 g) and TEA (0.0651 mL, 0.468 mmol) in DCM (2 mL) was stirred at rt for 2 h, followed by addition of sodium triacetoxyborohydride (66.13 mg, 0.312 mmol). The resulting mixture was stirred at rt overnight. The reaction was quenched by addition of saturated $NaHCO_3$ aqueous solution, extracted with DCM, and dried over $Na_2SO_4$. After removal of the solvent, the residue was purified by column chromatography (eluent: 5% 7N $NH_3$ in methanol in DCM) to give the product as a yellowish gel. $^1$H-NMR (400 MHz, $CDCl_3$): δ 1.52-1.95 (m, 4H), 2.34 (br. s., 1H), 2.61-2.89 (m, 6H), 3.03-3.61 (m, 11H), 3.63-4.13 (m, 7H), 4.27 (br. s., 1H), 4.57-5.11 (m, 2H), 7.69 (br. s., 1H), 8.71 (br. s., 1H); LC/MS: $C_{25}H_{34}F_3N_5O_4$: m/z 526.2 (M+H).

The following title compounds were synthesized using a similar procedure:

Example 14

(3aR,5R,6aR)-N-Isopropyl-5-(((3S*,4S*)-(3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxamide

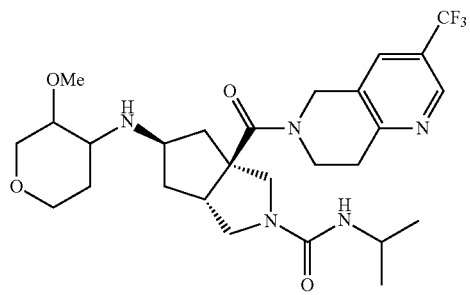 [SMILES: COC1COCCC1N[C@@H]1C[C@H]2CN(C(=O)NC(C)C)C[C@@]2(C(=O)N2CCc3ncc(C(F)(F)F)cc3C2)C1]

Prepared analogously to Example 13. $^1$H-NMR (400 MHz, $CDCl_3$): δ 1.15 (t, J=5.8 Hz, 6H), 1.57-2.18 (m, 3H), 2.40 (dd, J=12.6, 6.3 Hz, 1H), 2.81-4.19 (m, 24H), 4.57-5.02 (m, 2H), 7.70 (s, 1H), 8.71 (s, 1H); LC/MS: $C_{27}H_{38}F_3N_5O_4$: m/z 554.2 (M+H).

Example 15

(3aR,5R,6aR)-N-Isobutyl-5-(((3S*4S*)-(3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrole-2(1H)-carboxamide

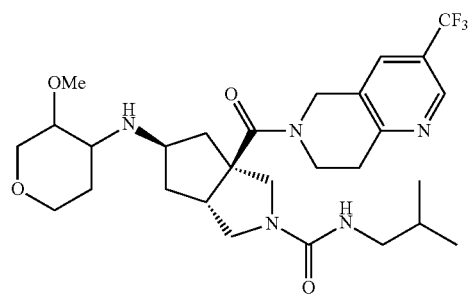

Prepared analogously to Example 13. $^1$H-NMR (400 MHz, $CD_3OD$): δ 0.87 (br. s., 6H), 1.48-1.98 (m, 6H), 2.29-4.28 (m, 26H), 8.05 (br. s., 1H), 8.69 (br. s., 1H); LC/MS: $C_{28}H_{40}F_3N_5O_4$: m/z 568.5 (M+H).

Example 16

(3aR,5R,6aR)-5-(((3S*,4S*)-(3-methoxytetrahydro-2H-pyran-4-yl)amino)-N-phenyl-3a-(3-(trifluoromethyl)-5,6,7,8-tetrahydro-1,6-naphthyridine-6-carbonyl)hexahydrocyclopenta-[c]pyrrole-2(1H)-carboxamide

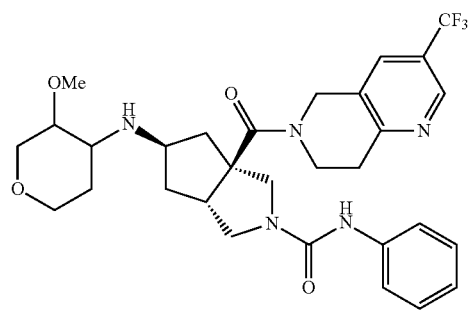 [SMILES: COC1COCCC1N[C@@H]1C[C@H]2CN(C(=O)Nc3ccccc3)C[C@@]2(C(=O)N2CCc3ncc(C(F)(F)F)cc3C2)C1]

Prepared analogously to Example 13. $^1$H-NMR (400 MHz, $CDCl_3$): δ 1.58-1.94 (m, 6H), 2.36 (br. s., 1H), 2.72 (br. s., 1H), 3.09-3.56 (m, 10H), 3.68-4.08 (m, 8H), 4.57-5.11 (m, 2H), 6.39 (d, J=14.9 Hz, 1H), 6.97-7.11 (m, 1H), 7.21-7.33 (m, 2H), 7.38 (d, J=7.8 Hz, 2H), 7.68 (br. s., 1H), 8.71 (br. s., 1H); LC/MS: $C_{30}H_{36}F_3N_5O_4$: m/z 588.3 (M+H).

Example 17

(3aR,5R,6aR)-N-benzyl-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrole-2(1H)-carboxamide

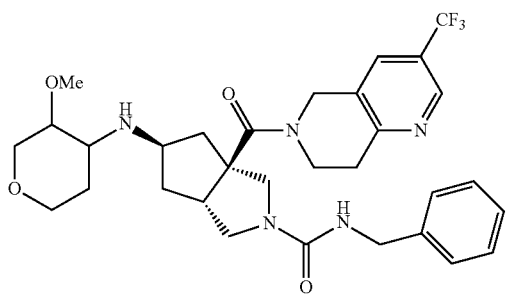 [SMILES: COC1COCCC1N[C@@H]1C[C@H]2CN(C(=O)NCc3ccccc3)C[C@@]2(C(=O)N2CCc3ncc(C(F)(F)F)cc3C2)C1]

Prepared analogously to Example 13. $^1$H-NMR (400 MHz, CDCl$_3$): δ 1.59-1.94 (m, 6H), 2.34 (br. s., 1H), 2.72 (br. s., 1H), 3.11-4.07 (m, 18H), 4.40 (d, J=5.1 Hz, 2H), 4.63-5.03 (m, 3H), 7.26-7.39 (m, 5H), 7.69 (br. s., 1H), 8.71 (br. s., 1H); LC/MS: C$_{31}$H$_{38}$F$_3$N$_5$O$_4$: m/z 602.5 (M+H).

Example 18

(3aR,5R,6aR)-5-(((3S*,4S*)-3-Methoxytetrahydro-2H-pyran-4-yl)amino)-N-neopentyl-3a-(3-(trifluoromethyl)-5,6,7,8-tetrahydro-1,6-naphthyridine-6-carbonyl)hexahydrocyclopenta[c]pyrrole-2(1H)-carboxamide

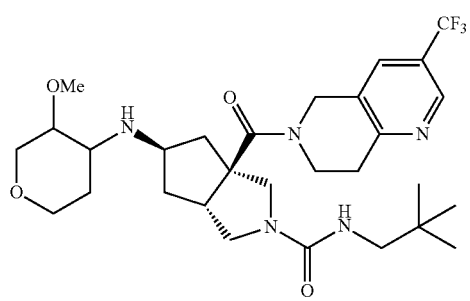 [SMILES: COC1COCCC1N[C@@H]1C[C@H]2CN(C(=O)NCC(C)(C)C)C[C@@]2(C(=O)N2CCc3ncc(C(F)(F)F)cc3C2)C1]

Step A. tert-Butyl((3aR,5R,6aR)-2-(neopentylcarbamoyl)-3a-(3-(trifluoromethyl)-5,6,7,8-tetrahydro-1,6-naphthyridine-6-carbonyl)octahydrocyclopenta[c]pyrrol-5-yl)carbamate A mixture of the intermediate 1 (0.10 g, 0.22 mmol) and TEA (0.128 mL, 0.924 mmol) in DCM (6 mL) was added dropwise to a solution of triphosgene (24.65 mg, 0.0814 mmol) in DCM (4 mL) at 0° C. The mixture was stirred at 0° C. for 30 min and treated with a solution of neopentylamine (23.73 mg, 0.264 mmol) in DCM (2 mL). The mixture was then stirred at rt overnight and quenched by the addition of saturated aqueous NaHCO$_3$ solution, extracted with DCM, and dried over Na$_2$SO$_4$. Filtration and purification by CombiFlash (eluent: 5% methanol in DCM) gave the product as a colorless gel. $^1$H-NMR (400 MHz, CDCl$_3$): δ 0.90 (d, J=3.8 Hz, 9H), 1.27-1.54 (m, 9H), 1.74-2.10 (m, 3H), 2.43 (br. s., 1H), 2.86-3.38 (m, 5H), 3.45-3.94 (m, 5H), 4.30 (t, J=5.9 Hz, 2H), 4.45-5.07 (m, 3H), 7.33-7.46 (m, 1H), 7.69 (br. s., 1H), 8.71 (br. s., 1H); LC/MS: C$_{28}$H$_{40}$F$_3$N$_5$O$_4$: m/z 568.2 (M+H).

Step B. (3aR,5R,6aR)-5-Amino-N-neopentyl-3a-(3-(trifluoromethyl)-5,6,7,8-tetrahydro-1,6-naphthyridine-6-carbonyl)hexahydrocyclopenta[c]pyrrole-2(1H)-carboxamide The title compound was prepared analogously to Step B in Example 13 as a TFA salt. LC/MS: C$_{23}$H$_{32}$F$_3$N$_5$O$_2$: m/z 468.2 (M+H).

Step C. (3aR,5R,6aR)-5-(((3S*,4S*)-3-Methoxytetrahydro-2H-pyran-4-yl)amino)-N-neopentyl-3a-(3-(trifluoromethyl)-5,6,7,8-tetrahydro-1,6-naphthyridine-6-carbonyl)hexahydrocyclopenta[c]pyrrole-2(1H)-carboxamide The title compound was prepared analogously to Step C in Example 13. $^1$H-NMR (400 MHz, CDCl$_3$): δ 0.79-0.97 (m, 9H), 1.07-1.35 (m, 2H), 1.54-2.07 (m, 5H), 2.36 (br. s., 1H), 2.72 (br. s., 1H), 2.95-3.22 (m, 4H), 3.22-3.65 (m, 8H), 3.68-4.00 (m, 6H), 4.00-4.15 (m, 1H), 4.28 (t, J=5.6 Hz, 1H), 4.60-4.78 (m, 1H), 4.90 (br. s., 1H), 7.69 (br. s., 1H), 8.71 (br. s., 1H); LC/MS: C$_{29}$H$_{42}$F$_3$N$_5$O$_4$: m/z 582.2 (M+H).

Example 19

(3aR,5R,6aR)-N-(2-Methoxyethyl)-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxamide

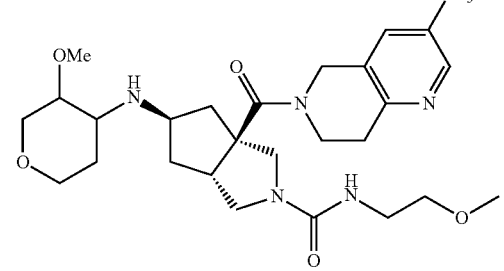

Prepared analogously to Example 18. $^1$H-NMR (400 MHz, CDCl$_3$): δ 0.77-0.94 (m, 1H), 1.14-1.34 (m, 3H), 1.53-1.90 (m, 7H), 2.33 (br. s., 1H), 2.70 (br. s., 1H), 3.12-3.50 (m, 13H), 3.62-3.95 (m, 7H), 4.05 (ddd, J=11.6, 7.6, 3.3 Hz, 1H), 4.57-5.04 (m, 2H), 7.69 (s, 1H), 8.71 (s, 1H); LC/MS: C$_{27}$H$_{38}$F$_3$N$_5$O$_5$: m/z 570.2 (M+H).

Example 20

(3aR,5R,6aR)-5-(((3S*,4S*)-3-Methoxytetrahydro-2H-pyran-4-yl)amino)-N-(2-morpholinoethyl)-3a-(3-(trifluoromethyl)-5,6,7,8-tetrahydro-1,6-naphthyridine-6-carbonyl)hexahydrocyclopenta[c]pyrrole-2(1H)-carboxamide

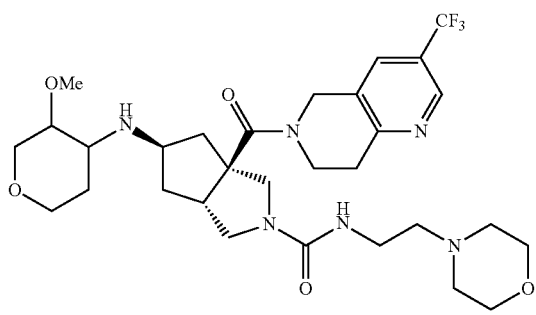 [SMILES: COC1COCCC1N[C@@H]1C[C@H]2CN(C(=O)NCCN3CCOCC3)C[C@@]2(C(=O)N2CCc3ncc(C(F)(F)F)cc3C2)C1]

Prepared analogously to Example 18. $^1$H-NMR (400 MHz, CDCl$_3$): δ 0.77-0.94 (m, 3H), 1.06-1.35 (m, 3H), 1.51-1.88 (m, 7H), 2.49 (d, J=11.1 Hz, 5H), 2.72 (br. s., 1H), 3.01-3.20 (m, 2H), 3.21-3.60 (m, 9H), 3.64-3.97 (m, 8H), 4.00-4.15 (m, 1H), 4.63-5.02 (m, 2H), 7.69 (s, 1H), 8.71 (s, 1H); LC/MS: C$_{30}$H$_{43}$F$_3$N$_6$O$_5$: m/z 625.5 (M+H).

Example 21

(3aR,5R,6aR)-5-(((3S*,4S*)-3-Methoxytetrahydro-2H-pyran-4-yl)amino)-N,N-dimethyl-3a-(3-(trifluoromethyl)-5,6,7,8-tetrahydro-1,6-naphthyridine-6-carbonyl)hexahydrocyclopenta[c]pyrrole-2(1H)-carboxamide

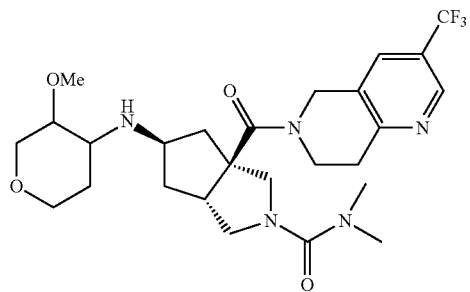 [SMILES: COC1COCCC1N[C@@H]1C[C@H]2CN(C(=O)N(C)C)C[C@@]2(C(=O)N2CCc3ncc(C(F)(F)F)cc3C2)C1]

Step A. tert-Butyl((3aR,5R,6aR)-2-(dimethylcarbamoyl)-3a-(3-(trifluoromethyl)-5,6,7,8-tetrahydro-1,6-naphthyridine-6-carbonyl)octahydrocyclopenta[c]pyrrol-5-yl)carbamate To a solution of Intermediate 1 (0.11 g, 0.242 mmol) in DCM (10 mL) at 0° C. were added DIPEA (0.101 mL, 0.581 mmol) and N,N-dimethylcarbamoyl chloride (0.0544 mL, 0.581 mmol). The mixture was stirred at 0° C. for 1 h and at rt overnight. Aqueous workup and purification by CombiFlash (eluent: 8% methanol in DCM) gave the product as a colorless gel. $^1$H-NMR (400 MHz, CDCl$_3$): δ 1.32-1.51 (m, 9H), 1.74-2.06 (m, 2H), 2.42 (dd, J=12.3, 5.7 Hz, 1H), 2.76-2.90 (m, 7H), 2.94-3.28 (m, 4H), 3.49-3.93 (m, 5H), 4.23 (br. s., 1H), 4.61-5.00 (m, 3H), 7.71 (s, 1H), 8.71 (br. s., 1H); LC/MS: C$_{25}$H$_{34}$F$_3$N$_5$O$_4$: m/z 526.5 (M+H).

Step B. (3aR,5R,6aR)-5-Amino-N,N-dimethyl-3a-(3-(trifluoromethyl)-5,6,7,8-tetrahydro-1,6-naphthyridine-6-carbonyl)hexahydrocyclopenta[c]pyrrole-2(1H)-carboxamide The title compound was prepared analogously to Step B in Example 13 as a TFA salt. LC/MS: C$_{20}$H$_{26}$F$_3$N$_5$O$_2$: m/z 426.5 (M+H).

Step C. (3aR,5R,6aR)-5-(((3S*,4S*)-3-Methoxytetrahydro-2H-pyran-4-yl)amino)-N,N-dimethyl-3a-(3-(trifluoromethyl)-5,6,7,8-tetrahydro-1,6-naphthyridine-6-carbonyl)hexahydrocyclopenta[c]pyrrole-2(1H)-carboxamide The title compound was prepared analogously to Step C in Example 13. $^1$H-NMR (400 MHz, CDCl$_3$): δ 1.59-2.11 (m, 5H), 2.34-2.51 (m, 1H), 2.74-2.95 (m, 7H), 3.06-3.23 (m, 5H), 3.24-3.47 (m, 7H), 3.47-3.70 (m, 4H), 3.76-4.00 (m, 4H), 4.10 (d, J=12.1 Hz, 1H), 4.79 (br. s., 2H), 7.71 (s, 1H), 8.71 (br. s., 1H); LC/MS: C$_{26}$H$_{36}$F$_3$N$_5$O$_4$: m/z 540.3 (M+H).

Example 22

((3aR,5R,6aR)-5-(((3S*,4S*)-3-Methoxytetrahydro-2H-pyran-4-yl)amino)-2-(morpholine-4-carbonyl)octahydrocyclopenta[c]pyrrol-3a-yl)(3-(trifluoromethyl)-7,8-dihydro-1,6-naphthyridin-6(5H)-yl)methanone

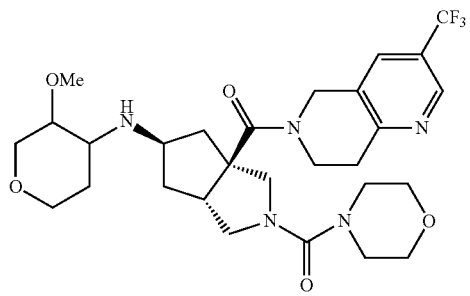 [SMILES: COC1COCCC1N[C@@H]1C[C@H]2CN(C(=O)N3CCOCC3)C[C@@]2(C(=O)N2CCc3ncc(C(F)(F)F)cc3C2)C1]

Prepared analogously to Example 21. $^1$H-NMR (400 MHz, CDCl$_3$): δ 1.84-2.14 (m, 4H), 2.33 (br. s., 1H), 3.01-3.35 (m, 11H), 3.51-3.96 (m, 14H), 4.45 (br. s., 1H), 4.61-4.97 (m, 2H), 7.71 (s, 1H), 8.73 (s, 1H); LC/MS: C$_{28}$H$_{35}$F$_3$N$_5$O$_5$: m/z 581.3 (M+H).

Example 23

((3aR,5R,6aR)-2-(1H-Imidazole-1-carbonyl)-5-(((3S*,4S*)-3-methoxytetrahydro-2H-pyran-4-yl)amino)octahydrocyclopenta[c]pyrrol-3a-yl)(3-(trifluoromethyl)-7,8-dihydro-1,6-naphthyridin-6(5H)-yl)methanone

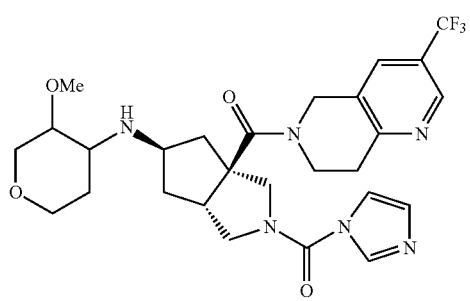 [SMILES: COC1COCCC1N[C@@H]1C[C@H]2CN(C(=O)n3ccnc3)C[C@@]2(C(=O)N2CCc3ncc(C(F)(F)F)cc3C2)C1]

Step A. tert-Butyl((3aR,5R,6aR)-2-(1H-imidazole-1-carbonyl)-3a-(3-(trifluoromethyl)-5,6,7,8-tetrahydro-1,6-naphthyridine-6-carbonyl)octahydrocyclopenta[c]pyrrol-5-yl)carbamate To a solution of Intermediate 1 (135 mg, 0.297 mmol) in THF (5 mL) was added carbonyl diimidazole (57.8 mg, 0.356 mmol). The mixture was stirred at rt under Ar for 1.5 h and evaporated to give an oil, which was partitioned between water and DCM. The DCM solution was washed with brine (3×), dried over $Na_2SO_4$. Filtration and evaporation to dryness gave the product as a white solid. $^1$H-NMR (400 MHz, $CDCl_3$): δ 1.35-1.45 (m, 9H), 1.73-2.13 (m, 2H), 2.27 (t, J=7.7 Hz, 1H), 2.46-2.56 (m, 1H), 3.17 (br. s., 2H), 3.41-3.55 (m, 1H), 3.76 (d, J=5.9 Hz, 3H), 3.89-4.10 (m, 3H), 4.23-4.32 (m, 1H), 4.49-5.02 (m, 3H), 7.10 (br. s., 1H), 7.29-7.35 (m, 1H), 7.72 (s, 1H), 7.98 (br. s., 1H), 8.74 (br. s., 1H); LC/MS: $C_{26}H_{31}F_3N_6O_4$: m/z 549.0 (M+H).

Step B. ((3aR,5R,6aR)-5-Amino-2-(1H-imidazole-1-carbonyl)octahydrocyclopenta-[c]pyrrol-3a-yl)(3-(trifluoromethyl)-7,8-dihydro-1,6-naphthyridin-6(5H)-yl)methanone The title compound was prepared analogously to Step B in Example 13 as a TFA salt. LC/MS: $C_{21}H_{23}F_3N_6O_2$: m/z 449.0 (M+H).

Step C. ((3aR,5R,6aR)-2-(1H-Imidazole-1-carbonyl)-5-(((3S*,4S*)-3-methoxytetrahydro-2H-pyran-4-yl)amino)octahydrocyclopenta[c]pyrrol-3a-yl)(3-(trifluoromethyl)-7,8-dihydro-1,6-naphthyridin-6(5H)-yl)methanone The title compound was prepared analogously to Step C in Example 13. $^1$H-NMR (400 MHz, $CD_3OD$): δ 1.76-2.41 (m, 5H), 3.03 (br. s., 1H), 3.36-3.83 (m, 13H), 3.85-4.38 (m, 7H), 4.98 (br. s., 2H), 7.70 (br. s., 1H), 8.08 (br. s., 1H), 8.66 (br. s., 1H), 9.09 (br. s., 1H), 9.53 (s, 1H); LC/MS: $C_{27}H_{33}F_3N_6O_4$: m/z 563.3 (M+H).

Example 24

((3aR,5R,6aR)-2-(1H-Imidazole-1-carbonyl)-5-(((3S*,4S*)-3-methoxytetrahydro-2H-pyran-4-yl)amino)octahydrocyclopenta[c]pyrrol-3a-yl)(7-(trifluoromethyl)-3,4-dihydroisoquinolin-2(1H)-yl)methanone

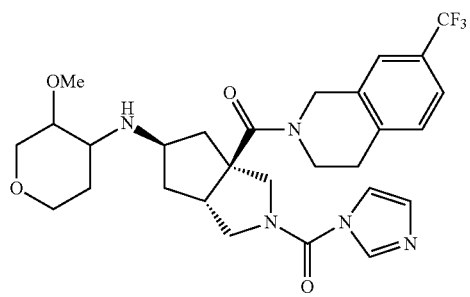 [SMILES: COC1COCCC1N[C@@H]1C[C@H]2CN(C(=O)n3ccnc3)C[C@@]2(C(=O)N2CCc3ccc(C(F)(F)F)cc3C2)C1]

Prepared analogously to Example 23 from Intermediate 2. $^1$H-NMR (400 MHz, $CD_3OD$): δ 1.80-2.40 (m, 5H), 3.01 (br. s., 3H), 3.24-4.33 (m, 18H), 4.66-4.84 (m, 2H), 7.40 (br. s., 1H), 7.45-7.80 (m, 3H), 8.06 (br. s., 1H), 9.50 (br. s., 1H); LC/MS: $C_{28}H_{34}F_3N_5O_4$: m/z 562 (M+H).

Example 25

(3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrole-2(1H)-carbothioamide

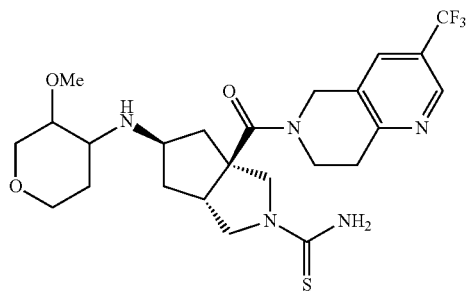 [SMILES: COC1COCCC1N[C@@H]1C[C@H]2CN(C(N)=S)C[C@@]2(C(=O)N2CCc3ncc(C(F)(F)F)cc3C2)C1]

Step A. tert-Butyl((3aR,5R,6aR)-2-carbamothioyl-3a-(3-(trifluoromethyl)-5,6,7,8-tetrahydro-1,6-naphthyridine-6-carbonyl)octahydrocyclopenta[c]pyrrol-5-yl)carbamate To a solution of Intermediate 1 (136.3 mg, 0.3 mmol) in THF (5 mL) was added 1,1'-thiocarbonyldiimidazole (64.2 mg, 0.36 mmol), and the mixture was stirred at rt overnight. To the mixture was added ammonium hydroxide (5.11 mg, 0.3 mmol) and the resolution was heated at 65° C. overnight. Aqueous workup and purification by CombiFlash (eluent: 5% methanol in DCM) gave the product as a white solid. $^1$H-NMR (400 MHz, $CDCl_3$): δ 1.31-1.46 (m, 9H), 1.82-2.09 (m, 4H), 2.42-2.63 (m, 1H), 3.16 (br. s., 3H), 3.59-3.88 (m, 4H), 3.98-4.41 (m, 3H), 4.57-4.98 (m, 3H), 5.59 (br. s., 1H), 7.72 (s, 1H), 8.72 (br. s., 1H); LC/MS: $C_{23}H_{30}F_3N_5O_3S$: m/z 514 (M+H).

Step B. (3aR,5R,6aR)-5-Amino-3a-(3-(trifluoromethyl)-5,6,7,8-tetrahydro-1,6-naphthyridine-6-carbonyl)hexahydrocyclopenta[c]pyrrole-2(1H)-carbothioamide The title compound was prepared analogously to Step B in Example 13 as a TFA salt as a TFA salt. LC/MS: $C_{18}H_{22}F_3N_5OS$: m/z 414 (M+H).

Step C. (3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrole-2(1H)-carbothioamide The title compound was prepared analogously to Step C in Example 13. $^1$H-NMR (400 MHz, DMSO-$d_6$): δ 1.87-2.35 (m, 9H), 2.59-2.91 (m, 3H), 3.29-4.73 (m, 14H), 4.90-5.22 (m, 4H), 7.90 (s, 1H), 8.48 (s, 1H); LC/MS: $C_{24}H_{32}F_3N_5O_3S$: m/z 528 (M+H).

Example 26

(3aR,5R,6aR)-N-Benzyl-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrole-2(1H)-carbothioamide

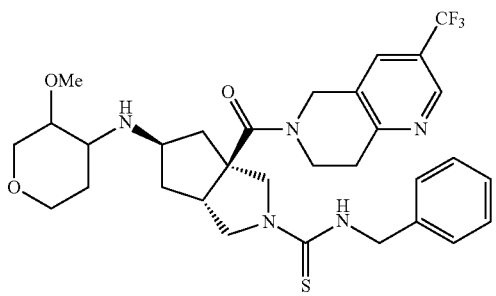

Step A. tert-Butyl((3aR,5R,6aR)-2-(benzylcarbamothioyl)-3a-(3-(trifluoromethyl)-5,6,7,8-tetrahydro-1,6-naphthyridine-6-carbonyl)octahydrocyclopenta[c]pyrrol-5-yl)carbamate To a solution of the Intermediate 1 (90.0 mg, 0.2 mmol) in THF (2 mL) was added a solution of benzyl isothiocyanate (29.84 mg, 0.2 mmol) in THF (1 mL). The mixture was stirred at rt for 1 h. Aqueous workup and purification by CombiFlash (eluent: 8% methanol in DCM) gave the product as a colorless oil. $^1$H-NMR (400 MHz, CDCl$_3$): δ 1.32-1.44 (m, 9H), 1.63 (br. s., 2H), 1.80-2.06 (m, 5H), 2.50 (t, J=8.3 Hz, 1H), 3.09-3.32 (m, 3H), 3.62-3.90 (m, 4H), 4.11 (d, J=12.0 Hz, 1H), 4.36 (t, J=7.1 Hz, 2H), 4.56-4.94 (m, 2H), 7.33-7.41 (m, 5H), 7.71 (s, 1H), 8.72 (s, 1H); LC/MS: C$_{30}$H$_{36}$F$_3$N$_5$O$_3$S: m/z 604.5 (M+H).

Step B. (3aR,5R,6aR)-5-Amino-N-benzyl-3a-(3-(trifluoromethyl)-5,6,7,8-tetrahydro-1,6-naphthyridine-6-carbonyl)hexahydrocyclopenta[c]pyrrole-2(1H)-carbothioamide The title compound was prepared analogously to Step B in Example 13 as a TFA salt. LC/MS: C$_{25}$H$_{28}$F$_3$N$_5$OS: m/z 504 (M+H).

Step C. (3aR,5R,6aR)-N-Benzyl-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrole 2(1H)-carbothioamide The title compound was prepared analogously to Step C in Example 13. $^1$H-NMR (400 MHz, CDCl$_3$): δ 1.66 (br. s., 5H), 2.06 (d, J=12.7 Hz, 2H), 2.33 (br. s., 1H), 2.46-2.76 (m, 2H), 3.13-3.55 (m, 9H), 3.79 (d, J=6.4 Hz, 4H), 4.00 (br. s., 1H), 4.17 (d, J=12.0 Hz, 2H), 4.68-4.94 (m, 5H), 7.31-7.40 (m, 5H), 7.69 (br. s., 1H), 8.71 (s, 1H); LC/MS: C$_{31}$H$_{38}$F$_3$N$_5$O$_3$S: m/z 618 (M+H).

Example 27

(3aR,5R,6aR)-5-(((3S*,4S*)-3-Methoxytetrahydro-2H-pyran-4-yl)amino)-N-methyl-3a-(3-(trifluoromethyl)-5,6,7,8-tetrahydro-1,6-naphthyridine-6-carbonyl)hexahydrocyclopenta[c]pyrrole-2(1H)-carbothioamide

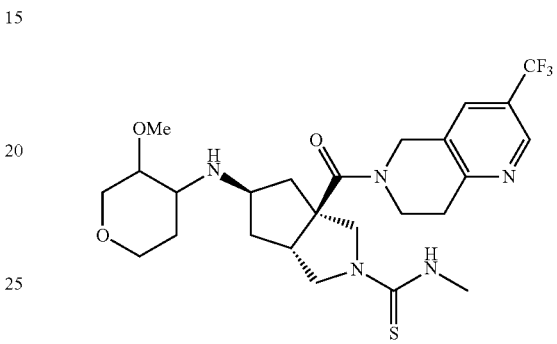

A solution of Example 1 (0.1 g, 0.213 mmol) in DCM (1 mL) was added methyl isothiocyanate (19.31 mg, 0.256 mmol) and the mixture was stirred at rt overnight. The reaction was quenched by addition of saturated aqueous NaHCO$_3$ solution, extracted with DCM, dried over Na$_2$SO$_4$. Filtration and purification by CombiFlash (eluent: 5% methanol in DCM) gave the product Example 27 as a white solid, $^1$H-NMR (400 MHz, CDCl$_3$): δ 1.56-1.89 (m, 6H), 2.41 (br. s., 1H), 2.71 (br. s., 1H), 3.08-3.57 (m, 13H), 3.64-4.12 (m, 7H), 4.33 (br. s., 1H), 4.62-5.02 (m, 2H), 5.46 (d, J=2.5 Hz, 1H), 7.71 (s, 1H), 8.71 (br. s., 1H); LC/MS: C$_{25}$H$_{34}$F$_3$N$_5$O$_3$S: m/z 542.3 (M+H).

Example 28

(3aR,5R,6aR)-5-(1-((3S*,4S*)-3-Methoxytetrahydro-2H-pyran-4-yl)-3-methylthioureido)-N-methyl-3a-(3-(trifluoromethyl)-5,6,7,8-tetrahydro-1,6-naphthyridine-6-carbonyl)hexahydrocyclopenta[c]pyrrole-2(1H)-carbothioamide

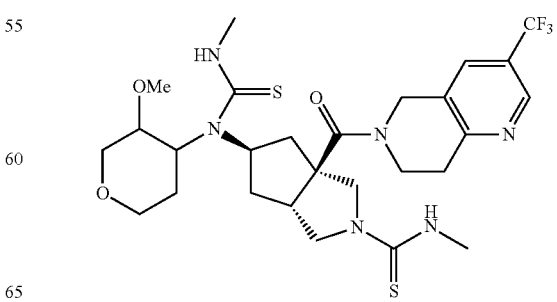

Prepared as a byproduct of the procedure used in Example 27, the title compound was isolated as a white solid. LC/MS: $C_{27}H_{37}F_3N_6O_3S_2$: m/z 615.2 (M+H).

Example 29

(3aR,5R,6aR)-N-Isobutyl-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carbothioamide

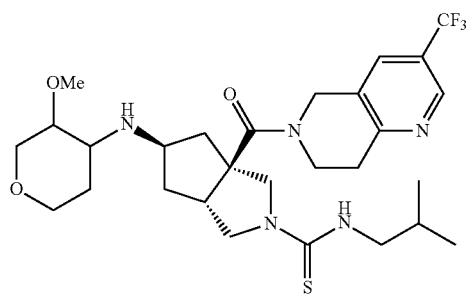 [SMILES: COC1COCCC1N[C@@H]1C[C@H]2CN(C(=S)NCC(C)C)C[C@@]2(C(=O)N2CCc3ncc(C(F)(F)F)cc3C2)C1]

Prepared analogously to Example 27, a white solid. $^1$H-NMR (400 MHz, CDCl$_3$): δ 0.89-0.99 (m, 6H), 1.56-1.99 (m, 6H), 2.31-2.53 (m, 1H), 2.71 (br. s., 1H), 3.08-3.58 (m, 13H), 3.63-4.17 (m, 7H), 4.34 (br. s., 1H), 4.61-5.02 (m, 2H), 5.31 (br. s., 1H), 7.71 (s, 1H), 8.72 (br. s., 1H); LC/MS: $C_{28}H_{40}F_3N_5O_3S$: m/z 584.2 (M+H).

Example 30

(3aR,5R,6aR)-N-Isobutyl-5-(((3S*,4S*)-3-isobutyl-1-(3-methoxytetrahydro-2H-pyran-4-yl)thioureido)-3a-(3-(trifluoromethyl)-5,6,7,8-tetrahydro-1,6-naphthyridine-6-carbonyl)hexahydrocyclopenta[c]pyrrole-2(1H)-carbothioamide

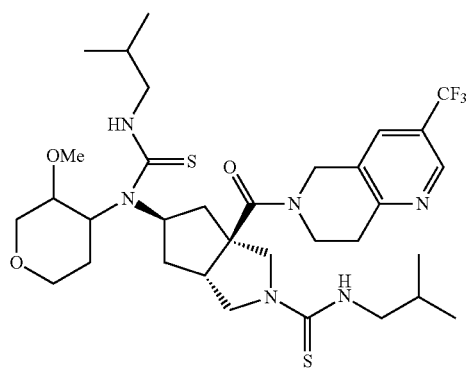 [SMILES: COC1COCCC1N(C(=S)NCC(C)C)[C@@H]1C[C@H]2CN(C(=S)NCC(C)C)C[C@@]2(C(=O)N2CCc3ncc(C(F)(F)F)cc3C2)C1]

Prepared analogously to Example 28, a white solid. LC/MS: $C_{33}H_{49}F_3N_6O_3S_2$: m/z 699.5 (M+H).

Example 31

((3aR,5R,6aR)-2-(1H-Imidazole-1-carbonothioyl)-5-(((3S*,4S*)-3-methoxytetrahydro-2H-pyran-4-yl)amino)octahydrocyclopenta[c]pyrrol-3a-yl)(3-(trifluoromethyl)-7,8-dihydro-1,6-naphthyridin-6(5H)-yl)methanone

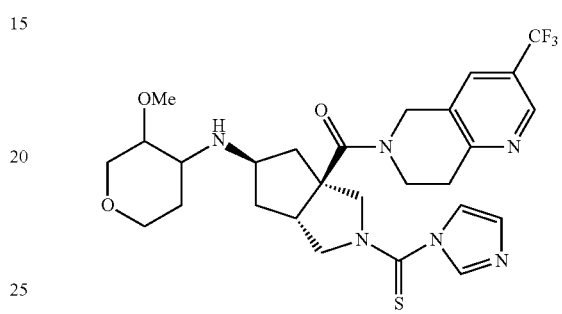

Step A. tert-Butyl((3aR,5R,6aR)-2-(1H-imidazole-1-carbonothioyl)-3a-(3-(trifluoromethyl)-5,6,7,8-tetrahydro-1,6-naphthyridine-6-carbonyl)octahydrocyclopenta[c]pyrrol-5-yl)carbamate To a solution of Intermediate 1 (409 mg, 0.9 mmol) in THF (15 mL) was added 1,1'-thiocarbonyldiimidazole (176.2 mg, 0.99 mmol), and the mixture was stirred at rt overnight. A little solid was filtered and the filtrate was evaporated. The residue was purified by CombiFlash (eluent: 5% methanol in DCM) gave the product as a colorless oil. $^1$H-NMR (400 MHz, CDCl$_3$): δ 1.30-1.44 (m, 9H), 1.78-2.15 (m, 2H), 2.50 (s, 1H), 3.18 (br. s., 1H), 3.39-3.89 (m, 6H), 3.96 (d, J=7.1 Hz, 1H), 4.35 (d, J=7.1 Hz, 3H), 4.71 (s, 3H), 7.08 (s, 1H), 7.38 (d, J=4.6 Hz, 1H), 7.75 (s, 1H), 7.94 (s, 1H), 8.74 (s, 1H); LC/MS: $C_{26}H_{31}F_3N_6O_3S$: m/z 565.5 (M+H).

Step B. ((3aR,5R,6aR)-5-Amino-2-(1H-imidazole-1-carbonothioyl)octahydrocyclopenta[c]pyrrol-3a-yl)(3-(trifluoromethyl)-7,8-dihydro-1,6-naphthyridin-6(5H)-yl)methanone trifluoroacetate The title compound was prepared analogously to Step B in Example 13 as a TFA salt. LC/MS: $C_{21}H_{23}F_3N_6OS$: m/z 465.5 (M+H).

Step C. ((3aR,5R,6aR)-2-(1H-Imidazole-1-carbonothioyl)-5-(((3S*,4S*)-3-methoxytetrahydro-2H-pyran-4-yl)amino)octahydrocyclopenta[c]pyrrol-3a-yl)(3-(trifluoromethyl)-7,8-dihydro-1,6-naphthyridin-6(5H)-yl)methanone The title compound was prepared analogously to Step C in Example 13 as an oil. $^1$H-NMR (400 MHz, CD$_3$OD): δ 1.79-2.45 (m, 5H), 2.97-4.50 (m, 22H), 4.96 (s, 1H), 7.70 (s, 1H), 8.11 (br. s., 1H), 8.43 (br. s., 1H), 8.96 (br. s., 1H), 9.54 (s, 1H); LC/MS: $C_{27}H_{33}F_3N_6O_3S$: m/z 579 (M+H).

Example 32

(3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrole-2(1H)-sulfonamide

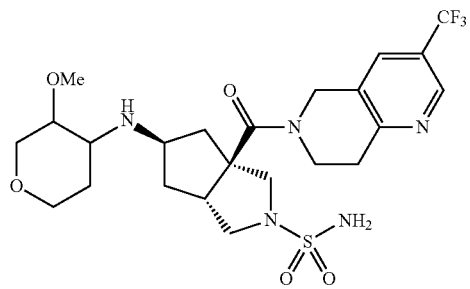 [SMILES: COC1COCCC1N[C@@H]1C[C@H]2CN(S(N)(=O)=O)C[C@@]2(C(=O)N2CCc3ncc(C(F)(F)F)cc3C2)C1]

Step A. tert-Butyl((3aR,5R,6aR)-5-((tert-butoxycarbonyl)amino)-3a-(3-(trifluoromethyl)-5,6,7,8-tetrahydro-1,6-naphthyridine-6-carbonyl)hexahydrocyclopenta[c]pyrrol-2(1H)-yl)sulfonylcarbamate To a cool (0° C.) solution of chlorosulfonyl isocyanate (0.1 mL, 1.129 mol) in DCM (2 mL) was added a solution of tert-butanol (83.7 mg, 1.129 mmol) in DCM (2 mL). After being stirred at 0° C. for 30 min, the resulting solution and TEA (0.318 mL, 2.257 mmol) were added dropwise to a solution of the Intermediate 1 (513 mg, 1.129 mmol) in DCM (3 mL) while keeping the temperature below 5° C. The reaction mixture was stirred at rt for 2 h, quenched by addition of brine. Aqueous workup and purification by CombiFlash (eluent: 5% methanol in DCM) gave the product as a yellow oil. $^1$H-NMR (400 MHz, CDCl$_3$): δ 1.33-1.49 (m, 18H), 1.72-1.95 (m, 3H), 2.42 (br. s., 1H), 3.02-3.33 (m, 4H), 3.48-3.60 (m, 1H), 3.69-3.98 (m, 4H), 4.25 (br. s., 1H), 4.55-4.95 (m, 3H), 7.41-7.62 (m, 1H), 7.71 (s, 1H), 8.72 (s, 1H); LC/MS: $C_{27}H_{38}F_3N_5O_7S$: m/z 634.2 (M+H).

Step B. (3aR,5R,6aR)-5-Amino-3a-(3-(trifluoromethyl)-5,6,7,8-tetrahydro-1,6-naphthyridine-6-carbonyl)hexahydrocyclopenta[c]pyrrole-2(1H)-sulfonamide The title compound was prepared analogously to Step B in Example 13 as a TFA salt. LC/MS: $C_{17}H_{22}F_3N_5O_3S$: m/z 434.5 (M+H).

Step C. (3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrole-2(1H)-sulfonamide The title compound was prepared analogously to Step C in Example 13 as a yellow gel. $^1$H-NMR (400 MHz, CDCl$_3$): δ 1.54-1.91 (m, 4H), 2.32 (d, J=6.6 Hz, 1H), 2.73 (br. s., 1H), 3.04-3.18 (m, 3H), 3.22-3.45 (m, 8H), 3.47-3.60 (m, 2H), 3.72-3.99 (m, 3H), 4.06 (ddd, J=15.9, 7.4, 3.5 Hz, 1H), 4.78 (br. s., 2H), 5.30 (d, J=10.4 Hz, 2H), 5.59-5.88 (m, 3H), 7.72 (s, 1H), 8.71 (br. s., 1H); LC/MS: $C_{23}H_{32}F_3N_5O_5S$: m/z 548.0 (M+H).

An alternative way to make Example 32:

A mixture of Example 1 (42 mg, 0.0896 mmol) and sulfamide (15 mg, 0.155 mmol) in DME (1 mL) in a sealed tube was heated at 90° C. overnight. After condensation, the residue was purified by CombiFlash (eluent: 5% 7N NH$_3$ in methanol in DCM) to give the product as a yellow oil. LC/MS: $C_{23}H_{32}F_3N_5O_5S$: m/z 548.2 (M+H).

Example 33

(3aR,5R,6aR)-N-Benzyl-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-sulfonamide

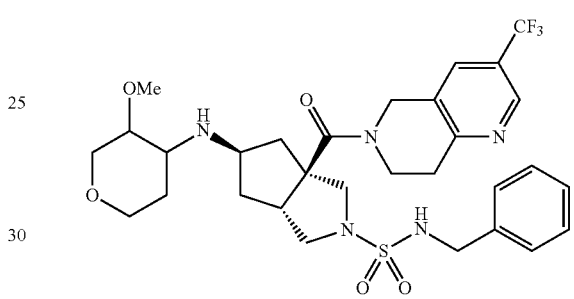

Step A. tert-Butyl benzyl(((3aR,5R,6aR)-5-((tert-butoxycarbonyl)amino)-3a-(3-(trifluoromethyl)-5,6,7,8-tetrahydro-1,6-naphthyridine-6-carbonyl)hexahydrocyclopenta-[c]pyrrol-2(1H)-yl)sulfonyl)carbamate To a cool (0° C.) solution of 34A (90 mg, 0.142 mol), TPP (37 mg, 0.141 mmol) and benzyl alcohol (15.1 mg, 0.14 mmol) in THF (3 mL) under Ar was added dropwise a solution of DIAD (29 mg, 0.143 mmol) in THF (0.5 mL). After being stirred at rt overnight, the mixture was condensed and dissolved in DMSO and purified by HPLC to give the product as a clear oil.

Step B. (3aR,5R,6aR)-5-Amino-N-benzyl-3a-(3-(trifluoromethyl)-5,6,7,8-tetrahydro-1,6-naphthyridine-6-carbonyl)hexahydrocyclopenta[c]pyrrole-2(1H)-sulfonamide The title compound was prepared analogously to Step B in Example 13 as a TFA salt. LC/MS: $C_{24}H_{28}F_3N_5O_3S$: m/z 524 (M+H).

Step C. (3aR,5R,6aR)-N-Benzyl-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-sulfonamide The title compound was prepared analogously to Step C in Example 13 as a yellow gel. $^1$H-NMR (400 MHz, CDCl$_3$): δ 1.70-2.19 (m, 5H), 2.65 (s, 1H), 2.97-3.62 (m, 15H), 3.64-4.03 (m, 5H), 4.19 (br. s., 3H), 4.74 (br. s., 2H), 7.08-7.38 (m, 5H), 8.05 (br. s., 1H), 8.73 (br. s., 1H); LC/MS: $C_{30}H_{38}F_3N_5O_5S$: m/z 638 (M+H).

Example 34

(3aR,5R,6aR)-Methyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxylate

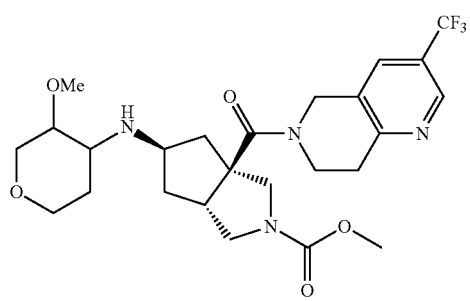 [SMILES: COC(=O)N1C[C@@H]2C[C@@H](NC3CCOCC3OC)C[C@]2(C(=O)N2CCc3ncc(C(F)(F)F)cc3C2)C1]

Step A. (3aR,5R,6aR)-Methyl 5-((tert-butoxycarbonyl)amino)-3a-(3-(trifluoromethyl)-5,6,7,8-tetrahydro-1,6-naphthyridine-6-carbonyl)hexahydrocyclopenta[c]pyrrole-2(1H)-carboxylate To a cool (0° C.) solution of Intermediate 1 (0.11 g, 0.242 mol), TEA (0.132, 0.944 mmol) in DCM (3 mL) under Ar was added methyl chloroformate (0.0564 mL, 0.726 mmol) dropwise. The mixture was then stirred at 0° C. for 30 min and rt overnight. The reaction was quenched by addition of saturated $NaHCO_3$, separated, extracted with DCM, and dried over $Na_2SO_4$. Purification by CombiFlash (eluent: EtOAc) gave the product as a white foam. $^1$H-NMR (400 MHz, $CDCl_3$): δ 1.32-1.46 (m, 9H), 1.73-2.03 (m, 3H), 2.31-2.52 (m, 1H), 2.93-3.36 (m, 3H), 3.55-3.88 (m, 9H), 4.24 (d, J=4.5 Hz, 1H), 4.48-5.01 (m, 3H), 7.71 (br. s., 1H), 8.72 (br. s., 1H); LC/MS: $C_{24}H_{31}F_3N_4O_5$: m/z 513.5 (M+H).

Step B. (3aR,5R,6aR)-Methyl 5-(methylamino)-3a-(3-(trifluoromethyl)-5,6,7,8-tetrahydro-1,6-naphthyridine-6-carbonyl)hexahydrocyclopenta[c]pyrrole-2(1H)-carboxylate The title compound was prepared analogously to Step B in Example 13 as a TFA salt. LC/MS: $C_{19}H_{23}F_3N_4O_2$: m/z 413.5 (M+H).

Step C. (3aR,5R,6aR)-Methyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxylate The title compound was prepared analogously to Step C in Example 13 as a yellow gel. $^1$H-NMR (400 MHz, $CDCl_3$): δ 1.54-1.92 (m, 5H), 2.21-2.38 (m, 2H), 2.53-2.65 (m, 3H), 2.66-2.78 (m, 1H), 3.09-4.28 (m, 18H), 4.65-4.95 (m, 2H), 7.70 (br. s., 1H), 8.72 (br. s., 1H); LC/MS: $C_{25}H_{33}F_3N_4O_5$: m/z 527.2 (M+H).

The following title compounds were synthesized using a similar procedure:

Example 35

(3aR,5R,6aR)-Propyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydro-cyclopenta[c]pyrrole-2(1H)-carboxylate

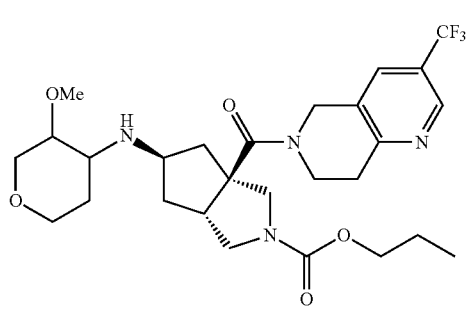 [SMILES: CCCOC(=O)N1C[C@@H]2C[C@@H](NC3CCOCC3OC)C[C@]2(C(=O)N2CCc3ncc(C(F)(F)F)cc3C2)C1]

Prepared analogously to Example 34. $^1$H-NMR (400 MHz, $CDCl_3$): δ 0.93 (d, J=6.3 Hz, 3H), 1.53-2.44 (m, 6H), 2.75 (br. s., 1H), 3.05-4.17 (m, 23H), 4.61-5.06 (m, 2H), 7.71 (br. s., 1H), 8.72 (br. s., 1H); LC/MS: $C_{27}H_{37}F_3N_4O_5$: m/z 555.2 (M+H).

Example 36

(3aR,5R,6aR)-Neopentyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydro-cyclopenta[c]pyrrole-2(1H)-carboxylate

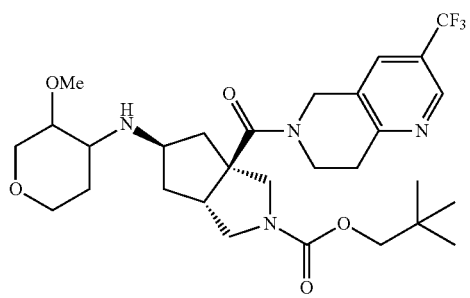 [SMILES: COC1COCCC1N[C@@H]1C[C@H]2CN(C(=O)OCC(C)(C)C)C[C@@]2(C(=O)N2CCc3ncc(C(F)(F)F)cc3C2)C1]

Prepared analogously to Example 34. $^1$H-NMR (400 MHz, $CDCl_3$): δ 0.93 (br. s., 9H), 1.53-2.04 (m, 3H), 2.32 (br. s., 1H), 2.74 (br. s., 1H), 3.05-4.14 (m, 23H), 4.60-5.03 (m, 2H), 7.69 (br. s., 1H), 8.71 (br. s., 1H); LC/MS: $C_{29}H_{41}F_3N_4O_5$: m/z 583.3 (M+H).

Example 37

(3aR,5R,6aR)-Phenyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydro-cyclopenta[c]pyrrole-2(1H)-carboxylate

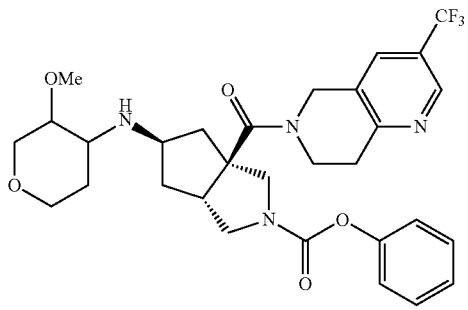 [SMILES: COC1COCCC1N[C@@H]1C[C@H]2CN(C(=O)Oc3ccccc3)C[C@@]2(C(=O)N2CCc3ncc(C(F)(F)F)cc3C2)C1]

Prepared analogously to Example 34. $^1$H-NMR (400 MHz, CDCl$_3$): δ 1.59-2.12 (m, 3H), 2.38 (br. s., 1H), 2.76 (br. s., 1H), 3.06-4.19 (m, 21H), 4.61-5.06 (m, 2H), 7.04-7.23 (m, 3H), 7.30-7.43 (m, 2H), 7.71 (br. s., 1H), 8.72 (br. s., 1H); LC/MS: C$_{30}$H$_{35}$F$_3$N$_4$O$_5$: m/z 589.3 (M+H).

Example 38

(3aR,5R,6aR)-Allyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxylate

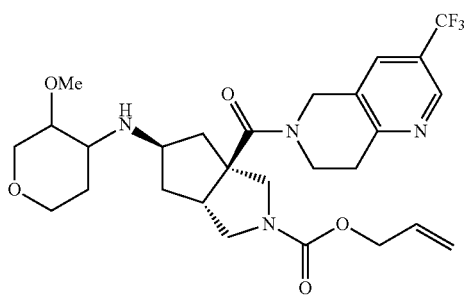 [SMILES: C=CCOC(=O)N1C[C@@H]2C[C@@H](NC3CCOCC3OC)C[C@]2(C(=O)N2CCc3ncc(C(F)(F)F)cc3C2)C1]

Prepared analogously to Example 34. $^1$H-NMR (400 MHz, CDCl$_3$): δ 1.54-1.93 (m, 3H), 2.31 (br. s., 1H), 2.73 (br. s., 1H), 3.06-4.12 (m, 21H), 4.58 (d, J=5.6 Hz, 2H), 4.65-5.00 (m, 2H), 5.16-5.36 (m, 2H), 5.83-6.00 (m, 1H), 7.70 (br. s., 1H), 8.72 (s, 1H); LC/MS: C$_{27}$H$_{35}$F$_3$N$_4$O$_5$: m/z 553.3 (M+H).

Example 39

(3aR,5R,6aR)-2-Morpholinoethyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxylate

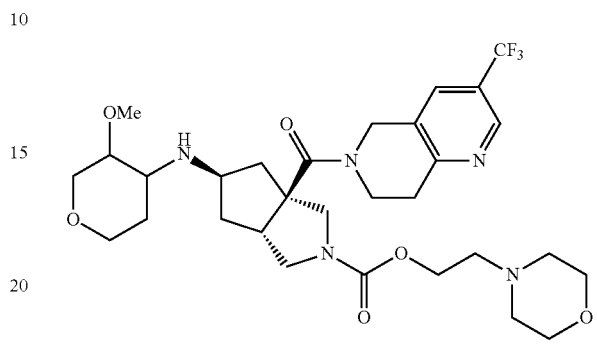

A. (3aR,5R,6aR)-2-Morpholinoethyl 5-((3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxylate To a mixture of 4-(2-hydroxyethyl)morpholine (0.0299 mL, 0.242 mmol), N,N'-disuccinimidyl carbonate (62.0 mg, 0.242 mmol) in acetonitrile (1.2 mL) and DCM (1.2 mL) was added DMAP (9.462 mg, 0.0774 mmol). The mixture was stirred at rt for 2 h and treated with intermediate 1 (110 mg, 0.242 mmol) and DMF (0.2 mL). After being stirred at rt overnight, the reaction mixture was concentrated and partitioned between aqueous NaHCO$_3$ solution and DCM, separated, and dried over Na$_2$SO$_4$. Purification by CombiFlash (eluent: 8% methanol in DCM) gave the product as a colorless gel. $^1$H-NMR (400 MHz, CDCl$_3$): δ 1.20-1.33 (m, 1H), 1.86 (br. s., 3H), 2.45 (br. s., 1H), 2.60-3.05 (m, 16H), 3.08-3.34 (m, 3H), 3.56-3.89 (m, 9H), 4.13-4.41 (m, 3H), 4.70-5.01 (m, 2H), 8.01 (s, 1H), 8.71 (br. s., 1H); LC/MS: C$_{29}$H$_{40}$F$_3$N$_5$O$_6$: m/z 612.3 (M+H).

B. (3aR,5R,6aR)-2-Morpholinoethyl 5-amino-3a-(3-(trifluoromethyl)-5,6,7,8-tetrahydro-1,6-naphthyridine-6-carbonyl)hexahydrocyclopenta[c]pyrrole-2(1H)-carboxylate The title compound was prepared analogously to Step B in Example 13 as a TFA salt. LC/MS: C$_{24}$H$_{32}$F$_3$N$_5$O$_4$: m/z 512.5 (M+H).

C. (3aR,5R,6aR)-2-Morpholinoethyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxylate The title compound was prepared analogously to Step C in Example 13 as a yellow gel. $^1$H-NMR (400 MHz, CDCl$_3$): δ 1.51-1.97 (m, 5H) 2.21-2.79 (m, 6H) 3.06-4.30 (m, 27H) 4.60-5.03 (m, 2H) 7.70 (br. s., 1H) 8.72 (br. s., 1H); LC/MS: C$_{30}$H$_{42}$F$_3$N$_5$O$_6$: m/z 626.2 (M+H).

The following title compounds were synthesized using a similar procedure:

Example 40

(3aR,5R,6aR)-2-Morpholinoethyl 5-(((3S*,4S*)-3-methoxytetrahydro-2H-pyran-4-yl)amino)-3a-(7-(trifluoromethyl)-1,2,3,4-tetrahydroisoquinoline-2-carbonyl)hexahydro-cyclopenta[c]pyrrole-2(1H)-carboxylate

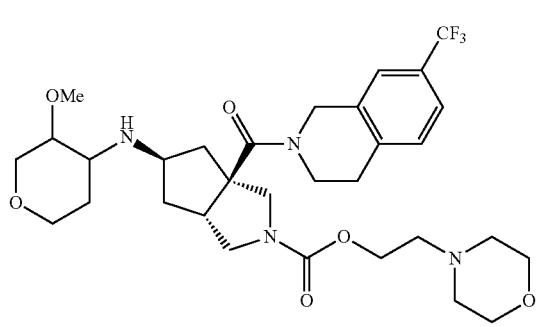 [SMILES: COC1COCCC1N[C@@H]1C[C@H]2CN(C(=O)OCCN3CCOCC3)C[C@@]2(C(=O)N2CCc3ccc(C(F)(F)F)cc3C2)C1]

Prepared analogously to Example 39. $^1$H-NMR (400 MHz, CDCl$_3$): δ 1.50-2.01 (m, 5H), 2.24-4.29 (m, 33H), 4.68-4.89 (m, 2H), 7.29 (br. s., 1H), 7.40 (br. s., 2H); LC/MS: C$_{31}$H$_{43}$F$_3$N$_4$O$_6$: m/z 625.3 (M+H).

Example 41

(3aR,5R,6aR)-2-(Diethylamino)ethyl 5-(((3S*,4S*)-3-methoxytetrahydro-2H-pyran-4-yl)amino)-3a-(7-(trifluoromethyl)-1,2,3,4-tetrahydroisoquinoline-2-carbonyl)hexahydrocyclopenta[c]pyrrole-2(1H)-carboxylate

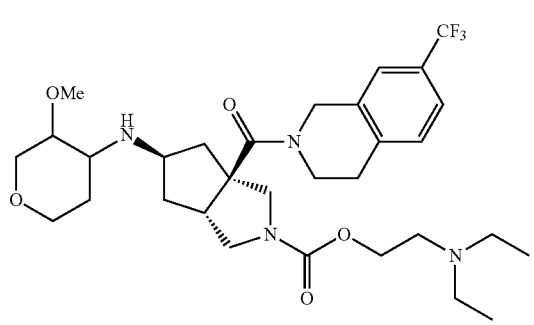 [SMILES: CCN(CC)CCOC(=O)N1C[C@@H]2C[C@@H](NC3CCOCC3OC)C[C@]2(C(=O)N2CCc3ccc(C(F)(F)F)cc3C2)C1]

Prepared analogously to Example 39. $^1$H-NMR (400 MHz, CDCl$_3$): δ 1.05 (t, J=6.7 Hz, 6H), 1.55-1.91 (m, 6H), 2.29 (br. s., 1H), 2.54-2.80 (m, 7H), 2.95 (br. s., 2H), 3.19-3.50 (m, 8H), 3.57-3.81 (m, 6H), 3.86-3.97 (m, 1H), 4.00-4.23 (m, 3H), 4.71 (br. s., 2H), 7.26 (br. s., 1H), 7.33-7.53 (m, 2H); LC/MS: C$_{31}$H$_{45}$F$_3$N$_4$O$_5$: m/z 611.2 (M+H).

Example 42

(3aR,5R,6aR)-2-(Tetrahydro-2H-pyran-4-yl)ethyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxylate

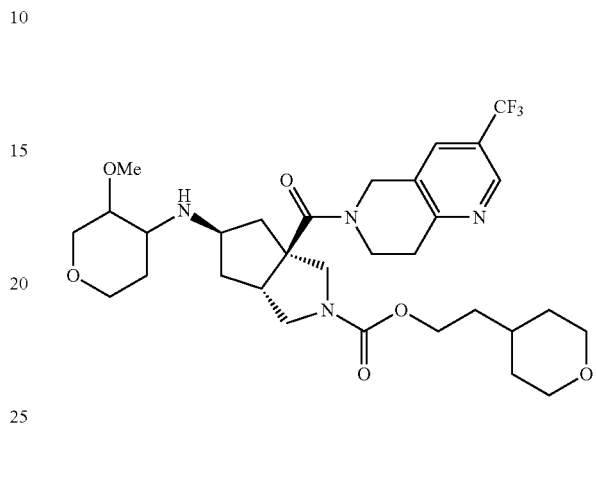

Prepared analogously to Example 39. $^1$H-NMR (400 MHz, CDCl$_3$): δ 1.14-1.33 (m, 2H), 1.45-1.89 (m, 10H), 2.25 (br. s., 1H), 2.67 (br. s., 1H), 2.98-4.13 (m, 25H), 4.51-5.01 (m, 2H), 7.63 (br. s., 1H), 8.65 (br. s., 1H); LC/MS: C$_{31}$H$_{43}$F$_3$N$_4$O$_6$: m/z 625.3 (M+H).

Example 43

(3aR,5R,6aR)-2-(Tetrahydro-2H-pyran-4-yl)ethyl 5-(((3S,4S)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxylate

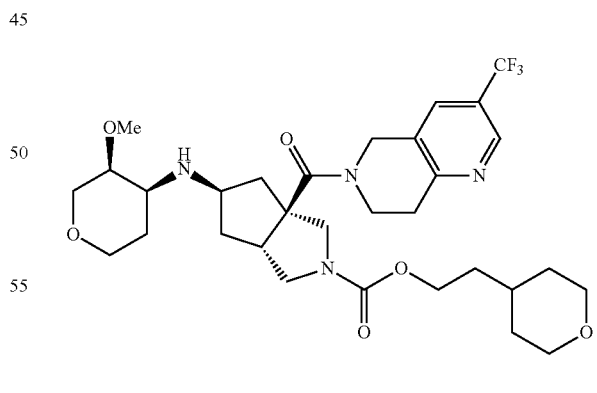

Isolated by chiral HPLC (Kromasil K40813, 10-Amycoat, 30×250 mm; eluent: 50% isopropyl alcohol in heptanes) from the product of Example 39. The first fraction. $^1$H-NMR (400 MHz, CDCl$_3$): δ 1.13-1.40 (m, 2H), 1.52-1.98 (m, 10H), 2.33 (br. s., 1H), 2.72 (br. s., 1H), 3.05-4.22 (m, 25H), 4.60-5.04 (m, 2H), 7.73 (br. s., 1H), 8.72 (br. s., 1H).

Example 44

(3aR,5R,6aR)-2-(Tetrahydro-2H-pyran-4-yl)ethyl 5-(((3R,4R)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxylate

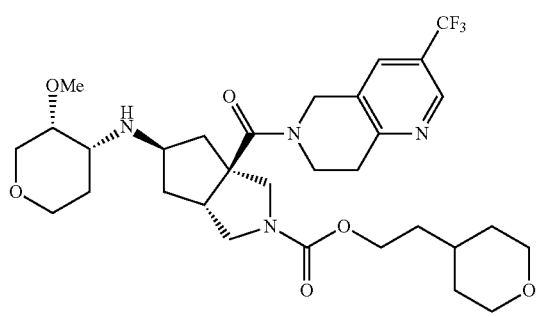 [SMILES: CO[C@H]1COCC[C@H]1N[C@@H]1C[C@H]2CN(C(=O)OCCC3CCOCC3)C[C@@]2(C(=O)N2CCc3ncc(C(F)(F)F)cc3C2)C1]

Isolated by chiral HPLC (Kromasil K40813, 10-Amycoat, 30×250 mm; eluent: 50% isopropyl alcohol in heptanes) from the product of Example 39. The second fraction. $^1$H-NMR (400 MHz, CDCl$_3$): δ 1.12-1.40 (m, 2H), 1.45-1.98 (m, 10H), 2.32 (br. s., 1H), 2.74 (br. s., 1H), 3.01-4.21 (m, 25H), 4.59-5.04 (m, 2H), 7.70 (br. s., 1H), 8.70 (br. s., 1H).

Example 45

(3aR,5R,6aR)-2-(Pyrrolidin-1-yl)ethyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxyl

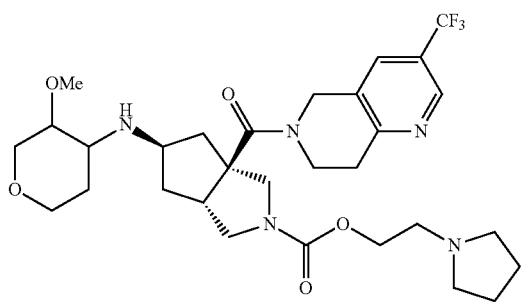 [SMILES: COC1COCCC1N[C@@H]1C[C@H]2CN(C(=O)OCCN3CCCC3)C[C@@]2(C(=O)N2CCc3ncc(C(F)(F)F)cc3C2)C1]

Prepared analogously to Example 39. $^1$H-NMR (400 MHz, CDCl$_3$): δ 1.53-1.96 (m, 6H), 2.12-2.85 (m, 10H), 2.92-4.32 (m, 22H), 4.59-5.05 (m, 2H), 7.71 (d, J=7.8 Hz, 1H), 8.72 (br. s., 1H); LC/MS: C$_{30}$H$_{42}$F$_3$N$_5$O$_5$: m/z 610.3 (M+H).

Example 46

(3aR,5R,6aR)-2-(Pyrrolidin-1-yl)ethyl 5-(((3S*,4S*)-3-methoxytetrahydro-2H-pyran-4-yl)amino)-3a-(7-(trifluoromethyl)-1,2,3,4-tetrahydroisoquinoline-2-carbonyl)hexahydrocyclopenta[c]pyrrole-2(1H)-carboxylate

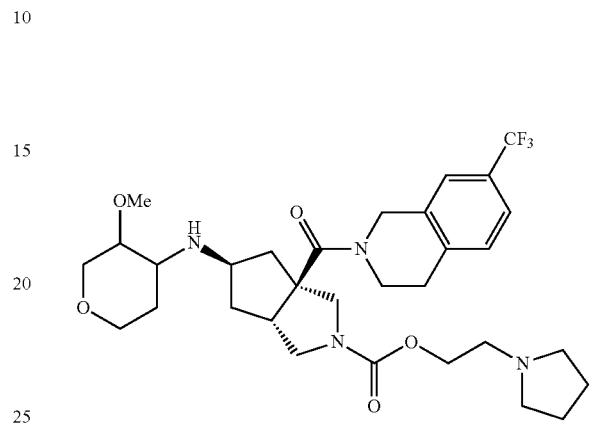

Prepared analogously to Example 39. $^1$H-NMR (400 MHz, CDCl$_3$): δ 1.41-1.86 (m, 9H), 2.05-2.36 (m, 1H), 2.39-2.98 (m, 9H), 3.05-4.04 (m, 17H), 4.07-4.25 (m, 2H), 4.64 (br. s., 2H), 7.14-7.23 (m, 1H), 7.24-7.44 (m, 2H); LC/MS: C$_{31}$H$_{43}$F$_3$N$_4$O$_5$: m/z 609.2 (M+H).

Example 47

(3aR,5R,6aR)-(Tetrahydro-2H-pyran-4-yl)methyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxylate

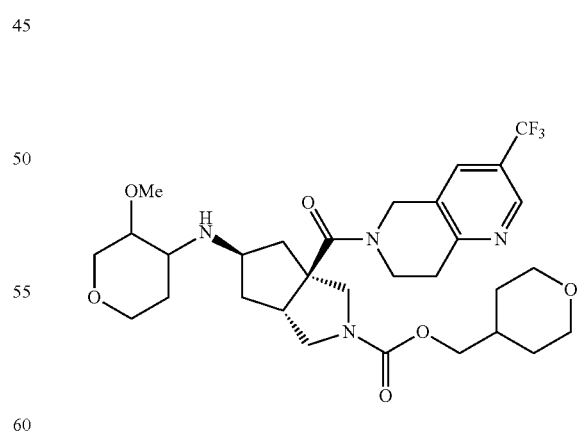

Prepared analogously to Example 39. $^1$H-NMR (400 MHz, CDCl$_3$): δ 1.21-1.46 (m, 2H), 1.50-2.17 (m, 5H), 2.32 (br. s., 1H), 2.74 (br. s., 1H), 3.03-4.14 (m, 28H), 4.60-5.06 (m, 2H), 7.71 (br. s., 1H), 8.72 (br. s., 1H); LC/MS: C$_{30}$H$_{41}$F$_3$N$_4$O$_6$: m/z 611.2 (M+H).

Example 48

(3aR,5R,6aR)-2-Methoxyethyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxylate

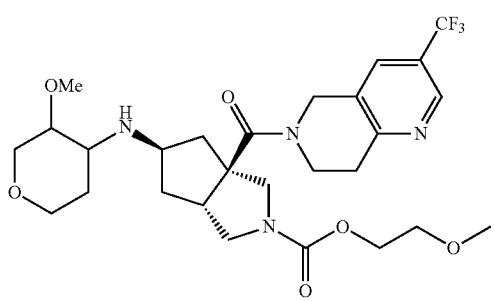 [SMILES: COCCOC(=O)N1C[C@@H]2C[C@@H](NC3CCOCC3OC)C[C@]2(C(=O)N2CCc3ncc(C(F)(F)F)cc3C2)C1]

Prepared analogously to Example 39. $^1$H-NMR (400 MHz, CDCl$_3$): δ 1.50-1.92 (m, 5H), 2.32 (br. s., 1H), 2.73 (br. s., 1H), 2.92-4.15 (m, 24H), 4.23 (br. s., 2H), 4.72 (m, 2H), 7.71 (br. s., 1H), 8.72 (br. s., 1H); LC/MS: $C_{27}H_{37}F_3N_4O_6$: m/z 571.3 (M+H).

Example 49

(3aR,5R,6aR)-2-Methoxyethyl 5-(((3S*,4S*)-3-methoxytetrahydro-2H-pyran-4-yl)amino)-3a-(7-(trifluoromethyl)-1,2,3,4-tetrahydroisoquinoline-2-carbonyl)hexahydrocyclopenta[c]pyrrole-2(1H)-carboxylate

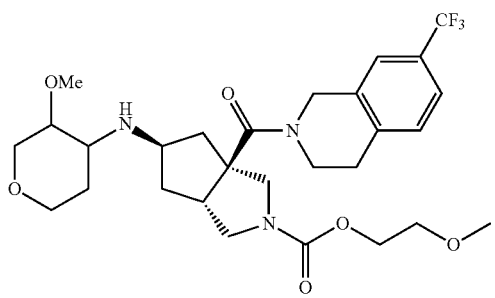 [SMILES: COCCOC(=O)N1C[C@@H]2C[C@@H](NC3CCOCC3OC)C[C@]2(C(=O)N2CCc3ccc(C(F)(F)F)cc3C2)C1]

Prepared analogously to Example 39. $^1$H-NMR (400 MHz, CDCl$_3$): δ 1.48-1.97 (m, 6H), 2.30 (br. s., 1H), 2.72 (br. s., 1H), 2.96 (br. s., 2H), 3.19-3.53 (m, 11H), 3.53-3.82 (m, 8H), 3.85-3.98 (m, 1H), 4.00-4.10 (m, 1H), 4.16-4.29 (m, 2H), 4.46-4.49 (m, 2H), 7.22-7.31 (m, 1H), 7.33-7.50 (m, 2H); LC/MS: $C_{28}H_{38}F_3N_3O_6$: m/z 571.3 (M+H).

Example 50

(3aR,5R,6aR)-3-Hydroxy-3-methylbutyl 5-(((3S*,4S*)-3-methoxytetrahydro-2H-pyran-4-yl)amino)-3a-(7-(trifluoromethoxy)-1,2,3,4-tetrahydroisoquinoline-2-carbonyl)hexahydrocyclopenta[c]pyrrole-2(1H)-carboxylate

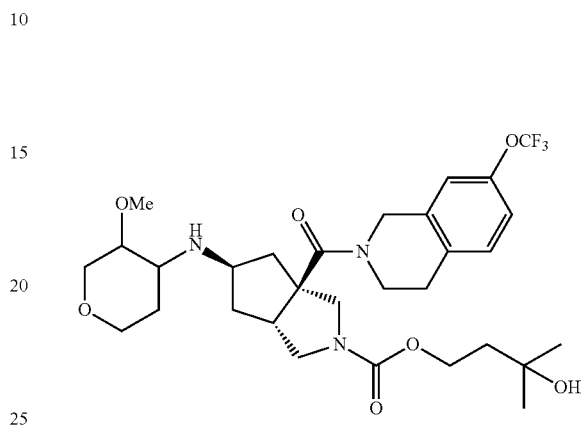

Prepared analogously to Example 39. $^1$H-NMR (400 MHz, CDCl$_3$): δ 1.26 (s, 6H), 1.53-2.05 (m, 9H), 2.28 (br. s., 1H), 2.72 (br. s., 1H), 2.89 (d, J=4.0 Hz, 2H), 3.16-3.52 (m, 8H), 3.51-3.83 (m, 6H), 3.83-3.98 (m, 1H), 3.99-4.11 (m, 1H), 4.25 (t, J=6.6 Hz, 2H), 4.66 (br. s., 2H), 6.91-7.11 (m, 2H), 7.17 (d, J=8.1 Hz, 1H); LC/MS: $C_{30}H_{42}F_3N_3O_7$: m/z 614.2 (M+H).

Example 51

(3aR,5R,6aR)-3,3,3-Trifluoropropyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclo-penta[c]pyrrole-2(1H)-carboxylate

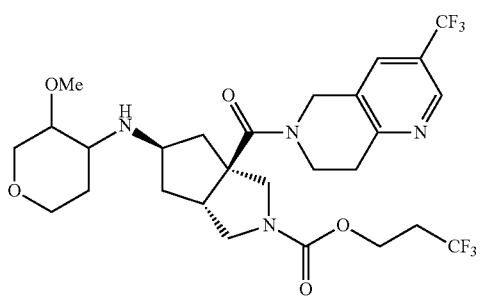 [SMILES: COC1COCCC1N[C@@H]1C[C@H]2CN(C(=O)OCCC(F)(F)F)C[C@@]2(C(=O)N2CCc3ncc(C(F)(F)F)cc3C2)C1]

Prepared analogously to Example 39. $^1$H-NMR (400 MHz, CDCl$_3$): δ 1.53-2.12 (m, 5H), 2.25-2.79 (m, 1H), 2.93-4.36

(m, 24H), 4.63-5.03 (m, 2H), 7.71 (br. s., 1H), 8.72 (br. s., 1H); LC/MS: $C_{27}H_{34}F_6N_4O_5$: m/z 609.2 (M+H).

Example 52

(3aR,5R,6aR)-2-Cyanoethyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxylate

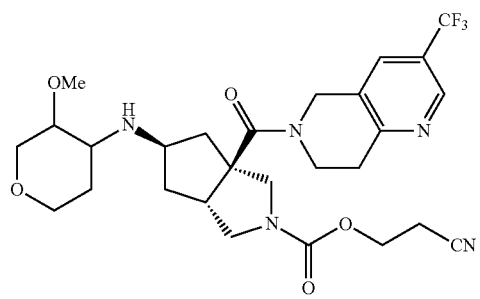 [SMILES: COC1COCCC1N[C@@H]1C[C@H]2CN(C(=O)OCCC#N)C[C@@]2(C(=O)N2CCc3ncc(C(F)(F)F)cc3C2)C1]

Prepared analogously to Example 39. $^1$H-NMR (400 MHz, CDCl$_3$): δ 1.55-1.90 (m, 5H), 2.33 (br. s., 1H), 2.62-2.80 (m, 3H), 3.07-3.57 (m, 11H), 3.60-4.12 (m, 8H), 4.18-4.37 (m, 2H), 4.62-5.02 (m, 2H), 7.71 (d, J=6.8 Hz, 1H), 8.72 (br. s., 1H); LC/MS: $C_{27}H_{34}F_3N_5O_5$: m/z 566.2 (M+H).

Example 53

(3aR,5R,6aR)-Prop-2-yn-1-yl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxylate

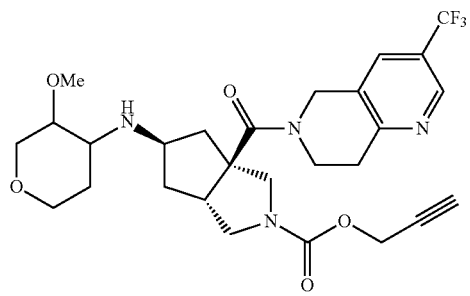 [SMILES: C#CCOC(=O)N1C[C@@H]2C[C@@H](NC3CCOCC3OC)C[C@]2(C(=O)N2CCc3ncc(C(F)(F)F)cc3C2)C1]

Prepared analogously to Example 39. $^1$H-NMR (400 MHz, CDCl$_3$): δ 1.56-2.03 (m, 3H), 2.23-2.80 (m, 3H), 3.07-4.29 (m, 21H), 4.65-4.95 (m, 4H), 7.71 (br. s., 1H), 8.72 (br. s., 1H); LC/MS: $C_{27}H_{33}F_3N_4O_5$: m/z 551.2 (M+H).

Example 54

(3aR,5R,6aR)-2-(Dimethylamino)ethyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)-hexahydrocyclopenta[c]pyrrole-2(1H)-carboxylate

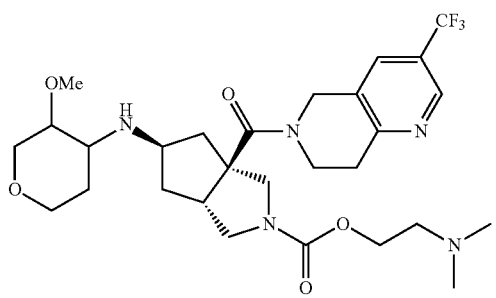 [SMILES: COC1COCCC1N[C@@H]1C[C@H]2CN(C(=O)OCCN(C)C)C[C@@]2(C(=O)N2CCc3ncc(C(F)(F)F)cc3C2)C1]

Prepared analogously to Example 39. $^1$H-NMR (400 MHz, CDCl$_3$): δ 1.55-1.98 (m, 5H), 2.25-2.36 (m, 7H), 2.51-2.81 (m, 3H), 3.05-3.55 (m, 11H), 3.59-4.28 (m, 10H), 4.60-5.00 (m, 2H), 7.62-7.77 (m, 1H), 8.72 (s, 1H); LC/MS: $C_{28}H_{40}F_3N_5O_5$: m/z 584.2 (M+H).

Example 55

(3aR,5R,6aR)-2-Acetamidoethyl 5-(((3S*,4S*)-3-methoxytetrahydro-2H-pyran-4-yl)amino)-3a-(7-(trifluoromethyl)-1,2,3,4-tetrahydroisoquinoline-2-carbonyl)hexahydrocyclopenta[c]pyrrole-2(1H)-carboxylate

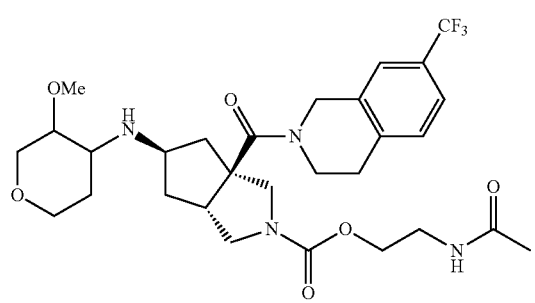 [SMILES: COC1COCCC1N[C@@H]1C[C@H]2CN(C(=O)OCCNC(C)=O)C[C@@]2(C(=O)N2CCc3ccc(C(F)(F)F)cc3C2)C1]

Prepared analogously to Example 39. $^1$H-NMR (400 MHz, CDCl$_3$): δ 1.45-1.91 (m, 6H), 1.98 (br. s., 3H), 2.31 (br. s., 1H), 2.72 (br. s., 1H), 2.97 (br. s., 2H), 3.18-4.28 (m, 20H), 4.70 (d, J=15.7 Hz, 2H), 6.08-6.46 (m, 1H), 7.30 (d, J=6.6 Hz, 1H), 7.43 (d, J=10.6 Hz, 2H); LC/MS: $C_{29}H_{39}F_3N_4O_6$: m/z 597.3 (M+H).

Example 56

(3aR,5R,6aR)-Benzyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxylate

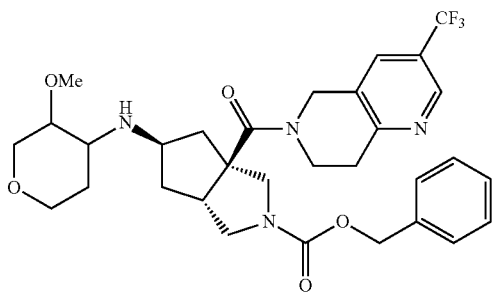

Prepared analogously to Example 39. $^1$H-NMR (400 MHz, CDCl$_3$): δ 1.51-2.44 (m, 4H), 2.88-4.23 (m, 22H), 4.73 (br. s., 2H), 5.08-5.33 (m, 2H), 7.35 (br. s., 5H), 7.69 (br. s., 1H), 8.72 (br. s., 1H); LC/MS: $C_{31}H_{37}F_3N_5O_5$: m/z 603.3 (M+H).

Example 57

(3aR,5R,6aR)-Benzyl 5-(1-((3S*,4S*)-3-methoxytetrahydro-2H-pyran-4-yl)-3-methylthioureido)-3a-(3-(trifluoromethyl)-5,6,7,8-tetrahydro-1,6-naphthyridine-6-carbonyl)hexahydrocyclopenta[c]pyrrole-2(1H)-carboxylate

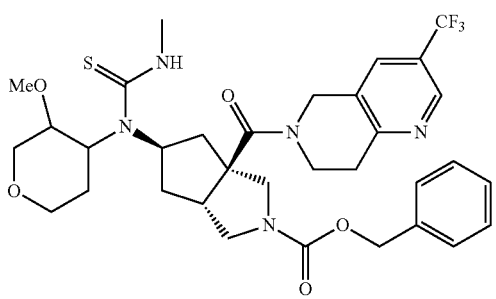 [SMILES: CNC(=S)N(C1CCOCC1OC)[C@@H]1C[C@H]2CN(C(=O)OCc3ccccc3)C[C@@]2(C(=O)N2CCc3ncc(C(F)(F)F)cc3C2)C1]

Prepared analogously to Example 28 from the product of Example 56. $^1$H-NMR (400 MHz, CDCl$_3$): δ 1.26 (br. s., 1H), 1.57-4.28 (m, 27H), 4.79 (br. s., 2H), 5.13 (br. s., 2H), 5.81 (br. s., 1H), 7.36 (br. s., 5H), 7.75-7.76 (br. s., 1H), 8.71 (br. s., 1H); LC/MS: $C_{33}H_{40}F_3N_5O_5S$: m/z 676.2 (M+H).

Example 58

(3aR,5R,6aR)-4-Cyanobenzyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrole-2(1H)-carboxylate

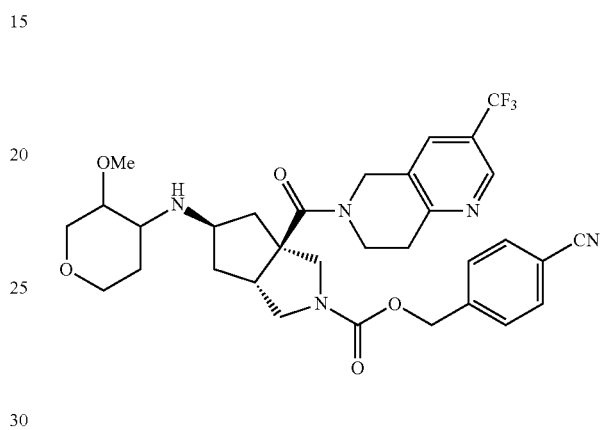

Prepared analogously to Example 39. $^1$H-NMR (400 MHz, CDCl$_3$): δ 1.55-1.91 (m, 2H), 2.33 (br. s., 1H), 2.73 (br. s., 1H), 3.08-4.28 (m, 22H), 4.60-5.03 (m, 2H), 5.08-5.25 (m, 2H), 7.38-7.51 (m, 2H), 7.58-7.75 (m, 3H), 8.72 (br. s., 1H); LC/MS: $C_{32}H_{36}F_3N_5O_5$: m/z 628.3 (M+H).

Example 59

(3aR,5R,6aR)-3-Cyanobenzyl 5-((3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrole-2(1H)-carboxylate

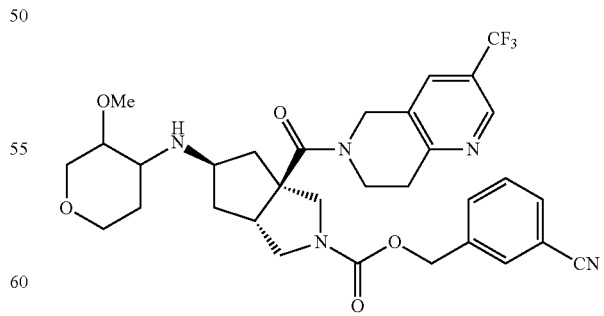

Prepared analogously to Example 39. $^1$H-NMR (400 MHz, CDCl$_3$): δ 1.53-1.99 (m, 2H), 2.24-2.43 (m, 1H), 2.56-2.81 (m, 1H), 3.12-4.28 (m, 22H), 4.67-4.96 (m, 2H), 5.14 (br. s., 2H), 7.49-7.75 (m, 5H), 8.71 (br. s., 1H); LC/MS: $C_{32}H_{36}F_3N_5O_5$: m/z 628.3 (M+H).

Example 60

(3aR,5R,6aR)-3-Methoxybenzyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrole-2(1H)-carboxylate

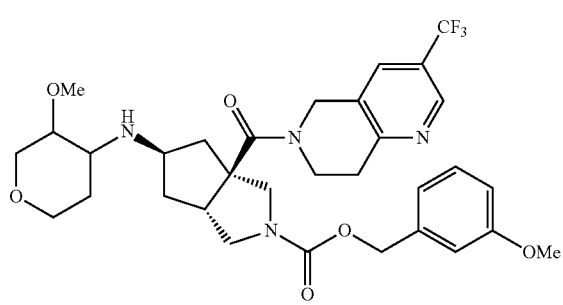 [SMILES: COc1cccc(COC(=O)N2C[C@@H]3C[C@@H](NC4CCOCC4OC)C[C@]3(C(=O)N3CCc4ncc(C(F)(F)F)cc4C3)C2)c1]

Prepared analogously to Example 39. $^1$H-NMR (400 MHz, CDCl$_3$): δ 1.55-2.41 (m, 3H), 2.64-2.79 (m, 1H), 3.07-4.13 (m, 25H), 4.63-4.96 (m, 2H), 5.09 (d, J=4.0 Hz, 2H), 6.80-6.97 (m, 3H), 7.24-7.32 (m, 1H), 7.69 (br. s., 1H), 8.71 (s, 1H); LC/MS: $C_{32}H_{39}F_3N_4O_5$: m/z 633.3 (M+H).

Example 61

(3aR,5R,6aR)-4-Methoxybenzyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrole-2(1H)-carboxylate

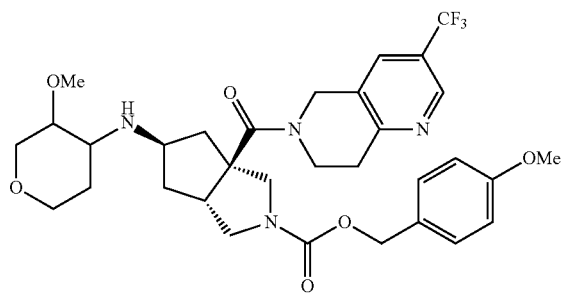 [SMILES: COc1ccc(COC(=O)N2C[C@@H]3C[C@@H](NC4CCOCC4OC)C[C@]3(C(=O)N3CCc4ncc(C(F)(F)F)cc4C3)C2)cc1]

To a mixture of 4-methoxybenzyl alcohol (7.05 mg, 0.05 mmol), N,N'-disuccinimidyl carbonate (12.8 mg, 0.05 mmol) in acetonitrile (0.3 mL) and DCM (0.3 mL) was added DMAP (1.955 mg, 0.016 mmol). The mixture was stirred at rt for 2 h and treated with Example 1 (23.43 mg, 0.05 mmol) and DMF (0.05 mL). After being stirred at rt overnight, the reaction mixture was concentrated and partitioned between aqueous NaHCO$_3$ solution and DCM, separated, and dried over Na$_2$SO$_4$. Purification by CombiFlash (eluent: 8% MeOH in DCM) gave the product as a colorless gel. $^1$H-NMR (400 MHz, CDCl$_3$): δ 1.64-1.99 (m, 2H), 2.21 (br. s., 1H), 2.40 (br. s., 1H), 2.94-3.45 (m, 8H), 3.55-4.20 (m, 17H), 4.76 (br. s., 2H), 5.04 (br. s., 2H), 6.88 (d, J=8.1 Hz, 2H), 7.24-7.35 (m, 2H), 7.71 (s, 1H), 8.70 (br. s., 1H); LC/MS: $C_{32}H_{39}F_3N_4O_6$: m/z 633.3 (M+H).

Example 62

(3aR,5R,6aR)-3-Hydroxy-3-methylbutyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)-hexahydrocyclopenta[c]pyrrole-2(1H)-carboxylate

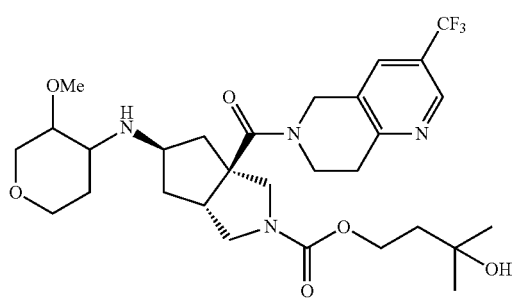 [SMILES: COC1COCCC1N[C@@H]1C[C@H]2CN(C(=O)OCCC(C)(C)O)C[C@@]2(C(=O)N2CCc3ncc(C(F)(F)F)cc3C2)C1]

Prepared analogously to Example 61. $^1$H-NMR (400 MHz, CDCl$_3$): δ 1.26 (s, 6H), 1.55-1.91 (m, 3H), 2.12-2.42 (m, 3H), 2.73 (br. s., 1H), 2.93-4.34 (m, 24H), 4.63-5.03 (m, 2H), 7.71 (br. s., 1H), 8.71 (br. s., 1H); LC/MS: $C_{29}H_{41}F_3N_4O_6$: m/z 599.2 (M+H).

Example 63

(3aR,5R,6aR)-2-Acetamidoethyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carboxylate

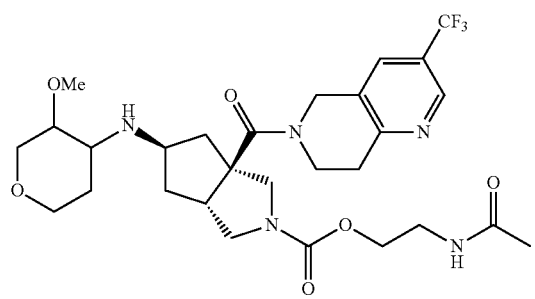 [SMILES: COC1COCCC1N[C@@H]1C[C@H]2CN(C(=O)OCCNC(C)=O)C[C@@]2(C(=O)N2CCc3ncc(C(F)(F)F)cc3C2)C1]

Prepared analogously to Example 61. $^1$H-NMR (400 MHz, CDCl$_3$): δ 1.56-2.04 (m, 7H), 2.33 (br. s., 1H), 2.73 (br. s., 1H), 3.10-4.27 (m, 24H), 4.61-5.04 (m, 2H), 6.13-6.45 (m, 1H), 7.64-7.83 (m, 1H), 8.72 (br. s., 1H); LC/MS: C$_{28}$H$_{38}$F$_3$N$_5$O$_6$: m/z 598.2 (M+H).

Example 64

(3aR,5R,6aR)-Isobutyl 5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydro-cyclopenta[c]pyrrole-2(1H)-carboxylate

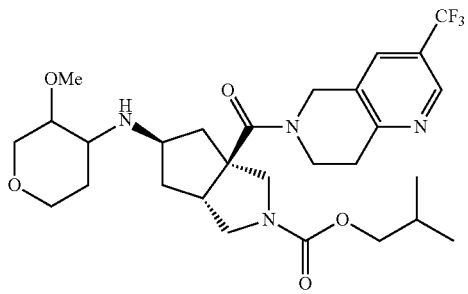

To a solution of Example 1 (0.1 g, 0.213 mmol) and TEA (0.12 mL, 0.854 mmol) in DCM (2.6 mL) at 0° C. was added isobutyl chloroformate (0.086 mL, 0.64 mmol). The mixture was stirred at 0° C. for 30 min and at rt overnight. The reaction was quenched by addition of saturated aqueous NaHCO$_3$ solution, extracted with DCM, dried over Na$_2$SO$_4$. Purification by CombiFlash (eluent: 5% methanol in DCM, then 5% 7N NH$_3$ in methanol in DCM) gave the title compound as a white solid. $^1$H-NMR (400 MHz, CDCl$_3$): δ 0.93 (d, J=6.3 Hz, 6H), 1.57-1.99 (m, 7H), 2.32 (br. s., 1H), 2.74 (br. s., 1H), 3.08-3.56 (m, 10H), 3.56-4.00 (m, 9H), 4.01-4.11 (m, 1H), 4.57-5.07 (m, 2H), 7.70 (br. s., 1H), 8.72 (br. s., 1H); LC/MS: C$_{28}$H$_{39}$F$_3$N$_4$O$_5$: m/z 569.3 (M+H).

Example 65

(E)-1-((3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrol-2(1H)-yl)-3-phenylprop-2-en-1-one

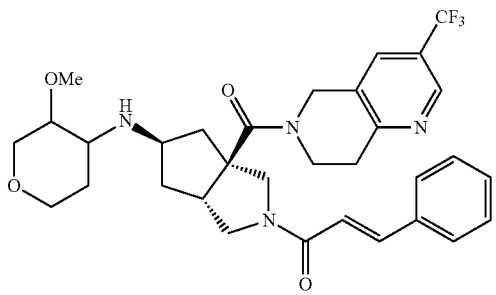 [SMILES: COC1COCCC1N[C@@H]1C[C@H]2CN(C(=O)/C=C/c3ccccc3)C[C@@]2(C(=O)N2CCc3ncc(C(F)(F)F)cc3C2)C1]

Step A. tert-Butyl((3aR,5R,6aR)-2-cinnamoyl-3a-(3-(trifluoromethyl)-5,6,7,8-tetrahydro-1,6-naphthyridine-6-carbonyl)octahydrocyclopenta[c]pyrrol-5-yl)carbamate To a solution of Intermediate 1 (0.11 g, 0.242 mmol) and TEA (0.0538 mL, 0.387 mmol) in DCM (2 mL) at 0° C. was added cinnamoyl chloride (45.26 mg, 0.266 mol). The mixture was stirred at 0° C. for 30 min and at rt for 2 days. The reaction mixture was quenched by addition of brine, extracted with DCM, and dried over Na$_2$SO$_4$. Purification by CombiFlash (eluent: 60% EtOAc in hexanes) gave the product as a yellow gel. $^1$H-NMR (400 MHz, CDCl$_3$): δ 1.32-1.44 (m, 9H), 1.85-1.97 (m, 3H), 2.47 (br. s., 1H), 3.17 (br. s., 2H), 3.55 (dd, J=10.1, 4.0 Hz, 1H), 3.70-4.36 (m, 7H), 4.63-5.05 (m, 3H), 6.68 (d, J=15.7 Hz, 1H), 7.31-7.43 (m, 3H), 7.52 (d, J=4.3 Hz, 2H), 7.63-7.77 (m, 2H), 8.72 (br. s., 1H); LC/MS: C$_{31}$H$_{35}$F$_3$N$_4$O$_4$: m/z 585.5 (M+H).

Step B. (E)-1-((3aR,5R,6aR)-5-Amino-3a-(3-(trifluoromethyl)-5,6,7,8-tetrahydro-1,6-naphthyridine-6-carbonyl)hexahydrocyclopenta[c]pyrrol-2(1H)-yl)-3-phenylprop-2-en-1-one The title compound was prepared analogously to Step B in Example 13 as a TFA salt. LC/MS: C$_{26}$H$_{27}$F$_3$N$_4$O$_2$: m/z 485.5 (M+H).

Step C. (E)-1-((3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrol-2(1H)-yl)-3-phenylprop-2-en-1-one The title compound was prepared analogously to Step C in Example 13 as a yellow gel. $^1$H-NMR (400 MHz, CDCl$_3$): δ 1.53-2.15 (m, 5H), 2.39 (br. s., 1H), 2.73 (br. s., 1H), 3.07-4.15 (m, 19H), 4.61-5.05 (m, 2H), 6.70 (d, J=15.4 Hz, 1H), 7.32-7.43 (m, 3H), 7.52 (d, J=4.8 Hz, 2H), 7.63-7.76 (m, 2H), 8.72 (br. s., 1H); LC/MS: C$_{32}$H$_{37}$F$_3$N$_4$O$_4$: m/z 599.2 (M+H).

The following title compounds were synthesized using a similar procedure:

Example 66

1-((3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrol-2(1H)-yl)ethanone

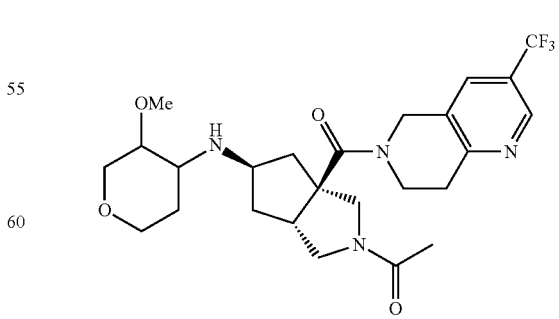

Prepared analogously to Example 65. $^1$H-NMR (400 MHz, CDCl$_3$): δ 1.53-1.96 (m, 5H), 2.04 (s, 3H), 2.35 (d, J=2.3 Hz, 1H), 2.72 (br. s., 1H), 3.05-4.17 (m, 19H), 4.58-5.06 (m, 2H), 7.58-7.79 (m, 1H), 8.72 (br. s., 1H); LC/MS: C$_{25}$H$_{33}$F$_3$N$_4$O$_4$: m/z 511.5 (M+H).

3H), 7.29 (t, J=7.6 Hz, 2H), 7.69 (br. s., 1H), 8.72 (br. s., 1H); LC/MS: C$_{31}$H$_{37}$F$_3$N$_4$O$_5$: m/z 603.3 (M+H).

Example 67

1-((3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrol-2(1H)-yl)-3-phenylpropan-1-one Example 69

((3aR,5R,6aR)-2-Benzoyl-5-(((3S*,4S*)-3-methoxytetrahydro-2H-pyran-4-yl)amino)-octahydrocyclopenta[c]pyrrol-3a-yl)(3-(trifluoromethyl)-7,8-dihydro-1,6-naphthyridin-6(5H)-yl)methanone

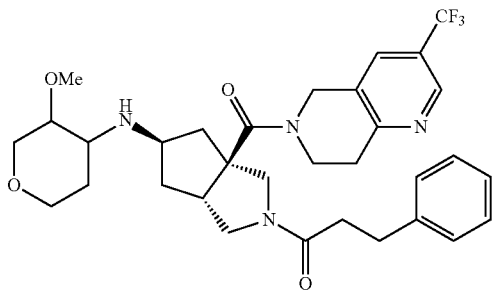 [SMILES: COC1COCCC1N[C@@H]1C[C@H]2CN(C(=O)CCc3ccccc3)C[C@@]2(C(=O)N2CCc3ncc(C(F)(F)F)cc3C2)C1]

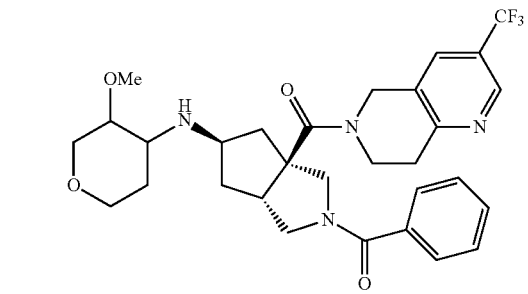

Prepared analogously to Example 65. $^1$H-NMR (400 MHz, CDCl$_3$): δ 1.54-1.91 (m, 5H), 2.31 (br. s., 1H), 2.46-2.60 (m, 2H), 2.70 (br. s., 1H), 2.87-4.15 (m, 21H), 4.59-5.04 (m, 2H), 7.17-7.33 (m, 5H), 7.69 (br. s., 1H), 8.72 (br. s., 1H); LC/MS: C$_{32}$H$_{39}$F$_3$N$_4$O$_4$: m/z 601.3 (M+H).

Prepared analogously to Example 65. $^1$H-NMR (400 MHz, CD$_3$OD): δ 1.79-2.32 (m, 5H), 2.75-3.16 (m, 2H), 3.25-4.20 (m, 17H), 4.27 (dd, J=13.3, 5.5 Hz, 2H), 4.75-5.05 (m, 2H), 7.49 (d, J=8.8 Hz, 5H), 8.56 (br. s., 1H), 9.05 (br. s., 1H); LC/MS: C$_{30}$H$_{35}$F$_3$N$_4$O$_4$: m/z 573 (M+H).

Example 68

1-((3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrol-2(1H)-yl)-2-phenoxyethanone Example 70

((3aR,5R,6aR)-5-(((3S*,4S*)-3-Methoxytetrahydro-2H-pyran-4-yl)amino)-2-(oxazole-2-carbonyl)octahydrocyclopenta[c]pyrrol-3a-yl)(3-(trifluoromethyl)-7,8-dihydro-1,6-naphthyridin-6(5H)-yl)methanone

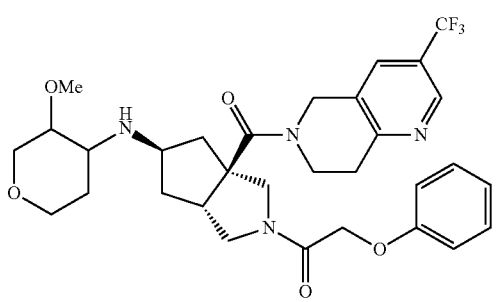 [SMILES: COC1COCCC1N[C@@H]1C[C@H]2CN(C(=O)COc3ccccc3)C[C@@]2(C(=O)N2CCc3ncc(C(F)(F)F)cc3C2)C1]

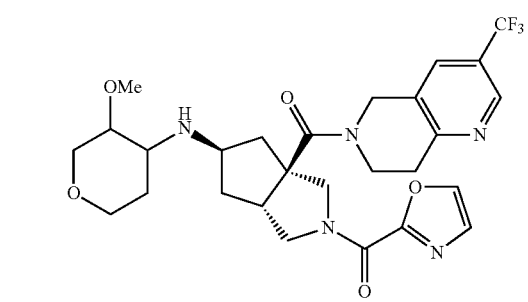

Prepared analogously to Example 65. $^1$H-NMR (400 MHz, CDCl$_3$): δ 1.49-1.92 (m, 5H), 2.13-2.39 (m, 1H), 2.67 (br. s., 1H), 3.04-4.10 (m, 19H), 4.53-5.06 (m, 4H), 6.82-7.04 (m, Prepared analogously to Example 65. $^1$H-NMR (400 MHz, CD$_3$OD): δ 1.75-2.29 (m, 5H), 2.86 (br. s., 1H), 3.09-3.60 (m, 11H), 3.79 (m, 1H), 3.88-4.62 (m, 8H), 4.80-4.90 (m, 2H), 7.39 (s, 1H), 7.97-8.15 (m, 2H), 8.73 (s, 1H); LC/MS: $C_{27}H_{32}F_3N_5O_5$: m/z 564 (M+H).

Example 71

Isoxazol-5-yl((3aR,5R,6aR)-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrol-2(1H)-yl)methanone

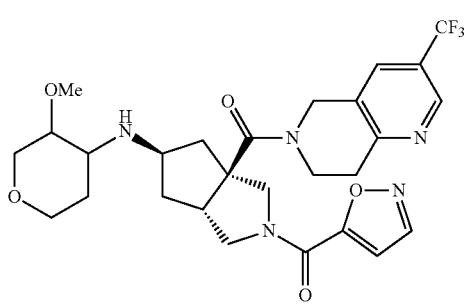 [SMILES: COC1COCCC1N[C@@H]1C[C@H]2CN(C(=O)c3ccno3)C[C@@]2(C(=O)N2CCc3ncc(C(F)(F)F)cc3C2)C1]

Prepared analogously to Example 65. $^1$H-NMR (400 MHz, CD$_3$OD): δ 1.80-2.35 (m, 5H), 2.85-3.00 (m, 1H), 3.22-3.85 (m, 11H), 3.92-4.40 (m, 9H), 4.84-5.05 (m, 2H), 6.97 (d, J=2.0 Hz, 1H), 8.53 (d, J=2.0 Hz, 2H), 9.07 (br. s., 1H); LC/MS: $C_{27}H_{32}F_3N_5O_5$: m/z 564 (M+H).

Example 72

((3aR,5R,6aR)-5-(((3S*,4S*)-3-Methoxytetrahydro-2H-pyran-4-yl)amino)-2-(oxazole-4-carbonyl)octahydrocyclopenta[c]pyrrol-3a-yl)(3-(trifluoromethyl)-7,8-dihydro-1,6-naphthyridin-6(5H)-yl)methanone

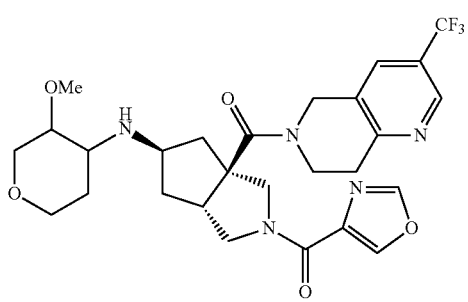 [SMILES: COC1COCCC1N[C@@H]1C[C@H]2CN(C(=O)c3cocn3)C[C@@]2(C(=O)N2CCc3ncc(C(F)(F)F)cc3C2)C1]

Prepared analogously to Example 65. $^1$H-NMR (400 MHz, CD$_3$OD): δ 1.84-2.38 (m, 5H), 2.93 (dd, J=13.8, 8.2 Hz, 1H), 3.28-4.57 (m, 20H), 4.88-5.12 (m, 2H), 8.28 (s, 1H), 8.47 (br. s., 1H), 8.65 (br. s., 1H), 9.09 (d, J=16.6 Hz, 1H); LC/MS: $C_{27}H_{32}F_3N_5O_5$: m/z 564 (M+H).

Example 73

1-((3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrol-2(1H)-yl)prop-2-yn-1-one

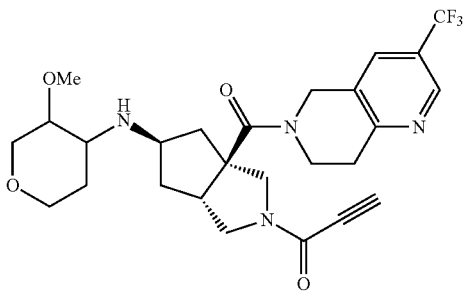 [SMILES: C#CC(=O)N1C[C@@H]2C[C@@H](NC3CCOCC3OC)C[C@]2(C(=O)N2CCc3ncc(C(F)(F)F)cc3C2)C1]

Step A. tert-Butyl((3aR,5R,6aR)-2-propioloyl-3a-(3-(trifluoromethyl)-5,6,7,8-tetrahydro-1,6-naphthyridine-6-carbonyl)octahydrocyclopenta[c]pyrrol-5-yl)carbamate To a solution of Intermediate 1 (91 mg, 0.2 mmol) in acetonitrile (5 mL) was added propiolic acid (23.46 mg, 0.22 mmol), HOBt (27.06 mg, 0.2 mmol), TEA (22.29 mg, 0.22 mmol), and EDAC (42.22 mg, 0.22 mmol). The resulting mixture was stirred at rt overnight. The reaction was quenched by addition of brine, extracted with EtOAc, dried over Na$_2$SO$_4$. Evaporation and purification by column chromatography (eluent: 80% EtOAc in hexanes to 100%) gave the product. LC/MS: $C_{25}H_{29}F_3N_4O_4$: m/z 507 (M+H).

Step B. 1-((3aR,5R,6aR)-5-Amino-3a-(3-(trifluoromethyl)-5,6,7,8-tetrahydro-1,6-naphthyridine-6-carbonyl)hexahydrocyclopenta[c]pyrrol-2(1H)-yl)prop-2-yn-1-one The title compound was prepared analogously to Step B in Example 13 as a TFA salt. LC/MS: $C_{20}H_{21}F_3N_4O_2$: m/z 407 (M+H).

Step C. 1-((3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrol-2(1H)-yl)prop-2-yn-1-one The title compound was prepared analogously to Step C in Example 13. $^1$H-NMR (400 MHz, CD$_3$OD): δ 1.75-2.25 (m, 5H), 2.83 (br. s., 1H), 3.08-4.33 (m, 21H), 4.74-4.94 (m, 2H), 8.06 (br. s., 1H), 8.72 (br. s., 1H); LC/MS: $C_{26}H_{31}F_3N_4O_4$: m/z 521 (M+H).

The following title compounds were synthesized using a similar procedure:

Example 74

(E)-4,4,4-Trifluoro-1-((3aR,5R,6aR)-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrol-2(1H)-yl)but-2-en-1-one

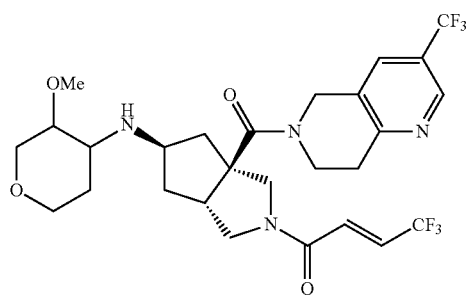 [SMILES: COC1COCCC1N[C@@H]1C[C@H]2CN(C(=O)/C=C/C(F)(F)F)C[C@@]2(C(=O)N2CCc3ncc(C(F)(F)F)cc3C2)C1]

Prepared analogously to Example 73. $^1$H-NMR (400 MHz, CDCl$_3$): δ 1.52-1.96 (m, 5H), 2.37 (br. s., 1H), 2.72 (br. s., 1H), 3.09-3.60 (m, 10H), 3.61-4.18 (m, 9H), 4.58-5.08 (m, 2H), 6.70-6.86 (m, 2H), 7.60-7.77 (m, 1H), 8.73 (br. s., 1H); LC/MS: $C_{27}H_{32}F_6N_4O_4$: m/z 591.2 (M+H).

Example 75

N-(2-((3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrol-2(1H)-yl)-2-oxoethyl)acetamide

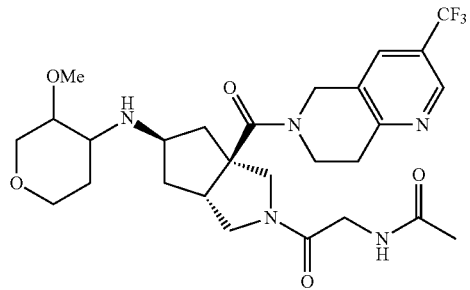 [SMILES: COC1COCCC1N[C@@H]1C[C@H]2CN(C(=O)CNC(C)=O)C[C@@]2(C(=O)N2CCc3ncc(C(F)(F)F)cc3C2)C1]

Prepared analogously to Example 73. $^1$H-NMR (400 MHz, CD$_3$OD): δ 0.25-0.78 (m, 5H), 1.22-1.42 (m, 1H), 1.67-2.76 (m, 26H), 3.29-3.52 (m, 2H), 7.15 (br. s., 1H), 7.59 (br. s., 1H); LC/MS: $C_{27}H_{36}F_3N_5O_5$: m/z 568 (M+H).

Example 76

2-(Dimethylamino)-1-((3aR,5R,6aR)-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrol-2(1H)-yl)ethanone

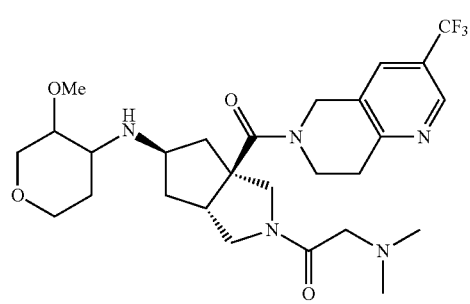

Prepared analogously to Example 73. $^1$H-NMR (400 MHz, CD$_3$OD): δ 0.27-0.81 (m, 5H), 1.29-1.57 (m, 7H), 1.67-3.03 (m, 22H), 3.30-3.57 (m, 2H), 7.00 (br. s., 1H), 7.49 (d, J=8.1 Hz, 1H); LC/MS: $C_{27}H_{38}F_3N_5O_4$: m/z 554 (M+H).

Example 77

3-(Dimethylamino)-1-((3aR,5R,6aR)-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrol-2(1H)-yl)propan-1-one

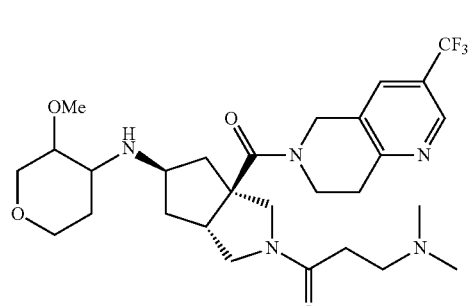

Prepared analogously to Example 73. $^1$H-NMR (400 MHz, CD$_3$OD): δ 0.27-0.79 (m, 5H), 1.23-2.81 (m, 31H), 3.29-3.55

(m, 2H), 7.07 (br. s., 1H), 7.53 (br. s., 1H); LC/MS: $C_{28}H_{40}F_3N_5O_4$: m/z 568 (M+H).

Example 78

4-(Dimethylamino)-1-((3aR,5R,6aR)-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)-hexahydrocyclopenta[c]pyrrol-2(1H)-yl)butan-1-one

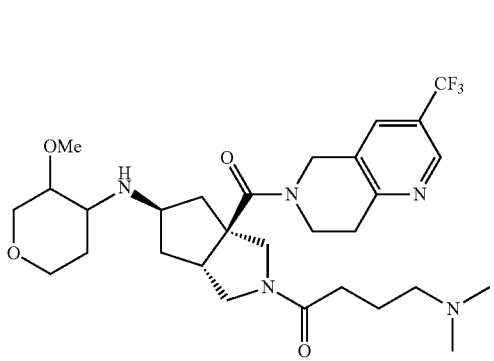 [SMILES: COC1COCCC1N[C@@H]1C[C@H]2CN(C(=O)CCCN(C)C)C[C@@]2(C(=O)N2CCc3ncc(C(F)(F)F)cc3C2)C1]

Prepared analogously to Example 73. $^1$H-NMR (400 MHz, CD$_3$OD): δ 1.89-2.33 (m, 5H), 2.46-2.77 (m, 2H), 2.89 (s, 7H), 3.13-4.32 (m, 24H), 4.94-5.08 (m, 2H), 8.73 (br. s., 1H), 9.16 (br. s., 1H); LC/MS: $C_{29}H_{42}F_3N_5O_4$: m/z 582 (M+H).

Example 79

1-((3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrol-2(1H)-yl)-3-(piperidin-1-yl)propan-1-one

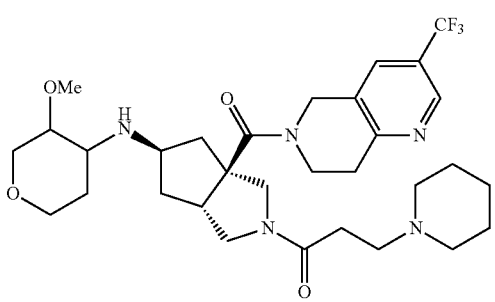 [SMILES: COC1COCCC1N[C@@H]1C[C@H]2CN(C(=O)CCN3CCCCC3)C[C@@]2(C(=O)N2CCc3ncc(C(F)(F)F)cc3C2)C1]

Prepared analogously to Example 73. $^1$H-NMR (400 MHz, CD$_3$OD): δ 1.53 (d, J=12.5 Hz, 1H), 1.75-2.36 (m, 10H), 2.81-3.14 (m, 5H), 3.34-4.34 (m, 24H), 5.01 (br. s., 2H), 8.85 (br. s., 1H), 9.22 (s, 1H); LC/MS: $C_{31}H_{44}F_3N_5O_4$: m/z 608 (M+H).

Example 80

1-((3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrol-2(1H)-yl)-3-morpholinopropan-1-one

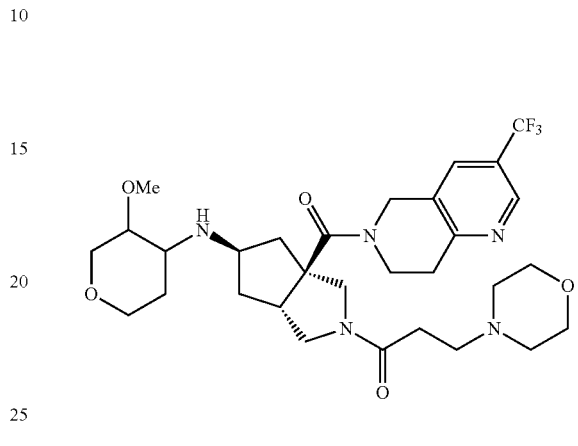

Prepared analogously to Example 73. $^1$H-NMR (400 MHz, CD$_3$OD): δ 1.82-2.35 (m, 5H), 2.81-4.34 (m, 33H), 4.97 (br. s., 2H), 8.70 (br. s., 1H), 9.14 (br. s., 1H); LC/MS: $C_{30}H_{42}F_3N_5O_5$: m/z 610 (M+H).

Example 81

((3aR,5R,6aR)-5-(((3S*,4S*)-3-Methoxytetrahydro-2H-pyran-4-yl)amino)-2-(thiazole-2-carbonyl)octahydrocyclopenta[c]pyrrol-3a-yl)(3-(trifluoromethyl)-7,8-dihydro-1,6-naphthyridin-6(5H)-yl)methanone

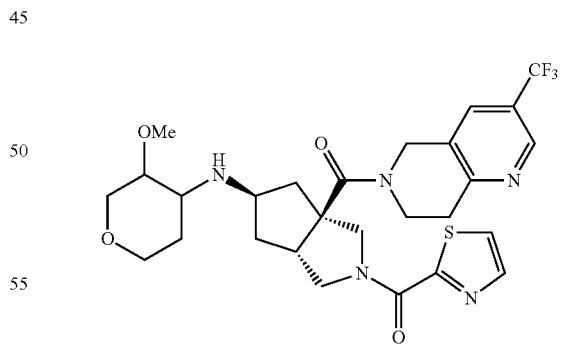

Prepared analogously to Example 73 while PyBOP was used instead of EDAC. $^1$H-NMR (400 MHz, CD$_3$OD): δ 1.78-2.05 (m, 2H), 2.08-2.36 (m, 3H), 2.81-2.98 (m, 1H), 3.19-3.84 (m, 12H), 3.91-4.31 (m, 7H), 4.45-4.77 (m, 1H), 4.84-5.06 (m, 2H), 7.79-8.05 (m, 2H), 8.50 (br. s., 1H), 9.02 (d, J=18.1 Hz, 1H); LC/MS: $C_{27}H_{32}F_3N_5O_4S$: m/z 580 (M+H).

Example 82

(E)-1-((3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrol-2(1H)-yl)-4,4-dimethylpent-2-en-1-one

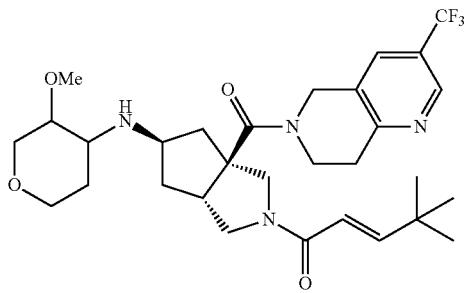 [SMILES: COC1COCCC1N[C@@H]1C[C@H]2CN(C(=O)/C=C/C(C)(C)C)C[C@@]2(C(=O)N2CCc3ncc(C(F)(F)F)cc3C2)C1]

Prepared analogously to Step A in Example 65, using the product of Example 1 as the starting material. $^1$H-NMR (400 MHz, CDCl$_3$): δ 1.08 (s, 9H), 1.52-1.97 (m, 6H), 2.36 (br. s., 1H), 2.72 (br. s., 1H), 3.08-4.20 (m, 18H), 4.57-5.05 (m, 2H), 5.95 (d, J=15.4 Hz, 1H), 6.93 (d, J=15.4 Hz, 1H), 7.70 (br. s., 1H), 8.72 (br. s., 1H); LC/MS: C$_{30}$H$_{41}$F$_3$N$_4$O$_4$: m/z 579.2 (M+H).

The following title compounds were synthesized using a similar procedure:

Example 83

2-((3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrol-2(1H)-yl)-2-oxoethyl acetate

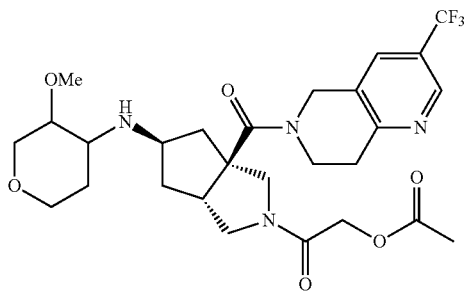 [SMILES: COC1COCCC1N[C@@H]1C[C@H]2CN(C(=O)COC(C)=O)C[C@@]2(C(=O)N2CCc3ncc(C(F)(F)F)cc3C2)C1]

Prepared analogously to Example 82. $^1$H-NMR (400 MHz, CDCl$_3$): δ 1.51-2.01 (m, 5H), 2.10-2.43 (m, 4H), 2.45-2.84 (m, 2H), 2.90-4.16 (m, 19H), 4.49-5.04 (m, 3H), 7.70 (br. s., 1H), 8.72 (br. s., 1H); LC/MS: C$_{27}$H$_{35}$F$_3$N$_4$O$_6$: m/z 569.3 (M+H).

Example 84

2-Methoxy-1-((3aR,5R,6aR)-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrol-2(1H)-yl)ethanone

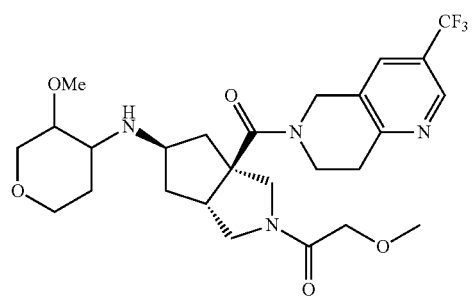 [SMILES: COCC(=O)N1C[C@@H]2C[C@@H](NC3CCOCC3OC)C[C@]2(C(=O)N2CCc3ncc(C(F)(F)F)cc3C2)C1]

Prepared analogously to Example 82. $^1$H-NMR (400 MHz, CDCl$_3$): δ 1.53-1.93 (m, 5H), 2.14-2.83 (m, 4H), 3.02-4.17 (m, 22H), 4.58-5.07 (m, 2H), 7.70 (br. s., 1H), 8.72 (br. s., 1H); LC/MS: C$_{26}$H$_{35}$F$_3$N$_4$O$_5$: m/z 541.3 (M+H).

Example 85

2-(tert-Butoxy)-1-((3aR,5R,6aR)-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydro-cyclopenta[c]pyrrol-2(1H)-yl)ethanone

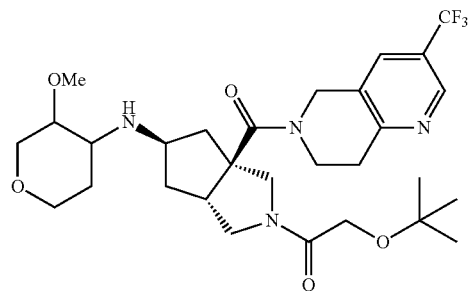 [SMILES: COC1COCCC1N[C@@H]1C[C@H]2CN(C(=O)COC(C)(C)C)C[C@@]2(C(=O)N2CCc3ncc(C(F)(F)F)cc3C2)C1]

Prepared analogously to Example 82. $^1$H-NMR (400 MHz, CDCl$_3$): δ 1.13-1.32 (m, 9H), 1.55-1.95 (m, 6H), 2.33 (br. s., 1H), 2.72 (br. s., 1H), 3.07-3.57 (m, 10H), 3.67-4.13 (m, 10H), 4.61-5.04 (m, 2H), 7.69 (br. s., 1H), 8.72 (br. s., 1H); LC/MS: $C_{29}H_{41}F_3N_4O_5$: m/z 583.3 (M+H).

Example 86

3-Cyclopropyl-1-((3aR,5R,6aR)-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydro-cyclopenta[c]pyrrol-2(1H)-yl)prop-2-yn-1-one

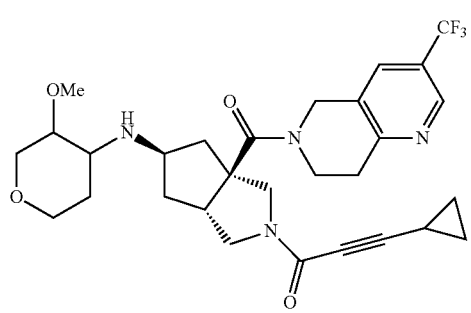 [SMILES: COC1COCCC1N[C@@H]1C[C@H]2CN(C(=O)C#CC3CC3)C[C@@]2(C(=O)N2CCc3ncc(C(F)(F)F)cc3C2)C1]

Prepared analogously to Step A in Example 73. ¹H-NMR (400 MHz, CDCl₃): δ 0.78-0.99 (m, 4H), 1.31-1.53 (m, 2H), 1.58-2.44 (m, 6H), 2.80-4.19 (m, 19H), 4.72-4.98 (m, 2H), 7.64-7.78 (m, 1H), 8.71 (br. s., 1H); LC/MS: $C_{29}H_{35}F_3N_4O_4$: m/z 561.3 (M+H).

The following were synthesized using a similar procedure:

Example 87 tert-Butyl (2-((3aR,5R,6aR)-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrol-2(1H)-yl)-2-oxoethyl)carbamate

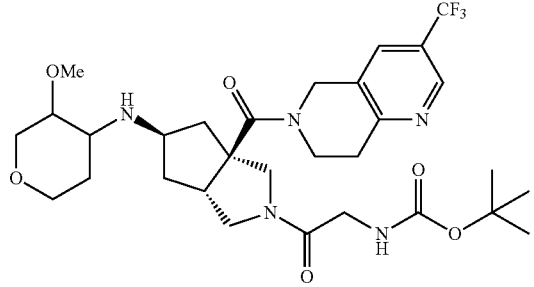 [SMILES: COC1COCCC1N[C@@H]1C[C@H]2CN(C(=O)CNC(=O)OC(C)(C)C)C[C@@]2(C(=O)N2CCc3ncc(C(F)(F)F)cc3C2)C1]

Prepared analogously to Example 82. LC/MS: $C_{30}H_{42}F_3N_5O_6$: m/z 626.2 (M+H).

Example 88

(E)-1-((3aR,5R,6aR)-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydro-cyclopenta[c]pyrrol-2(1H)-yl)-4-(pyrrolidin-1-yl)but-2-en-1-one

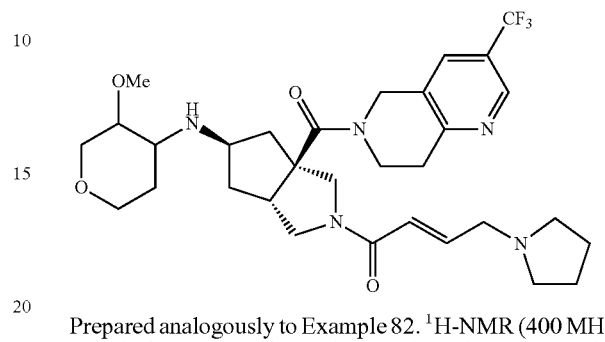

Prepared analogously to Example 82. ¹H-NMR (400 MHz, CD₃OD): δ 1.76-2.27 (m, 8H), 2.85 (s, 1H), 3.06-4.08 (m, 26H), 4.25 (m, 1H), 4.78-5.00 (m, 2H), 6.68-6.79 (m, 2H), 8.06 (br. s., 1H), 8.73 (br. s., 1H); LC/MS: $C_{31}H_{42}F_3N_5O_4$: m/z 606 (M+H).

Intermediate 7

(E)-3-(4-Methoxyphenyl)-1-((3aR,5R,6aR)-5-((3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrol-2(1H)-yl)prop-2-en-1-one

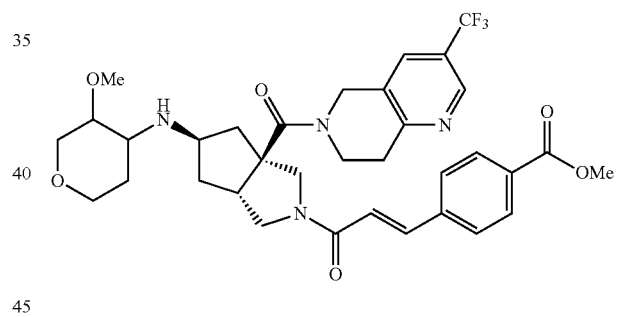

Prepared analogously to Example 73. LC/MS: $C_{35}H_{40}F_3N_3O_6$: m/z 656 (M+H).

Intermediate 8

(E)-3-(3-Methoxyphenyl)-1-((3aR,5R,6aR)-5-((3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrol-2(1H)-yl)prop-2-en-1-one

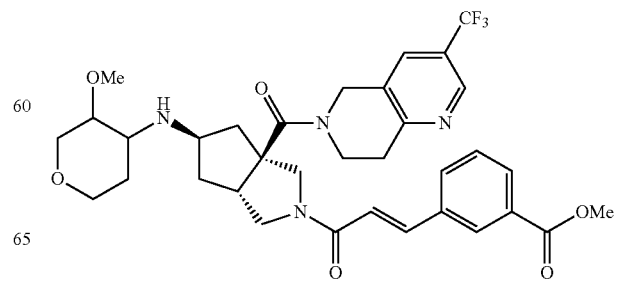

Prepared analogously to Example 73. LC/MS: $C_{35}H_{40}F_3N_3O_6$: m/z 656 (M+H).

Example 89

4-((E)-3-((3aR,5R,6aR)-5-(((3S*,4S*)-3-methoxytetrahydro-2H-pyran-4-yl)amino)-3a-(7-(trifluoromethyl)-1,2,3,4-tetrahydroisoquinoline-2-carbonyl)hexahydrocyclopenta-[c]pyrrol-2(1H)-yl)-3-oxoprop-1-en-1-yl)benzoic acid

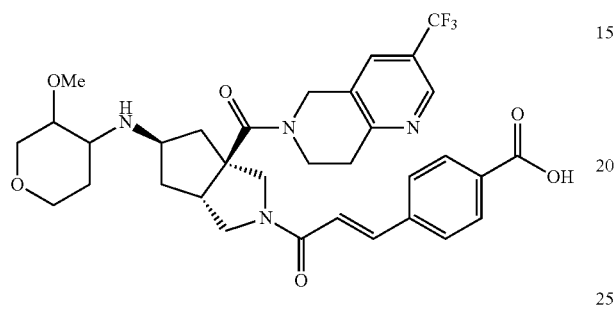

To a solution of Intermediate 7 (120 mg, 0.183 mmol) in methanol (20 mL) was added a 0.1 M LiOH aqueous solution (2 mL). The mixture was heated at gentle reflux for 5 h. After cooling to rt, the solvent was removed by evaporation and the residue was purified by HPLC to give a TFA solid, which was then converted to a HCl salt by adding 1N aqueous HCl solution and evaporating to dryness for three cycles. $^1$H-NMR (400 MHz, CD$_3$OD): δ 1.81 (m, 1H), 1.89-2.29 (m, 4H), 2.84 (m, 1H), 3.05 (m, 2H), 3.23-3.59 (m, 10H), 3.64-4.13 (m, 8H), 4.28 (m, 1H), 4.75-4.96 (m, 2H), 7.09 (d, J=16 Hz, 1H), 7.41 (d, J=6.8 Hz, 1H), 7.73 (m, 5H), 8.04 (d, J=7.8 Hz, 2H); LC/MS: $C_{34}H_{38}F_3N_3O_6$: m/z 642 (M+H).

Example 90

3-((E)-3-((3aR,5R,6aR)-5-(((3S*,4S*)-3-methoxytetrahydro-2H-pyran-4-yl)amino)-3a-(7-(trifluoromethyl)-1,2,3,4-tetrahydroisoquinoline-2-carbonyl)hexahydrocyclopenta-[c]pyrrol-2(1H)-yl)-3-oxoprop-1-en-1-yl)benzoic acid

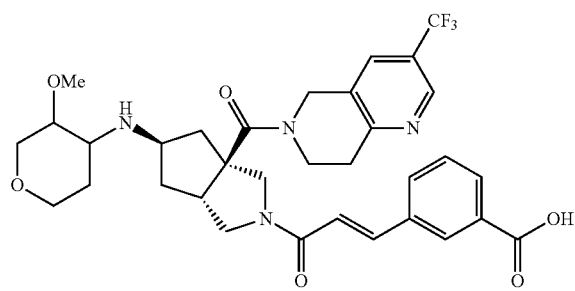 [SMILES: COC1COCCC1N[C@@H]1C[C@H]2CN(C(=O)/C=C/c3cccc(C(=O)O)c3)C[C@@]2(C(=O)N2CCc3ncc(C(F)(F)F)cc3C2)C1]

The title compound was prepared analogously to Example 89 using Intermediate 8. $^1$H-NMR (400 MHz, CD$_3$OD): δ 1.74-2.30 (m, 5H), 2.79-2.94 (m, 1H), 3.05 (m, 2H), 3.26-4.37 (m, 19H), 4.70-4.97 (m, 2H), 7.03 (d, J=15.4 Hz, 1H), 7.40 (d, J=6.8 Hz, 1H), 7.45-7.75 (m, 4H), 7.86 (d, J=7.6 Hz, 1H), 8.04 (d, J=7.8 Hz, 1H), 8.25 (s, 1H); LC/MS: $C_{34}H_{38}F_3N_3O_6$: m/z 642 (M+H).

Example 91

((3aR,5R,6aR)-5-(((3S*,4S*)-3-Methoxytetrahydro-2H-pyran-4-yl)amino)-2-(methylsulfonyl)octahydrocyclopenta[c]pyrrol-3a-yl)(3-(trifluoromethyl)-7,8-dihydro-1,6-naphthyridin-6(5H)-yl)methanone

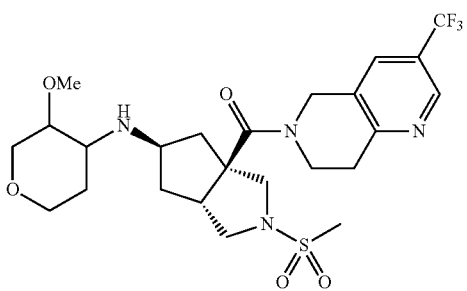 [SMILES: COC1COCCC1N[C@@H]1C[C@H]2CN(S(C)(=O)=O)C[C@@]2(C(=O)N2CCc3ncc(C(F)(F)F)cc3C2)C1]

Step A. tert-Butyl((3aR,5R,6aR)-2-(methylsulfonyl)-3a-(3-(trifluoromethyl)-5,6,7,8-tetrahydro-1,6-naphthyridine-6-carbonyl)octahydrocyclopenta[c]pyrrol-5-yl)carbamate To a solution of Intermediate 1 (0.11 g, 0.242 mmol) and TEA (0.0344 mL, 0.247 mmol) in DCM (3 mL) at 0° C. was added methanesulfonyl chloride (0.0188 mL, 0.242 mol). The mixture was stirred at 0° C. for 30 min and at rt overnight. The reaction mixture was quenched by addition of brine, extracted with DCM, dried over Na$_2$SO$_4$. Purification by CombiFlash (eluent: 60% EtOAc in hexanes) gave the product as a yellow gel. $^1$H-NMR (400 MHz, CDCl$_3$): δ 1.14-1.55 (m, 9H), 1.67-2.16 (m, 4H), 2.27-2.47 (m, 1H), 2.76-2.94 (m, 1H), 3.06-3.93 (m, 10H), 4.25 (d, J=5.1 Hz, 1H), 4.54-5.01 (m, 3H), 7.73 (s, 1H), 8.72 (s, 1H); LC/MS: $C_{23}H_{31}F_3N_4O_5S$: m/z 555.5 (M+Na).

Step B. ((3aR,5R,6aR)-5-Amino-2-(methylsulfonyl)octahydrocyclopenta[c]pyrrol-3a-yl)(3-(trifluoromethyl)-7,8-dihydro-1,6-naphthyridin-6(5H)-yl)methanone The title compound was prepared analogously to Step B in Example 13 as a TFA salt. LC/MS: $C_{18}H_{23}F_3N_4O_3S$: m/z 433.5 (M+H).

Step C. ((3aR,5R,6aR)-5-(((3S*,4S*)-3-Methoxytetrahydro-2H-pyran-4-yl)amino)-2-(methylsulfonyl)octahydrocyclopenta[c]pyrrol-3a-yl)(3-(trifluoromethyl)-7,8-dihydro-1,6-naphthyridin-6(5H)-yl)methanone The title compound was prepared analogously to Step C in Example 13. $^1$H-NMR (400 MHz, CDCl$_3$): δ 1.51-2.04 (m, 5H), 2.16-2.43 (m, 2H), 2.53-2.88 (m, 6H), 3.05-4.32 (m, 16H), 4.65-5.01 (m, 2H), 7.70 (s, 1H), 8.73 (br. s., 1H); LC/MS: $C_{24}H_{33}F_3N_4O_5S$: m/z 547.5 (M+H).

The following title compounds were synthesized using a similar procedure:

Example 92

((3aR,5R,6aR)-2-(Benzylsulfonyl)-5-(((3S*,4S*)-3-methoxytetrahydro-2H-pyran-4-yl)amino)octahydro-cyclopenta[c]pyrrol-3a-yl)(3-(trifluoromethyl)-7,8-dihydro-1,6-naphthyridin-6(5H)-yl)methanone

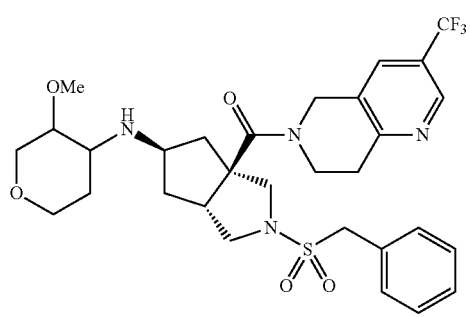 [SMILES: COC1COCCC1N[C@@H]1C[C@H]2CN(S(=O)(=O)Cc3ccccc3)C[C@@]2(C(=O)N2CCc3ncc(C(F)(F)F)cc3C2)C1]

The title compound was prepared analogously to Example 91. $^1$H-NMR (400 MHz, CDCl$_3$): δ 1.54-1.88 (m, 5H), 2.18 (br. s., 2H), 2.71 (br. s., 1H), 2.83-3.14 (m, 3H), 3.19-3.96 (m, 14H), 3.99-4.12 (m, 1H), 4.16-4.35 (m, 2H), 4.45-4.96 (m, 2H), 7.09-7.42 (m, 5H), 7.70 (br. s., 1H), 8.74 (s, 1H); LC/MS: C$_{30}$H$_{37}$F$_3$N$_4$O$_5$S: m/z 623.2 (M+H).

Example 93

((3aR,5R,6aR)-5-(((3S*,4S*)-3-Methoxytetrahydro-2H-pyran-4-yl)amino)-2-(phenethylsulfonyl)octahydrocyclopenta[c]pyrrol-3a-yl)(3-(trifluoromethyl)-7,8-dihydro-1,6-naphthyridin-6(5H)-yl)methanone

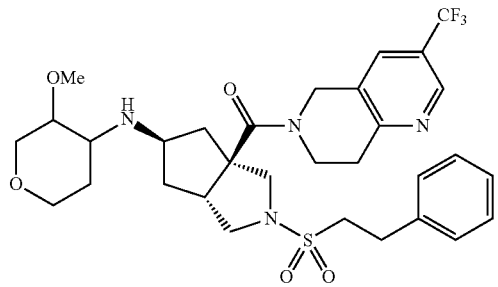 [SMILES: COC1COCCC1N[C@@H]1C[C@H]2CN(S(=O)(=O)CCc3ccccc3)C[C@@]2(C(=O)N2CCc3ncc(C(F)(F)F)cc3C2)C1]

The title compound was prepared analogously to Example 91. $^1$H-NMR (400 MHz, CDCl$_3$): δ 1.59-1.98 (m, 5H), 2.31 (d, J=6.6 Hz, 2H), 2.75 (br. s., 1H), 3.04-4.13 (m, 22H), 4.63-4.92 (m, 2H), 7.16-7.32 (m, 5H), 7.69 (s, 1H), 8.72 (s, 1H); LC/MS: C$_{31}$H$_{39}$F$_3$N$_4$O$_5$S: m/z 637.3 (M+H).

Example 94

((3aR,5R,6aR)-2-Cyclopropyl-5-(((3S*,4S*)-3-methoxytetrahydro-2H-pyran-4-yl)amino)octahydro-cyclopenta[c]pyrrol-3a-yl)(3-(trifluoromethyl)-7,8-dihydro-1,6-naphthyridin-6(5H)-yl)methanone

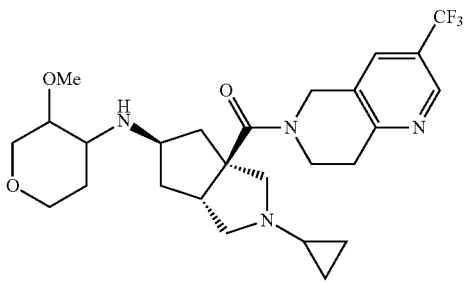 [SMILES: COC1COCCC1N[C@@H]1C[C@H]2CN(C3CC3)C[C@@]2(C(=O)N2CCc3ncc(C(F)(F)F)cc3C2)C1]

Step A. tert-Butyl((3aR,5R,6aR)-2-cyclopropyl-3a-(3-(trifluoromethyl)-5,6,7,8-tetrahydro-1,6-naphthyridine-6-carbonyl)octahydrocyclopenta[c]pyrrol-5-yl)carbamate A solution of Intermediate 1 (0.1213 g, 0.267 mmol) in methanol (2 mL) was added (1-ethoxycyclopropoxy)-trimethylsilane (0.0813 mL, 0.4 mol), sodium cyanoborohydride (70.62 mg, 1.068 mmol) and acetic acid (0.153 mL, 2.669 mmol). The mixture was heated at reflux overnight. The reaction mixture was quenched by addition of saturated aqueous NaHCO$_3$ solution, extracted with EtOAc, and dried over Na$_2$SO$_4$. Purification by CombiFlash (eluent: 5% methanol in DCM) gave the product as a colorless gel. $^1$H-NMR (400 MHz, CDCl$_3$): δ 0.39 (d, J=6.1 Hz, 4H), 1.31-1.46 (m, 11H), 1.65-1.98 (m, 3H), 2.15-2.31 (m, 1H), 2.55 (dd, J=9.0, 3.2 Hz, 1H), 2.66-2.81 (m, 2H), 2.94-3.19 (m, 3H), 3.61 (br. s., 1H), 3.77-3.92 (m, 1H), 4.20 (d, J=6.1 Hz, 1H), 4.64-4.84 (m, 3H), 7.70 (s, 1H), 8.70 (br. s., 1H); LC/MS: C$_{25}$H$_{33}$F$_3$N$_4$O$_3$: m/z 495.2 (M+H).

Step B. ((3aR,5R,6aR)-5-Amino-2-cyclopropyloctahydrocyclopenta[c]pyrrol-3a-yl)(3-(trifluoromethyl)-7,8-dihydro-1,6-naphthyridin-6(5H)-yl)methanone The title compound was prepared analogously to Step B in Example 13 as a TFA salt. LC/MS: C$_{20}$H$_{25}$F$_3$N$_4$O: m/z 395.2 (M+H).

Step C. ((3aR,5R,6aR)-2-Cyclopropyl-5-(((3S*,4S*)-3-methoxytetrahydro-2H-pyran-4-yl)amino)octahydrocyclopenta[c]pyrrol-3a-yl)(3-(trifluoromethyl)-7,8-dihydro-1,6-naphthyridin-6(5H)-yl)methanone The title compound was prepared analogously to Step C in Example 13. $^1$H-NMR (400 MHz, CDCl$_3$): δ 0.26-0.47 (m, 4H), 0.98-1.10 (m, 1H), 1.46-1.80 (m, 6H), 2.16 (br. s., 1H), 2.43-4.15 (m, 19H), 4.79 (br. s., 2H), 7.69 (br. s., 1H), 8.70 (br. s., 1H); LC/MS: C$_{26}$H$_{35}$F$_3$N$_4$O$_3$: m/z 509.2 (M+H).

Example 95

((3aR,5R,6aR)-2-Cyclopropyl-5-(((3S*,4S*)-3-methoxytetrahydro-2H-pyran-4-yl)amino)octahydro-cyclopenta[c]pyrrol-3a-yl)(7-(trifluoromethyl)-3,4-dihydroisoquinolin-2(1H)-yl)methanone

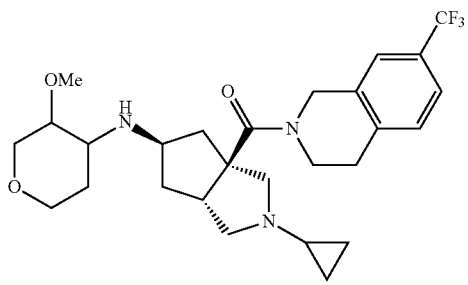 [SMILES: COC1COCCC1N[C@@H]1C[C@H]2CN(C3CC3)C[C@@]2(C(=O)N2CCc3ccc(C(F)(F)F)cc3C2)C1]

The title compound was prepared analogously to Example 94. $^1$H-NMR (400 MHz, CDCl$_3$): δ 0.19-0.40 (m, 4H), 1.38-1.78 (m, 7H), 2.05 (br. s., 1H), 2.39 (dt, J=9.0, 4.4 Hz, 1H), 2.60-2.91 (m, 6H), 3.12-3.44 (m, 7H), 3.52-4.01 (m, 5H), 4.66 (br. s., 2H), 7.13-7.23 (m, 1H), 7.25-7.41 (m, 2H); LC/MS: C$_{27}$H$_{36}$F$_3$N$_3$O$_3$: m/z 508.3 (M+H).

Example 96

((3aR,5R,6aR)-2-Isopropyl-5-(((3S*,4S*)-3-methoxytetrahydro-2H-pyran-4-yl)amino)octahydrocyclopenta[c]pyrrol-3a-yl)(3-(trifluoromethyl)-7,8-dihydro-1,6-naphthyridin-6(5H)-yl)methanone

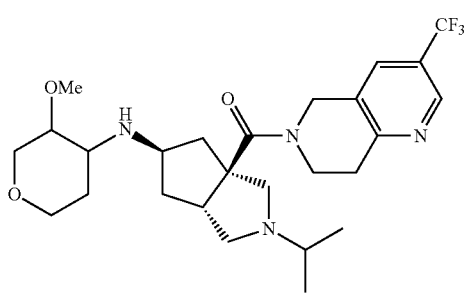 [SMILES: COC1COCCC1N[C@@H]1C[C@H]2CN(C(C)C)C[C@@]2(C(=O)N2CCc3ncc(C(F)(F)F)cc3C2)C1]

Step A. tert-Butyl((3aR,5R,6aR)-2-Isopropyl-3a-(3-(trifluoromethyl)-5,6,7,8-tetrahydro-1,6-naphthyridine-6-carbonyl)octahydrocyclopenta[c]pyrrol-5-yl)carbamate A mixture of Intermediate 1 (0.11 g, 0.242 mmol) and acetone (19.5 μL, 0.266 mmol) in DCM (2 mL) was stirred at rt for 20 min, followed by addition of NaBH(OAc)$_3$ (076.9 mg, 0.363 mmol). The mixture was stirred at rt overnight and quenched by addition of saturated aqueous NaHCO$_3$ solution, extracted with DCM, dried over Na$_2$SO$_4$. Purification by CombiFlash (eluent: 8% MeOH in DCM) gave the product as a colorless gel. $^1$H-NMR (400 MHz, CDCl$_3$): δ 0.95-1.12 (m, 6H), 1.31-1.47 (m, 9H), 1.68-1.78 (m, 1H), 1.78-1.99 (m, 2H), 2.20-2.39 (m, 2H), 2.46-2.74 (m, 3H), 2.93 (br. s., 1H), 3.12 (br. s., 2H), 3.61 (br. s., 1H), 3.85 (br. s., 2H), 4.25 (d, J=6.1 Hz, 1H), 4.58-4.93 (m, 3H), 7.70 (s, 1H), 8.71 (s, 1H); LC/MS: C$_{25}$H$_{35}$F$_3$N$_4$O$_3$: m/z 497.2 (M+H).

Step B. ((3aR,5R,6aR)-5-Amino-2-isopropyloctahydrocyclopenta[c]pyrrol-3a-yl)(3-(trifluoromethyl)-7,8-dihydro-1,6-naphthyridin-6(5H)-yl)methanone The title compound was prepared analogously to Step B in Example 93 as a TFA salt. LC/MS: C$_{20}$H$_{27}$F$_3$N$_4$O: m/z 397.2 (M+H).

Step C. ((3aR,5R,6aR)-2-Isopropyl-5-(((3S*,4S*)-3-methoxytetrahydro-2H-pyran-4-yl)amino)octahydro-cyclopenta[c]pyrrol-3a-yl)(3-(trifluoromethyl)-7,8-dihydro-1,6-naphthyridin-6(5H)-yl)methanone The title compound was prepared analogously to Step C in Example 93 as a colorless gel. $^1$H-NMR (400 MHz, CDCl$_3$): δ 0.93-1.14 (m, 6H), 1.52-1.87 (m, 5H), 2.12-2.41 (m, 3H), 2.49-2.88 (m, 5H), 3.02-3.67 (m, 10H), 3.75-4.13 (m, 4H), 4.80 (br. s., 2H), 7.69 (br. s., 1H), 8.70 (s, 1H); LC/MS: C$_{26}$H$_{37}$F$_3$N$_4$O$_3$: m/z 511.2 (M+H).

Example 97

((3aR,5R,6aR)-5-(((3S*,4S*)-3-Methoxytetrahydro-2H-pyran-4-yl)amino)-2-methyloctahydrocyclopenta[c]pyrrol-3a-yl)(3-(trifluoromethyl)-7,8-dihydro-1,6-naphthyridin-6(5H)-yl)methanone

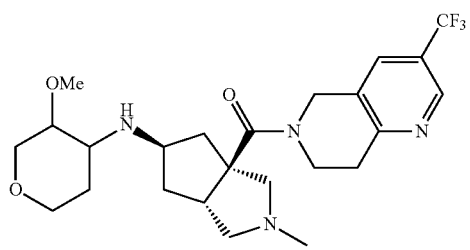

The title compound was prepared analogously to Example 96. $^1$H-NMR (400 MHz, CDCl$_3$): δ 1.49-1.88 (m, 5H), 2.15-2.42 (m, 5H), 2.56-2.85 (m, 5H), 2.93-3.58 (m, 9H), 3.62-4.12 (m, 5H), 4.78 (br. s., 2H), 7.69 (br. s., 1H), 8.70 (br. s., 1H); LC/MS: C$_{24}$H$_{33}$F$_3$N$_4$O$_3$: m/z 483.3 (M+H).

Example 98

((3aR,5R,6aR)-2-Ethyl-5-(((3S*,4S*)-3-methoxytetrahydro-2H-pyran-4-yl)amino)octahydrocyclopenta[c]pyrrol-3a-yl)(3-(trifluoromethyl)-7,8-dihydro-1,6-naphthyridin-6(5H)-yl)methanone

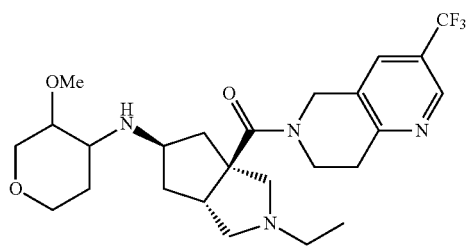 [SMILES: CCN1C[C@@H]2C[C@@H](NC3CCOCC3OC)C[C@]2(C(=O)N2CCc3ncc(C(F)(F)F)cc3C2)C1]

The title compound was prepared analogously to Example 96. ¹H-NMR (400 MHz, CDCl₃): δ 0.98-1.21 (m, 3H), 1.48-1.97 (m, 5H), 2.12-2.53 (m, 4H), 2.58-2.92 (m, 4H), 3.04-4.21 (m, 15H), 4.79 (br. s., 2H), 7.69 (br. s., 1H), 8.71 (br. s., 1H); LC/MS: $C_{25}H_{35}F_3N_4O_3$: m/z 497.2 (M+H).

Example 99

((3aR,5R,6aR)-5-(((3S*,4S*)-3-methoxytetrahydro-2H-pyran-4-yl)amino)-2-(oxetan-3-yl)octahydrocyclopenta[c]pyrrol-3a-yl)(3-(trifluoromethyl)-7,8-dihydro-1,6-naphthyridin-6(5H)-yl)methanone

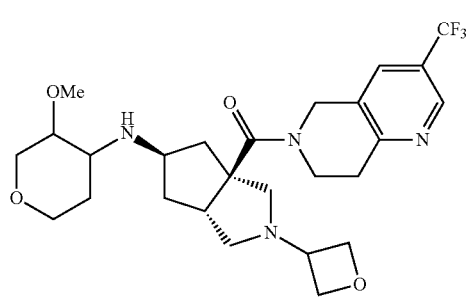 [SMILES: COC1COCCC1N[C@@H]1C[C@H]2CN(C3COC3)C[C@@]2(C(=O)N2CCc3ncc(C(F)(F)F)cc3C2)C1]

The title compound was prepared analogously to Example 96. ¹H-NMR (400 MHz, CDCl₃): δ 1.54-1.89 (m, 5H), 1.91-2.32 (m, 2H), 2.32-2.46 (m, 1H), 2.48-2.67 (m, 2H), 2.67-3.21 (m, 4H), 3.21-4.12 (m, 13H), 4.50-5.00 (m, 6H), 7.71 (s, 1H), 8.71 (s, 1H); LC/MS: $C_{26}H_{35}F_3N_4O_4$: m/z 525.3 (M+H).

Example 100

((3aR,5R,6aR)-5-(((3S*,4S*)-3-Methoxytetrahydro-2H-pyran-4-yl)amino)-2-(oxetan-3-yl)octahydrocyclopenta[c]pyrrol-3a-yl)(7-(trifluoromethyl)-3,4-dihydroisoquinolin-2(1H)-yl)methanone

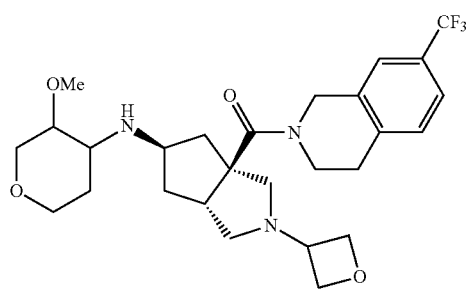 [SMILES: COC1COCCC1N[C@@H]1C[C@H]2CN(C3COC3)C[C@@]2(C(=O)N2CCc3ccc(C(F)(F)F)cc3C2)C1]

The title compound was prepared analogously to Example 96. ¹H-NMR (400 MHz, CDCl₃): δ 1.51-1.93 (m, 6H), 2.11-2.26 (m, 1H), 2.34-2.45 (m, 1H), 2.48-2.62 (m, 2H), 2.78 (d, J=8.8 Hz, 2H), 2.92 (br. s., 2H), 3.16-3.45 (m, 6H), 3.47-3.62 (m, 2H), 3.62-3.83 (m, 3H), 3.85-4.00 (m, 1H), 3.99-4.09 (m, 1H), 4.48-4.95 (m, 6H), 7.22-7.30 (m, 1H), 7.34-7.51 (m, 2H); LC/MS: $C_{27}H_{36}F_3N_3O_4$: m/z 524.3 (M+H).

Example 101

((3aR,5R,6aR)-2-Benzyl-5-(((3S*,4S*)-3-methoxytetrahydro-2H-pyran-4-yl)amino)octahydrocyclopenta[c]pyrrol-3a-yl)(3-(trifluoromethyl)-7,8-dihydro-1,6-naphthyridin-6(5H)-yl)methanone

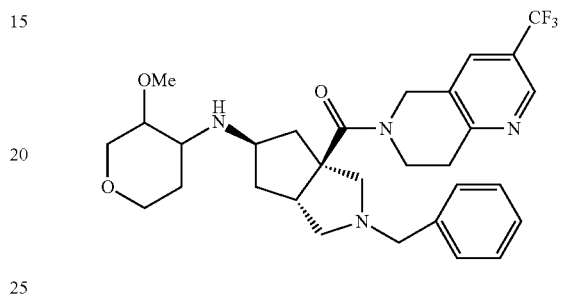

The title compound was prepared analogously to Example 96. ¹H-NMR (400 MHz, CDCl₃): δ 1.47-2.06 (m, 6H), 2.21 (d, J=5.8 Hz, 1H), 2.39-2.68 (m, 3H), 2.71-2.90 (m, 2H), 2.93-3.18 (m, 2H), 3.23-3.73 (m, 10H), 3.74-4.01 (m, 3H), 4.02-4.16 (m, 1H), 4.76 (br. s., 2H), 7.18-7.37 (m, 5H), 7.66 (br. s., 1H), 8.70 (br. s., 1H); LC/MS: $C_{30}H_{37}F_3N_4O_3$: m/z 559.2 (M+H).

Example 102

((3aR,5R,6aR)-5-(((3S*,4S*)-3-Methoxytetrahydro-2H-pyran-4-yl)amino)-2-phenethyloctahydrocyclopenta[c]pyrrol-3a-yl)(3-(trifluoromethyl)-7,8-dihydro-1,6-naphthyridin-6(5H)-yl)methanone

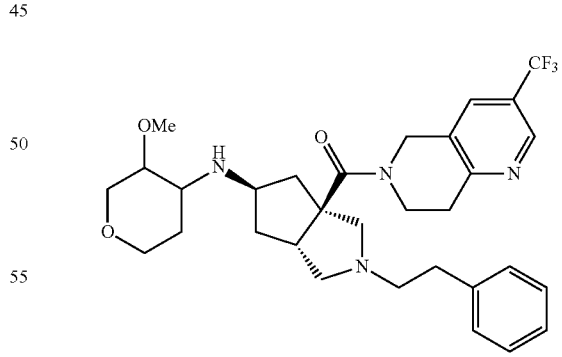

The title compound was prepared analogously to Example 96. ¹H-NMR (400 MHz, CDCl₃): δ 1.53-1.90 (m, 5H), 2.18 (br. s., 1H), 2.30-2.96 (m, 10H), 2.96-3.71 (m, 10H), 3.76-4.22 (m, 4H), 4.76 (br. s., 2H), 7.13-7.32 (m, 5H), 7.66 (br. s., 1H), 8.69 (br. s., 1H); LC/MS: $C_{31}H_{39}F_3N_4O_3$: m/z 573.3 (M+H).

Example 103

((3aR,5R,6aR)-5-(((3S*,4S*)-3-Methoxytetrahydro-2H-pyran-4-yl)amino)-2-(3-phenylpropyl)octahydro-cyclopenta[c]pyrrol-3a-yl)(3-(trifluoromethyl)-7,8-dihydro-1,6-naphthyridin-6(5H)-yl)methanone

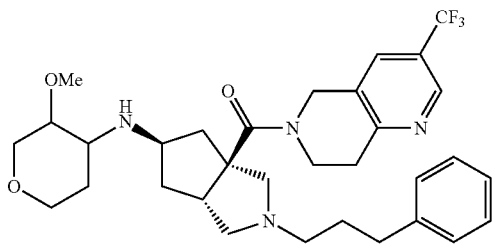 [SMILES: COC1COCCC1N[C@@H]1C[C@H]2CN(CCCc3ccccc3)C[C@@]2(C(=O)N2CCc3ncc(C(F)(F)F)cc3C2)C1]

The title compound was prepared analogously to Example 96. $^1$H-NMR (400 MHz, CDCl$_3$): δ 1.52-1.90 (m, 8H), 2.20 (br. s., 1H), 2.30-2.49 (m, 3H), 2.49-2.69 (m, 4H), 2.78 (d, J=3.5 Hz, 2H), 3.00-3.16 (m, 2H), 3.20-3.41 (m, 6H), 3.50-3.71 (m, 2H), 3.79-4.13 (m, 4H), 4.78 (br. s., 2H), 7.15-7.32 (m, 5H), 7.68 (s, 1H), 8.70 (s, 1H); LC/MS: C$_{32}$H$_{41}$F$_3$N$_4$O$_3$: m/z 587.2 (M+H).

Example 104

((3aR,5R,6aR)-2-((3S*,4S*)-3-Methoxytetrahydro-2H-pyran-4-yl)-5-(((3S*,4S*)-3-methoxytetrahydro-2H-pyran-4-yl)amino)octahydrocyclopenta[c]pyrrol-3a-yl)(3-(trifluoromethyl)-7,8-dihydro-1,6-naphthyridin-6(5H)-yl)methanone

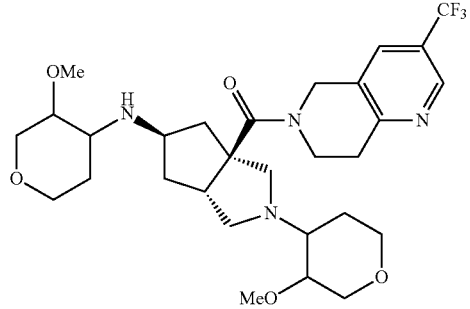 [SMILES: COC1COCCC1N[C@@H]1C[C@H]2CN(C3CCOCC3OC)C[C@@]2(C(=O)N2CCc3ncc(C(F)(F)F)cc3C2)C1]

The title compound was prepared analogously to Example 96, a mixture of at least four diastereoisomers. $^1$H-NMR (400 MHz, CDCl$_3$): δ 1.36-2.07 (m, 8H), 2.14-2.38 (m, 2H), 2.45-2.60 (m, 1H), 2.67-3.20 (m, 6H), 3.23-3.69 (m, 14H), 3.82-4.16 (m, 6H), 4.68-4.96 (m, 2H), 7.71 (d, J=4.8 Hz, 1H), 8.70 (s, 1H); LC/MS: C$_{29}$H$_{41}$F$_3$N$_4$O$_5$: m/z 583.3 (M+H).

Example 105

((3aR,5R,6aR)-2-((3S*,4S*)-3-Methoxytetrahydro-2H-pyran-4-yl)-5-(((3S*,4S*)-3-methoxytetrahydro-2H-pyran-4-yl)amino)octahydrocyclopenta[c]pyrrol-3a-yl)(7-(trifluoromethyl)-3,4-dihydroisoquinolin-2(1H)-yl)methanone

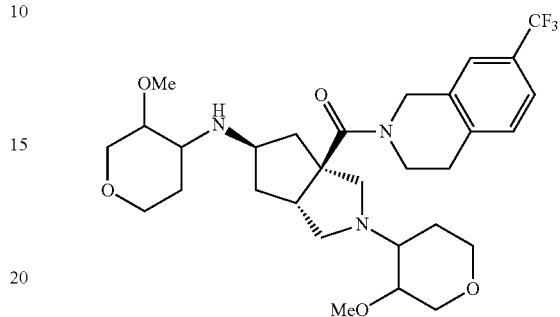

The title compound was prepared analogously to Example 96, a mixture of at least four diastereoisomers. $^1$H-NMR (400 MHz, CDCl$_3$): δ 1.48-2.05 (m, 8H), 2.20 (dd, J=11.2, 4.9 Hz, 2H), 2.45-2.59 (m, 1H), 2.65-3.05 (m, 6H), 3.20-4.16 (m, 20H), 4.73 (br. s., 2H), 7.20-7.30 (m, 1H), 7.33-7.50 (m, 2H); LC/MS: C$_{30}$H$_{42}$F$_3$N$_3$O$_5$: m/z 582.2 (M+H).

Example 106

2-((3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrol-2(1H)-yl)-N,N-dimethylacetamide

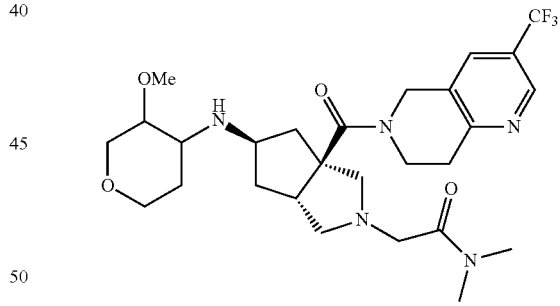

Step A. 2-((3aR,5R,6aR)-5-((tert-Butoxycarbonyl)amino)-3a-(3-(trifluoromethyl)-5,6,7,8-tetrahydro-1,6-naphthyridine-6-carbonyl)hexahydrocyclopenta[c]pyrrol-2(1H)-yl)acetic acid A solution of Intermediate 1 (0.22 g, 0.484 mmol), glyoxylic acid monohydrate (0.136 g, 1.452 mmol) and 4 Å molecular sieves (0.8 g) in DCM (8 ml) at 0° C. was added NaBH(OAc)$_3$ (0.216 g, 0.968 mol). The mixture was stirred at 0° C. for 30 min and at rt overnight. The reaction was quenched by addition of saturated NaHCO$_3$ solution, separated, extracted with DCM, and dried over Na$_2$SO$_4$. The crude product was obtained by evaporation. LC/MS: C$_{24}$H$_{31}$F$_3$N$_4$O$_5$: m/z 513.3 (M+H).

Step B. tert-Butyl((3aR,5R,6aR)-2-(2-(dimethylamino)-2-oxoethyl)-3a-(3-(trifluoromethyl)-5,6,7,8-tetrahydro-1,6-naphthyridine-6-carbonyl)octahydrocyclopenta-[c]pyrrol-5-yl)carbamate A solution the product from Step A (37 mg, 0.072 mmol), dimethylamine (0.0433 mL, 0.0866 mmol, 2 M in THF), EDAC (18 mg, 0.0938 mmol), HOBt (19.51 mg, 0.144 mmol) and DIPEA (0.0252 mL, 0.144 mmol) in DMF (3 mL) was stirred at rt over the weekend. The reaction was quenched by addition of brine, extracted with EtOAc, dried over $Na_2SO_4$ and purified by CombiFlash (eluent: 8% methanol in DCM) to give the product as a yellowish gel. $^1$H-NMR (400 MHz, $CDCl_3$): δ 1.29-1.43 (m, 9H), 1.75-2.09 (m, 4H), 2.20-2.35 (m, 1H), 2.55-2.71 (m, 3H), 2.86-3.00 (m, 4H), 3.05-3.22 (m, 6H), 3.60-3.93 (m, 2H), 4.25 (d, J=5.6 Hz, 1H), 4.59-4.92 (m, 3H), 7.70 (s, 1H), 8.70 (s, 1H); LC/MS: $C_{26}H_{36}F_3N_5O_4$: m/z 540.3 (M+H).

Step C. 2-((3aR,5R,6aR)-5-Amino-3a-(3-(trifluoromethyl)-5,6,7,8-tetrahydro-1,6-naphthyridine-6-carbonyl)hexahydrocyclopenta[c]pyrrol-2(1H)-yl)-N,N-dimethylacetamide The title compound was prepared analogously to Step B in Example 13 as a TFA salt. LC/MS: $C_{21}H_{28}F_3N_5O_2$: m/z 440.2 (M+H).

Step D. 2-((3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrol-2(1H)-yl)-N,N-dimethylacetamide The title compound was prepared analogously to Step C in Example 13 as a colorless gel. $^1$H-NMR (400 MHz, $CDCl_3$): δ 1.54-1.87 (m, 5H), 2.23 (br. s., 1H), 2.52-2.86 (m, 5H), 2.94 (s, 3H), 3.04 (s, 3H), 3.06-3.44 (m, 11H), 3.48-3.59 (m, 1H), 3.68 (d, J=4.8 Hz, 1H), 3.73-3.97 (m, 3H), 4.00-4.09 (m, 1H), 4.77 (br. s., 2H), 7.69 (s, 1H), 8.70 (s, 1H); LC/MS: $C_{27}H_{38}F_3N_5O_4$: m/z 554.5 (M+H).

Example 107

Methyl 2-((3aR,5R,6aR)-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrol-2(1H)-yl)acetate

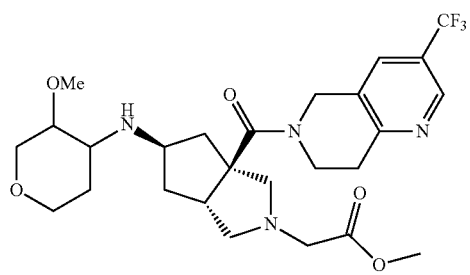 [SMILES: COC(=O)CN1C[C@@H]2C[C@@H](NC3CCOCC3OC)C[C@]2(C(=O)N2CCc3ncc(C(F)(F)F)cc3C2)C1]

Step A. Methyl 2-((3aR,5R,6aR)-5-((tert-butoxycarbonyl)amino)-3a-(3-(trifluoromethyl)-5,6,7,8-tetrahydro-1,6-naphthyridine-6-carbonyl)hexahydrocyclopenta[c]pyrrol-2(1H)-yl)acetate A solution of the product from Step A in Example 106 (52 mg, 0.101 mmol) in methanol (4 mL) was treated with (trimethylsilyl)diazomethane (2 M in hexanes, 0.304 mL, 0.609 mmol), and the resulting mixture was stirred at rt overnight. After removal of solvent, the residue was purified by CombiFlash (eluent: EtOAc) to give the product as a colorless gel. $^1$H-NMR (400 MHz, $CDCl_3$): δ 1.31-1.46 (m, 9H), 1.64-2.05 (m, 3H), 2.29 (br. s., 1H), 2.62 (dd, J=8.6, 3.0 Hz, 1H), 2.67-2.84 (m, 2H), 3.01-3.19 (m, 3H), 3.20-3.37 (m, 2H), 3.58-3.95 (m, 6H), 4.24 (br. s., 1H), 4.53-4.94 (m, 3H), 7.70 (s, 1H), 8.71 (s, 1H); LC/MS: $C_{25}H_{33}F_3N_4O_5$: m/z 527.2 (M+H).

Step B. Methyl 2-((3aR,5R,6aR)-5-amino-3a-(3-(trifluoromethyl)-5,6,7,8-tetrahydro-1,6-naphthyridine-6-carbonyl)hexahydrocyclopenta[c]pyrrol-2(1H)-yl)acetate The title compound was prepared analogously to Step B in Example 13 as a TFA salt. LC/MS: $C_{20}H_{25}F_3N_4O_3$: m/z 427.2 (M+H).

Step C. Methyl 2-((3aR,5R,6aR)-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrol-2(1H)-yl)acetate The title compound was prepared analogously to Step C in Example 13 as a colorless gel. $^1$H-NMR (400 MHz, $CDCl_3$): δ 1.85-2.08 (m, 3H), 2.19-2.45 (m, 2H), 2.49-2.82 (m, 4H), 3.06-3.49 (m, 12H), 3.56-3.75 (m, 5H), 3.80-4.06 (m, 4H), 4.17 (d, J=13.1 Hz, 1H), 4.70-5.00 (m, 2H), 7.73 (br. s., 1H), 8.70 (br. s., 1H); LC/MS: $C_{26}H_{35}F_3N_4O_5$: m/z 541.5 (M+H).

Example 108

((3aR,5R,6aR)-5-(((3S*,4S*)-3-Methoxytetrahydro-2H-pyran-4-yl)amino)-2-phenyloctahydrocyclopenta[c]pyrrol-3a-yl)(3-(trifluoromethyl)-7,8-dihydro-1,6-naphthyridin-6(5H)-yl)methanone

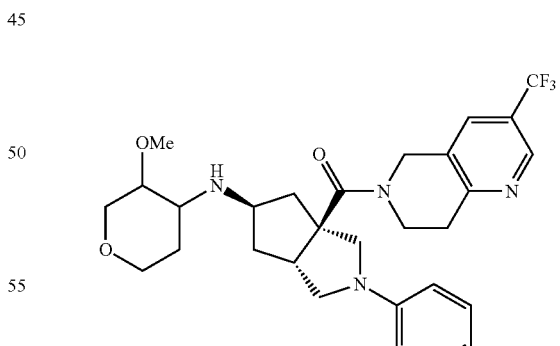

Step A. tert-Butyl((3aR,5R,6aR)-2-phenyl-3a-(3-(trifluoromethyl)-5,6,7,8-tetrahydro-1,6-naphthyridine-6-carbonyl)octahydrocyclopenta[c]pyrrol-5-yl)carbamate A mixture of Intermediate 1 (133 mg, 0.293 mmol), 2,6-lutidine (28.91 mg, 0.27 mmol), myristic acid (11.6 mg, 0.051 mmol), phenylboronic acid (52 mg, 0.427 mmol) and copper acetate (52 mg, 0.287 mmol) in toluene (6 mL) was stirred at rt for 2 days and diluted with toluene (25 mL), filtered. The filtrate was washed with saturated NaHCO₃ solution, brine and dried over Na₂SO₄. Filtration and evaporation to dryness gave the crude product as a clear oil. LC/MS: $C_{28}H_{33}F_3N_4O_3$: m/z 531 (M+H).

Step B. ((3aR,5R,6aR)-5-Amino-2-phenyloctahydro-cyclopenta[c]pyrrol-3a-yl)(3-(trifluoromethyl)-7,8-dihydro-1,6-naphthyridin-6(5H)-yl)methanone The title compound was prepared analogously to Step B in Example 13 as a TFA salt. LC/MS: $C_{23}H_{25}F_3N_4O$: m/z 431 (M+H).

Step C. ((3aR,5R,6aR)-5-(((3S*,4S*)-3-Methoxytetrahydro-2H-pyran-4-yl)amino)-2-phenyloctahydro-cyclopenta[c]pyrrol-3a-yl)(3-(trifluoromethyl)-7,8-dihydro-1,6-naphthyridin-6(5H)-yl)methanone The title compound was prepared analogously to Step C in Example 13 as a colorless gel. ¹H-NMR (400 MHz, CDCl₃): δ 1.80 (br. s., 1H), 1.89-2.32 (m, 4H), 2.76 (br. s., 1H), 3.08-3.59 (m, 16H), 3.76-4.08 (m, 5H), 4.25 (d, J=13.2 Hz, 1H), 6.66-6.81 (m, 3H), 7.19 (t, J=7.9 Hz, 2H), 8.05 (s, 1H), 8.72 (s, 1H); LC/MS: $C_{29}H_{35}F_3N_4O_3$: m/z 545 (M+H).

Example 109

((3aR,5R,6aR)-5-(((3S*,4S*)-3-Methoxytetrahydro-2H-pyran-4-yl)amino)-2-phenyloctahydro-cyclo-penta[c]pyrrol-3a-yl)(3-(trifluoromethyl)-7,8-dihy-dro-1,6-naphthyridin-6(5H)-yl)methanone

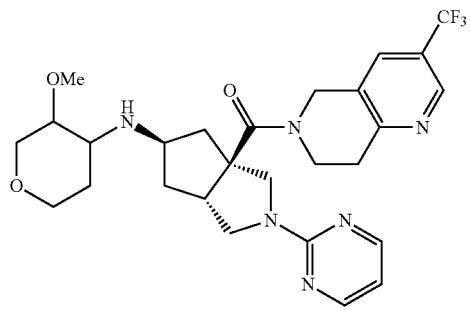 [SMILES: COC1COCCC1N[C@@H]1C[C@H]2CN(c3ccccc3)C[C@@]2(C(=O)N2CCc3ncc(C(F)(F)F)cc3C2)C1]

A mixture of Example 1 (32 mg, 0.0554 mmol), 2-bromopyrimidine (13.9 mg, 0.0831 mmol) in TEA (0.0385 mL, 0.277 mmol) and EtOH (2 mL) in a sealed tube was heated at 90° C. overnight. After removal of solvent by evaporation, the residue was purified by CombiFlash (eluent: 5% 7N NH₃ in methanol in DCM) to give the product as a colorless gel. ¹H-NMR (400 MHz, CDCl₃): δ 1.55-2.01 (m, 5H), 2.39 (br. s., 1H), 2.73 (m, 2H), 3.05-3.67 (m, 11H), 3.77-4.12 (m, 7H), 4.63-5.00 (m, 2H), 6.53 (t, J=4.7 Hz, 1H), 7.70 (s, 1H), 8.31 (d, J=4.5 Hz, 2H), 8.72 (br. s., 1H); LC/MS: $C_{27}H_{33}F_3N_6O_3$: m/z 547.2 (M+H).

Example 110

((3aR,5R,6aR)-5-(((3S*,4S*)-3-Methoxytetrahydro-2H-pyran-4-yl)amino)-2-(thiazol-2-yl)octahydrocy-clopenta[c]pyrrol-3a-yl)(3-(trifluoromethyl)-7,8-dihydro-1,6-naphthyridin-6(5H)-yl)methanone

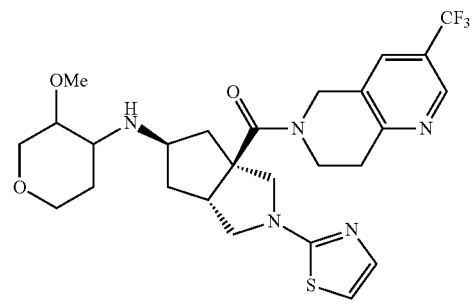 [SMILES: COC1COCCC1N[C@@H]1C[C@H]2CN(c3nccs3)C[C@@]2(C(=O)N2CCc3ncc(C(F)(F)F)cc3C2)C1]

A mixture of Example 1 (HCl salt, 32 mg, 0.0554 mmol), 2-bromothiazole (13.62 mg, 0.0831 mmol), TEA (0.0385 mL, 0.277 mmol) and potassium fluoride (1.61 mg, 0.0277 mmol) in ethanol (1 mL) in a sealed tube was heated at 90° C. for 6 days. After aqueous work up, the residue was purified by CombiFlash (eluent: 5% methanol in DCM) to give the product. ¹H-NMR (400 MHz, CDCl₃): δ 1.50-1.93 (m, 5H), 2.12-2.47 (m, 2H), 2.65-2.80 (m, 2H), 3.03-4.19 (m, 17H), 4.64-5.01 (m, 2H), 6.55 (d, J=3.5 Hz, 1H), 7.20 (d, J=3.5 Hz, 1H), 7.69 (br. s., 1H), 8.71 (d, J=5.1 Hz, 1H); LC/MS: $C_{26}H_{32}F_3N_5O_3S$: m/z 552.2 (M+H).

Example 111

((3aR,5R,6aR)-5-(((3S*,4S*)-3-Methoxytetrahydro-2H-pyran-4-yl)amino)-2-(3-methyl-1,2,4-oxadiazol-5-yl)octahydrocyclopenta[c]pyrrol-3a-yl)(3-(trifluo-romethyl)-7,8-dihydro-1,6-naphthyridin-6(5H)-yl)methanone

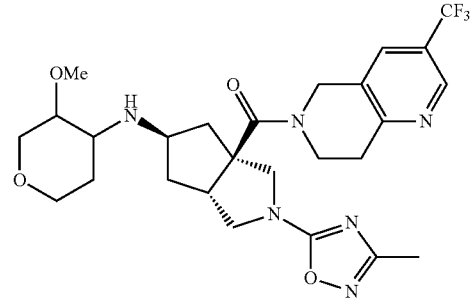 [SMILES: COC1COCCC1N[C@@H]1C[C@H]2CN(c3nc(C)no3)C[C@@]2(C(=O)N2CCc3ncc(C(F)(F)F)cc3C2)C1]

A mixture of 3-methyl-1,2,4-oxadiazol-5(4H)-one (21.36 mg, 0.213 mmol), DIPEA (0.184 mL, 1.067 mmol) and PyBrOP (99.5 mg, 0.213 mmol) in 1,4-dioxane (3 mL) was stirred at 50° C. for 1 h, followed by addition of Example 1 (HCl salt, 50 mg, 0.107 mmol). The resulting mixture was stirred at 50° C. overnight. After aqueous work up, the residue was purified by CombiFlash (eluent: 6% 7N NH₃ in methanol in DCM) to give the product. ¹H-NMR (400 MHz, CD₃OD): δ 1.55-1.96 (m, 8H), 2.12-2.27 (5, 3H), 2.30-2.45 (m, 1H), 2.74 (d, J=1.0 Hz, 1H), 3.11-3.56 (m, 10H), 3.77-3.97 (m, 5H), 4.01-4.13 (m, 1H), 4.65-5.02 (m, 2H), 7.70 (s, 1H), 8.73 (s, 1H); LC/MS: $C_{26}H_{33}F_3N_6O_4$: m/z 551 (M+H).

Example 112

((3aR,5R,6aR)-2-(4,5-Dihydrothiazol-2-yl)-5-(((3S*,4S*)-3-methoxytetrahydro-2H-pyran-4-yl)amino)octahydrocyclopenta[c]pyrrol-3a-yl)(3-(trifluoromethyl)-7,8-dihydro-1,6-naphthyridin-6(5H)-yl)methanone

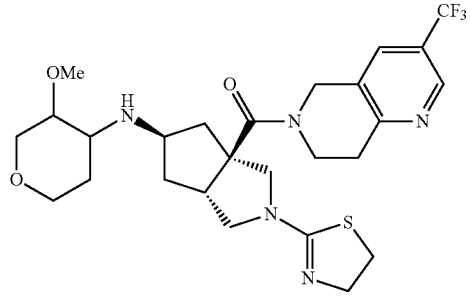 [SMILES: COC1COCCC1N[C@@H]1C[C@H]2CN(C3=NCCO3)C[C@@]2(C(=O)N2CCc3ncc(C(F)(F)F)cc3C2)C1]

Step A. tert-Butyl((3aR,5R,6aR)-2-(4,5-dihydrothiazol-2-yl)-3a-(3-(trifluoromethyl)-5,6,7,8-tetrahydro-1,6-naphthyridine-6-carbonyl)octahydrocyclopenta[c]pyrrol-5-yl)carbamate To a solution of Intermediate 1 (0.114 mg, 0.251 mmol) and TEA (253 mg, 2.503 mmol) in DCM (5 mL) was added 2-bromoethyl isothiocyanate (50 mg, 0.301 mmol). The mixture was stirred at rt overnight. The reaction mixture was quenched by addition of brine, extracted with DCM, dried over $Na_2SO_4$. Filtration and evaporation to dryness gave the product as a tan solid. LC/MS: $C_{25}H_{32}F_3N_5O_3S$: m/z 540 (M+H).

Step B. ((3aR,5R,6aR)-5-Amino-2-(4,5-dihydrothiazol-2-yl)octahydrocyclopenta-[c]pyrrol-3a-yl)(3-(trifluoromethyl)-7,8-dihydro-1,6-naphthyridin-6(5H)-yl)methanone ditrifluoroacetate The title compound was prepared analogously to Step B in Example 13 as a TFA salt. LC/MS: $C_{20}H_{24}F_3N_5OS$: m/z 440 (M+H).

Step C. ((3aR,5R,6aR)-2-(4,5-Dihydrothiazol-2-yl)-5-(((3S*,4S*)-3-methoxytetrahydro-2H-pyran-4-yl)amino)octahydrocyclopenta[c]pyrrol-3a-yl)(3-(trifluoromethyl)-7,8-dihydro-1,6-naphthyridin-6(5H)-yl)methanone The title compound was prepared analogously to Step C in Example 13 as a yellow gel. $^1$H-NMR (400 MHz, $CD_3OD$): δ 1.80-2.02 (m, 2H), 2.09-2.36 (m, 3H), 2.94-3.17 (m, 1H), 3.21-3.75 (m, 13H), 3.80-4.32 (m, 11H), 4.85-5.05 (m, 2H), 8.55 (br. s., 1H), 9.03 (br. s., 1H); LC/MS: $C_{26}H_{34}F_3N_5O_3S$: m/z 554 (M+H).

Example 113

((3aR,5R,6aR)-2-(4,5-Dihydrooxazol-2-yl)-5-(((3S*,4S*)-3-methoxytetrahydro-2H-pyran-4-yl)amino)octahydrocyclopenta[c]pyrrol-3a-yl)(3-(trifluoromethyl)-7,8-dihydro-1,6-naphthyridin-6(5H)-yl)methanone

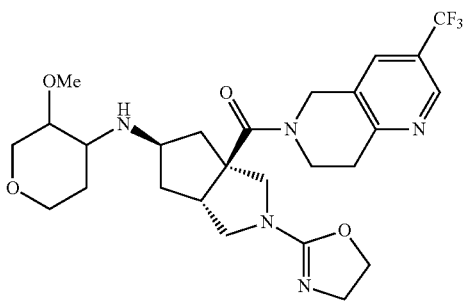

The title compound was prepared analogously to Example 112 while using 2-bromoethyl isocyanate instead of 2-bromoethyl isothiocyanate in Step A; the product was isolated as a white salt. $^1$H-NMR (400 MHz, $CD_3OD$): δ 1.82-2.01 (m, 2H), 2.06-2.38 (m, 3H), 2.79-3.16 (m, 1H), 3.23-4.30 (m, 23H), 4.78-5.12 (m, 2H), 8.77 (br. s., 1H), 9.10-9.24 (m, 1H); LC/MS: $C_{26}H_{34}F_3N_5O_4$: m/z 538 (M+H).

Example 114

(3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrole-2(1H)-carbaldehyde

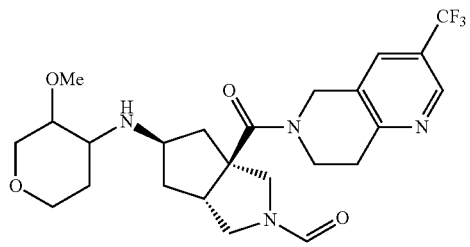 [SMILES: COC1COCCC1N[C@@H]1C[C@H]2CN(C=O)C[C@@]2(C(=O)N2CCc3ncc(C(F)(F)F)cc3C2)C1]

A mixture of Example 1 (70.28 mg, 0.15 mmol) in ethyl formate (1 mL) in a sealed tube was heated at 70° C. overnight. After cooling to rt, the mixture was concentrated and purified by CombiFlash (eluent: 8% methanol in DCM) gave the product as a yellowish gel. $^1$H-NMR (400 MHz, $CDCl_3$): δ 1.50-1.97 (m, 5H), 2.28 (br. s., 1H), 2.72 (br. s., 1H), 2.92-3.51 (m, 11H), 3.59-4.16 (m, 8H), 4.61-5.02 (m, 2H), 7.70 (br. s., 1H), 8.08-8.24 (m, 1H), 8.73 (br. s., 1H); LC/MS: $C_{24}H_{31}F_3N_4O_4$: m/z 497.2 (M+H).

Example 115

(3aR,5R,6aR,E)-N'-Cyano-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydrocyclopenta-[c]pyrrole-2(1H)-carboximidamide

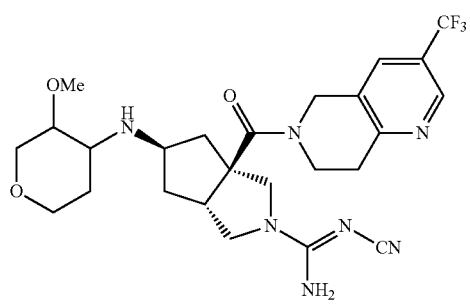 [SMILES: COC1COCCC1N[C@@H]1C[C@H]2CN(/C(N)=N/O)C[C@@]2(C(=O)N2CCc3ncc(C(F)(F)F)cc3C2)C1]

A mixture of Example 1 (HCl salt, 50 mg, 0.0865 mmol), sodium dicyanamide (10.32 mg, 0.116 mmol) in 5% water in i-PrOH (1.2 mL) in a sealed tube was flushed with Ar and heated at 120° C. for 5 h. After cooling to rt, the mixture was diluted with DCM, filtered and evaporated. The residue was purified by CombiFlash (eluent: 10% 7N $NH_3$ in methanol in DCM) to give the product as a colorless gel. $^1$H-NMR (400 MHz, $CDCl_3$): δ 1.54-1.92 (m, 5H), 2.37 (br. s., 1H), 2.71 (br. s., 1H), 3.07-4.23 (m, 19H), 4.66-4.96 (m, 2H), 5.80 (m, 2H), 7.73 (s, 1H), 8.71 (br. s., 1H); LC/MS: $C_{25}H_{32}F_3N_7O_3$: m/z 536.2 (M+H).

Example 116

(3aR,5R,6aR,E)-N'-Hydroxy-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydro-cyclopenta[c]pyrrole-2(1H)-carboximidamide

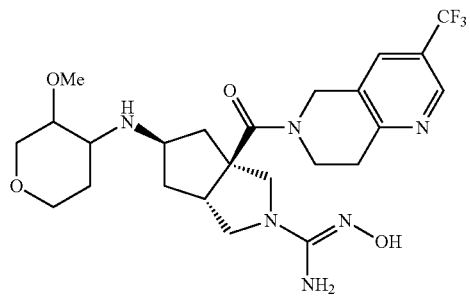

Step A. tert-Butyl((3aR,5R,6aR)-2-((E)-N'-hydroxycarbamimidoyl)-3a-(3-(trifluoromethyl)-5,6,7,8-tetrahydro-1,6-naphthyridine-6-carbonyl)octahydrocyclopenta-[c]pyrrol-5-yl)carbamate A mixture of the product of Step A of Example 2 (0.12 g, 0.25 mmol), hydroxylamine hydrochloride (43.48 mg, 0.626 mmol) and TEA (0.087 mL, 0.626 mmol) in ethanol (1.2 mL) in a sealed tube in Ar was heated at 80° C. overnight. After removal of solvent, the residue was partitioned between EtOAc and brine, separated, dried over $Na_2SO_4$. Purification by CombiFlash (eluent: 8% methanol in DCM) gave the product as a white solid. $^1$H-NMR (400 MHz, $CDCl_3$): δ 1.30-1.45 (m, 9H), 1.70-1.99 (m, 3H), 2.38 (br. s., 1H), 3.09 (d, J=9.3 Hz, 3H), 3.28-3.54 (m, 3H), 3.65-3.89 (m, 3H), 4.23 (d, J=5.1 Hz, 1H), 4.44-4.93 (m, 5H), 7.72 (br. s., 1H), 8.69 (s, 1H); LC/MS: $C_{23}H_{31}F_3N_6O_4$: m/z 513 (M+H).

Step B. (3aR,5R,6aR,E)-5-Amino-N'-hydroxy-3a-(3-(trifluoromethyl)-5,6,7,8-tetrahydro-1,6-naphthyridine-6-carbonyl)hexahydrocyclopenta[c]pyrrole-2(1H)-carboximidamide The title compound was prepared analogously to Step B in Example 13 as TFA salt. LC/MS: $C_{18}H_{23}F_3N_6O_2$: m/z 413.0 (M+H).

Step C. (3aR,5R,6aR,E)-N'-Hydroxy-5-(((3S*,4S*)-3-methoxytetrahydro-2H-pyran-4-yl)amino)-3a-(3-(trifluoromethyl)-5,6,7,8-tetrahydro-1,6-naphthyridine-6-carbonyl)hexahydro-cyclopenta[c]pyrrole-2(1H)-carboximidamide The title compound was prepared analogously to Step C in Example 13 as a colorless gel. $^1$H-NMR (400 MHz, $CDCl_3$): δ 1.53-1.91 (m, 6H), 2.28 (br. s., 1H), 2.73 (br. s., 1H), 2.95-3.58 (m, 14H), 3.67-3.98 (m, 4H), 4.00-4.14 (m, 1H), 4.39 (br. s., 2H), 4.63-4.95 (m, 2H), 7.69 (s, 1H), 8.70 (s, 1H); LC/MS: $C_{24}H_{33}F_3N_6O_4$: m/z 527.2 (M+H).

Example 117

(3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydrocyclopenta[c]pyrrole-2(1H)-carbonitrile

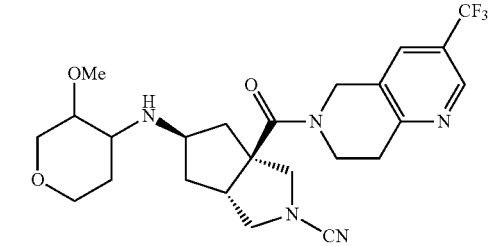 [SMILES: COC1COCCC1N[C@@H]1C[C@H]2CN(C#N)C[C@@]2(C(=O)N2CCc3ncc(C(F)(F)F)cc3C2)C1]

A mixture of Example 1 (0.05 g, 0.107 mmol) and potassium carbonate (17.7 mg, 0.128 mmol) in acetonitrile (1 mL) was added cyanogen bromide (5M in acetonitrile, 0.0213 mL, 0.107 mmol) and stirred at rt overnight. The mixture was filtered and the filtrate was concentrated in vacuo. The residue was purified by CombiFlash (eluent: 8% methanol in DCM) to give Example 117 as a colorless gel.

$^1$H-NMR (400 MHz, $CDCl_3$): δ 1.15-1.87 (m, 5H), 2.22-2.38 (m, 2H), 2.73 (br. s., 1H), 3.06-4.22 (m, 18H), 4.73 (br. s., 2H), 7.70 (br. s., 1H), 8.73 (br. s., 1H); LC/MS: $C_{24}H_{30}F_3N_5O_3$: m/z 494.2 (M+H).

Intermediate 9

(3aR,5R,6aS)-tert-Butyl 5-((tert-butoxycarbonyl) amino)-1-oxo-6a-(3-(trifluoromethyl)-5,6,7,8-tetrahydro-1,6-naphthyridine-6-carbonyl)hexahydrocyclopenta-[c]pyrrole-2(1H)-carboxylate

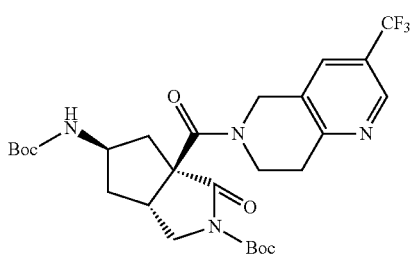 [SMILES: CC(C)(C)OC(=O)N[C@@H]1C[C@H]2CN(C(=O)OC(C)(C)C)C(=O)[C@@]2(C(=O)N2CCc3ncc(C(F)(F)F)cc3C2)C1]

Step A. (3aR,5R,6aR)-2-tert-Butyl 3a-methyl 5-((tert-butoxycarbonyl)amino)-hexahydrocyclopenta[c]pyrrole-2,3a(1H)-dicarboxylate A solution of the product from Step D in Intermediate 1 (1.314 g, 4.62 mmol), TEA (3 mL, 21.583 mmol) and di-tert-butyl dicarbonate (1.559 g, 6.93 mmol) in DCM (30 mL) was stirred at rt overnight. The reaction was quenched by addition of 0.5 N aqueous hydrochloric acid. The organic phase was washed with saturated NaHCO$_3$ solution, brine, and dried over Na$_2$SO$_4$. Purification by CombiFlash (eluent: 20% EtOAc in hexanes to 40%) gave the product as a colorless gel. $^1$H-NMR (400 MHz, CDCl$_3$): δ 1.36-1.55 (m, 18H), 1.83-1.98 (m, 2H), 2.07-2.21 (m, 2H), 2.96 (br. s., 1H), 3.23 (br. s., 2H), 3.49-3.67 (m, 1H), 3.74 (s, 3H), 3.81-3.95 (m, 1H), 4.23 (d, J=6.1 Hz, 1H), 4.85 (br. s., 1H); LC/MS: C$_{19}$H$_{32}$N$_2$O$_6$: m/z 791 (2M+H).

Step B. (3aR,5R,6aR)-2-tert-Butyl 3a-methyl 5-((tert-butoxycarbonyl)amino)-3-oxohexahydrocyclopenta[c]pyrrole-2,3a(1H)-dicarboxylate and (3aR,5R,6aR)-2-tert-butyl 3a-methyl 5-((tert-butoxycarbonyl)amino)-1-oxohexahydrocyclopenta[c]pyrrole-2,3a(1H)-dicarboxylate To a solution of the product from Step A (0.17 g, 0.442 mmol) in ACN (0.5 mL) was added RuCl$_3$ (1.834 mg, 0.00884 mmol), followed by a solution of sodium bromate (0.1 g, 0.663 mmol) in water (1.2 mL). The resulting biphasic mixture was stirred at rt for 12 h. The mixture was diluted with EtOAc and the organic phase was washed with Na$_2$S$_2$O$_3$, brine, and dried over Na$_2$SO$_4$. Purification by CombiFlash (eluent: 20% EtOAc in hexanes to 30%) gave a mixture of two isomers as a colorless gel. LC/MS: C$_{19}$H$_{30}$N$_2$O$_7$: m/z 819.2 (2M+H).

Step C. (3aR,5R,6aR)-2-(tert-Butoxycarbonyl)-5-((tert-butoxycarbonyl)amino)-3-oxooctahydrocyclopenta[c]pyrrole-3a-carboxylic acid and (3aR,5R,6aR)-2-(tert-butoxycarbonyl)-5-((tert-butoxycarbonyl)amino)-1-oxooctahydrocyclopenta[c]pyrrole-3a-carboxylic acid A solution of the products from Step B (0.46 g, 1.154 mmol) in THF (0.6 mL) and methanol (0.6 mL) was added 6 N KOH solution (0.577 mL, 3.463 mL). The mixture was stirred at rt for 4 h. After concentration, the residue was acidified by a cooled 1N hydrochloric acid, extracted with EtOAc, and dried over Na$_2$SO$_4$. Filtration and evaporation to dryness gave the crude product as a mixture. LC/MS: C$_{18}$H$_{28}$N$_2$O$_7$: m/z 569.3 (2M+H-2Boc).

Step D. (3aR,5R,6aS)-tert-Butyl 5-((tert-butoxycarbonyl)amino)-1-oxo-6a-(3-(trifluoromethyl)-5,6,7,8-tetrahydro-1,6-naphthyridine-6-carbonyl)hexahydrocyclopenta-[c]pyrrole-2(1H)-carboxylate and (3aR,5R,6aR)-tert-butyl 5-((tert-butoxycarbonyl)amino)-1-oxo-3a-(3-(trifluoromethyl)-5,6,7,8-tetrahydro-1,6-naphthyridine-6-carbonyl)hexahydrocyclopenta[c]pyrrole-2(1H)-carboxylate To a solution of the products from Step C (0.37 g, 0.962 mmol) and 3-(trifluoromethyl)-5,6,7,8-tetrahydro-1,6-naphthyridine dihydrochloride (0.318 g, 1.155 mmol) in DMF (5 mL) was added DIPEA (1.327 mL, 7.7 mmol), EDAC (0.24 g, 1.251 mol) and HOBt (0.26 g, 1.925 mmol). The resulting mixture was stirred at rt overnight. The reaction was quenched by addition of brine, extracted with EtOAc, and dried over Na$_2$SO$_4$. Evaporation and purification by column chromatography (eluent: 40% EtOAc in hexanes to 60%) gave the Intermediate 9 (less polar fraction) as a colorless gel and the Intermediate 10 (polar fraction). Spectra for 9: $^1$H-NMR (400 MHz, CDCl$_3$): δ 1.35 (br. s., 9H), 1.46-1.58 (m, 9H), 1.84 (dt, J=13.1, 9.0 Hz, 1H), 2.00-2.19 (m, 1H), 2.49 (dd, J=12.1, 6.3 Hz, 2H), 3.17 (br. s., 2H), 3.76-4.20 (m, 6H), 4.52-5.02 (m, 3H), 7.72 (br. s., 1H), 8.73 (br. s., 1H); LC/MS: C$_{27}$H$_{35}$F$_3$N$_4$O$_6$: m/z 469.2 (M-Boc).

Intermediate 10

(3aR,5R,6aR)-tert-Butyl 5-((tert-butoxycarbonyl) amino)-1-oxo-3a-(3-(trifluoromethyl)-5,6,7,8-tetrahydro-1,6-naphthyridine-6-carbonyl)hexahydrocyclopenta[c]pyrrole-2(1H)-carboxylate

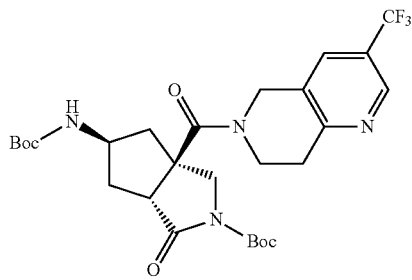 [SMILES: CC(C)(C)OC(=O)N[C@@H]1C[C@H]2C(=O)N(C(=O)OC(C)(C)C)C[C@@]2(C(=O)N2CCc3ncc(C(F)(F)F)cc3C2)C1]

The title compound was prepared as described in the procedure for Intermediate 9. $^1$H-NMR (400 MHz, CDCl$_3$): δ 1.30-1.45 (m, 18H), 1.84 (s, 1H), 2.21-2.37 (m, 1H), 2.52-2.67 (m, 1H), 3.03-3.45 (m, 3H), 3.56-3.98 (m, 1H), 4.02-4.34 (m, 3H), 4.52-4.64 (m, 1H), 4.80-4.95 (m, 2H), 5.10 (br. s., 1H), 7.69 (br. s., 1H), 8.70 (br. s., 1H); LC/MS: C$_{27}$H$_{35}$F$_3$N$_4$O$_6$: m/z 469.2 (M-Boc).

Example 118

(3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydro-cyclopenta[c]pyrrol-(2H)-one

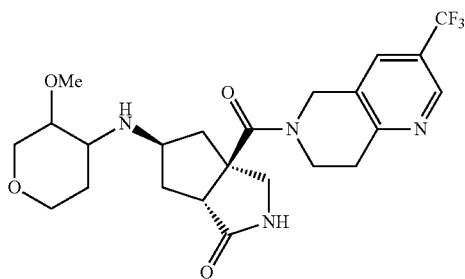 [SMILES: COC1COCCC1N[C@@H]1C[C@H]2C(=O)NC[C@@]2(C(=O)N2CCc3ncc(C(F)(F)F)cc3C2)C1]

Step A. (3aR,5R,6aR)-5-Amino-3a-(3-(trifluoromethyl)-5,6,7,8-tetrahydro-1,6-naphthyridine-6-carbonyl)hexahydrocyclopenta[c]pyrrol-1(2H)-one The title compound was prepared from Intermediate 10 analogously to Step B in Example 13 as a TFA salt. LC/MS: $C_{17}H_{19}F_3N_4O_2$: m/z 369.2 (M+H).

Step B. (3aR,5R,6aR)-5-(((3S*,4S*)-3-Methoxytetrahydro-2H-pyran-4-yl)amino)-3a-(3-(trifluoromethyl)-5,6,7,8-tetrahydro-1,6-naphthyridine-6-carbonyl)hexahydro-cyclopenta[c]pyrrol-1(2H)-one The title compound was prepared analogously to Step C in Example 13. $^1$H-NMR (400 MHz, CDCl$_3$): δ 1.25 (s, 2H), 1.63 (br. s., 5H), 2.23 (t, J=5.3 Hz, 1H), 2.82 (br. s., 1H), 3.04-3.74 (m, 13H), 3.89-4.31 (m, 5H), 7.59 (s, 1H), 8.68 (br. s., 1H); LC/MS: $C_{23}H_{29}F_3N_4O_4$: m/z 483.3 (M+H).

Example 119

(3aR,5R,6aR)-5-(((3S*,4S*)-3-Methoxytetrahydro-2H-pyran-4-yl)amino)-6a-(3-(trifluoromethyl)-5,6,7,8-tetrahydro-1,6-naphthyridine-6-carbonyl)hexahydrocyclopenta-[c]pyrrol-1(2H)-one

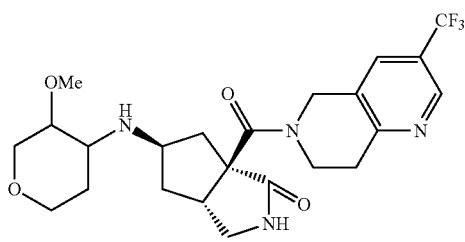 [SMILES: COC1COCCC1N[C@@H]1C[C@H]2CNC(=O)[C@@]2(C(=O)N2CCc3ncc(C(F)(F)F)cc3C2)C1]

The title compound was prepared from Intermediate 9 analogously to Example 118. $^1$H-NMR (400 MHz, CDCl$_3$): δ 1.58-1.77 (m, 4H), 1.91-2.05 (m, 1H), 2.32-2.47 (m, 2H), 2.69-2.84 (m, 1H), 3.08-3.45 (m, 9H), 3.53 (d, J=9.1 Hz, 1H), 3.67-4.18 (m, 6H), 4.80 (br. s., 2H), 6.54 (d, J=13.6 Hz, 1H), 7.70 (br. s., 1H), 8.73 (br. s., 1H); LC/MS: $C_{23}H_{29}F_3N_4O_4$: m/z 483.3 (M+H).

Example 120

In Vitro Biological Data

Compounds of the invention were subjected to various representative biological tests. The results of these tests are intended to illustrate the invention in a non-limiting fashion. MCP-1 Receptor Binding Assay in THP-1 Cells Human monocytic cell line THP-1 cells were obtained from American Type Culture Collection (Manassas, Va., USA). The THP-1 cells were grown in RPMI-1640 (RPMI: Roswell Park Memorial Institute Medium-cell culture growth media) supplemented with 10% fetal bovine serum in a humidified 5% $CO_2$ atmosphere at 37° C. The cell density was maintained between $0.5×10^6$ cells/mL.

THP-1 (cells were incubated with 0.5 nM $^{125}$I labeled MCP-1 (Perkin-Elmer Life Sciences, Inc. Boston, Mass.) in the presence of varying concentrations of either unlabeled MCP-1 (R & D Systems, Minneapolis, Minn.) or test compound for 2 hours at 30° C. in a 96 well plate. Cells were then harvested onto a filter plate, dried, and 20 μL of Microscint 20 was added to each well. Plates were counted in a TopCount NXT, Microplate Scintillation & Luminescence Counter (Perkin-Elmer Life Sciences, Inc. Boston, Mass.). Blank values (buffer only) were subtracted from all values and drug treated values were compared to vehicle treated values. 1 μM cold MCP-1 was used for nonspecific binding.

$IC_{50}$ values for inhibition of MCP-1 binding to CCR2 were obtained for test compounds of the invention.

| example | MCP1B_v3 IC50 (μM) |
|---|---|
| 1 | 0.78 |
| 2 | 0.06 |
| 3 | 0.03 |
| 4 | 0.04 |
| 5 | 1.35 |
| 6 | 0.01 |
| 7 | 5.06 |
| 8 | 0.17 |
| 9 | 0.19 |
| 10 | 0.32 |
| 11 | 0.32 |
| 12 | 0.10 |
| 13 | 0.08 |
| 14 | 0.41 |
| 15 | 0.11 |
| 16 | 0.47 |
| 17 | 0.06 |
| 18 | 0.41 |
| 19 | 0.38 |
| 20 | |
| 21 | 0.22 |
| 22 | 0.42 |
| 23 | 0.28 |
| 24 | 0.05 |
| 25 | 0.09 |
| 26 | 0.20 |
| 27 | 0.03 |
| 28 | 0.25 |
| 29 | 0.03 |
| 30 | 0.09 |
| 31 | 0.08 |
| 32 | 0.13 |
| 33 | 0.41 |
| 34 | 0.05 |
| 35 | 0.06 |
| 36 | 0.56 |
| 37 | 0.15 |
| 38 | 0.04 |
| 39 | 0.01 |
| 41 | 0.01 |

| example | MCP1B_v3 IC50 (μM) |
|---|---|
| 42 | 0.03 |
| 43 | 0.03 |
| 44 | 0.08 |
| 45 | 0.07 |
| 46 | 0.03 |
| 47 | 0.03 |
| 48 | 0.08 |
| 49 | 0.01 |
| 50 | 0.03 |
| 51 | 0.14 |
| 52 | 0.13 |
| 53 | 0.20 |
| 54 | 0.15 |
| 55 | 0.01 |
| 56 | 0.12 |
| 57 | 2.03 |
| 58 | 0.20 |
| 59 | 0.22 |
| 60 | 0.10 |
| 61 | 0.39 |
| 62 | 0.06 |
| 63 | 0.05 |
| 64 | 0.04 |
| 65 | 0.03 |
| 66 | 0.40 |
| 67 | 0.11 |
| 68 | 0.13 |
| 69 | 0.15 |
| 70 | 0.08 |
| 71 | 0.16 |
| 72 | 0.03 |
| 73 | 0.36 |
| 74 | |
| 75 | 0.17 |
| 76 | 0.16 |
| 77 | 0.23 |
| 78 | 0.23 |
| 79 | 0.50 |
| 80 | 0.23 |
| 81 | 0.04 |
| 82 | No Data |
| 83 | No Data |
| 84 | No Data |
| 85 | No Data |
| 86 | 0.09 |
| 87 | 0.36 |
| 88 | 0.04 |
| 89 | 0.01 |
| 90 | 0.01 |
| 91 | 0.61 |
| 92 | 1.10 |
| 93 | 0.98 |
| 94 | 0.18 |
| 95 | 0.03 |
| 96 | 1.22 |
| 97 | 0.30 |
| 98 | 0.63 |
| 99 | 0.13 |
| 100 | 0.03 |
| 101 | 0.37 |
| 102 | 1.00 |
| 103 | 1.00 |
| 104 | 1.98 |
| 105 | 0.12 |
| 106 | 2.80 |
| 107 | 1.10 |
| 108 | 0.12 |
| 109 | 1.30 |
| 110 | 0.15 |
| 111 | 0.27 |
| 112 | 3.66 |
| 113 | 0.10 |
| 114 | 0.37 |
| 115 | 0.04 |
| 116 | 1.80 |
| 117 | 5.40 |
| 118 | 22.78 |
| 119 | 12.01 |

Example 121

Animals

Mouse CCR2 knock-out/human CCR2 knock-in mice are generated using targeted 129Sv/Evbrd embryonic stem cell clones injected into C57BL/6 mice. Expression of the hCCR2 transcript is confirmed by quantitative reverse transcription-polymerase chain reaction performed on spleen and blood total RNA from homozygous hCCR2 knock-in mice. Backcrossing into C57BL/6 genetic background continued to the eighth generation. Transgenic mice are housed in a specific-pathogen-free, temperature-controlled facility that maintained a 12-hour light/12-hour dark cycle. Mice have free access to water and food. Experimental procedures are carried out in accordance with institutional standards for animal care and are approved by the institute's animal care and use committee.

Example 122

Murine In Vivo Cell Migration Assay

Animals are orally dosed with vehicle or CCR2 antagonists at 3, 10 and 30 mg/kg bid. Animals undergo anesthesia and laparotomy. A distal loop of small bowel (5 cm in length) is gently eventrated onto moist sterile gauze. Synthetic human MCP-1 (1 mg/100 ml sterile PBS) or PBS alone is administered drop-wise onto the serosa of the eventrated loop. A suture knot is placed into the mesentery to mark the terminus of the treated area. Twenty-four hours later, the animal is sacrificed and the segment of bowel plus the adjacent region is removed. The tissue is opened along the mesenteric border, pinned flat and the mucosa removed. The remaining muscle layer is fixed briefly in 100% EtOH and then stained using Hanker-Yates reagent to detect myeloperoxidase-containing immune cells. At 10 mpk, P.O. bid, a compound is deemed efficacious if the inhibition of cell migration reaches 30% compared with vehicle-treated animals.

Example 123

Thiolycollate-Induced Peritonitis in Mice

Animals are orally dosed with vehicle or CCR2 antagonists at 3, 10, 30 and 100 mg/kg bid). One hour later, the animals are intraperiponeally injected with sterile thioglycollate (25 mL/kg, ip, Sigma) for induction of peritonitis. Animals are orally treated twice daily with vehicle or CCR2 antagonists. At the 72-hour time point, perinoteal cavities are lavaged with 10 mL of sterile saline. Total cell counts in the peritoneal lavage fluid are performed using a microscope and cell differentiation is performed using cytospin analysis after Giemsa staining (Hema Tek 2000). Percent inhibition of the thioglycollate-induced peritonitis is calculated by comparing the change in number of leukocytes of CCR2 antagonist treated mice to the vehicle-treated mice.

Example 124

MCP-1-Induced Monocyte Recruitment to Airway of Mice

Animals are orally treated with vehicle or CCR2 antagonists at 3, 10, and 30 mg/kg po bid). One hour later, the animals are intranasally dosed with 4 µg of MCP-1 in sterile saline. The animals are orally treated twice daily with vehicle or CCR2 antagonists. After 48 h, mice are euthanized by intraperitoneal injection of anesthesia solution (Sleepaway-Sodium pentobarbital). Whole bronchoalveolar lavage (BAL) is performed using 1.4 ml of ice-cold PBS containing 3 mM EDTA. Total cell counts in the BAL lavage fluid are performed using a microscope and cell differentiation is performed using cytospin analysis after Giemsa staining (Hema Tek 2000). Percent inhibition is calculated by comparing the change in number of total leukocyte counts (including monocytes/macrophages and lymphocytes) of compound-treated mice to the vehicle-treated mice. Compounds are deemed efficacious if percent inhibition reaches 30%.

Example 125

High-Fat Diet Induced Obesity and Insulin Resistance in Mice

Obesity is induced by a high-fat diet that derived approximately 60% calories from lipids (D-12492; Research Diets Inc.) in animals for 10-24 weeks at age of 7 weeks. Prior to age 7 weeks, animals are fed a standard pellet diet, in which 5% of calories were provided as fat. Obese animals were randomized by body weight and fat mass. The obese animals are orally treated with vehicle or CCR2 antagonists at 3, 10 and 30 mg/kg, po bid. Body weight and food intake and were fasting blood glucose levels monitored. Body mass was determined by a NMR analyzer (Burker MiniSpec). Insulin tolerance test is carried out in animals that were fasted for 3 hours. After an intraperitoneal bolus injection of recombinant human insulin (1.5 U/kg), blood glucose concentrations are measured using a Glucometer before and 15, 30, 45, 60, 90 and 120 minutes after injection. Glucose tolerance tests are performed after an overnight (17-hour) fast. Blood glucose concentrations are measured before and after 15, 30, 60, 90, 120 minutes after an oral dose of glucose dissolved in water (1 g/kg). Energy expenditure analysis was monitored by a complete laboratory animal monitor system. After 40 days treatment with vehicle or CCR2 antagonists, the animals are sacrificed by $CO_2$ asphyxiation. Percent of weight loss is calculated by comparing the body weight changes of the compound-treated mice with the vehicle-treated mice.

Example 126

Mouse Model of Allergic Asthma

Animals are sensitized by intraperitoneal injection of 10 µg chicken egg albumin (OVA) absorbed to 1 mg Imject® in 100 µL phosphate-buffered saline (PBS) on days 0 and 5. Control animals received PBS ip. OVA-immunized animals were challenged by inhalation of 0.5% OVA aerosol for 10 minutes by an ultrasonic nebulizer on days 12, 16 and 20. Control animals were challenged with PBS in similar fashion. The OVA-sensitized animals receive vehicle (0.5% Methocel) or CCR2 antagonists orally at 3, 10, 30 mg/kg twice daily from days 9-20 and once daily on Day 21, 2 hours before sacrifice. Dexamethason (5 mg/kg) and Montelukast (1 mg/kg) are given orally once a day. On day 21, 2 hours post the last dose of CCR2 compounds, bronchial reactivity to aerosolized methacholine is measured using a Buxco whole body plethysmograpgh. On day 21, the animals are sacrificed. Bronchoalveolar lavage fluid is collected (1 mL) and total cells counted. The numbers of eosinophils, lymphocytes, monocytes and neutrophils are determined using cytospin analysis after Giemsa staining (Hema Tek 2000). Percent inhibition of total BAL leukocyte count (and eosinophil count) is calculated by comparing the compound-treated mice with vehicle-treated mice. Compounds are deemed efficacious if the inhibition reaches 30%.

Example 127

Oral Formulation

Prophetic Example

As a specific embodiment of an oral composition, 100 mg of the compound prepared as in any of Examples 1 to 119 is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. The compounds of Formula I

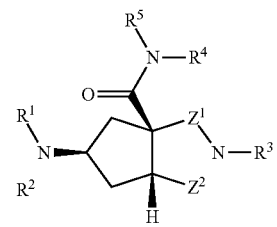

wherein $R^1$ is $C_{(1-4)}$alkylO$C_{(1-4)}$alkyl, cyclohexyl, or tetrahydropyranyl, wherein said cyclohexyl or tetrahydropyranyl may be optionally substituted with one substituent selected from the group consisting of: $OC_{(1-4)}$alkyl, OH, $CH_2CH_3$, —CN, $NH_2$, $NH(CH_3)$, $N(CH_3)_2$, or $OCF_3$;

$R^2$ is H, $C(S)NHCH_2CH(CH_3)_2$, or $C(S)NHCH_3$;

$R^3$ is

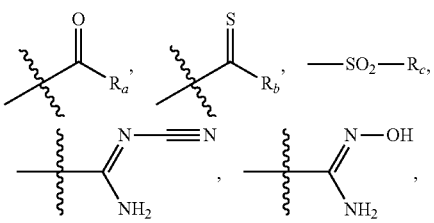

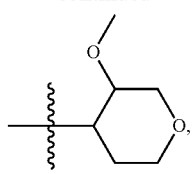

H, —CN, $C_{(1-4)}$alkyl, $C_{(1-4)}$alkylNA$^1$A$^2$, $C_{(1-3)}$alkylC(O)NA$^1$A$^2$, $C_{(3-6)}$cycloalkyl, oxetan-3-yl, —(CH$_2$)$_n$Ph-R$_{aa}$, —$C_{(1-4)}$alkylCO$_2$C$_{(1-4)}$alkyl, 4,5 dihydro thiazolyl, 4,5 dihydro oxazolyl, thiazolyl, oxazolyl, pyrimidinyl, pyridyl, pyrazyl, furyl, or 3-methyl 1,2,4 oxadiazol-5-yl; wherein said 4,5 dihydro thiazolyl, 4,5 dihydro oxazolyl, thiazolyl, oxazolyl, pyrimidinyl, pyridyl, pyrazyl, and furyl may be optionally substituted with up to two substituent independently selected from R$_{aa}$, n is 0, 1, 2, or 3;

R$_a$ is H, NA$^1$A$^2$, NHCH$_2$CH$_2$NA$_1$A$_2$, $C_{(1-4)}$alkylNA$^1$A$^2$, OC$_{(1-4)}$alkylNA$^1$A$^2$, $C_{(1-6)}$alkyl, OC$_{(1-6)}$alkyl, —CN, —CH$_2$CH$_2$Ph, —CH$_2$OPh, —CH$_2$OC(O)C$_{(1-4)}$alkyl, —CH$_2$OC$_{(1-4)}$alkyl, —CH$_2$NHBoc, —OCH$_2$CH=CH$_2$, —OCH$_2$CH$_2$CF$_3$, —OCH$_2$CH$_2$C(CH$_3$)$_2$OH, —OCH$_2$CH$_2$OC$_{(1-4)}$alkyl, —OCH$_2$CH$_2$CN, —OPh-R$_{aa}$,

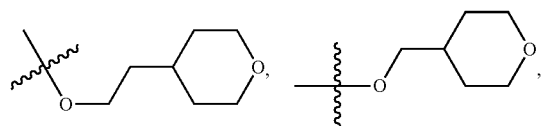

—OC$_{(1-4)}$alkyl-Ph—R$_{aa}$, phenyl-R$_{aa}$, oxazol-2-yl, oxazol-4-yl, isoxazol-5-yl, or thiazol-2-yl;

R$_{aa}$ is H, OC$_{(1-4)}$alkyl, OCF$_3$, —CO$_2$H, Cl, Br, F, or —CN;

R$_b$ is NA$^1$A$^2$;

R$_c$ is NA$^1$A$^2$, CH$_2$Ph, CH$_2$CH$_2$Ph, or C$_{(1-4)}$alkyl;

A$^1$ is H, C$_{(1-6)}$alkyl, Ph-R$_{aa}$, C(O)CH$_3$, CH$_2$Ph-R$_{aa}$, or C$_{(1-4)}$alkylOC$_{(1-4)}$alkyl;

A$^2$ is H, C$_{(1-6)}$alkyl; or

A$^1$ and A$^2$ may be taken together with the nitrogen to which they are attached to form a ring selected from the group consisting of:

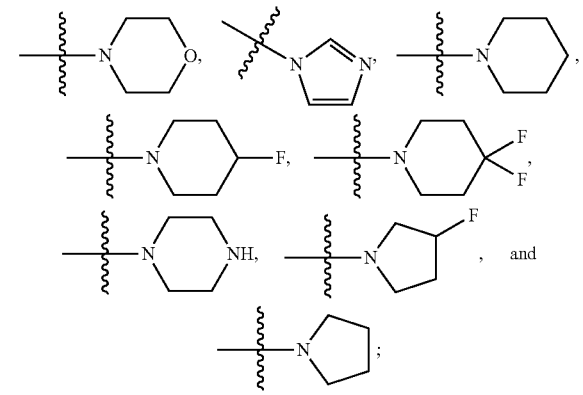

R$^4$ is CH$_2$Ph, wherein said Ph is optionally substituted with up to two groups selected from CF$_3$, OCF$_3$, and F;

R$^5$ is H; or

R$^4$ and R$^5$ are taken together with their attached nitrogen to form a pair of fused rings selected from the group consisting of:

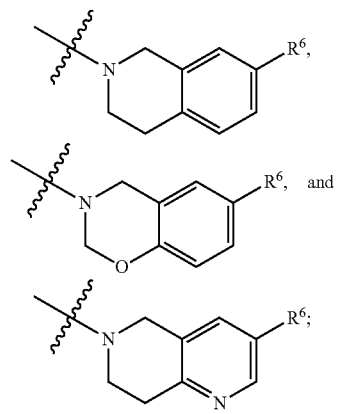

R$^6$ is CF$_3$, or OCF$_3$;

Z$^1$ is CH$_2$ or C=O;

Z$^2$ is CH$_2$ or Z$^2$ may be C=O provided that Z$^1$ and Z$^2$ are not both simultaneously C=O;

and pharmaceutically acceptable salts thereof.

2. A compound of claim 1, wherein:

R$^1$ is C$_{(1-4)}$alkylOCH$_3$, cyclohexyl, 1-methoxy cyclohex-2-yl, tetrahydropyran-4-yl, or 3-C$_{(1-4)}$alkoxy tetrahydropyran-4-yl;

R$^3$ is

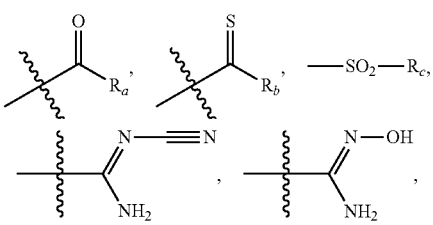

149
-continued

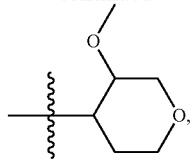

H, —CN, $C_{(1-4)}$alkyl, $C_{(1-4)}$alkylNA$^1$A$^2$, $C_{(1-3)}$alkylC(O)N($C_{(1-2)}$alkyl)$_2$, $C_{(3-6)}$cycloalkyl, oxetan-3-yl, —(CH$_2$)$_n$Ph, —$C_{(1-4)}$alkylCO$_2$C$_{(1-4)}$alkyl, 4,5 dihydro thiazolyl, 4,5 dihydro oxazolyl, thiazolyl, oxazolyl, pyrimidinyl, pyridyl, pyrazyl, furyl, or 3-methyl 1,2,4 oxadiazol-5-yl;

R$_a$ is H, NA$^1$A$^2$, NHCH$_2$CH$_2$NA$_1$A$_2$, $C_{(1-4)}$alkylNA$^1$A$^2$, OC$_{(1-4)}$alkylNA$^1$A$^2$, $C_{(1-6)}$alkyl, OC$_{(1-6)}$alkyl, —CN, —CH$_2$CH$_2$Ph, —CH$_2$OPh, —CH$_2$OC(O)C$_{(1-4)}$alkyl, —CH$_2$OC$_{(1-4)}$alkyl, —CH$_2$NHBoc, —OCH$_2$CH=CH$_2$, —OCH$_2$CH$_2$CF$_3$, —OCH$_2$CH$_2$C(CH$_3$)$_2$OH, —OCH$_2$CH$_2$OC$_{(1-4)}$alkyl, —OCH$_2$CH$_2$CN, —OPh,

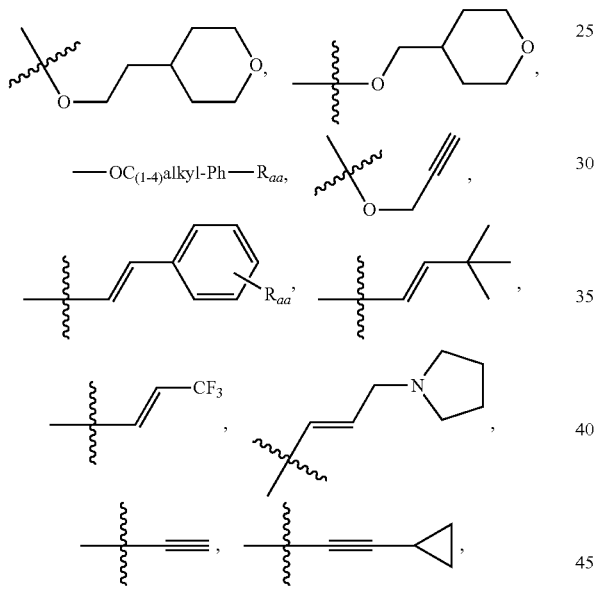

phenyl, oxazol-2-yl, oxazol-4-yl, isoxazol-5-yl, or thiazol-2-yl;

R$_{aa}$ is H, OC$_{(1-4)}$alkyl, —CO$_2$H, Cl, Br, F, or —CN;

R$_c$ is NH$_2$, NHCH$_2$Ph, CH$_2$Ph, CH$_2$CH$_2$Ph, or $C_{(1-4)}$alkyl;

R$^4$ is CH$_2$Ph, wherein said Ph is optionally substituted with up to two groups selected from CF$_3$, OCF$_3$, and F;

R$^5$ is H; or

R$^4$ and R$^5$ are taken together with their attached nitrogen to form a pair of fused rings selected from the group consisting of:

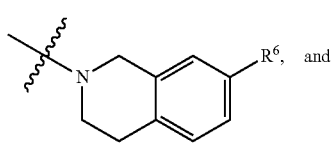

150
-continued

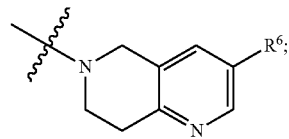

and pharmaceutically acceptable salts thereof.

3. A compound of claim 2, wherein:

R$^1$ is $C_{(1-4)}$alkylOCH$_3$, 3-$C_{(1-4)}$alkoxy tetrahydropyran-4-yl, or tetrahydropyran-4-yl;

R$^3$ is

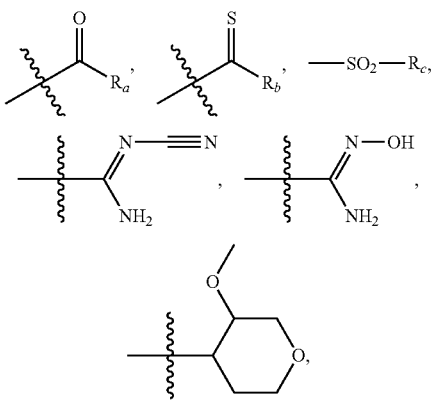

H, —CN, $C_{(1-4)}$alkyl, —C$_{(1-3)}$alkylC(O)N(C$_{(1-2)}$alkyl)$_2$, $C_{(3-6)}$cycloalkyl, oxetan-3-yl, —(CH$_2$)$_n$Ph, —C$_{(1-4)}$alkylCO$_2$C$_{(1-4)}$alkyl, 4,5 dihydro thiazolyl, 4,5 dihydro oxazolyl, thiazolyl, oxazolyl, pyrimidinyl, pyridyl, pyrazyl, furyl, or 3-methyl 1,2,4 oxadiazol-5-yl;

R$_a$ is H, NA$^1$A$^2$, NHCH$_2$CH$_2$NA$_1$A$_2$, $C_{(1-4)}$alkylNA$^1$A$^2$, OC$_{(1-4)}$alkylNA$^1$A$^2$, $C_{(1-6)}$alkyl, OC$_{(1-6)}$alkyl, —CN, —CH$_2$CH$_2$Ph, —CH$_2$OPh, —CH$_2$OC(O)C$_{(1-4)}$alkyl, —CH$_2$OC$_{(1-4)}$alkyl, —CH$_2$NHBoc, —OCH$_2$CH=CH$_2$, —OCH$_2$CH$_2$CF$_3$, —OCH$_2$CH$_2$C(CH$_3$)$_2$OH, —OCH$_2$CH$_2$OCH$_3$, —OCH$_2$CH$_2$CN, —OPh,

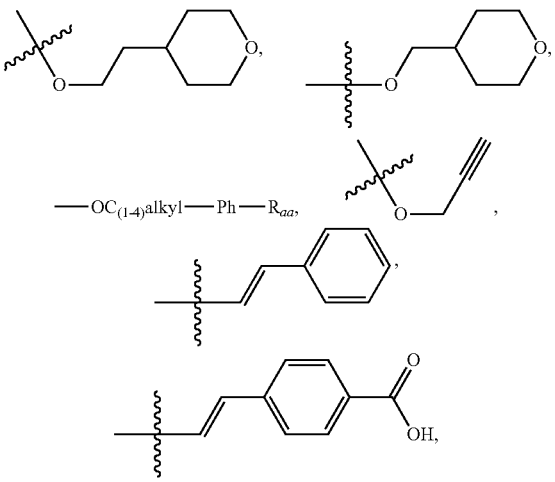

-continued

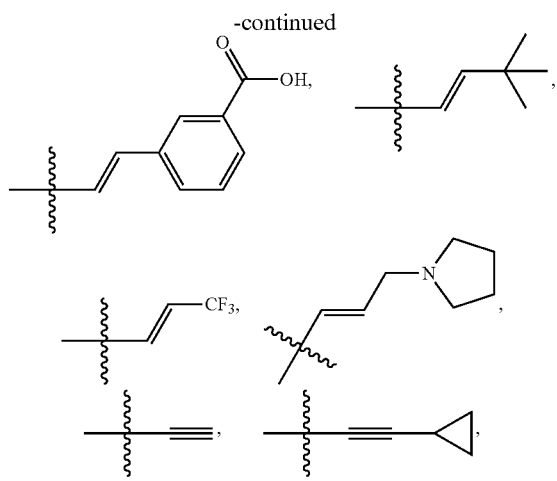

phenyl, oxazol-2-yl, oxazol-4-yl, isoxazol-5-yl, or thiazol-2-yl;

$R_{aa}$ is H, $OC_{(1-4)}$alkyl, or —CN;

$R_b$ is

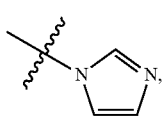 [SMILES: *n1ccnc1]

$NH_2$, $NHCH_3$, $NHCH_2Ph$, or $NHCH_2CH(CH_3)_2$;

$R_c$ is $NH_2$, $NHCH_2Ph$, $CH_2Ph$, $CH_2CH_2Ph$, or $CH_3$;

$A^1$ is H, $C_{(1-6)}$alkyl, Ph, or $C(O)CH_3$, $CH_2Ph$, $C_{(1-4)}$alkyl $OC_{(1-4)}$alkyl;

$A^2$ is H, $C_{(1-6)}$alkyl; or $A^1$ and $A^2$ may be taken together with the nitrogen to which they are attached to form a ring selected from the group consisting of:

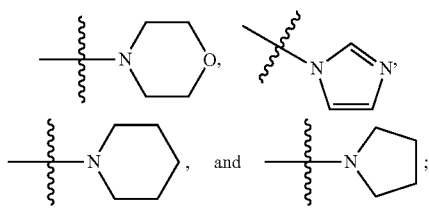

and pharmaceutically acceptable salts thereof.

4. A compound of claim 3, wherein:

$R^1$ is $CH_2CH_2OCH_3$, 3-$C_{(1-4)}$alkoxy tetrahydropyran-4-yl, or tetrahydropyran-4-yl;

$R^3$ is

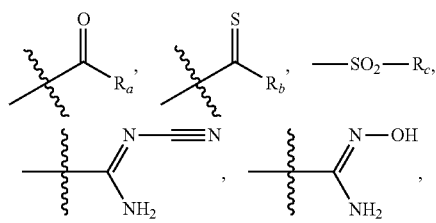

-continued

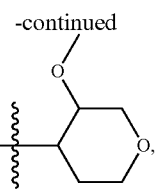

H, —CN, $C_{(1-4)}$alkyl, —$C_{(1-3)}$alkylC(O)N($C_{(1-2)}$alkyl)$_2$, cyclopropyl, cyclobutanyl, oxetan-3-yl, —$(CH_2)_n$Ph, —$C_{(1-4)}$alkylCO$_2C_{(1-4)}$alkyl, 4,5 dihydro thiazol-2-yl, 4,5 dihydro oxazol-2-yl, thiazol-2-yl, pyrimidin-2-yl, or 3-methyl 1,2,4 oxadiazol-5-yl;

$R_a$ is H, $NA^1A^2$, $NHCH_2CH_2NA_1A_2$, $C_{(1-4)}$alkyl$NA^1A^2$, $OC_{(1-4)}$alkyl$NA^1A^2$, $C_{(1-6)}$alkyl, $OC_{(1-6)}$alkyl, —CN, —$CH_2CH_2Ph$, —$CH_2OPh$, —$CH_2NHBoc$, —$OCH_2Ph$, —$CH_2OC(O)C_{(1-4)}$alkyl, —$CH_2OC_{(1-4)}$alkyl, —$OCH_2Ph$-CN, —$OCH_2Ph$-OCH$_3$, —$OCH_2CH=CH_2$, —$OCH_2CH_2CF_3$, —$OCH_2CH_2C(CH_3)_2OH$, —$OCH_2CH_2OCH_3$, —$OCH_2CH_2CN$, —OPh,

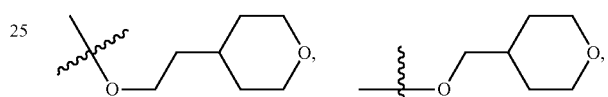

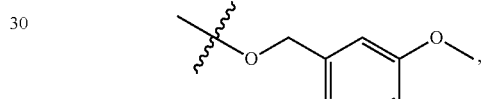

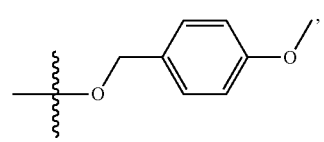

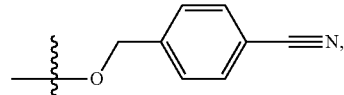

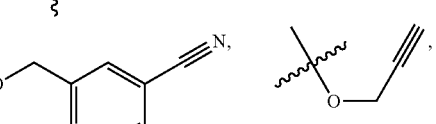

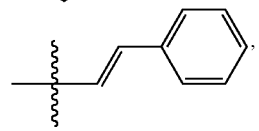

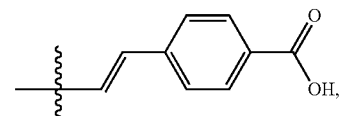

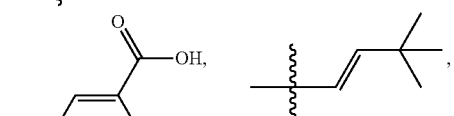

153

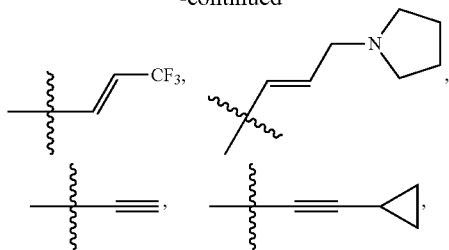

phenyl, oxazol-2-yl, oxazol-4-yl, isoxazol-5-yl, or thiazol-2-yl;

$A^1$ is H, $C_{(1-6)}$alkyl, Ph, or $C(O)CH_3$, $CH_2Ph$, $C_{(1-4)}$alkyl $OC_{(1-4)}$alkyl;

$A^2$ is H, $C_{(1-6)}$alkyl; or $A^1$ and $A^2$ may be taken together with the nitrogen to which they are attached to form a ring selected from the group consisting of:

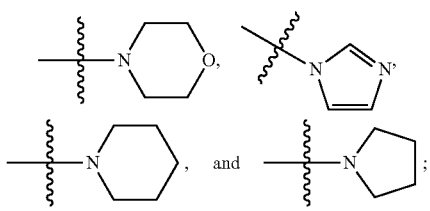

and pharmaceutically acceptable salts thereof.

5. A compound of claim 4, wherein:

$R^1$ is $CH_2CH_2OCH_3$, 3-$C_{(1-2)}$alkoxy tetrahydropyran-4-yl, or tetrahydropyran-4-yl;

$R^3$ is

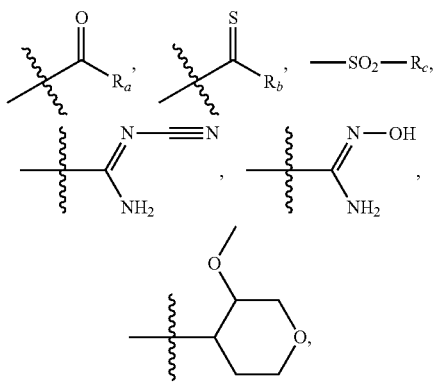

H, —CN, $C_{(1-3)}$alkyl, —$CH_2C(O)N(CH_3)_2$, cyclopropyl, oxetan-3-yl, —$(CH_2)_n$Ph, —$CH_2CO_2CH_3$, 4,5 dihydro thiazol-2-yl, 4,5 dihydro oxazol-2-yl, thiazol-2-yl, pyrimidin-2-yl, or 3-methyl 1,2,4 oxadiazol-5-yl;

$R_a$ is H, $NH_2$, $NHCH_3$, $N(CH_3)_2$, $NHCH_2CH(CH_3)_2$, $NHCH(CH_3)_2$, $NHCH_2C(CH_3)_3$, $NHCH_2CH_2OCH_3$, $NHCH_2CH_2$-morpholinyl, NHPh, $NHCH_2Ph$, $CH_2CH_2N(CH_3)_2$, $CH_2CH_2CH_2N(CH_3)_2$, —CN, —$CH_3$, —$CH_2CH_2Ph$, —$CH_2OPh$, —$CH_2OC(O)CH_3$, —$CH_2OCH_3$, —$CH_2OC(CH_3)_3$, —$CH_2NHC(O)CH_3$, —$CH_2N(CH_3)_2$, —$CH_2NHBoc$, —$OCH_3$, —$OCH_2C(CH_3)_3$, —$OCH_2CH(CH_3)_2$, —$OCH_2CH_2CH_3$, —$OCH_2Ph$, —$OCH_2Ph$-CN, —$OCH_2Ph$-$OCH_3$,

154

—$OCH_2CH=CH_2$, —$OCH_2CH_2CF_3$, —$OCH_2CH_2C(CH_3)_2OH$, —$OCH_2CH_2OCH_3$, —$OCH_2CH_2CN$, —$OCH_2CH_2N(C_{(1-2)}alkyl)_2$, —$OCH_2CH_2NHC(O)CH_3$, —OPh,

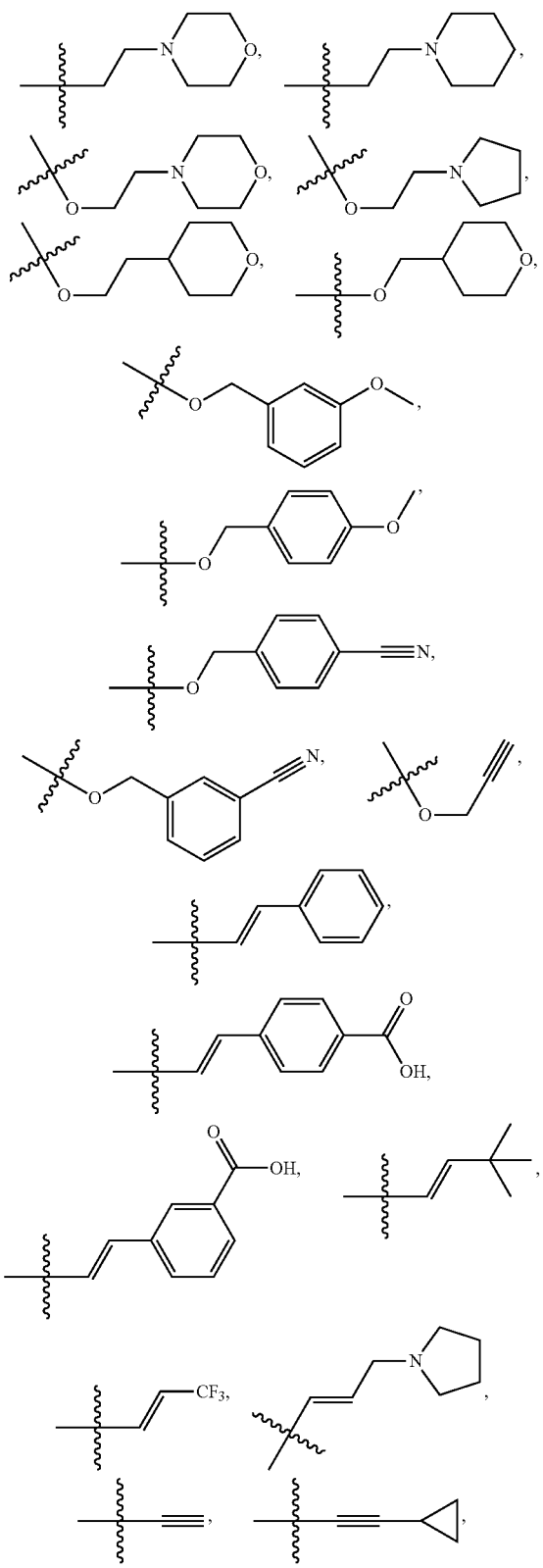

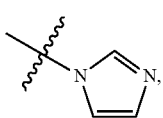

phenyl, oxazol-2-yl, oxazol-4-yl, isoxazol-5-yl, thiazol-2-yl,

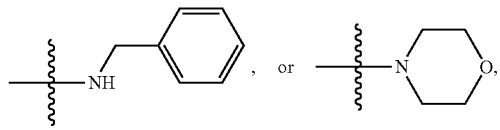

R⁴ is 1,3-bis(trifluoromethyl)benz-5-yl, 1-fluoro-3-(trifluoromethyl)benz-5-yl, or 1-(trifluoromethyl)benz-5-yl;

R⁵ is H; or

R⁴ and R⁵ are taken together with their attached nitrogen to form a pair of fused rings selected from the group consisting of:

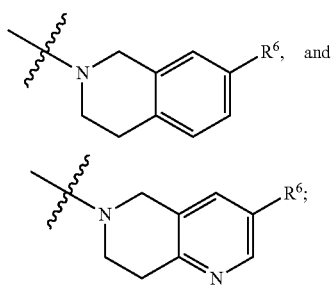

and pharmaceutically acceptable salts thereof.

6. A compound of claim 1, selected from the group consisting of:

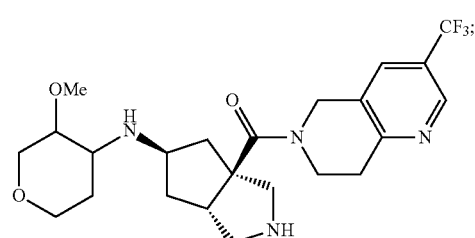

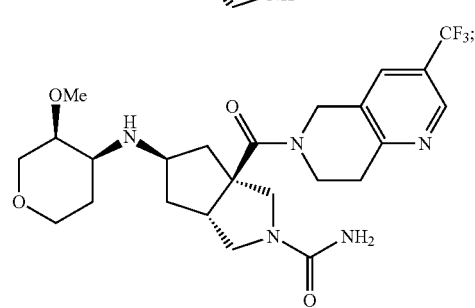

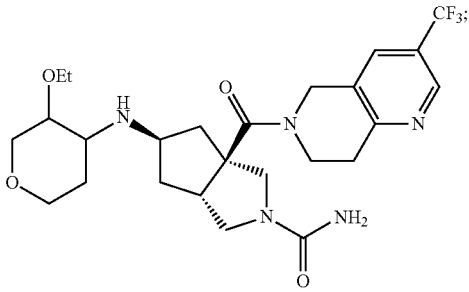

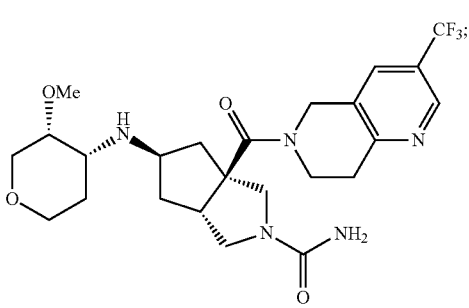

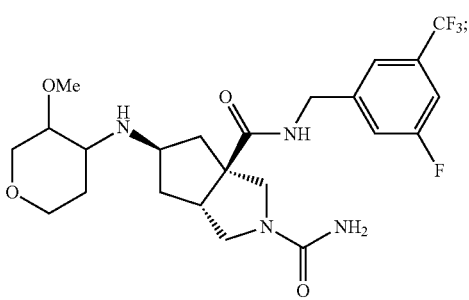

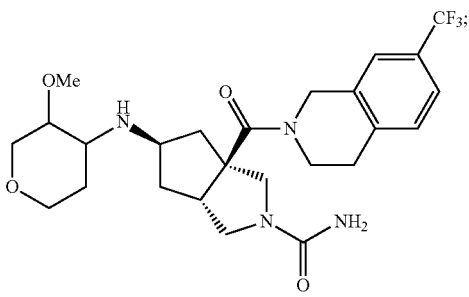

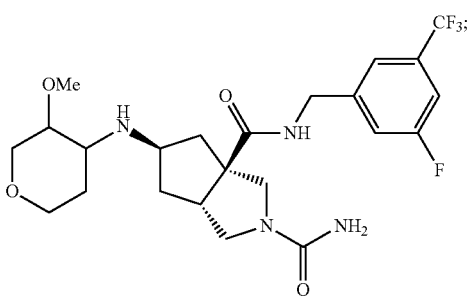

157
-continued
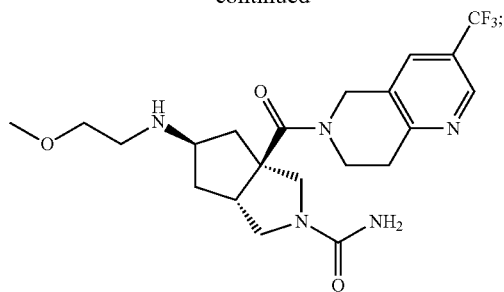
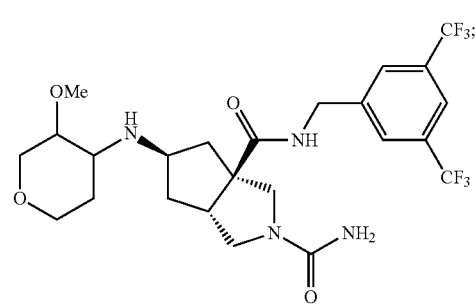
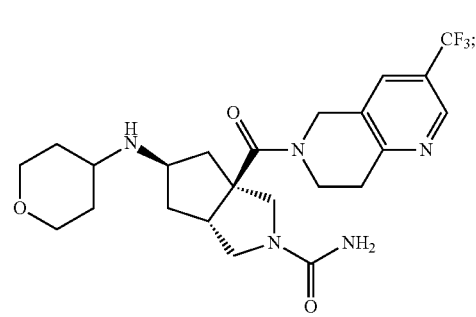
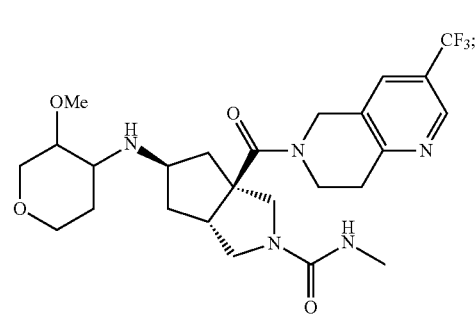
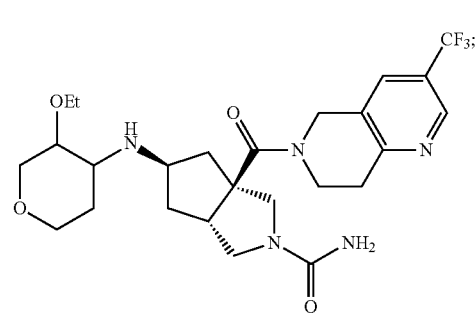
158
-continued
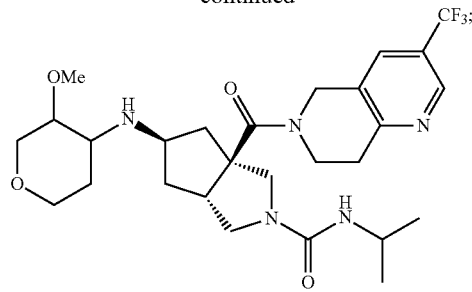
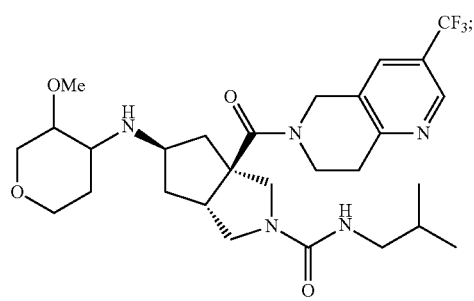
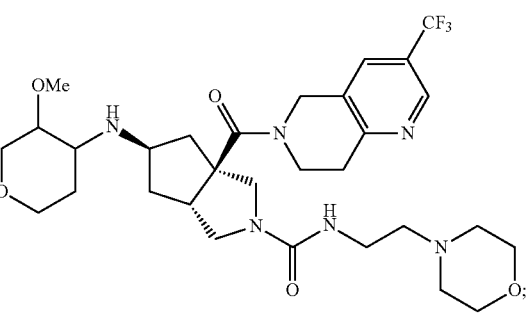
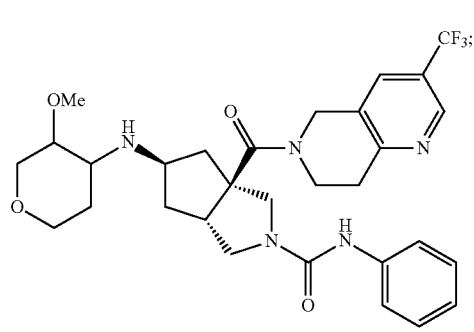
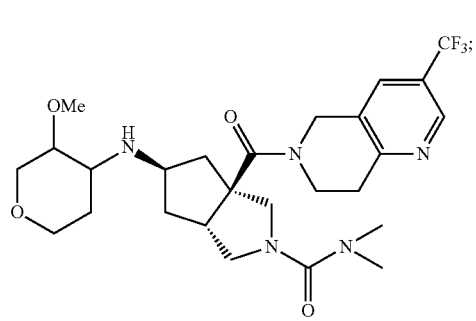

159
-continued
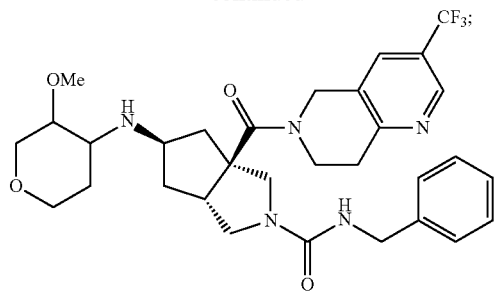
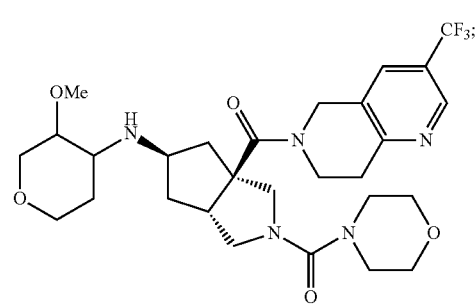
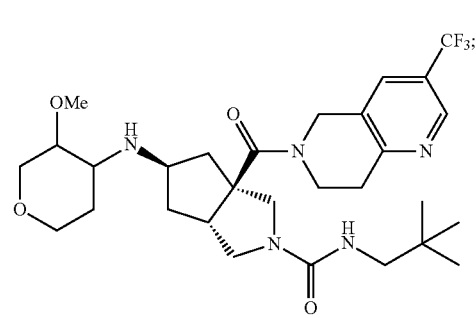
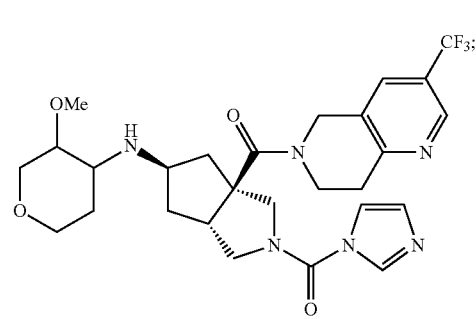
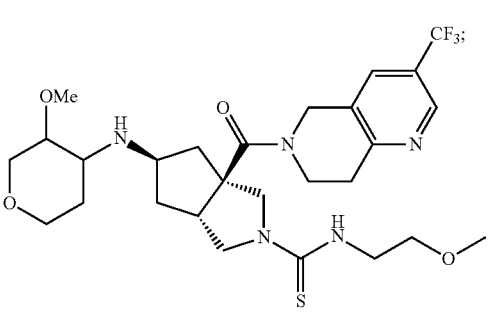
160
-continued
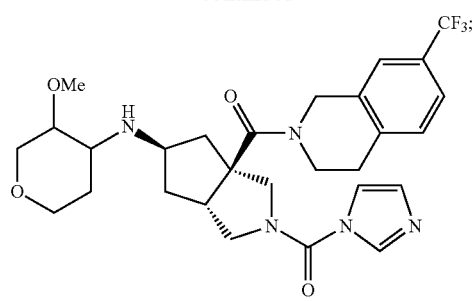
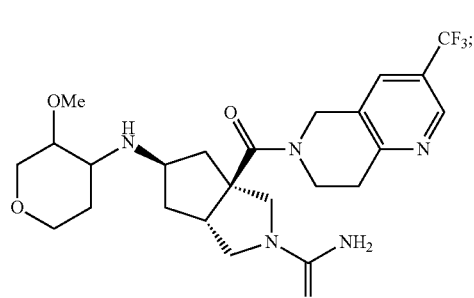
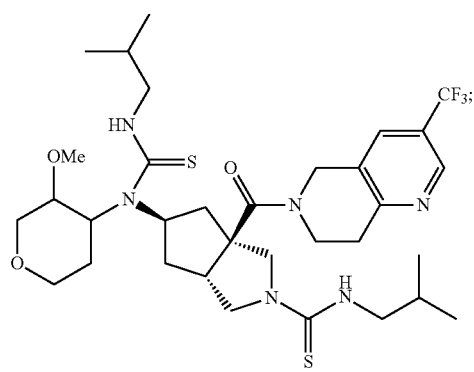
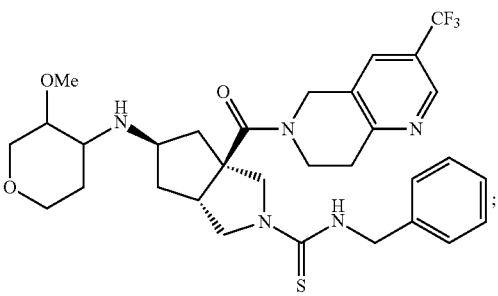
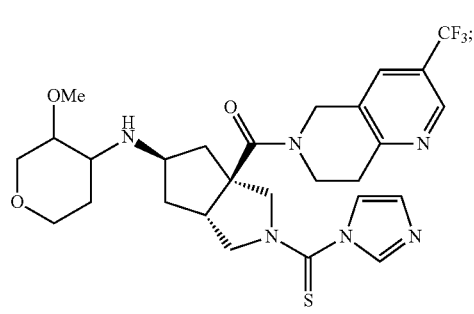

161
-continued
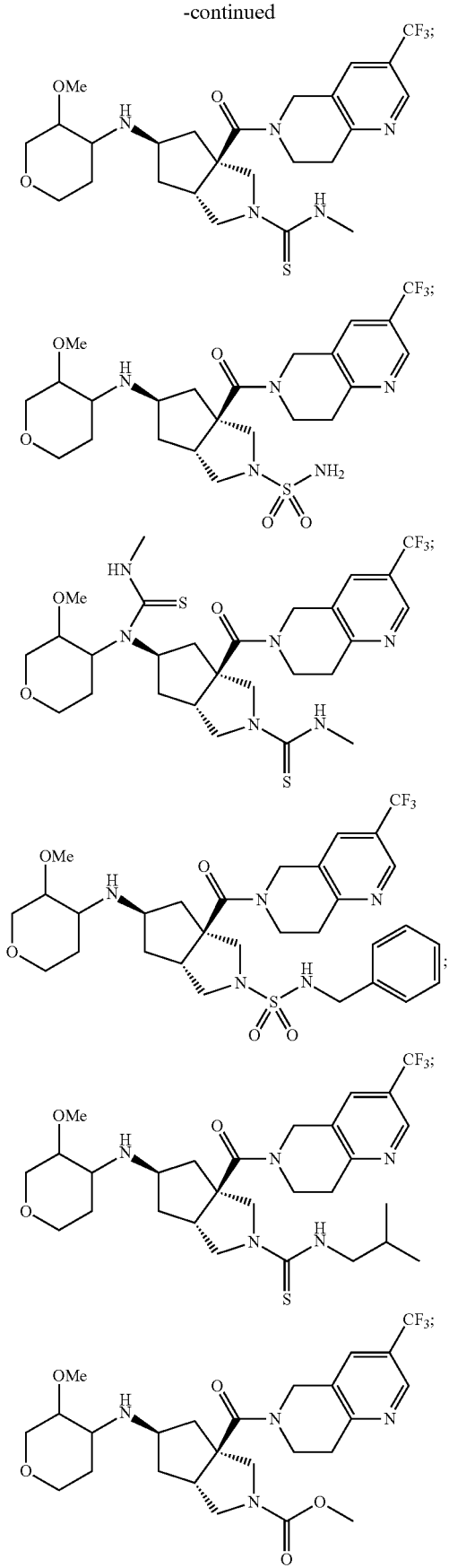
162
-continued
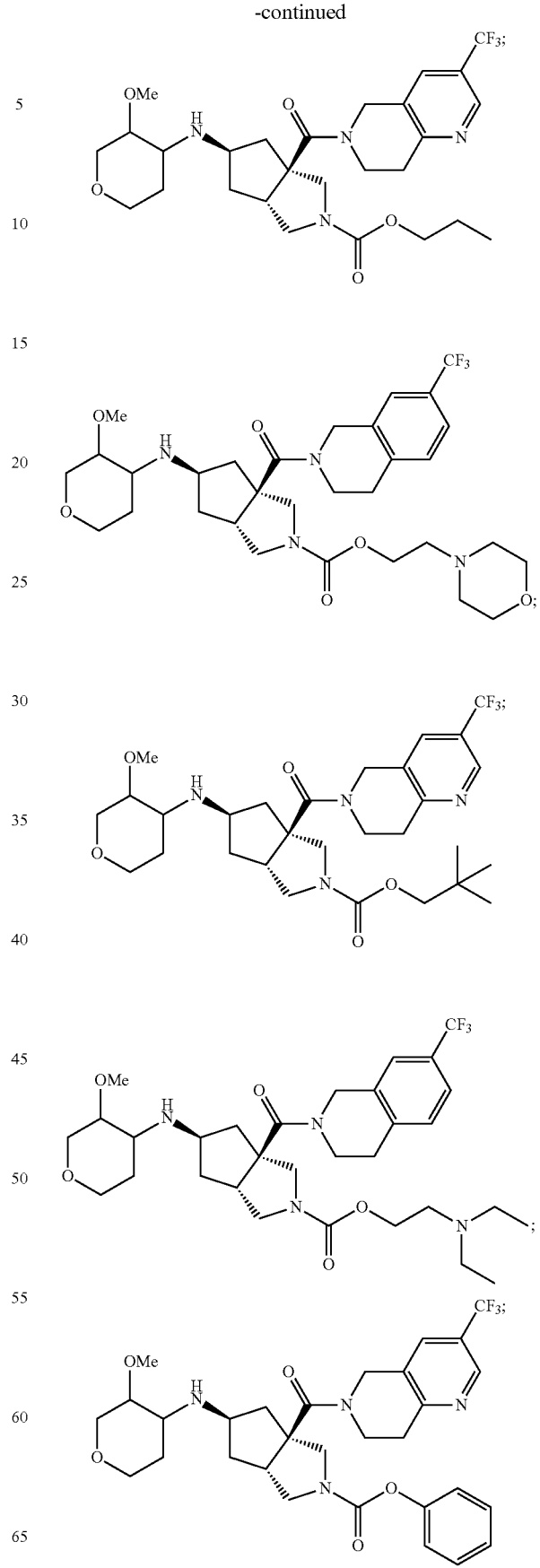

163
-continued
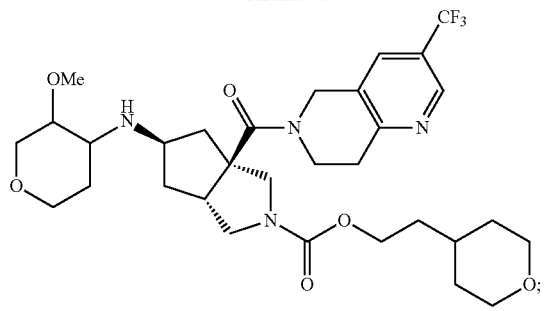
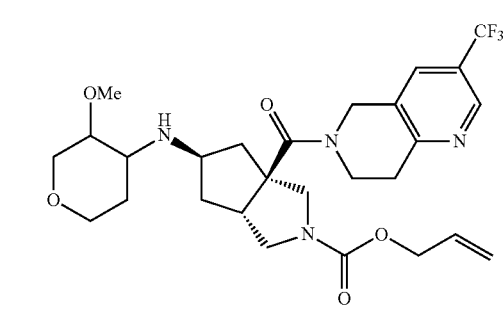
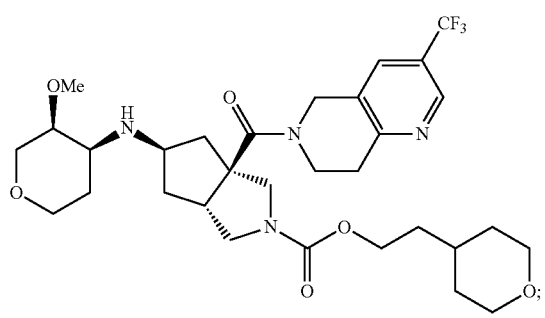
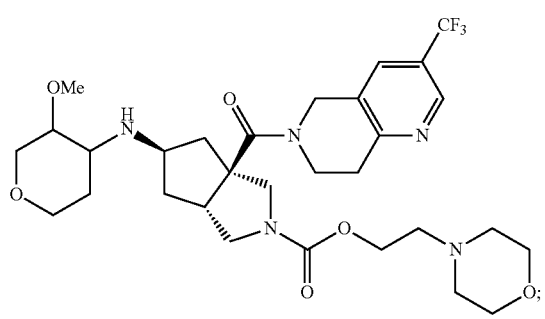
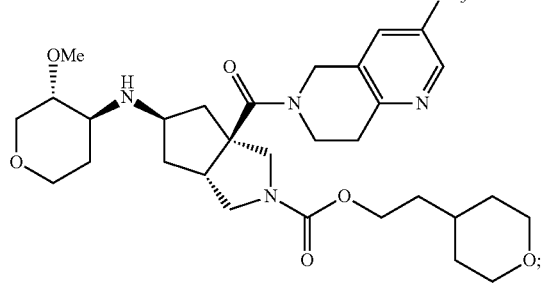
164
-continued
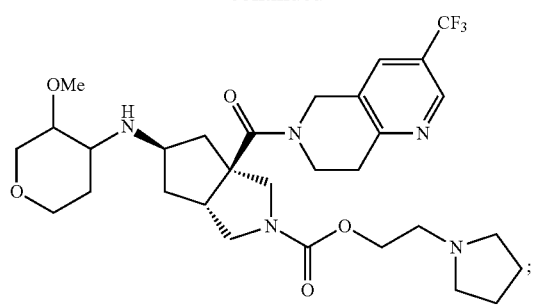
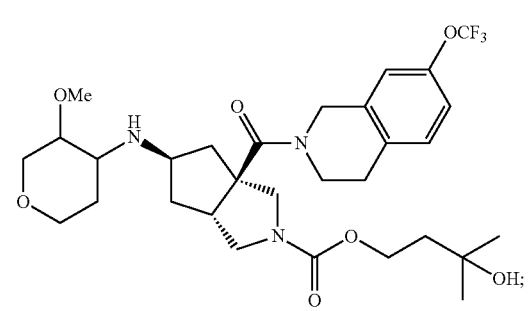
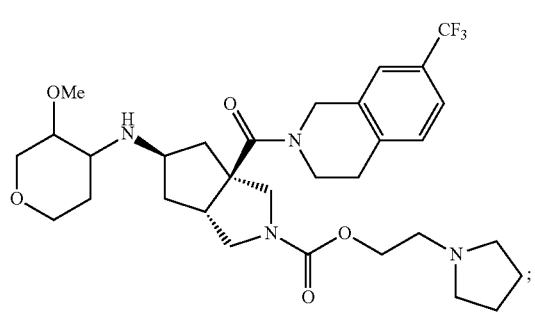
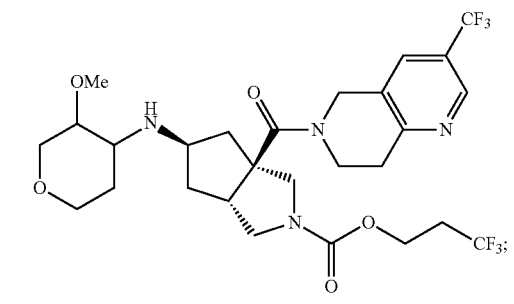
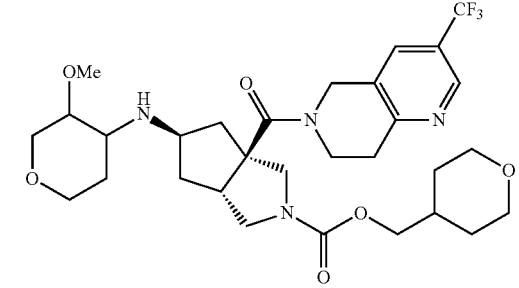

165
-continued
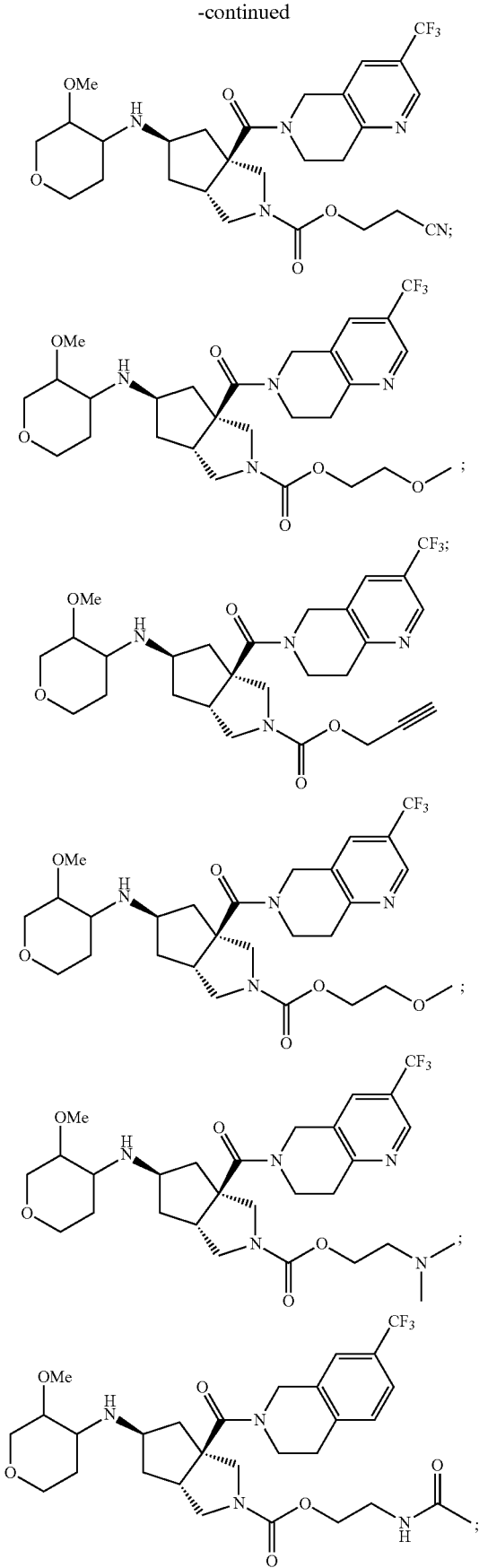
166
-continued
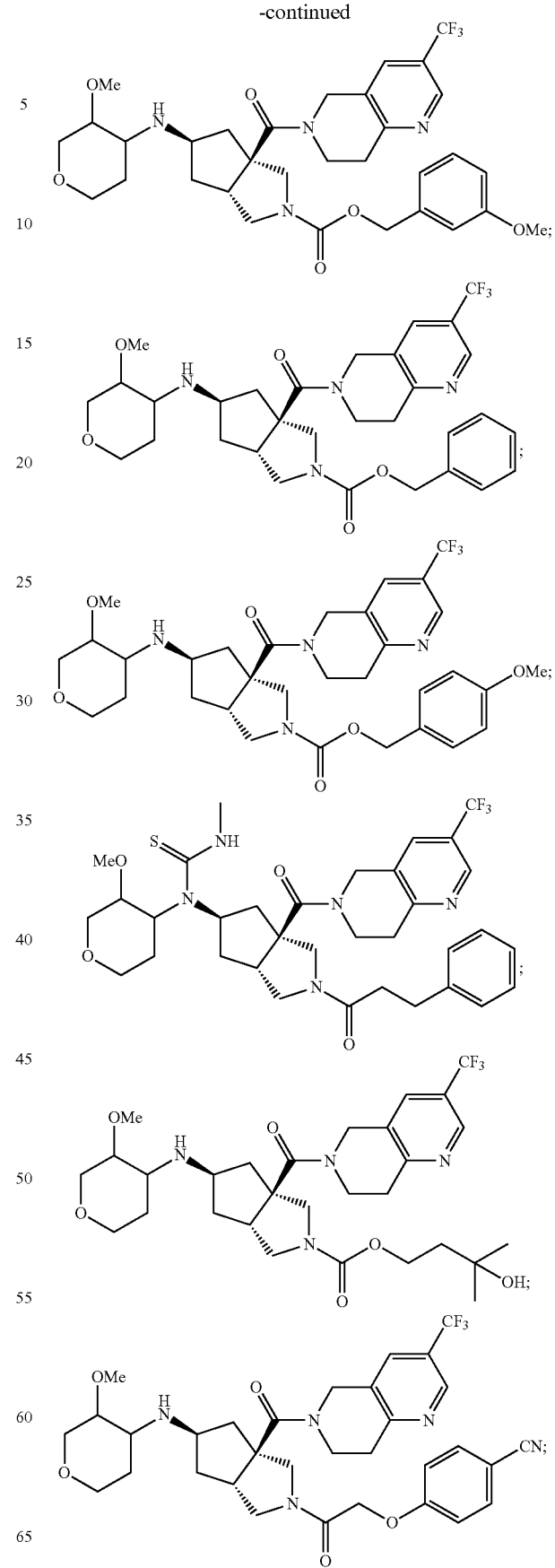

167
-continued
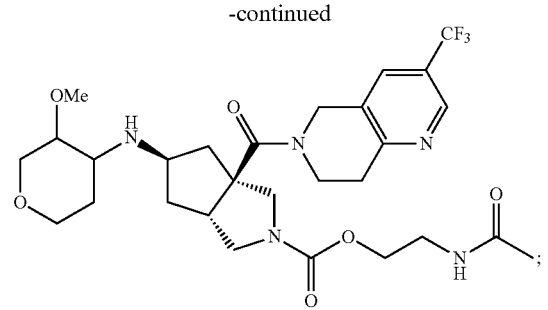
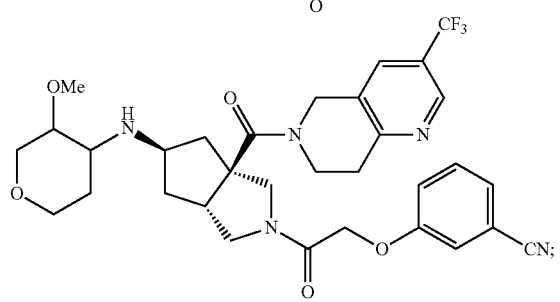
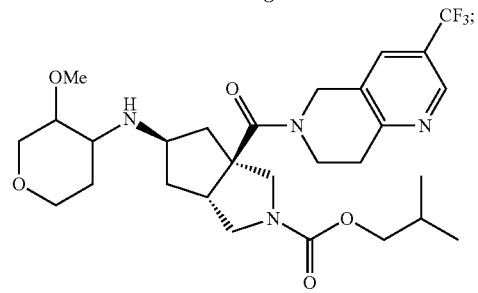
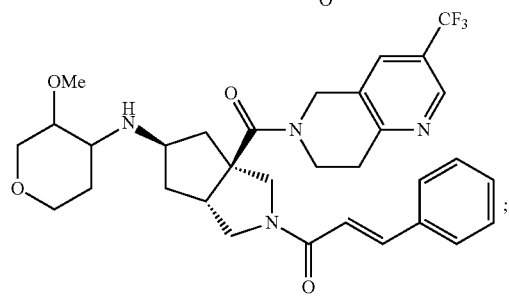
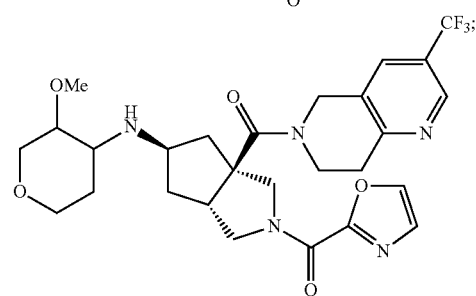
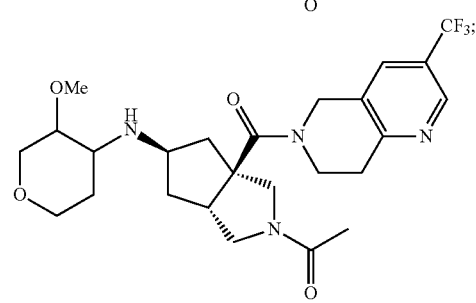
168
-continued
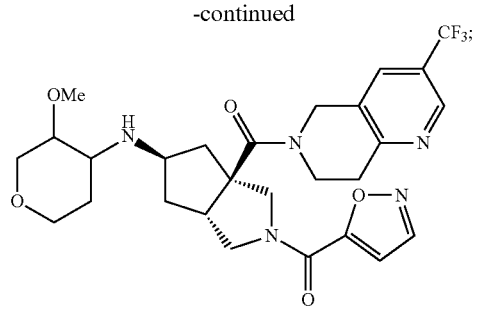
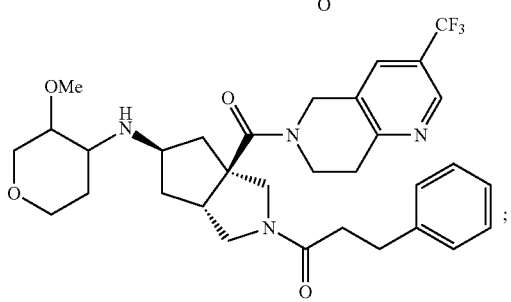
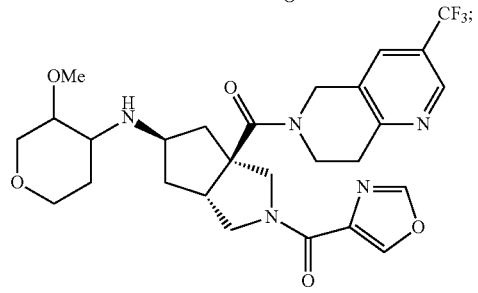
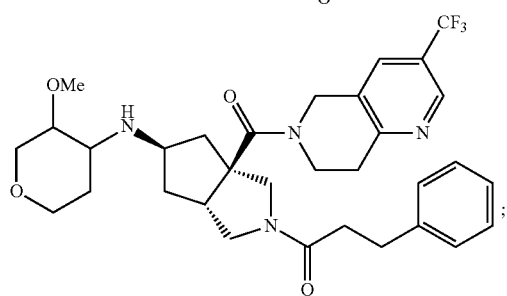
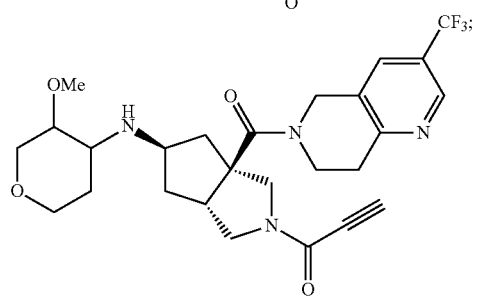
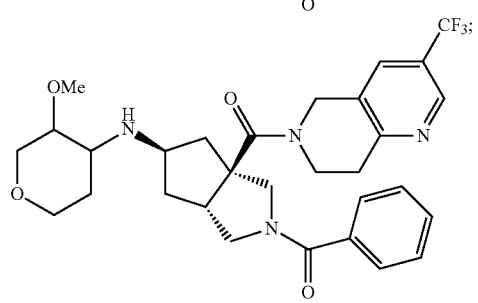

-continued
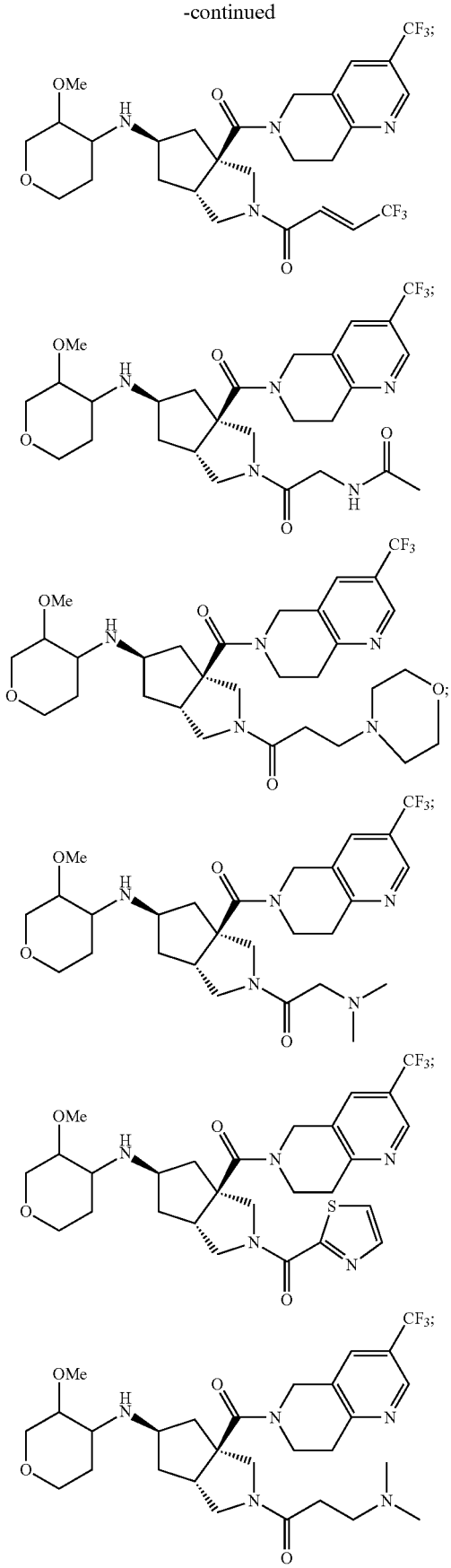
-continued
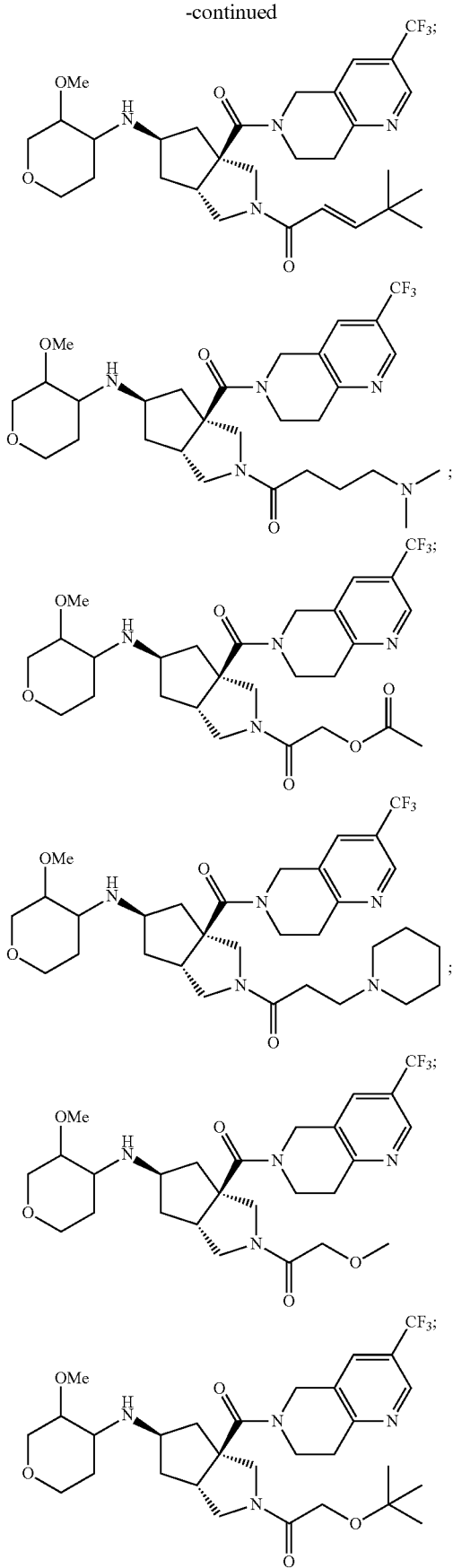

171
-continued
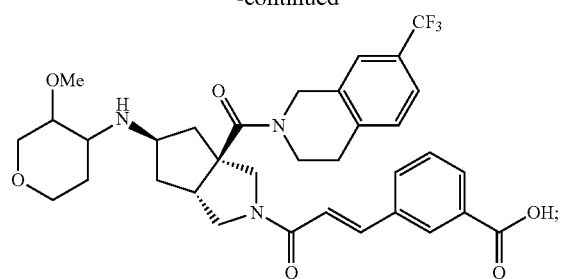
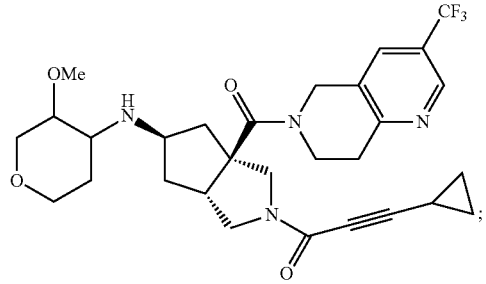
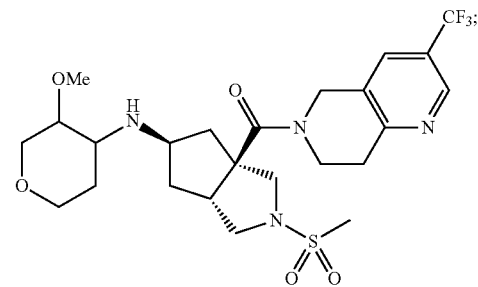
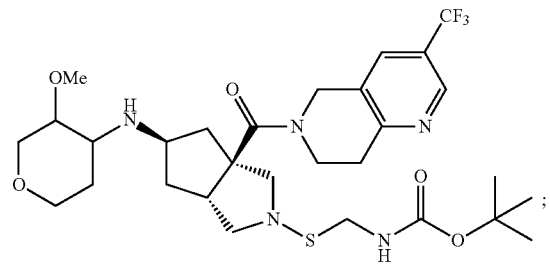
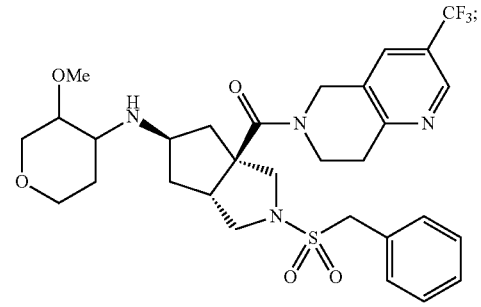
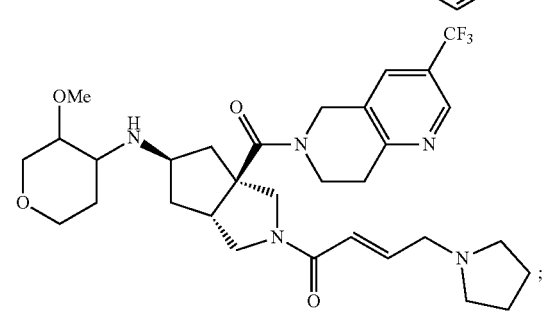
172
-continued
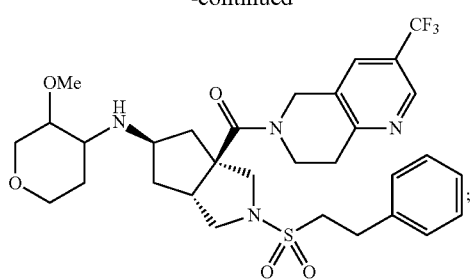
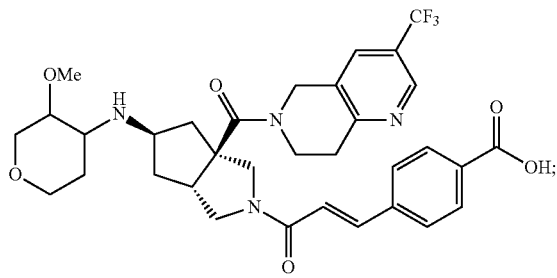
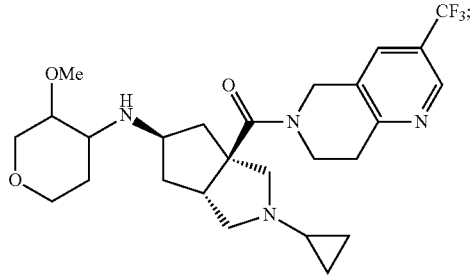
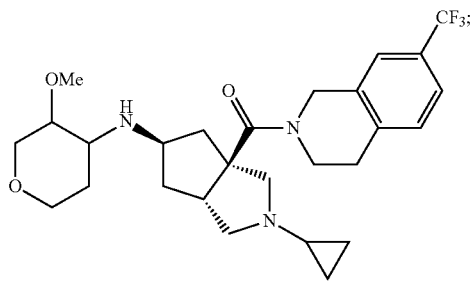
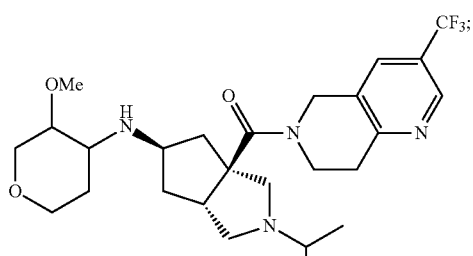
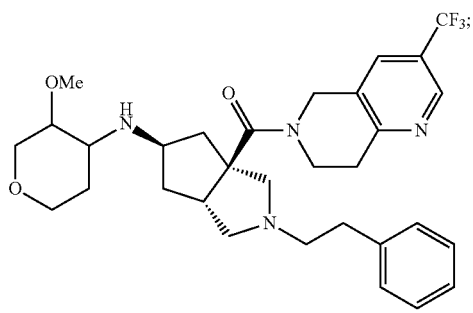

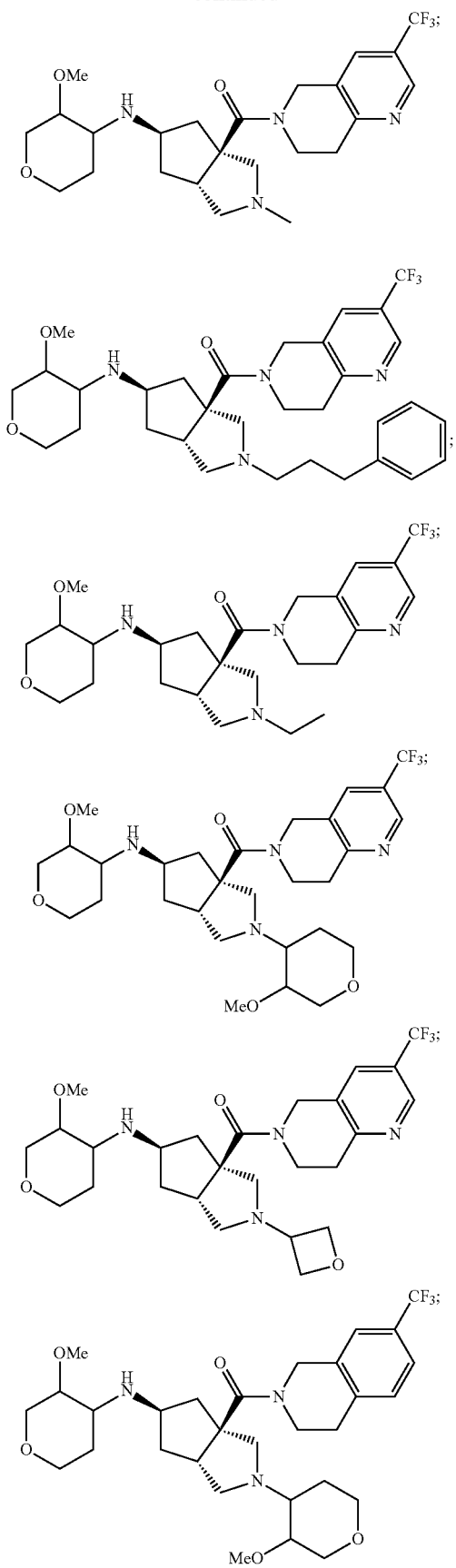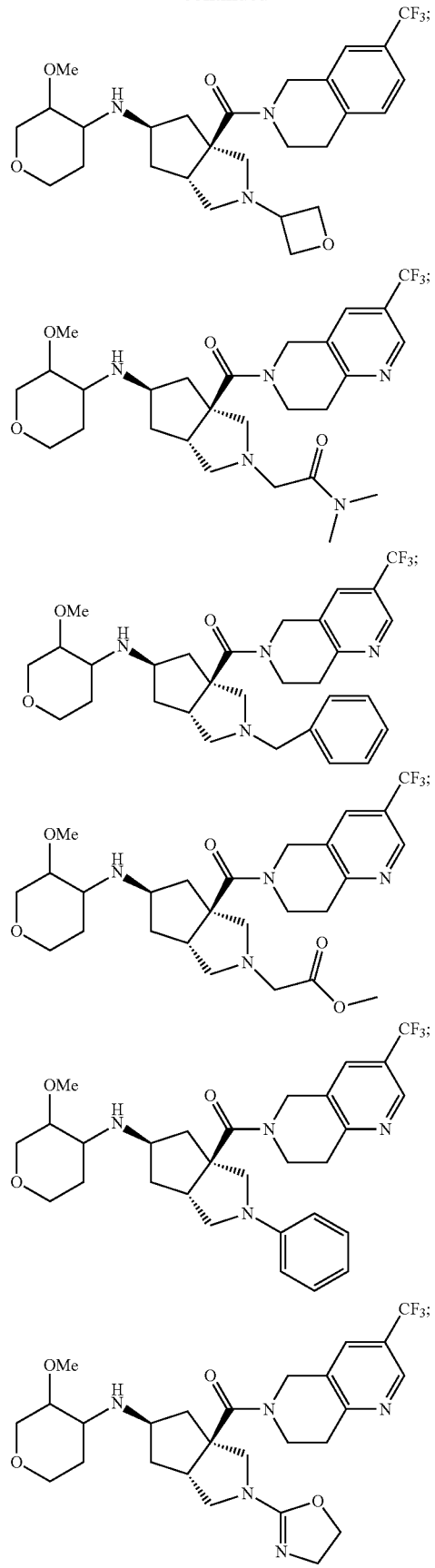

-continued

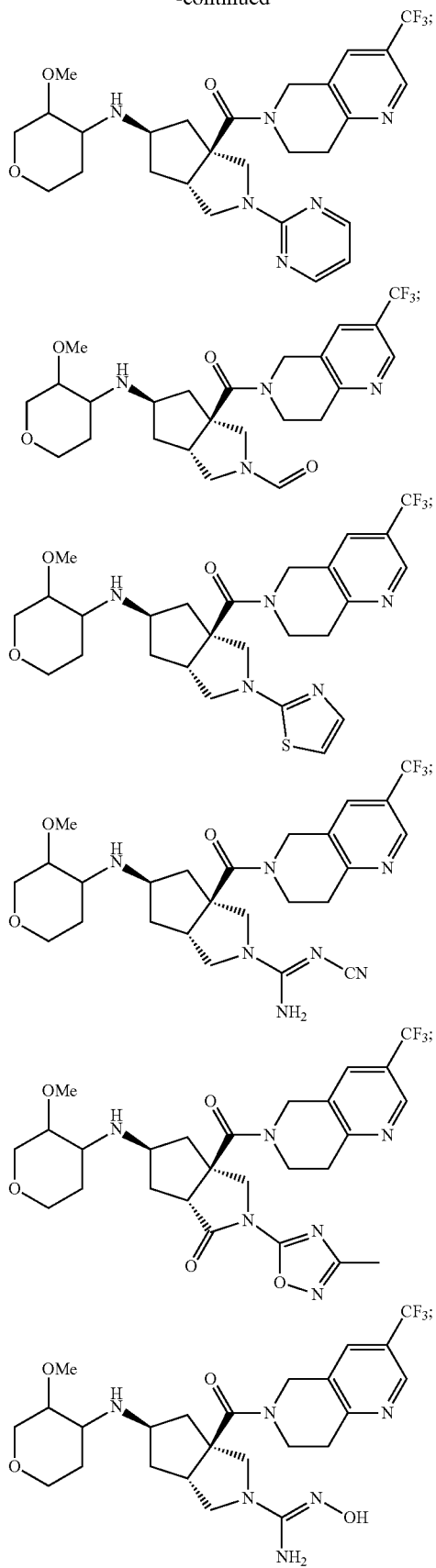

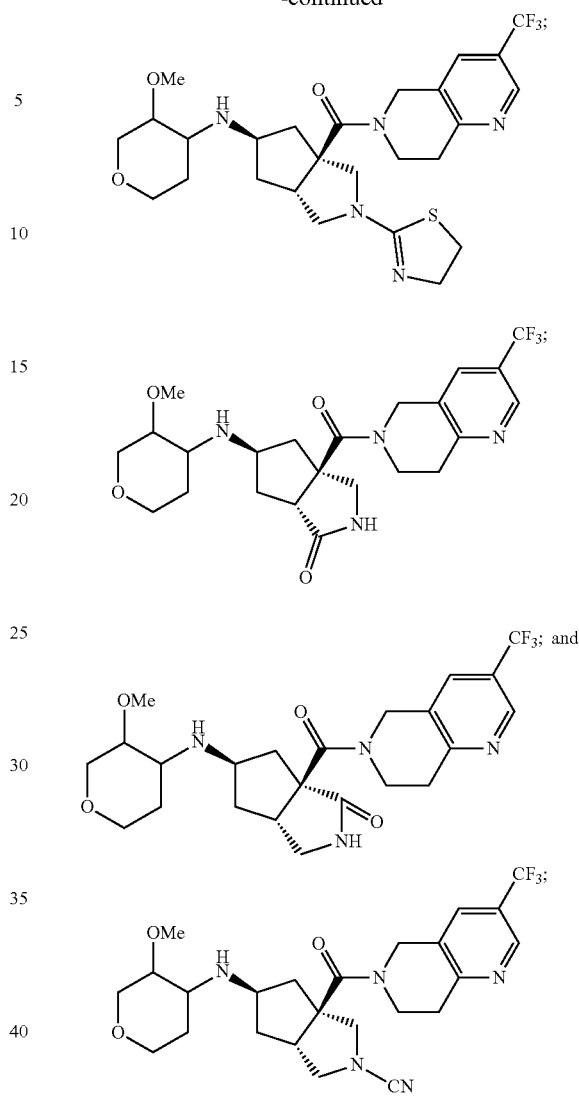

and pharmaceutically acceptable salts thereof.

7. A pharmaceutical composition, comprising a compound of claim 1 and a pharmaceutically acceptable carrier.

8. A pharmaceutical composition made by mixing a compound of claim 1 and a pharmaceutically acceptable carrier.

9. A process for making a pharmaceutical composition comprising mixing a compound of claim 1 and a pharmaceutically acceptable carrier.

10. A method of treating a disorder selected from the group consisting of type II diabetes, obesity and asthma comprising administering to a subject in need thereof a therapeutically effective amount of a compound of claim 1.

11. The method of claim 10, wherein the disorder is type II diabetes.

12. The method of claim 10, wherein the disorder is obesity.

13. The method of claim 10, wherein the disorder is asthma.

* * * * *

UNITED STATES PATENT AND TRADEMARK OFFICE
CERTIFICATE OF CORRECTION

PATENT NO. : 9,024,017 B2
APPLICATION NO. : 13/943099
DATED : May 5, 2015
INVENTOR(S) : Chaozhong Cai et al.

It is certified that error appears in the above-identified patent and that said Letters Patent is hereby corrected as shown below:

In the claims

COL. 156, Claim 6, lines 5-14, delete first chemical structure, and substitute therefor:

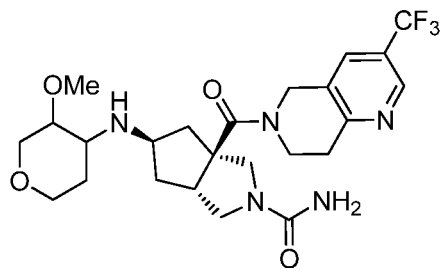

COL. 156, Claim 6, between lines 26 and 30, after 2<sup>nd</sup> chemical structure, insert the following:

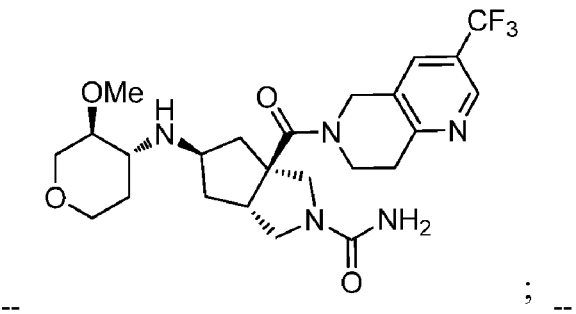

-- ; --

COL. 156, Claim 6, lines 30-40, delete 3<sup>rd</sup> chemical structure and substitute therefor:

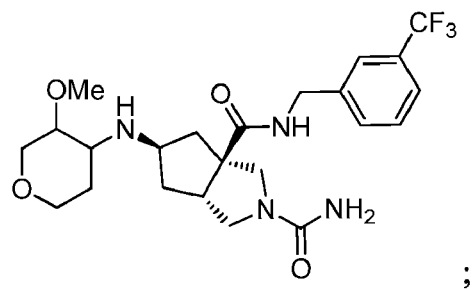

;

Signed and Sealed this
Twenty-third Day of February, 2016

Michelle K. Lee
*Director of the United States Patent and Trademark Office*